US012063858B2

(12) United States Patent
Abramov

(10) Patent No.: US 12,063,858 B2
(45) Date of Patent: Aug. 13, 2024

(54) APPARATUSES BASED ON JET-EFFECT AND THERMOELECTRIC EFFECT

(71) Applicant: SOLITON HOLDINGS CORPORATION, DELAWARE CORPORATION, New York, NY (US)

(72) Inventor: Yuri Abramov, Holon (IL)

(73) Assignee: SOLITON HOLDINGS CORPORATION, DELAWARE CORPORATION, New York, NY (US)

(*) Notice: Subject to any disclaimer, the term of this patent is extended or adjusted under 35 U.S.C. 154(b) by 416 days.

(21) Appl. No.: 17/107,982

(22) Filed: Dec. 1, 2020

(65) Prior Publication Data

US 2022/0173299 A1   Jun. 2, 2022

(51) Int. Cl.
*H10N 10/13*     (2023.01)
*B05B 1/24*      (2006.01)
(Continued)

(52) U.S. Cl.
CPC .............. *H10N 10/13* (2023.02); *B05B 1/24* (2013.01); *B05B 1/3402* (2018.08); *B64C 3/36* (2013.01);
(Continued)

(58) Field of Classification Search
None
See application file for complete search history.

(56) References Cited

U.S. PATENT DOCUMENTS 4,556,122 A    12/1985  Goode
6,981,366 B2    1/2006  Sharpe
(Continued)

FOREIGN PATENT DOCUMENTS

AU    2018200099 A1    1/2019
AU    2020201929 A1    4/2020
(Continued)

OTHER PUBLICATIONS

Co-pending U.S. Appl. No. 16/412,805, filed May 15, 2019.
(Continued)

*Primary Examiner* — Tamir Ayad
(74) *Attorney, Agent, or Firm* — Momentum IP; Marc Van Dyke

(57) ABSTRACT

The invention discloses a method and modified aerodynamic apparatuses: fluid pushers-off and fluid motion-sensors, making enable efficient implementation and use of a controllable enhanced jet-effect, either the waving jet-effect, the Coanda jet-effect, the lift-effect, the effect of thrust, the Venturi effect, and/or the de Laval jet-effect, all are controllable using the Peltier effect and/or the Seebeck effect. The modified aerodynamic apparatuses are geometrically shaped and supplied with built-in thermoelectric devices, wherein the presence of the thermoelectric devices provides for new functional properties of the modified aerodynamic apparatuses. The method solves the problem of effective control of the operation of modified aerodynamic apparatuses such as airfoil wings of a flying vehicle, convergent-divergent nozzles, loudspeakers, and detectors of acoustic waves, all of a highly-efficient functionality.

2 Claims, 31 Drawing Sheets

(51) Int. Cl.
| | |
|---|---|
| *B05B 1/34* | (2006.01) |
| *B64C 3/36* | (2006.01) |
| *B64D 27/18* | (2006.01) |
| *F15D 1/00* | (2006.01) |
| *H02J 7/02* | (2016.01) |
| *H02J 50/15* | (2016.01) |
| *H04R 1/10* | (2006.01) |
| *H04R 1/46* | (2006.01) |
| *H10N 10/17* | (2023.01) |
| *A61B 7/04* | (2006.01) |

(52) U.S. Cl.
CPC .......... *B64D 27/18* (2013.01); *F15D 1/0065* (2013.01); *H02J 7/02* (2013.01); *H02J 50/15* (2016.02); *H04R 1/1016* (2013.01); *H04R 1/46* (2013.01); *H10N 10/17* (2023.02); *A61B 7/04* (2013.01)

(56) References Cited

U.S. PATENT DOCUMENTS

| | | | |
|---|---|---|---|
| 7,156,201 | B2 | 1/2007 | Peshkovskiy et al. |
| 7,516,054 | B2 | 4/2009 | Tanji et al. |
| 8,221,514 | B2 | 7/2012 | Abramov |
| 8,268,030 | B2 | 9/2012 | Abramov |
| 8,611,787 | B2 | 12/2013 | Shiraki et al. |
| 9,724,241 | B2 | 8/2017 | Ogura et al. |
| 9,781,520 | B1 | 10/2017 | Huang |
| 2005/0027498 | A1 | 2/2005 | Tanji et al. |
| 2008/0061559 | A1 | 3/2008 | Hirshberg |
| 2008/0170941 | A1 | 7/2008 | Ghosh et al. |
| 2008/0236175 | A1* | 10/2008 | Chaparro Monferrer .................. F25B 21/02 257/713 |
| 2011/0083420 | A1 | 4/2011 | Clay et al. |
| 2013/0205798 | A1* | 8/2013 | Kwok ...................... F02K 1/82 60/783 |
| 2014/0288906 | A1 | 9/2014 | Sakaguchi et al. |
| 2017/0206291 | A1 | 7/2017 | Abramov |
| 2017/0316133 | A1 | 11/2017 | Abramov |
| 2017/0332179 | A1 | 11/2017 | Bright et al. |
| 2018/0266394 | A1 | 9/2018 | Abramov |
| 2018/0266395 | A1 | 9/2018 | Abramov |

FOREIGN PATENT DOCUMENTS

| | | |
|---|---|---|
| AU | 2020201562 B2 | 10/2020 |
| AU | 2020281012 B1 | 6/2021 |
| AU | 2021205020 B1 | 12/2021 |
| EP | 0227180 A3 | 1/1989 |
| EP | 2275671 A1 | 1/2011 |
| GB | 894450 A | 4/1962 |
| GB | 2546570 A | 7/2017 |
| GB | 2546571 A | 7/2017 |
| GB | 2546834 A | 8/2017 |
| GB | 2546834 B | 8/2017 |
| GB | 2558814 A | 7/2018 |
| JP | 2012188957 A | 10/2012 |
| TW | I467087 B | 1/2015 |
| WO | 2009006360 A3 | 2/2009 |
| WO | 2010006033 A1 | 1/2010 |

OTHER PUBLICATIONS

Co-pending U.S. Appl. No. 16/412,834, filed May 15, 2019.
Co-pending U.S. Appl. No. 16/412,848, filed May 15, 2019.
William Robert Freed; An Investigation of a Variable Geometry Diffuser for FTU's Four Inch Supersonic Wind Tunnel; dated 1977.
William Bugden et al.; Design and Construction of a Supersonic Wind Tunnel with Diagnostics JB3-SWT3; published Apr. 17, 2013.
Andrew Michael Carter; Nozzle Design for the Supersonic Wind Tunnel Ramjet Attachment; published Jun. 2013.
Avik Arora et. al.; Design of a Tri-sonic Wind Tunnel; published Oct. 2014 Journal of Basic and Applied Engineering Research Print ISSN: 2350-0077; Online ISSN: 2350-0255; vol. 1, No. 4; Oct. 2014 pp. 21-32.
JP2012188957A Machine Translation (from Google Patents)—published Oct. 4, 2012; IHI Corp.
TWI467087B Machine Translation (from Google Patents)—published Jan. 1, 2015 ; Clay and Hockaday.
AU2019200817, First Examination report, Mar. 20, 2019.
AU2019200817, Second Examination report , May 14, 2019.
AU2020201562, First Examination report , May 12, 2020.
AU2020201562, Second Examination report , Sep. 2, 2020.
AU2020201568, First Examination report , Apr. 14, 2020.
AU2020201929, First Examination report ,Dec. 21, 2021.
AU2020201929, Second Examination report, Mar. 14, 2022.
AU2018204546, First Examination report , Jan. 11, 2019.
AU2018204546, Second Examination report , Mar. 20, 2019.
AU2018204546, Third Examination report , Jul. 31, 2019.
AU2018204546, Fourth Examination report , Oct. 4, 2019.
AU2018204546, Fifth Examination report , Nov. 29, 2019.
AU2021205020, Second Examination report , Oct. 22, 2021.
AU2018200099, First Examination report , Dec. 14, 2018.
AU2018200099, Second Examination report , Mar. 20, 2019.
GB1609906.1 , Combined search and examination report, sent, (Jun. 28, 2016).
GB1613335.7, examination report, Mar. 3, 2017.
GB1613335.7, examination report, Dec. 14, 2016.
GB1613335.7, Abbreviated examination report, Sep. 28, 2016.
GB1613336.5, Search report, Sep. 27, 2016.
Au2021205020, First Examination report , Aug. 31, 2021.
Requirement for Restriction/Election for co-pending U.S. Appl. No. 16/412,848, filed Dec. 16, 2021.
Notice of allowance for co-pending U.S. Appl. No. 15/982,585, filed Jun. 20, 2022.

\* cited by examiner

Prior Art Fig. 1a
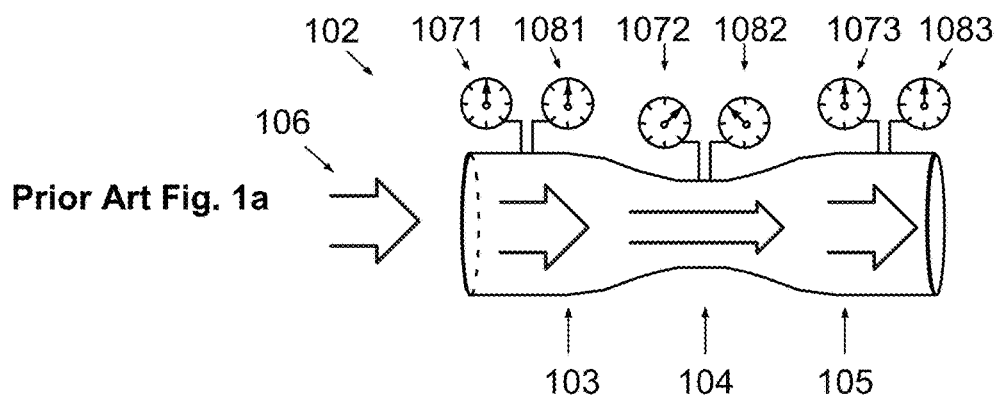
Prior Art Fig. 1b
Prior Art Fig. 1c
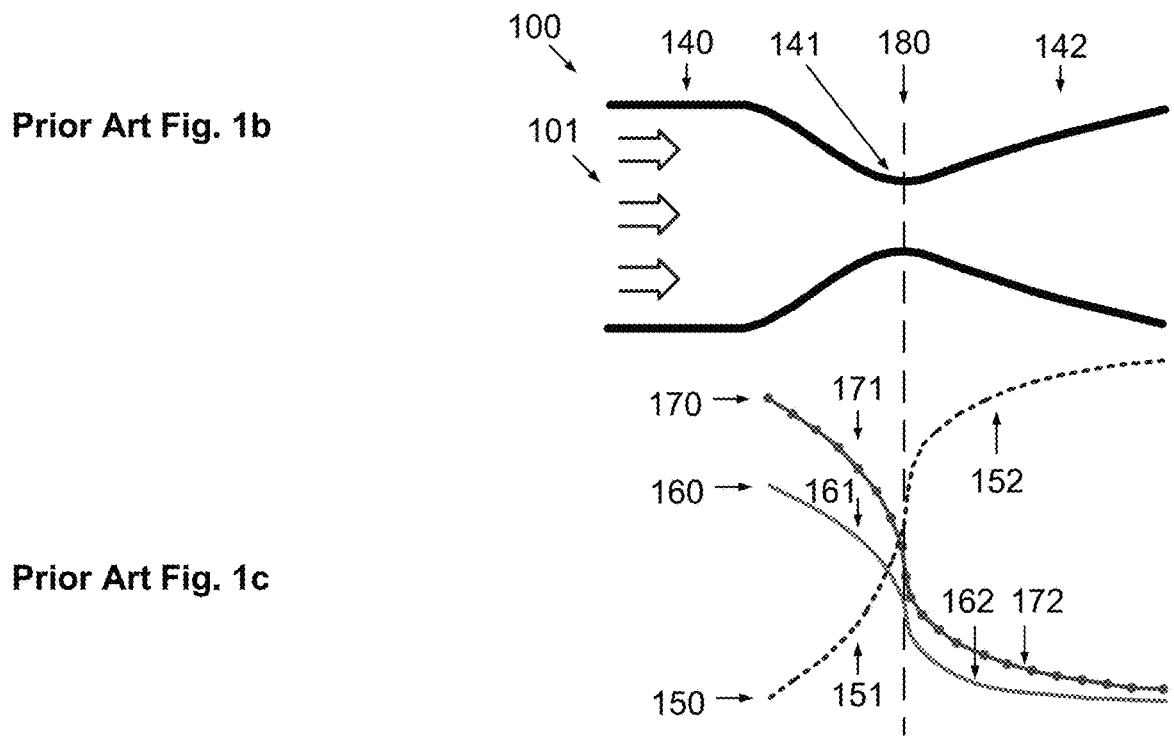

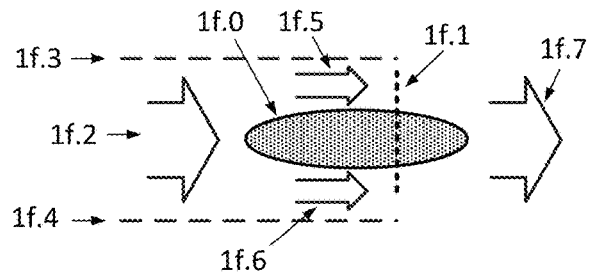
Prior Art Fig. 1d
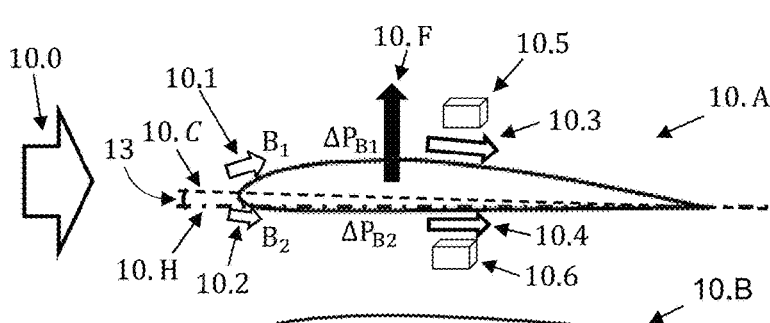
Prior Art Fig. 1e
Case (A)
Case (B)
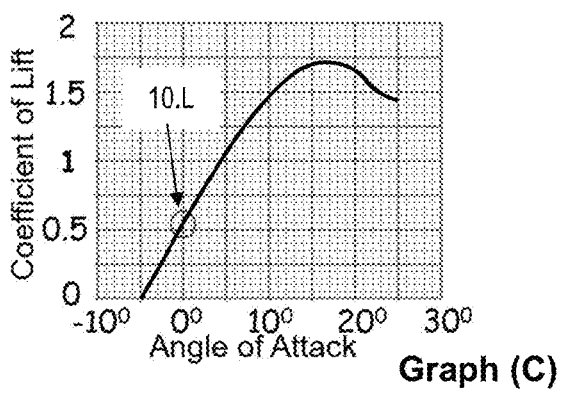
Graph (C)
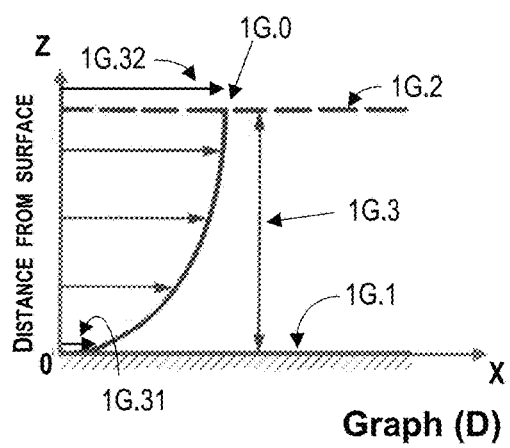
Graph (D)
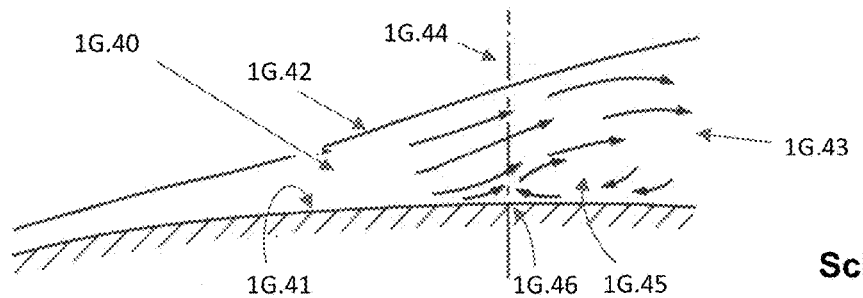
Scheme (E)

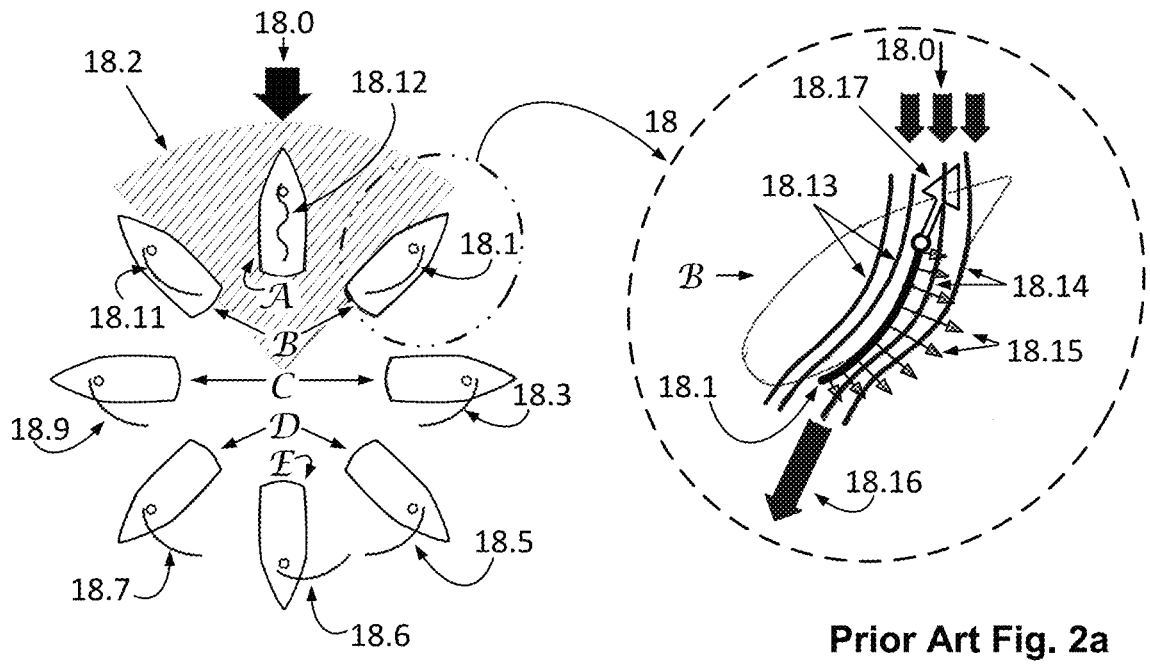
Prior Art Fig. 2a
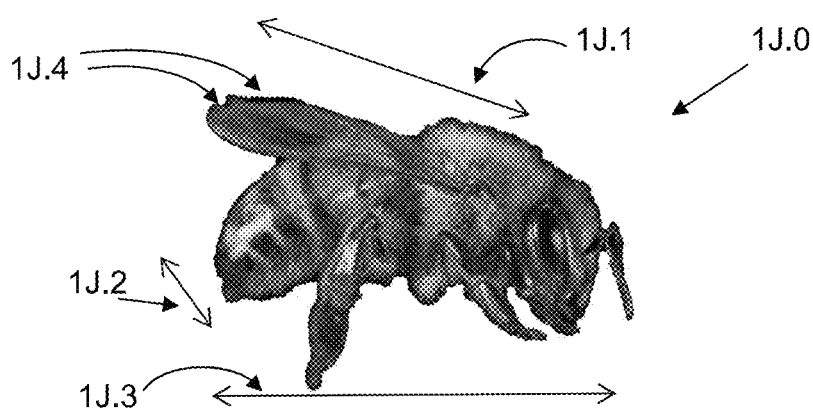
Prior Art Fig. 2b
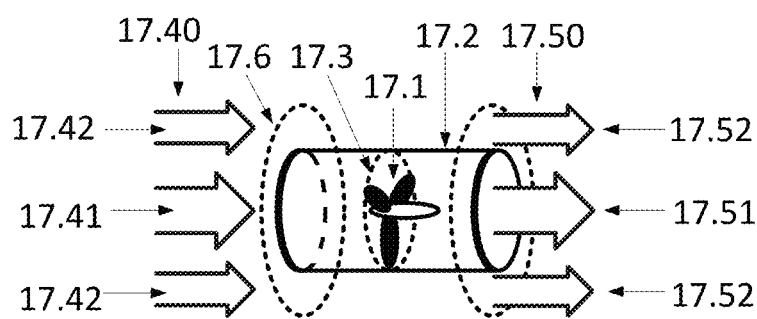
Prior Art Fig. 2c

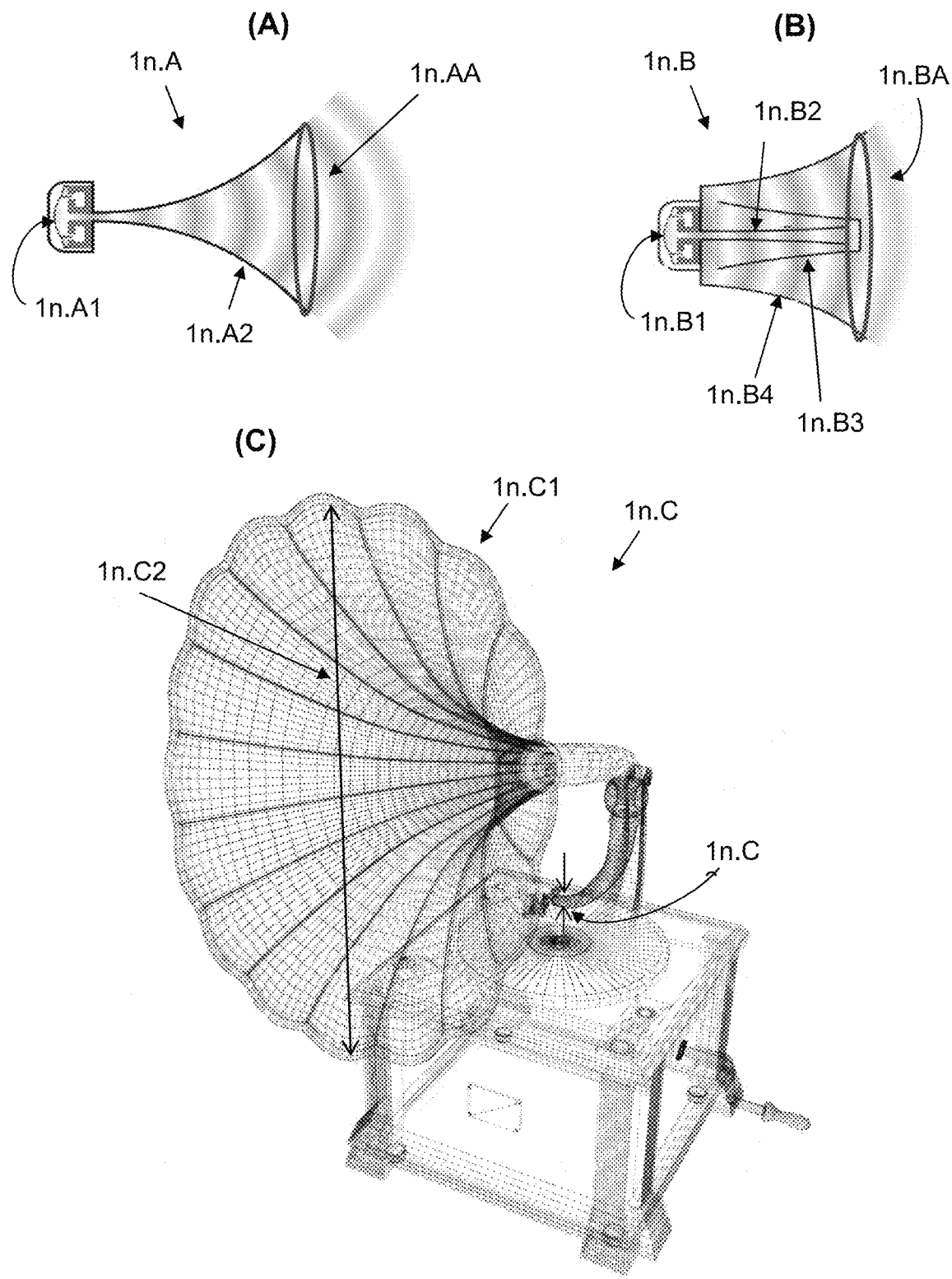
Prior Art Fig. 3a

Prior Art Fig. 3b
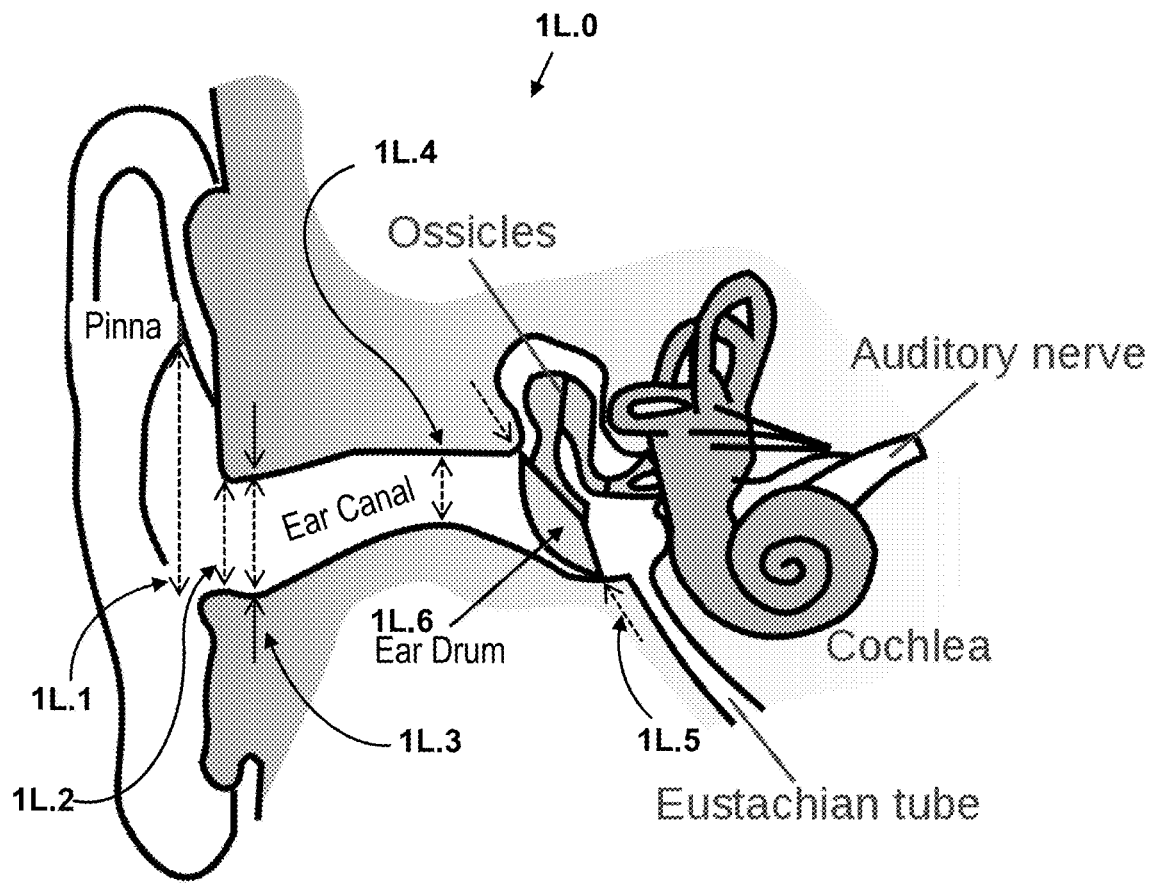
Prior Art Fig. 4a
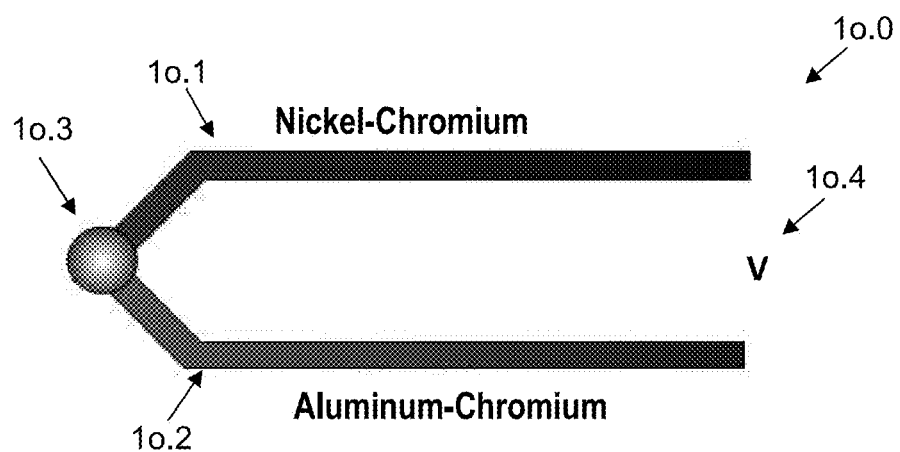

Prior Art Fig. 4b
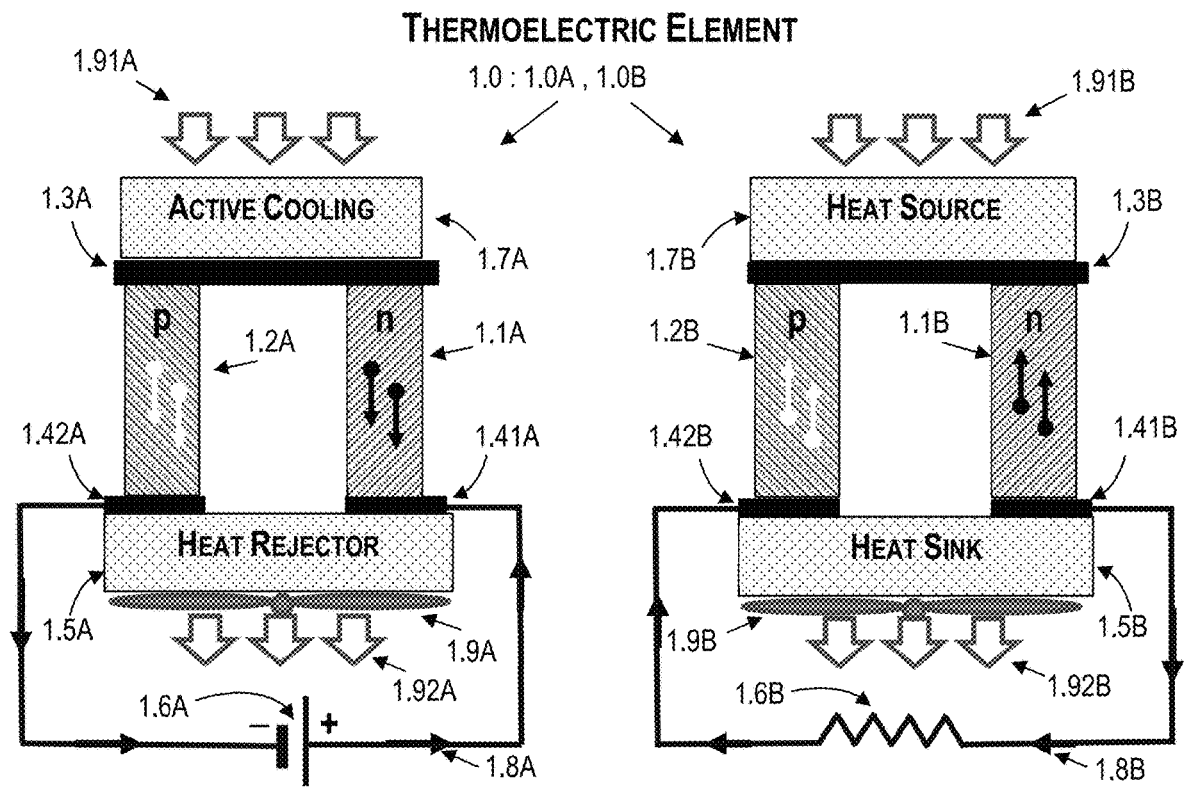
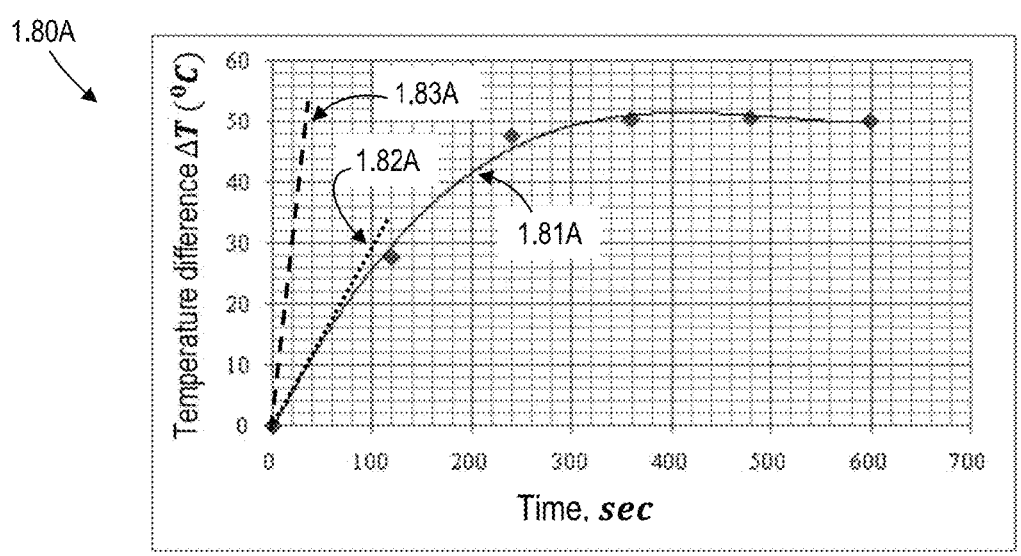
Case (A) Time Characteristic

Prior Art Fig. 4c
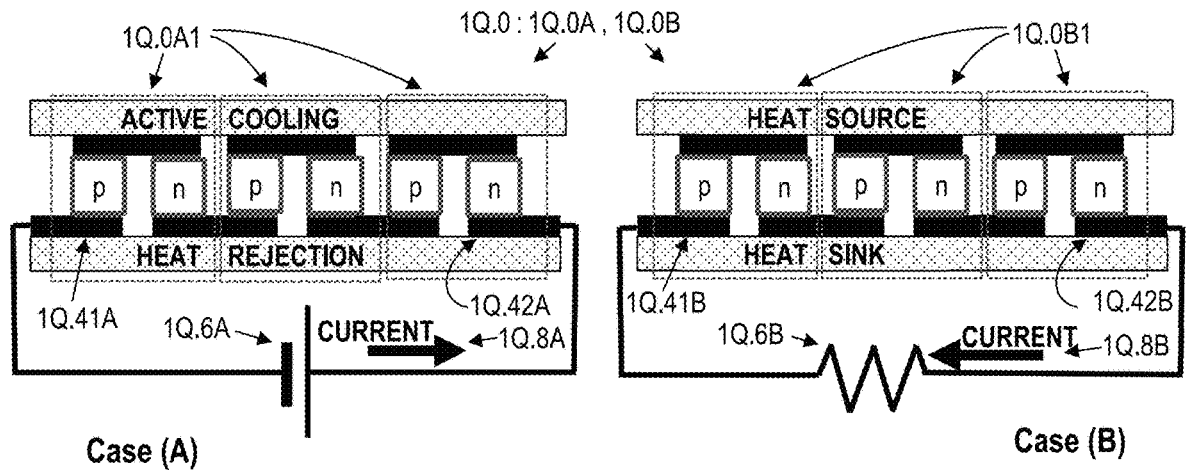
Case (A)  Case (B)
Prior Art Fig. 4d
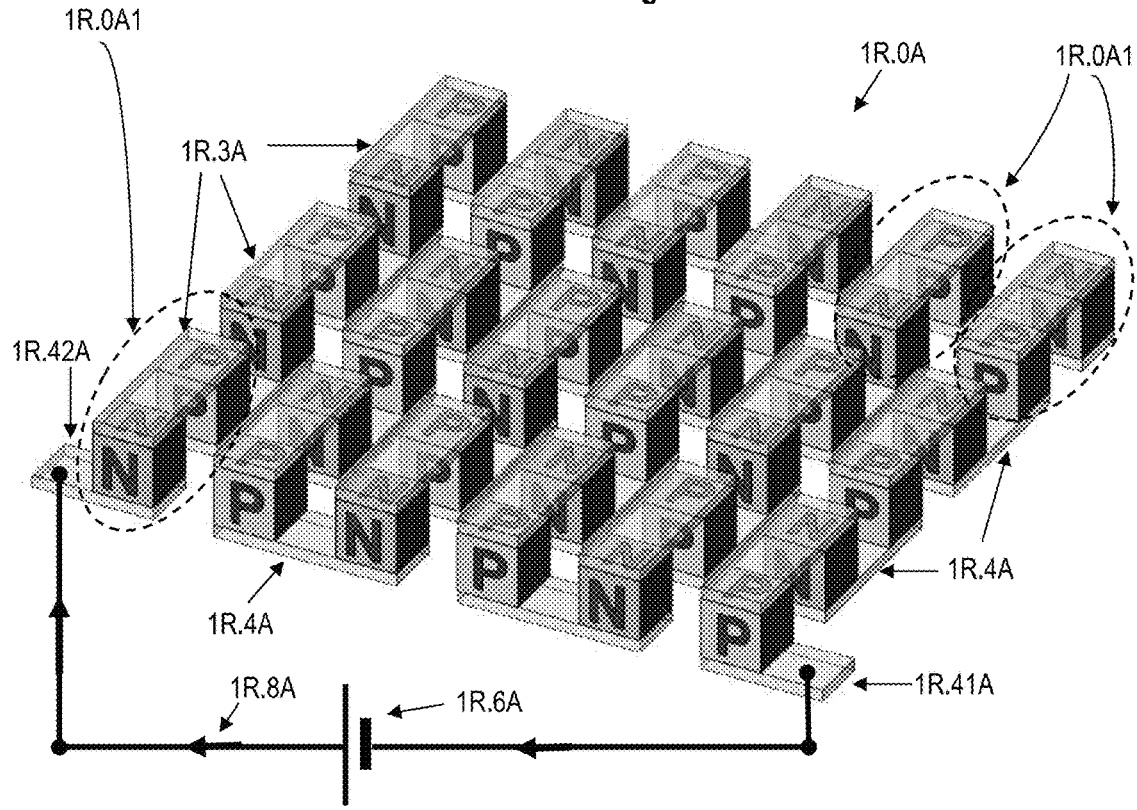

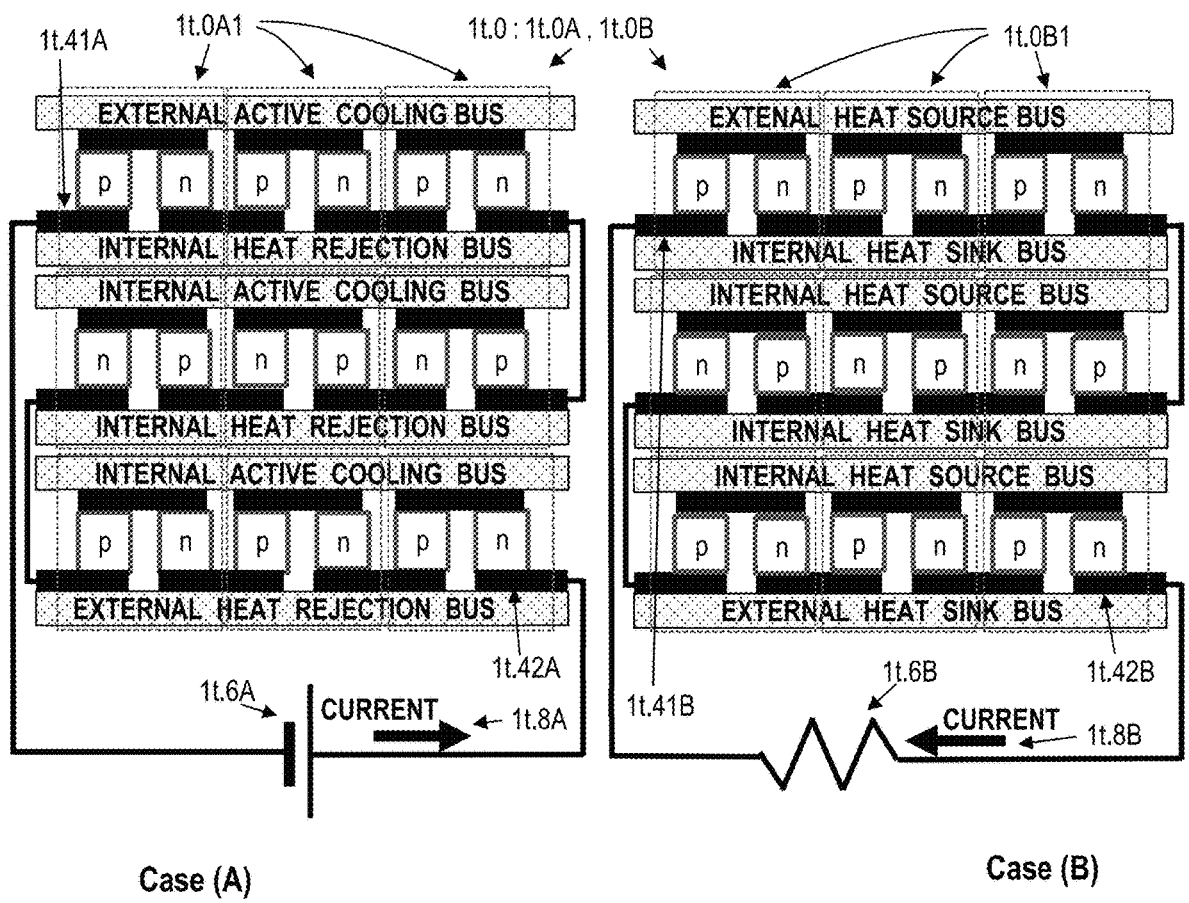
Prior Art Fig. 4e

Fig. 5b
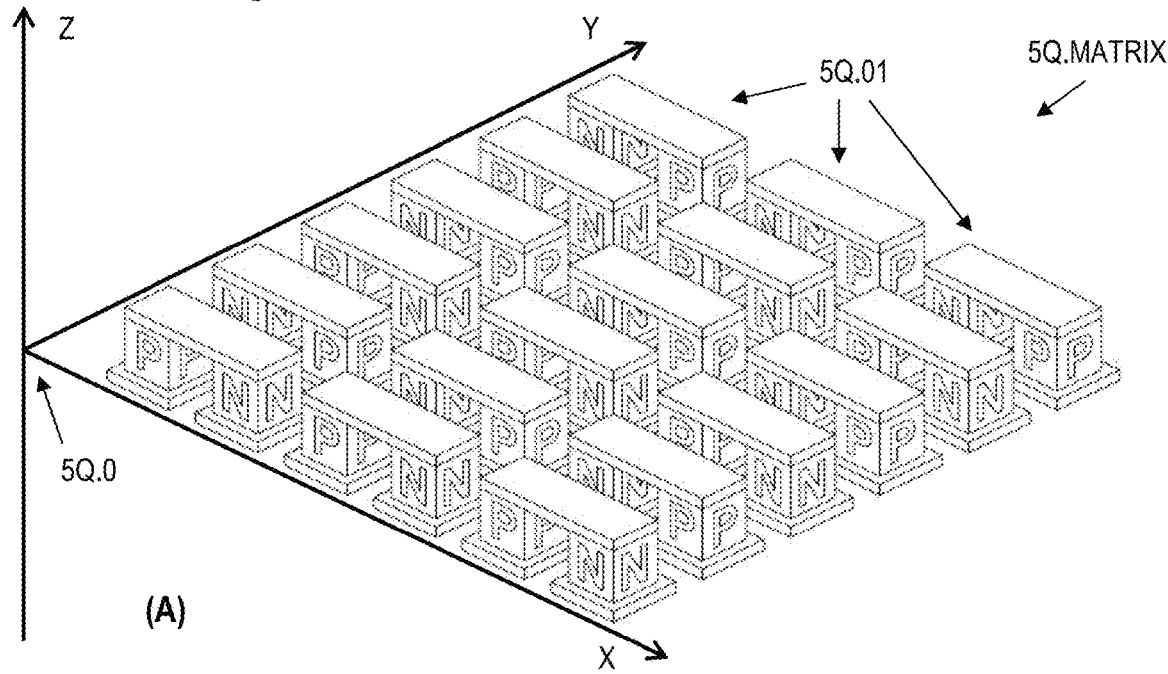
(A)
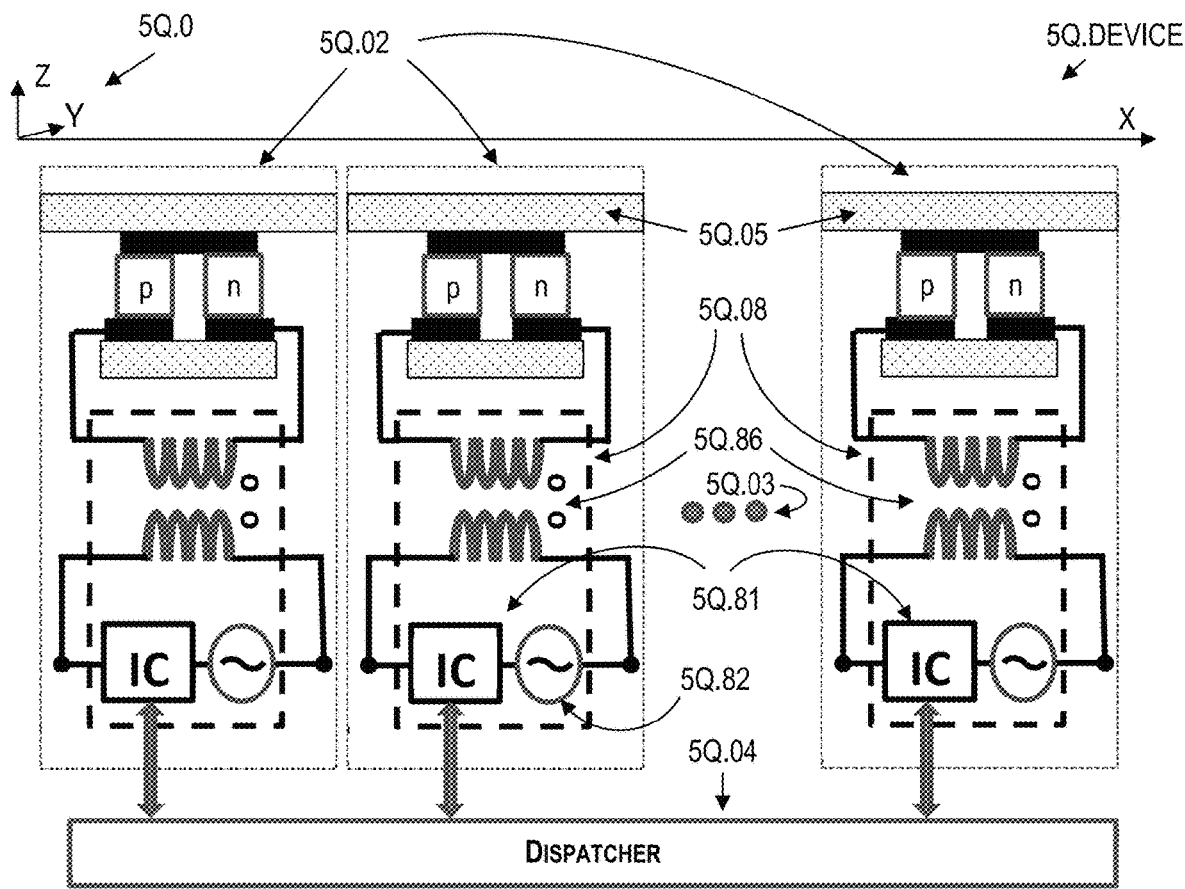
(B)

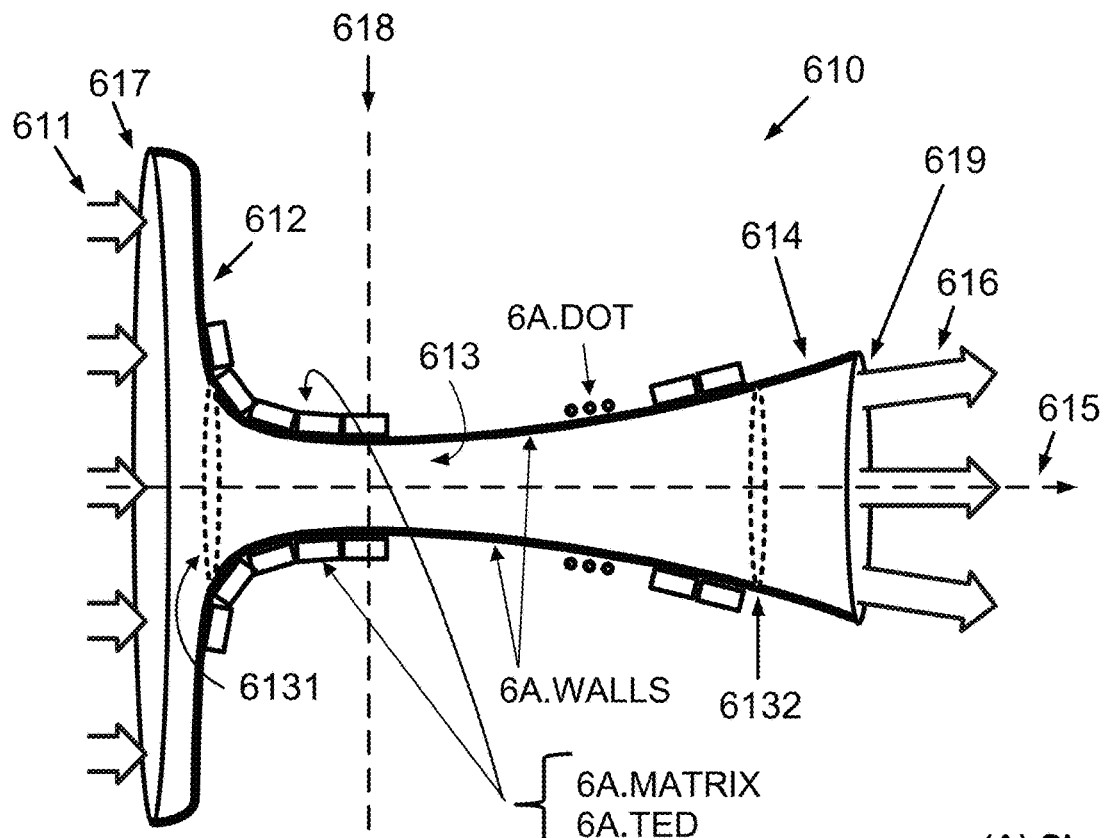
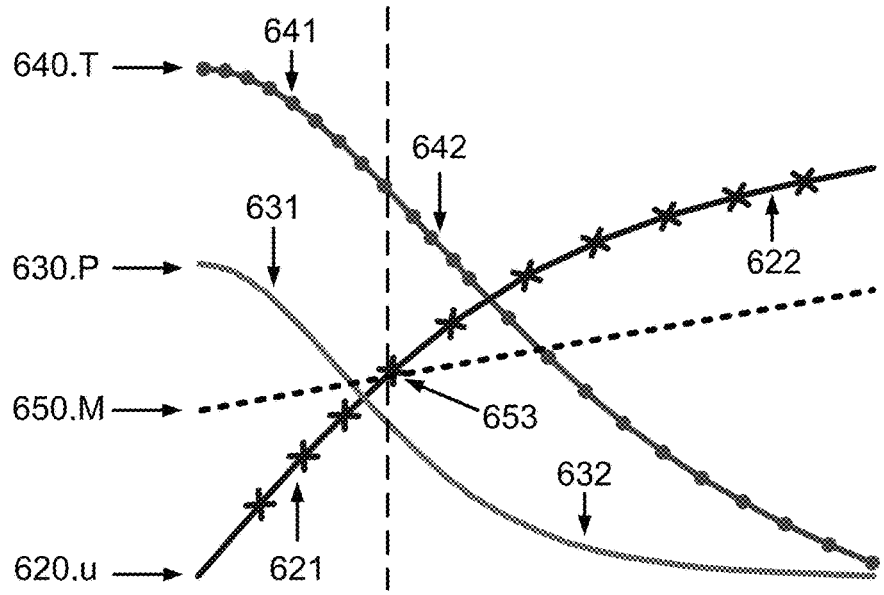
Fig. 6a

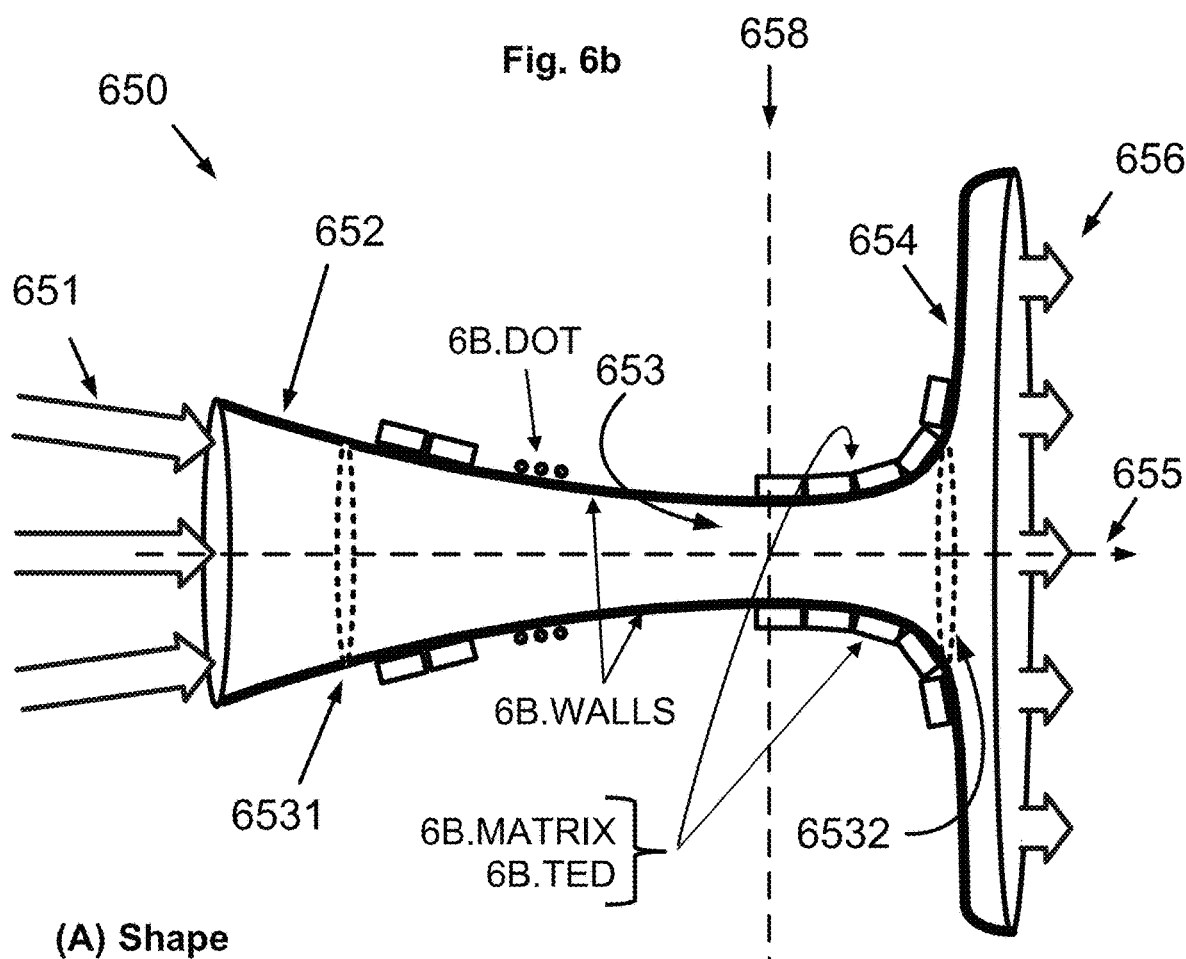
(A) Shape
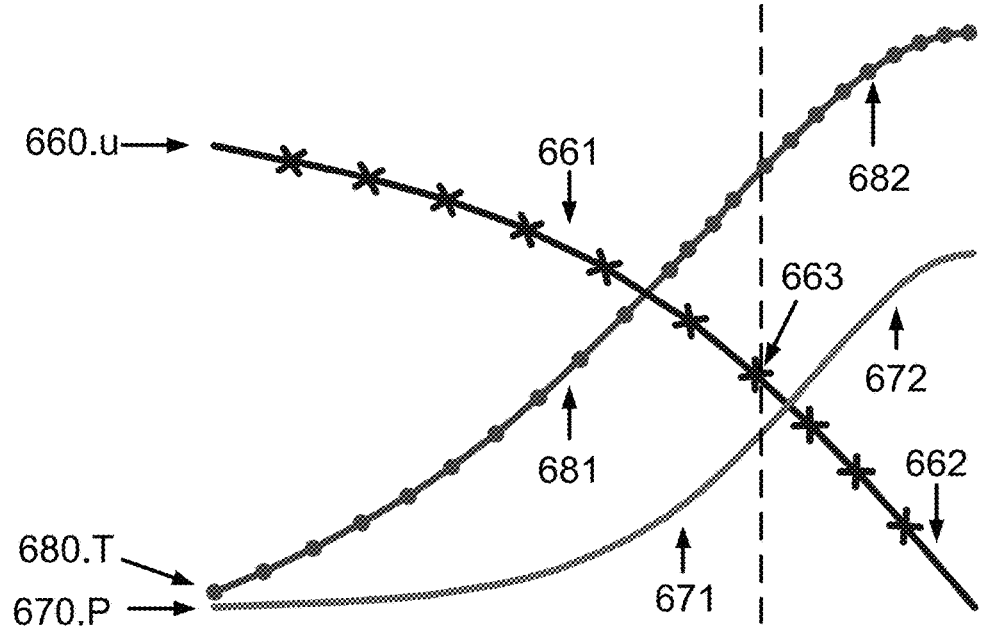
Fig. 6b
(B) Graph

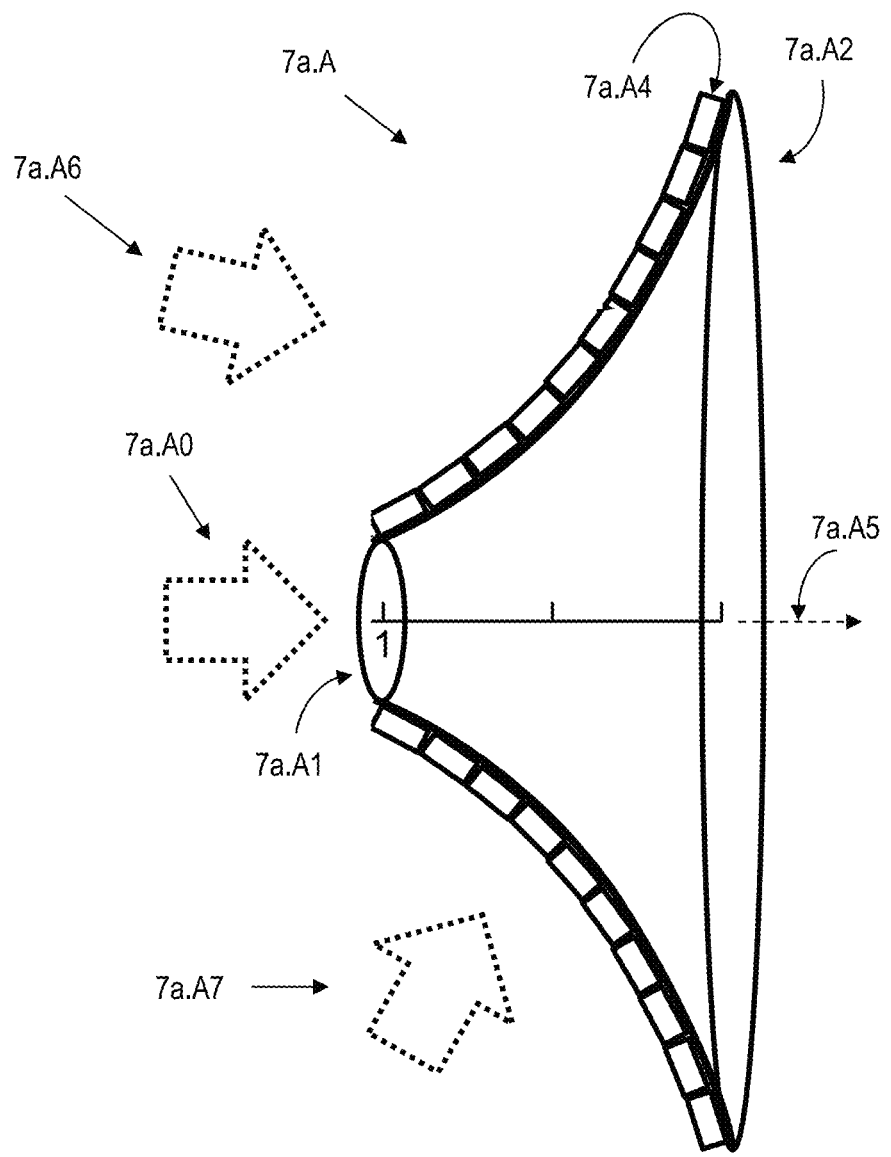

Fig. 7a case (B)
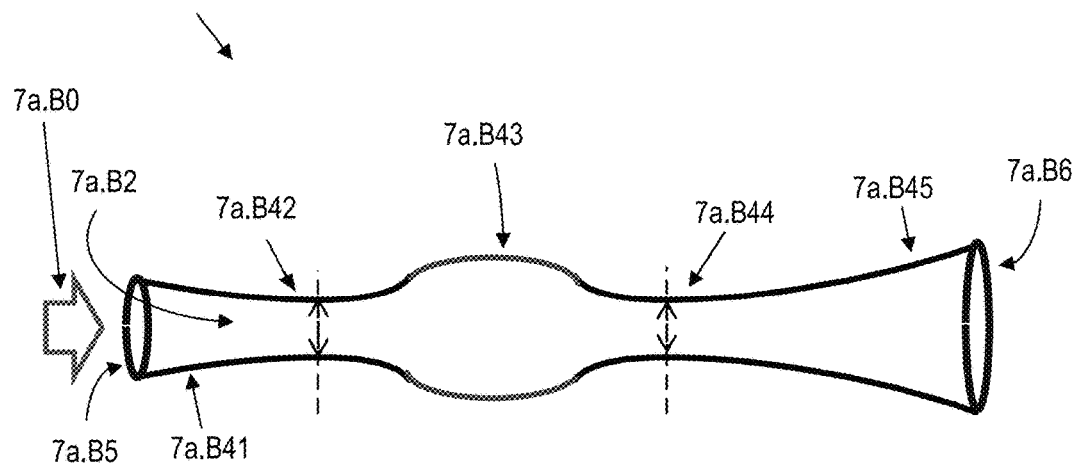
Fig. 7a case (C)
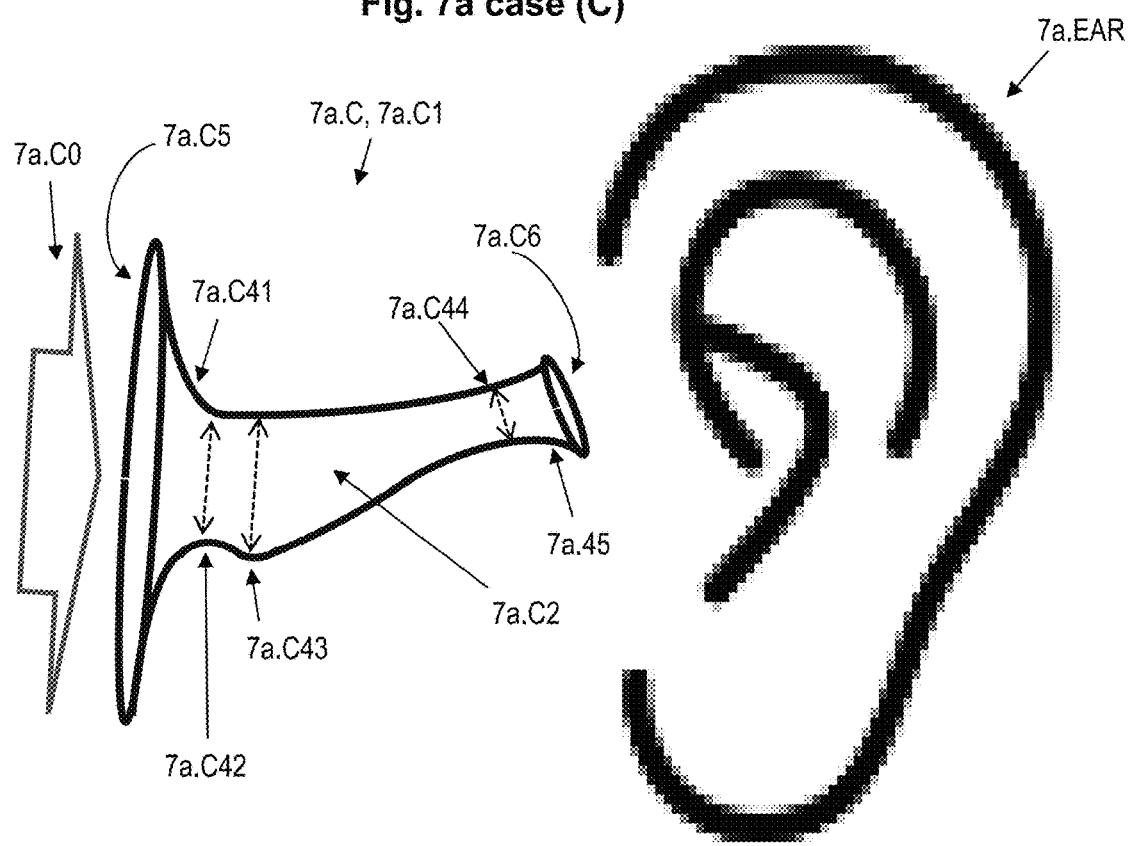

Fig. 7b
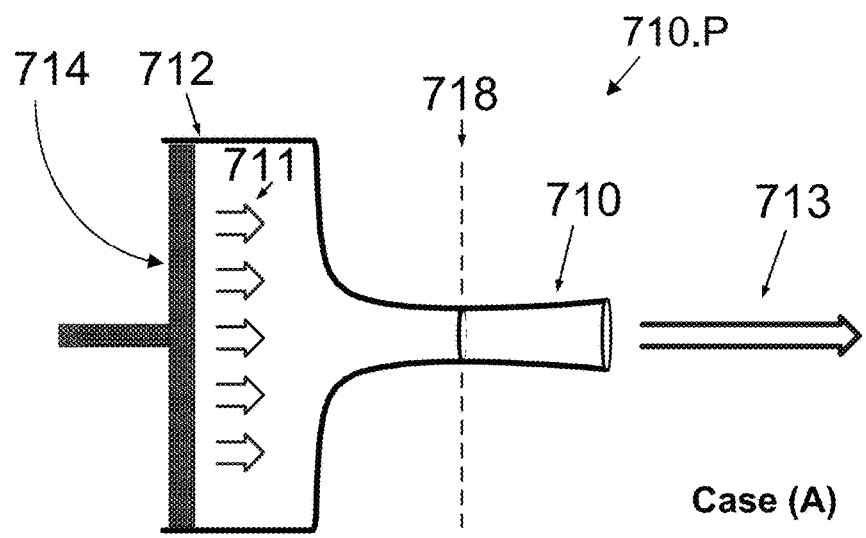
Case (A)
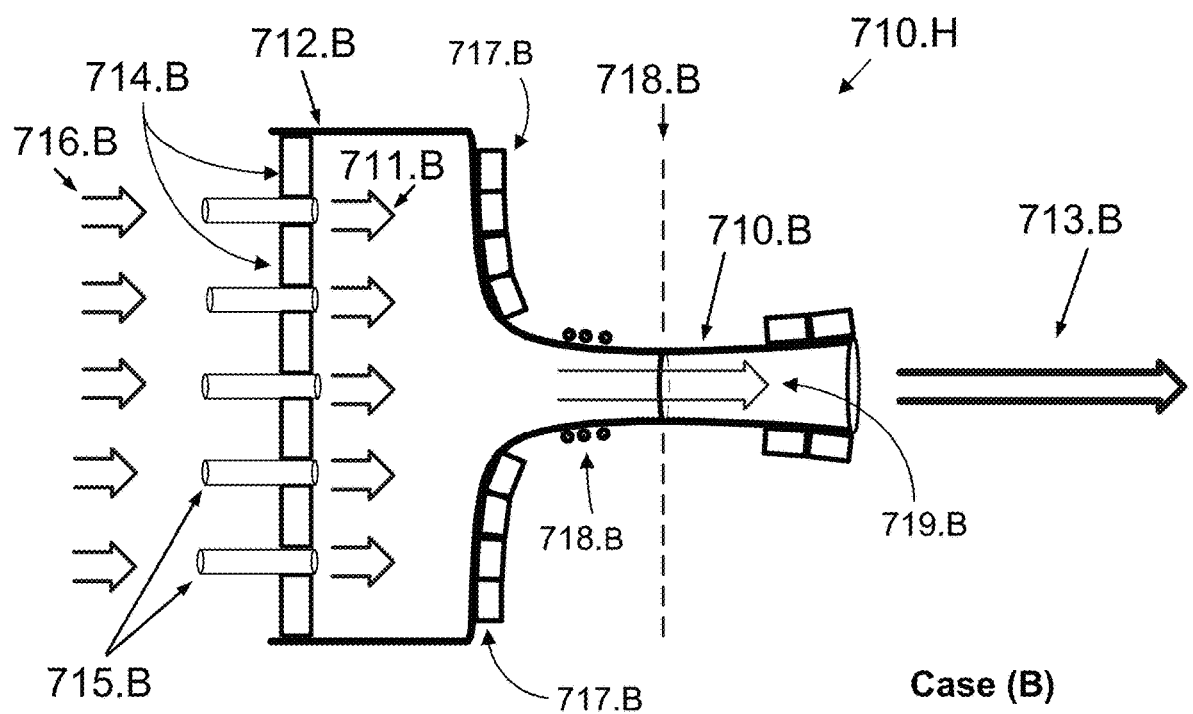
Case (B)

Fig. 8
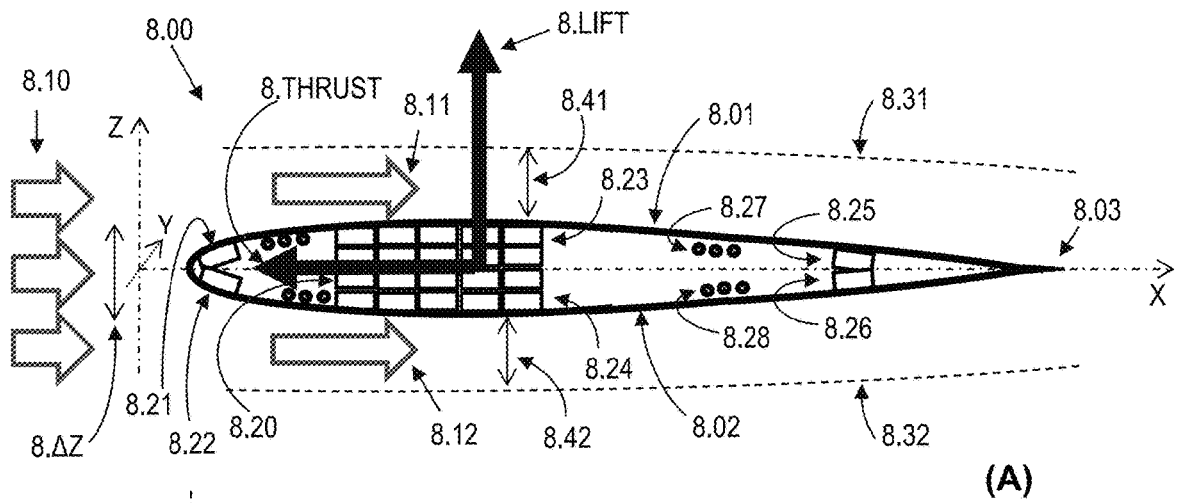
(A)
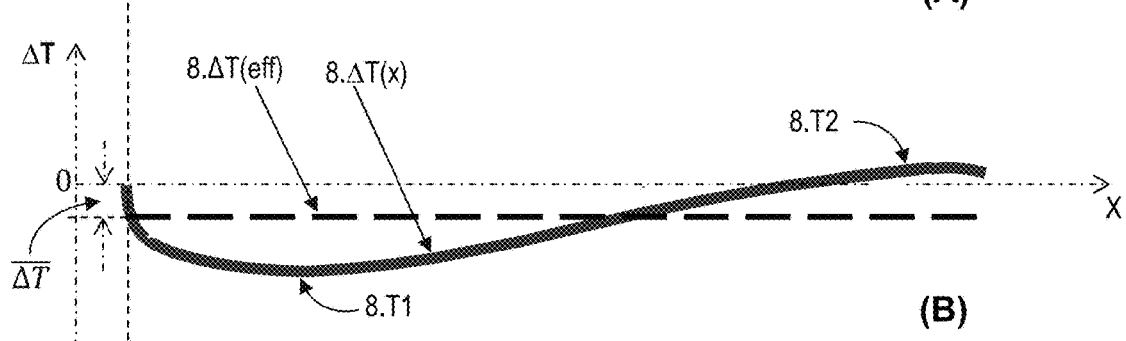
(B)
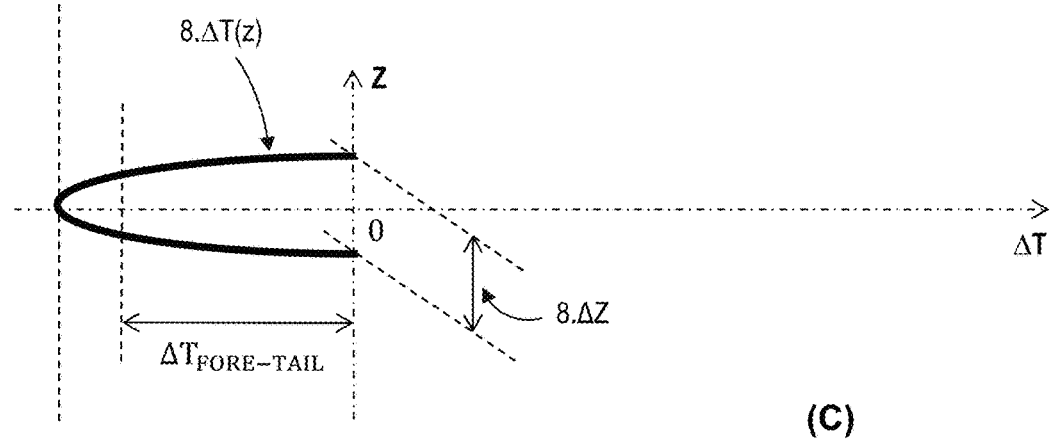
(C)

Fig. 8c
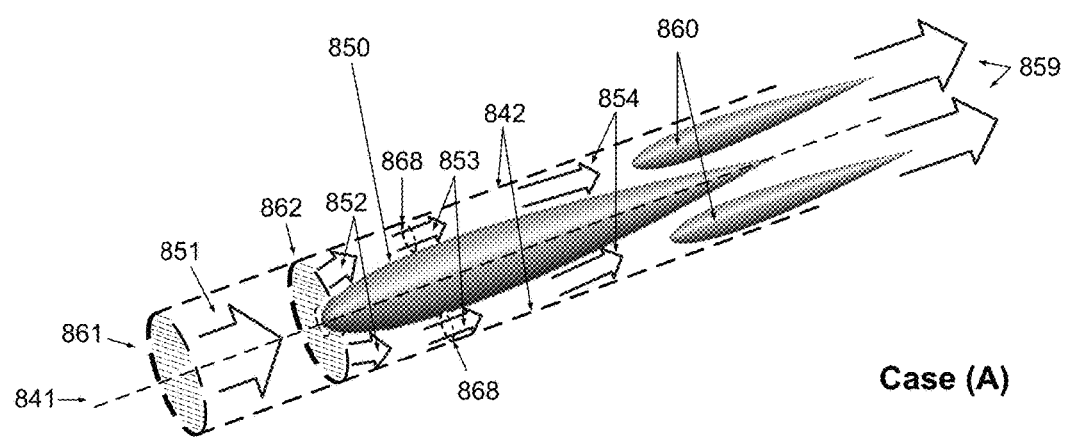
Case (A)
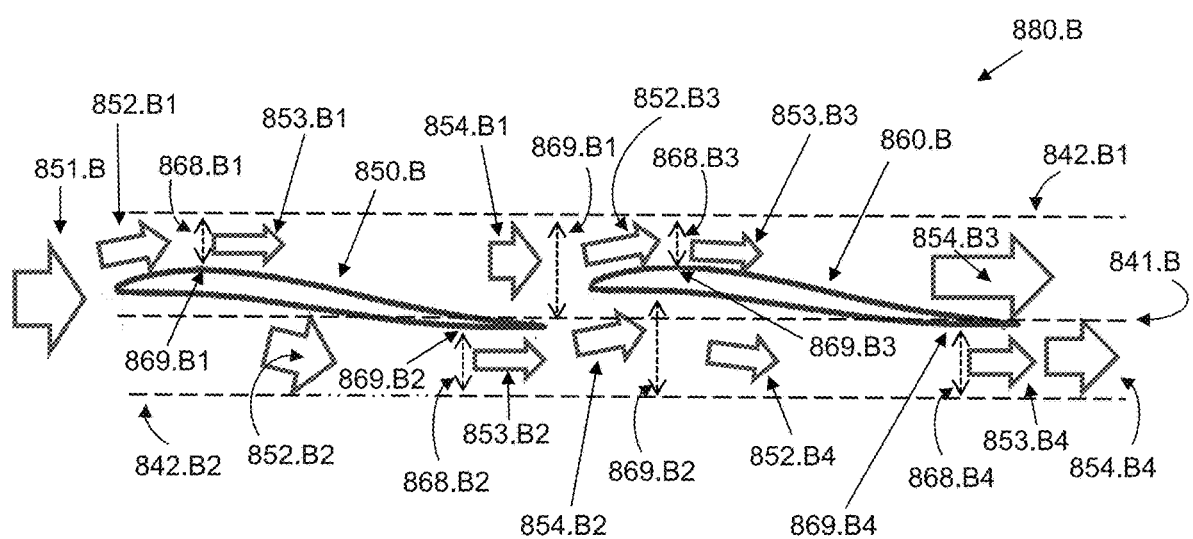
Case (B)

Fig. 8d
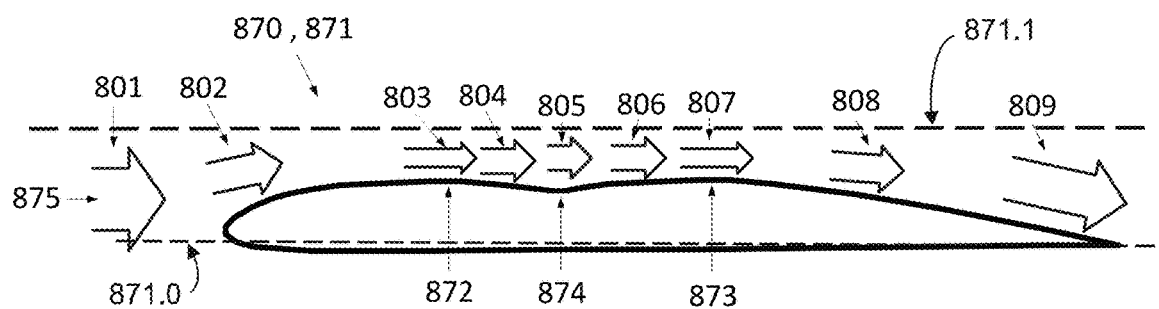
(A)
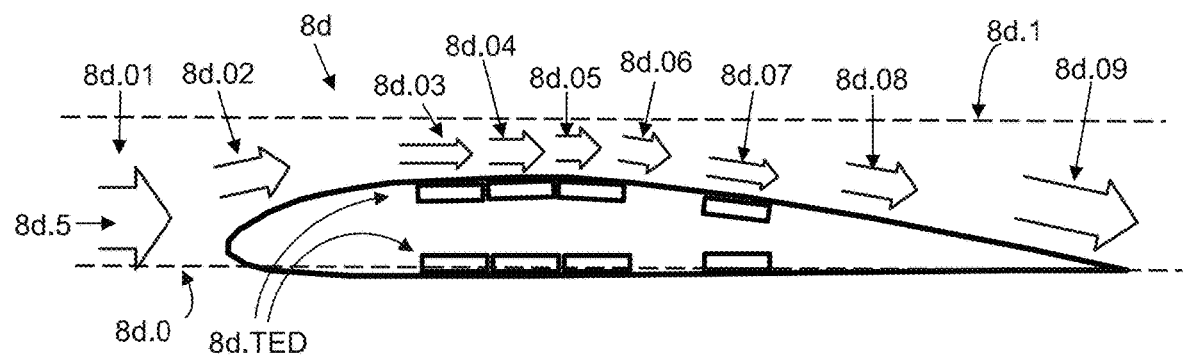
(B)

Front View  Side View

Front View  Side View

APPARATUSES BASED ON JET-EFFECT AND THERMOELECTRIC EFFECT

FIELD OF THE INVENTION

The invention relates generally to the use of a jet-effect in combination with a thermoelectric effect destined for controlling both the jet-effect and the laminarity of a headway moving fluid flow, and, more particularly, to a method for designing an aerodynamic apparatus controllably pulling-in and pushing-off a portion of fluid; the apparatus comprises a matrix of thermoelectric elements which are controllable to trigger origination of desired temperature differences and, thereby, to suppress the concomitant turbulence in the accelerated fluid portion.

BACKGROUND OF THE INVENTION

The following issued patents and publications provide potentially relevant background material, and are all incorporated by reference in their entirety:
  GB2546834 by Abramov, further indicated by A01,
  US 20190280561 by Abramov, further indicated by A02,
  AU 2018204546 by Abramov, further indicated by A03,
  the paper "*Thermoelectric Materials: Principles, Structure, Properties, and Applications*" by T. M. Trill [book: "Encyclopedia of Materials: Science and Technology (Second Edition)" ELSEVIER-2002, Pages 1-11] further indicated by D01;
  the paper "*Thermoelectric Materials: Principles, Structure, Properties, and Applications*" by I. Terasaki ["Reference Module in Materials Science and Material Engineering" ELSEVIER-2016], further indicated by D02;
  the paper "Thermo-Electric Cooler: Peltier Device Characteristics" by Jeethendra Kumar P. K. and Ajeya PadmaJeeth, KamalJeeth Instrumentation & Service Unit, Tata Nagar, Bengaluru-560092, Karnataka, India, further indicated by D03;
  US20090272417 A1 by Jurgen Schulz-Harder, further indicated by D04,
  NASA EP-89, 1971, p. 68, further indicated by D05,
  NASA TN-1384, 1947, further indicated by D06,
  U.S. Pat. No. 6,981,366 by Sharpe, further indicated by D07,
  US 200810061559 A1 by Hirshberg, further indicated by D08,
  U.S. Pat. No. 8,268,030 by Abramov, further indicated by D09,
  U.S. Pat. No. 8,221,514 by Abramov, further indicated by D10,
  U.S. Pat. No. 8,601,787 by Bulman, further indicated by D11,
  Patent FR577087 "Pile électrique" by Karpen, further indicated by D12;
  Bernd Heinrich, "Thermoregulation in Endothermic Insects"—Science, New Series, Vol. 185, No. 4153. (Aug. 30, 1974), pp. 747-756, further indicated by D13;
  Jose Eduardo Bicudo, "Control and Regulatory Mechanisms Associated with Thermogenesis in Flying Insects and Birds"—D01:10.10071s10540-005-2883-8, further indicated by D14; and
  Ono, M.; Okada, I.; Sasaki, M. (1987), "Heat production by balling in the Japanese honeybee, *Apis cerana japonica* as a defensive behavior against the hornet, *Vespa simillima xanthoptera* (Hymenoptera: Vespidae)", Cellular and Molecular Life Sciences, 43 (9): 1031-1034, doi:10.1007BF01952231, further indicated by D15.

Preamble and Terminology

For the purposes of the present patent application, the term "corpus of body" should be understood as a geometrically configurational (but not mass) aspect of the body.

The prior art applications A01, A02, and A03 disclose a nozzle with a through-hole tunnel having a specific shape, in general, configured as either converging, or divergent, or convergent-divergent, or two-stage convergent-divergent, optimized such that, when the nozzle is exposed to laminar flow of a certain fluid moving with a certain velocity, the fluid flow becomes accelerated and remains laminar as moving within and along the through-hole tunnel. As well, when the fluid flows around a body, an airfoil corpus of the body plays the role of such a nozzle while a boundary layer originated around the corpus is interpreted as a flow portion moving through an imaginary tunnel optimized to have the mentioned specific shape. In this relation, the introduced term "actually-airfoil" applied to the corpus should be understood as characterizing such a geometrical configuration of the corpus having a smooth curvature and optionally having a fluid-repellent (for instance, hydrophobic) surface that provides for the fluid flow remaining laminar when moving around as well as downstream behind the corpus.

In THE BACKGROUND OF THE INVENTION, a portion of descriptions of the prior art applications, which comprises aspects introducing to the claims of the present patent application, is repeated and amended. In particular, the inventor points out again to the feature that:
  a portion of a molecular fluid moving within a through-hole tunnel,
  a portion of a molecular fluid flowing around a body, for instance, an airfoil wing, and
  an elastic wave in a molecular fluid as a kind of motion of a portion of the molecular fluid around another portion of the molecular fluid, all are accompanied by changes in thermodynamic parameters of portions of the molecular fluid, i.e., in other words, each of them comprises a fluid stream subjected to the jet-effect at least one of headway-accelerating and waving.

For the purposes of the present patent application, the introduced term "molecular fluid" should be understood as a fluid substance composed of randomly moving and interacting molecules, according to the kinetic theory of matter. In this relation:
  symbols a, b should be understood as the van der Waals parameters;
  symbol $\gamma$ should be understood as the effective adiabatic compressibility parameter of the fluid, which (the $\gamma$) is defined such that, for a hypothetically ideal gas, it becomes equal to adiabatic compressibility-constant j, in turn, specified as equal to $1+2/n$, where n is the number of degrees of freedom per molecule of the hypothetical ideal gas wherein n depends on a configuration of the hypothetical ideal gas molecules; for instance, for air having dominantly bi-atomic molecules, n=5, and j=7/5 that is a good approximation for the generalized adiabatic compressibility parameter $\gamma$;
  the terms "partial pressure-a $P_a$", "partial pressure-b $P_b$", and "partial pressure-c $P_c$", description of which is in A01, A02, and A03 and is not narrated herein for brevity, should be understood as characterizing fluid state subjected to different kinds of action; wherein: (a) a partial deep-stagnation pressure-a $\delta P_a$ is characterized by varying $\delta a$ in the van der Waals parameter a; (b)

a partial stagnation pressure-b $\delta P_b$ is interrelated with a change of a moving portion's volume V and, thereby, of the compression ratio r defined as V/(V−b), while retaining the same inter-molecular forces defined by van der Waals parameter a; and (c) a partial pressure-c $\delta P_c$ associated with the Coanda-effect, is a measure of the cumulative aligning-impact of the fluid molecules on the imaginary boundaries of a fluid portion moving in the imaginary boundary layer adjacent to stationary walls of a body; and the symbol $a_w$ should be understood as the van der Waals parameter of attraction between, on the one hand, molecules of a solid wall, and, on the other hand, molecules of adjacent fluid.

The well-known and widely-used jet-effect provides for the effect of gas extension and thereby acceleration. Accelerated flow is widely applied to push-off some kinds of vehicles having jet-engines usually supplied by either converging or convergent-divergent nozzles, to which the term "jet-nozzle" is also applied to emphasize the jet-effect importance.

In D07, numerous modifications of the jet-effect implementation are overviewed.

In D08, the author points out that the jet-effect is accompanied by decreasing static pressure and temperature, and suggests applying the phenomenon as a trigger for vapor-to-water condensation.

In D09 and D10, the author points out that a long cascade of streamlined nozzles provides a convergence of a wider front of fluid flow, and provides for an adaptation of the jet-effect use for big-scale devices.

In the present patent application, a diversity of embodiments, in which additional degrees of freedom allowing to control thermodynamic parameters of moving fluid are utilized to solve aerodynamic problems of controlling the moving fluid, is disclosed. The diversity includes:
    an improved acoustic device,
    an actually-airfoil convergent-divergent jet-nozzle,
    an actually-airfoil wing similar to a wing of a warm-blooded bird,
    a jet-nozzle applied to boost a sound, and
    a levitating capsule.

In relation to the molecular fluid, to analyze the equation of the molecular fluid motion, for the purposes of the present patent application, the term "jet-effect" is used in a wide sense as the effect of fluid flow portion convective acceleration at the expense of fluid portion heat. In particular, the jet-effect occurs when the fluid portion moves adjacent to configured walls and is subjected to the walls accelerating action, as seemingly "negative drag". For example, the fluid is gas and the walls are configured to form a converging or convergent-divergent nozzle. In particular, the term "jet-effect" is applied to the well-known and widely-used effect of convective acceleration of a wind-portion, which is flowing over a convex upper-side surface of an airplane wing and is thereby being subjected to the varying of flow front cross-section in an imaginary convergent-divergent nozzle. Another example is a case, wherein the fluid is water and the configured walls have a hydrophobic surface. Thus, the term "jet-effect", used here in a wide sense, assumes that the process of fluid extension may be insignificant or latent.

The jet-effect is the nature of the well-known Coanda-effect, defined as a tendency of a fluid jetstream to be attracted to and aligned with a nearby airfoil surface, i.e. to be specifically accelerated at the expense of the fluid warmth. For the purposes of the present patent application, to emphasize the jet-effect nature of the Coanda-effect, the term "Coanda-jet-effect" is also applied as equivalent to the commonly known term "Coanda-effect". As the Coanda-effect assumes a laminar flow, looking ahead, the term "airfoil" will be specified as "actually-airfoil" in contrast to "seemingly-airfoil".

For the purposes of the present patent application, further terms are specified as follows:
    the term "imaginary wall", applied to a flowing fluid's streamlines, should be understood as a material (but not virtual) wall, formed by the fluid's matter, forcedly-bordering a portion of the flowing fluid. I.e. the material but optionally invisible by the human eye and thereby imaginary wall acts on adjoining fluid portions, enforcing the fluid portions to move along the streamlines, i.e. in alignment with the imaginary wall. When flowing plasma is subjected to an action of a magnetic field, "imaginary walls" are formed by the magnetic field's force-lines defining the streamlines of the flowing plasma;
    the term "fluid pusher-off" should be understood in a broad sense as a device interacting with a portion of the ambient fluid, gaseous or liquid, to cause pulling-in and/or pushing-off the fluid portion resulting in motion of the fluid portion relative to the device corpus;
    the term "fluid motion-sensor" should be understood in a broad sense as a device interacting with a portion of the ambient fluid, gaseous or liquid, to detect motions of the fluid portion relative to the device corpus;
    the term "velocity of a flying body" should be understood as the body motion velocity relative to a stationary fluid; and vice-versa, the term "flow velocity" should be understood as the fluid flow velocity relative to the considered body submerged in the fluid stream. These two terms are interrelated according to Galilean relativity;
    the term "M-velocity" should be understood as the fluid velocity measured in Mach numbers or velocity normalized to the temperature-dependent velocity of sound in the fluid;
    the term "specific M-velocity" is as introduced and specified in detail in A01, A02, and A03 to separate the terms "low M-velocities", associated with M-velocities lower than the specific M-velocity indicated by $M_*$ and "high M-velocities", associated with M-velocities higher than the specific M-velocity $M_*$. Namely, the value of specific M-velocity is quantified via the effective adiabatic compressibility parameter of the fluid $\gamma$ as $M_* = \sqrt{(\gamma-1)/\gamma}$; for air as a diatomic molecular gas, the generalized adiabatic compressibility parameter $\gamma$ equals $\gamma = 7/5 = 1.4$, and $M_* = \sqrt{(\gamma-1)/\gamma} \approx 0.5345$ Mach; and
    the well-known terms "low-subsonic", "high-subsonic", "transonic", "supersonic", and "hypersonic" are used to specify the flow velocity ranges as the following:
    (a) the low-subsonic velocity range is defined as the M-velocity range comprising M-velocities lower than 0.3 Mach;
    (b) the high-subsonic velocity range is defined as the M-velocity range comprising M-velocities higher than 0.3 Mach and lower than 0.8 Mach;
    (c) the transonic velocity range is defined as the M-velocity range comprising M-velocities higher than 0.8 Mach and lower than 1.2 Mach;
    (d) the supersonic velocity range is defined as the M-velocity range comprising M-velocities higher than 1 Mach and lower than 5 Mach; and (e) the hypersonic velocity range is defined as the M-velocity range comprising M-velocities higher than 5 Mach.

the well-known terms "audible sound" and "ultrasound" are used to specify frequency ranges of acoustic waves as follows:

(a) the audible frequency range is defined as including frequencies from 20 Hertz to 20 kHertz; and (b) the ultrasound frequencies are defined as frequencies higher than 20 kHertz. and the well-known terms "direct current (DC)" and "alternating current (AC)" should be understood in a broader sense:

(a) the direct current (DC) should be understood as a current, value of which can vary but remaining either positive or negative; and (b) the alternating current (AC) should be understood as a current, value of which changes in a sign during a considered time.

Referring to the defined term "molecular fluid", the earlier defined term "flow velocity" is further specified as a measure of the molecular fluid's molecules motion in a prevalent direction in addition to the random Brownian motion. For instance, the air is considered as a molecular fluid, and the wind is considered as a natural process, bringing fresh portions of air, storing at least both: the heat energy of molecules Brownian random motion and the kinetic energy of the wind motion. Normally, in nature, when the wind is of 10 m/sec, the proportion is such that 99.96% is the heat energy [i.e. warmth] and only 0.04% is the kinetic energy of the wind motion as a whole. A phenomenon of a transformation of warmth into hurricane power is well-known; however, the warmth of ambient natural air remains largely unused in the world industry. Possession of a technology to control the transformation of the surrounding air and/or water warmth into a directional motion of the fluid could provide a renewable cycle, comprising:

transformation of the flowing fluid heat-power into acquired kinetic-power of an arisen jetstream (and/or into acquired wave power of an arisen wave);

conversion of the jetstream kinetic-power into useful electric power; and consumption of the electric power, in the final analysis, inevitably dissipating back into the warmth of the surrounding matter.

There is, therefore, a need in the art for a method and apparatus to provide a proper optimal design of a system, implementing a controllable jet-effect appropriate for use in industry.

Venturi Effect

Reference is now made to prior art FIG. 1a. FIG. 1a is a schematic illustration of an airfoil-shaped convergent-divergent nozzle 102, pipe-section in a sagittal plane. The shape can be described as comprising an inlet part 103 constricting into a narrow throat 104, further followed by a divergent outlet part 105. When a fluid 106 flows slowly through convergent-divergent nozzle 102, a jet-effect is observed in an adiabatic process, i.e. velocity increases in narrow throat 104 at the expense of the static pressure in fluid 106. Speedometers 1071, 1072, 1073, and barometers 1081, 1082, 1083 illustrate the interrelated behavior of the velocity and static pressure. This jet-effect is known also as the Venturi effect. Thus, the Venturi acceleration effect is observed in the case of a slow and converging flow, and the Venturi retarding effect is observed in the case of slow and divergent flow.

The inventor points out and emphasizes that the phenomenon of the Venturi effect is the self-acceleration and self-retarding of an airflow portion, i.e. is the airflow velocity self-oscillation, at the expense of the air portion's warmth. I.e., in other words, the Venturi effect of the airflow velocity self-oscillation (as well as the Coanda-jet-effect) has the jet-effect nature. When observing a freely falling water jetstream, one explains a conic constriction of the water jetstream by the Venturi effect, where the accelerated jetstream becomes accompanied by a decrease of the cross-sectional area.

De Laval Effect

Reference is now made to prior art FIGS. 1b and 1c. FIG. 1b shows schematically pipe 100 referred to the de Laval nozzle that, in principle, is similar to pipe 102 shown in FIG. 1a, but now the incoming fluid-flow 101 is sufficiently fast such that fluid 101 becomes substantially compressible-expandable. In this case, in an adiabatic process, the de Laval effect is observed. This is the effect of the extension of fluid 101 in the divergent outlet part 142 resulting in a further decrease of the static pressure and temperature and a correlated increase of the flow velocity.

FIG. 1c illustrates schematically graphics of distributions of the fluid-flow 101's (FIG. 1b) three mutually-scaled parameters: headway velocity 150, static pressure 160, and temperature 170, each along the length of nozzle 100. A standard rocket convergent-divergent jet-nozzle 100 can be modeled as a cylinder 140 that leads to a constriction 141, known as the "throat", which leads into a widening "exhaust bell" 142 open at the end. The location of the narrowest cross-section of the throat is called the "critical condition" point 180. High speed and therefore compressible-expandable hot fluid 101 flows through throat 141, where the velocity picks up as a jump 151 and the pressure and temperature suddenly fall, 161 and 171, correspondingly. Hot fluid 101 exits throat 141 and enters the widening exhaust bell 142. It expands rapidly, and this expansion drives the velocity up 152, while the pressure and temperature continue to fall, 162 and 172 correspondingly. This jet-effect phenomenon of fluid 101 extra-acceleration at the expense of the fluid 101 heat energy, defined by the static pressure, absolute temperature, and mass density, is applied to jet-engines, particularly, to accelerate a rocket. A sharp slope of the static pressure, observed in throat 141, results in pressure waves, called Mach waves. An undesired influence of the Mach waves in the de Laval nozzle is described, in particular, in D11—U.S. Pat. No. 8,601,787 "Rocket nozzles for unconventional vehicles" by Bulman.

In A01, A02, and A03, the enhanced implementations of jet-effects: the Venturi effect, the de Laval jet-effect, and the de Laval retarding-effect, are suggested, wherein the essence of the improvement is in stationary geometrical configurations of a Venturi pipe and a de Laval jet-nozzle, correspondingly, such that the stationary geometrical configurations are passively adapted to certainly-given velocity and thermodynamic parameters of an incoming fluid flow to provide for laminar flow. Namely, the prior art improved passively adapted stationary geometrical configuration of a de Laval jet-nozzle is such that the varying cross-sectional area characterized by a passively adapted cross-sectional area profile function $A_0(x)$ given by an equation expressed as:

$$A_0(x) = \frac{A_*}{M(x)} \left(\frac{\gamma-1}{\gamma}\right)^{\frac{1}{2}} \left(\frac{2+\gamma(M(x))^2}{\gamma+1}\right)^{\frac{\gamma+1}{2(\gamma-1)}}, \quad \text{Eq. (1.a)}$$

where $A_*$ is the minimal cross-sectional area of a narrow throat, $\gamma$ is an adiabatic compressibility parameter of the fluid flow, and $M(x)$ is a gradually-smoothed monotonic function of x representing a profile of an M-velocity of the fluid flow moving within and through the nozzle. In particular, to accelerate a certain gas flow characterized by a specific gas constant R, entering the open inlet of the improved passively adapted stationary geometrical configuration of a de Laval jet-nozzle with an initial velocity $u_{in}$ and temperature $T_{in}$, and to result in the enhanced de Laval jet-effect, the stationary geometrical configuration of the de Laval jet-nozzle must have the ratio $A/A_*$ of the cross-sectional area of the open inlet to the minimal cross-sectional area of a narrow throat strictly quantified as $$\frac{A_{in}}{A_*} = \frac{1}{u_{in}}\sqrt{(\gamma-1)RT_{in}}\left(\frac{2+u_{in}^2/(RT_{in})}{\gamma+1}\right)^{\frac{\gamma+1}{2(\gamma-1)}}. \qquad \text{Eq. (1.b)}$$

However, the prior art stationary geometrical configuration remains not optimized for arbitrary velocity and thermodynamic parameters of the incoming fluid flow that makes the prior art solution not universal for practical use in industry.

For the purposes of the present patent application:
the term "de Laval effect" should be understood in a wide sense as comprising both: the de Laval jet-effect, defined as an effect of flow extra-acceleration, and the de Laval retarding-effect, defined as an effect of flow extra-slowing; thus, the de Laval jet-effect is a particular case of the de Laval effect; also,
the term "de Laval-like jet-effect" should be understood in a wider sense including a case when an enhanced jet-effect occurs in an open space imaginarily bordered by the flow streamlines, wherein the imaginary borders constitute a convergent-divergent shape, i.e. similar to a de Laval nozzle.

The Phenomenon of Convective Self-Acceleration

FIG. 1d is a prior art schematic drawing of a body 1f.0 blown by an initially laminar airflow having portion 1f.2 enveloping body 1f.0. It is assumed that the velocity of the airflow motion is much lower than 0.5 Mach, for instance, 1 m/sec. For simplicity and without loss of reasoning, consider a case when the body 1f.0 corpus has at least partially airfoil shape providing for that ambient-adjoining sub-portions 1f.5 and 1f.6 of airflow portion 1f.2 remain laminar at least upstream afore a frontal plane, crossing the body 1f.0 corpus. Here:

such a frontal plane is marked with the dotted line having numeral 1f.1;
dashed lines 1f.3 and 1f.4 are imaginary streamlines bordering airflow portion 1f.2 as a whole and being sufficiently far from body 1f.0 that allows ignoring the airflow streamlines minor curving when bordering ambient-adjoining sub-portions 1f.5 and 1f.6; and
arrow 1f.7 symbolizes a portion of downstream airflow, not obligatorily laminar.

When flowing around body 1f.0, ambient-adjoining sub-portions 1f.5 and 1f.6 of airflow portion 1f.2 become subjected to reshaping and can be considered as moving through an imaginary tunnel, which is characterized by varying cross-sectional area. According to the mass conservation law, called also the equation of continuity: $A\rho u = \text{Const}$, where $\rho$ is the mass density of flux; u is the flux velocity, and A is the flux cross-sectional area, the ambient-adjoining sub-portions: 1f.5 and 1f.6, both move faster than yet to be reshaped airflow portion 1f.2 because the air mass density changes are minor at low airflow velocities and the sub-portions have the cumulative cross-sectional area smaller than the cross-sectional area of yet to be reshaped airflow portion 1fi. Therefore, the cumulative kinetic energy of ambient-adjoining sub-portions: 1f.5 and 1f.6, together, is higher than the kinetic energy of oncoming airflow portion 1f.2 yet to be subjected to the reshaping.

One of the key questions about the origin of flowing fluid portion acceleration is the following. At the expense of what kind of energy, the sub-portions became accelerated, if the case is adiabatic? The answer to the question is the self-acceleration occurs at the expense of the internal heat energy of the flowing fluid portion itself, wherein the initial velocity of the flowing fluid portion plays a role of a "trigger-catalyst" defining the intensity of the self-acceleration, namely, a higher velocity results in a greater self-acceleration. The answer shows that the phenomenon of convective self-acceleration is inevitable for fluid flowing around a body with relatively low velocities in an adiabatic process, i.e. upon conditions usually provided in the actual practice.

The inventor points out and emphasizes that a portion of the flowing fluid can play the role of a body subjected to blowing by another portion of the flowing fluid—this situation occurs, for instance, in acoustic waves.

Airfoil Wing (Definition of Attack Angle)

FIG. 1e comprises five parts: Case (A), Case (B), Graph (C), Graph (D), and Scheme (E).

FIG. 1e Case (A) is a prior art schematic drawing of a classic airfoil profile of an airplane wing 10.A oriented horizontally in a sagittal plane. The wing profile is recognizable by a rounded leading edge, a convex profile contour, having smoothly curved, elongated sides: more convex and lesser convex, and a sharp trailing end.

To move the wing 10.A with the velocity $u_0$ through a real fluid (for instance, air), an engine "ENGINE-A", which is not shown here, consumes power to overcome a certain resistance of the ambient fluid. The certain resistance (sometimes, called a drag in a wide sense) against the headway motion is defined as the cumulative resistance including:

drag in the direct sense against a cross-sectional area; the drag is determined by the wing's cross-sectional area and shape;
skin-friction determined by the chemical composition of the air and shell of the wing and manifested as the fluid viscosity and stickiness between the fluid and the wing 10.A; and
the additional resistance, determined by turbulence (as the turbulent portions draw other portions of the fluid thereby further increasing the drag and inter-air friction).

Again, the consumed power (for instance, the energy of burned fuel) goes to overcome the certain drag in the wide sense.

A horizontal oncoming airstream 10.0 runs on the rounded leading edge and flows around wing 10.A, thereby being divided into two dominantly-laminarly moving portions: upper-side air portion $B_1$ 10.1 forming an upper-side air flux 10.3 (called also an upper-side boundary layer) and lower-side air portion $B_2$ 10.2 forming a lower-side air flux 10.4 (called also a lower-side boundary layer), both going off from the sharp trailing end.

For the purposes of the present patent application, the introduced terms "upper-side" and "lower-side" applied to an object should be understood as indicating the location of the object: adjacently above an upper side and adjacently under a lower side, correspondingly.

The axis 10.C of wing 10.A is codirectional with a so-called chord of the wing, which (the chord of the wing), sometimes, is defined relatively arbitrary, based on a side-view profile of the wing. Since a wing can have a twist, a chord line of the whole wing may not be definable, so an alternate reference line is simply defined. Often, the chord line of the so-called "root of the wing" is chosen as the reference line. Another choice is to use a horizontal line on the fuselage as the reference line (and also as the longitudinal axis) 10.H. Axis 10.C of wing 10.A and the axis 10.H constitute an angle of the wing asymmetry 13. To define "an angle of attack", some authors use a so-called "zero lift axis" where, by the specific definition, "a zero angle of attack" corresponds to zero coefficient of lift. In contrast, for the purposes of the present patent application, taking into account the dual nature of lift-force 10.F: by impact and by the Coanda-effect, an "attack angle" or "angle of attack" should be understood as an angle between the horizontal direction of oncoming airstream 10.0 and the longitudinal axis 10.H, while the chord of the wing 10.C is conditionally defined as separating the upper-side and lower-side fluxes. In other words, the attack angle is defined relative to the zero attack angle that, in turn, is specified by a manifestation such that the zero attack angle provides for minimized impact by the oncoming flow and, thereby, for the lift-force 10.F generation due to the Coanda-jet-effect only or at least dominantly. The more convex upper side provides a slippery surface, and the lesser convex lower side, exposed to oncoming air stream 10.0 with the attack angle (zero or non-zero positive) and so subjected to friction and impact by lower air flux 10.4, has thereby more frictional-dragging surface.

Thereby, the shown profile of wing 10.A oriented horizontally is defined as a profile of wing exposed to the oncoming wind 10.0 at the zero attack angle and subjected to the minimum drag and a certain lift originated due to the Conada-effect.

Lift-Force Mechanism

The well-known lift-effect of an airplane wing 10.A arises due to the non-symmetrical profile of wing 10.A when the upper side is more convex determining the angle of the wing asymmetry 13. Firstly, a lift-force 10.F is defined by the attack angle, which redirects the flowing wind. Secondly, when the attack angle is equal to zero, wing 10.A, having an ideally streamlined contour, provides that the sliding upper-side air flux 10.3 and the impacting lower-side air flux 10.4, both subjected to the Coanda-jet-effect operation, meet behind wing 10.A. Sliding upper-side air flux 10.3 and impacting lower-side air flux 10.4, flowing around wing 10.A, incur changes in their cross-sectional areas and are accelerated convectively according to the mass conservation law. Considering relatively low velocities, the varying cross-sectional areas result in that the sliding upper-side air flux 10.3 runs faster than the impacting lower-side flux 10.4. According to Bernoulli's principle, this results in less so-called static pressure on wing 10.A from sliding upper-side flux 10.3 than the static pressure from the impacting lower-side flux 10.4. If upper-side flux 10.3 and lower-side flux 10.4 flow around wing 10.A laminarly, the difference between the static pressures is defined as $\Delta P_L = C_L \rho u_0^2/2$, where $\Delta P_L$ is the static pressure difference defining the lift-force 10.F, $C_L$ is the coefficient of lift depending on wing 10.A's non-symmetrical profile shape and orientation, $\rho$ is the mass density of the air, and $u_0$ is the velocity of the ambient airflow relative to wing 10.A.

FIG. 1e Graph (C) illustrates the dependence of the coefficient of lift $C_L$ for the classic airplane wing 10.A on the attack angle, wherein the marked range 10.L of the coefficient of lift $C_L$ corresponds to the attack angles close to zero. In practice, "the zero attack angle" has a tolerance $\delta\varphi$ of several degrees [for instance, it is well-known for an airplane pilot that, when Boing 777 is flying strictly horizontally, the orientation of fuselage is at a positive $\delta\varphi$]. In this case, the lift-force is substantial and the drag is minimal.

Thus, quintessentially, a frequently cited explanation of a mechanism of the lift-force origination is that the static pressure in a shaped boundary layer above the upper side of the wing 10.A is lower than the static pressure in a shaped boundary layer under the lower side of the wing 10.A. In addition, for the purpose of the present patent application, to introduce to claimed method and devices, a more detailed explanation of the mechanism of the lift-force origination is expounded hereinafter in the sub-paragraph "Boundary-Laver". In particular, it will be emphasized that the two portions of air: $B_1$ 10.1 and $B_2$ 10.2 (which originally being portions of the oncoming airstream 10.0 characterized by the ambient static pressure), when becoming portions of the upper-side and lower-side shaped boundary layers 10.3 and 10.4, both are subjected to just-sudden changes in the static pressures: $\Delta P_{B1}$ and $\Delta P_{B2}$, correspondingly, and the coefficient of lift $C_L$ is determined by the interrelated wing's shape and suddenness of pressure changes. A wing, having an elaborated airfoil profile, provides for an unbroken, gradual variation of the airflow static pressure along the profile's smoothly curved contour that, when flying with a certain velocity, results in an unbroken distribution of the airflow velocities along the profile's smoothly curved contour, i.e. satisfies a condition preventing an origination of turbulences. Consider an air portion flowing around wing 10.A, referring to the Clapeyron-Mendeleev law concerning a so-called hypothetical ideal gas state: $P = \rho R_0 T/\mu$, where P is the gas static pressure, $\rho$ is the gas mass density, T is the absolute temperature of the gas, $\mu$ is the gas molar mass, and $R_0$ is the universal gas constant. One could apply rough and more exact explanations for changes in the gas state parameters of the air portion flowing around wing 10.A.

Roughly, for the sake of estimation of a relatively slow wind tendency only, considering the flowing air as substantially incompressible gas, Gay-Lussac's law for an isochoric process interrelates the static pressure P and absolute temperature T by the equation $\Delta P/P = \Delta T/T$, i.e. the reducing static pressure is accompanied by the decreasing absolute temperature.

More exactly, for the wind at low speeds as well as at higher speeds running, in general, at a non-zero attack angle, the air (being compressible-extendable as an ideal or van der Walls gas), when flowing around wing 10.A, is subjected to an adiabatic process rather than to an isochoric process. An adiabatic process in gas is described by the condition $P/\rho^\gamma = \text{Const}$ or $P/T^{\gamma/(\gamma-1)} = \text{Const}$ or the equivalent thermodynamic differential equations interrelating changes in absolute temperature T, mass density, and static pressure P of gas as follows:

$$\begin{cases} \dfrac{d\rho}{\rho} = \dfrac{1}{\gamma}\dfrac{dP}{P} & \text{Eq. (1.1a)} \\ \dfrac{dT}{T} = \dfrac{\gamma-1}{\gamma}\dfrac{dP}{P} & \text{Eq. (1.1b)} \end{cases}$$

In general, when a portion of air flows nearby a solid surface, attraction forces between the air molecules differ from the attraction forces between, on the one hand, molecules of the air and, on the other hand, molecules of the solid surface. Normally, the effect of stiction of the flowing air to the solid surface is observed.

FIG. 1e Graph (D) is a prior art schematic drawing extracted from D05 showing a flow velocity profile u(z) 1G.0 in height within a flat boundary layer nearby a solid surface 1G.1, when the ambient velocity $u_0$ 1G.32 above the dashed line 1G.2 is in the low-subsonic velocity range. The dashed line 1G.2 indicates an imaginary boundary between the flat boundary layer characterized by the effective thickness S 1G.3 and an outer ambient portion of the flow moving substantially free. The velocity profile u(z) 1G.0 is shown as a function of the x-component (projection to the axis X) of velocity-dependent on Z-coordinate, where the axis Z shows the distance from the solid surface 1G.1. It is well-known that, normally, solid surface 1G.1 is sticky for a real flow (in particular, airflow) such that an airflow portion adjacent to the solid surface 1G.1 moves slower than a portion moving farther from the solid surface 1G.1. The stickiness, in particular, says that the effective thickness S 1G.3 of the flat boundary layer is specified as a thickness, for simulation of which a spatial temperature distribution and heat exchange between the flow and the solid surface 1G.1 should be taken into account. The ambient velocity $u_0$ 1G.32 above the dashed line 1G.2 is much higher than the velocity $u(z \ll \delta)$ 1G.31 near the solid surface 1G.1, wherein there are extremely low velocities $u(z \ll \delta)$ in close proximity above the solid surface 1G.1. Moreover, normally, the condition $u(0) \to 0$ of the zero velocity at the zero height above the solid surface 1G.1 is satisfied for much higher ambient velocities, including the supersonic velocity range. The velocity profile u(z) 1G.0 and the effective thickness δ 1G.3, both are velocity-dependent: the higher the ambient velocity $u_0$ 1G.32, the thinner the boundary layer. In frames of the aerodynamics, one estimates the thickness δ 1G.3 of a boundary layer, dependent on both a so-called "characteristic size" $L_*$ and the so-called Reynolds Number Re, as, for example, approximation by Prandtl: $\delta = 0.37 \times L_* / Re^{0.2}$, where $L_*$ has the sense of a chord of an airfoil wing 10.A. As well, the thickness δ 1G.3 of the boundary layer can be specified experimentally for a kind of body corpus. Looking ahead, it will be pointed out that, if the temperature of the solid surface is maintained forcibly; on the one hand, a tiny portion of airflow moving adjacent to the solid surface can be heated or cooled by the solid surface and get the temperature of the solid surface and, on the other hand, a big portion of the airflow moving farther from the solid surface is capable of removing or, vice-versa, reverting an increased or, vice-versa, a reduced portion of the heat, correspondingly, thereby, providing for the two useful tendencies: on the one hand, the faster airflow the faster heat removing and/or reverting, and, on the other hand, the tiny portion always tends to have the temperature of the solid surface.

According to the Bernoulli theorem, the distributed velocity u(z) is interrelated with the distributed static pressure $\overline{P_B}(z)$ and mass density ρ(z) of the air within the flat boundary layers as follows:

$$\frac{\overline{P_B}(Z)}{\rho(Z)} - \frac{\overline{P_B}(0)}{\rho(0)} = \frac{u(0)^2}{2} - \frac{u(z)^2}{2} \quad \text{Eq. (1.1c)}$$

A common convention is that u(0) is extremely low and for low velocities the assumption $\rho(z) \cong \text{const}$ is a good approximation, so the equation Eq. (1.1c) can be rewritten as $$\overline{\Delta P_B}(z) \approx -\rho_0 \frac{u(z)^2}{2} \quad \text{Eq. (1.1d)}$$

where $\overline{\Delta P_B}(z)$ is a change in static pressure within the flat boundary layer and $\rho_0$ is the mass density of the ambient airflow. Thus, the effective change $\overline{\Delta P_B}$ in the static pressure of the flat boundary layer due to the effect of stiction relative to the ambient static pressure is positive because the velocities u(z) within the flat boundary layer are lower than the ambient velocity $u_0$. When considering convexly curved surfaces of wing 10.A, in addition to the effect of stiction, the Coanda-effect is observed. The Coanda-effect makes the boundary layers shaped; in other words, the motion of airflow within the shaped boundary layers is accompanied by changes in the cross-sectional area of the airflow. I.e. the air portions, $B_1$ 10.1 and $B_2$ 10.2, both become subjected to acceleration interrelated with the cross-sectional area convergence and divergence due to the Venturi effect. The partial static pressures, indicated by $\widetilde{\Delta P}_{B1}$ and $\widetilde{\Delta P}_{B2}$, originated due to the convective accelerations of the Coanda-effect plus the Venturi effect and contributed to the resulting changes $\Delta P_{B1}$ and $\Delta P_{B2}$ of the static pressures of the shaped boundary layers, are interrelated with the resulting effective velocities, indicated by $u_1$ and $u_2$, of the upper-side and lower-side shaped boundary layers, correspondingly. The resulting changes $\Delta P_{B1}$ and $\Delta P_{B2}$ of the static pressures of the shaped boundary layers are specified as:

$$\Delta P_{B1} = \overline{\Delta P_B} + \widetilde{\Delta P}_{B1} \quad \text{Eq. (1.1e)}$$

$$\Delta P_{B2} = \overline{\Delta P_B} + \widetilde{\Delta P}_{B2} \quad \text{Eq. (1.1f)}$$

and, according to the Bernoulli theorem:

$$\Delta P_{B1} \approx \rho_0 \frac{u_0^2 - u_1^2}{2} \quad \text{Eq. (1.1g)}$$

$$\Delta P_{B2} \approx \rho_0 \frac{u_0^2 - u_2^2}{2} \quad \text{Eq. (1.1h)}$$

wherein, again, the symbol of approximate equality, '≈', is used as the mass density is approximated by the constant $\rho_0$. Thereby, the resulting static pressure difference $(\Delta P_{B1} - \Delta P_{B2})$ is approximated by:

$$(\Delta P_{B1} - \Delta P_{B2}) \approx \rho_0 \frac{u_2^2 - u_1^2}{2}. \quad \text{Eq. (1.1i)}$$

As the curvature of the upper side is more convex than the curvature of the lower side of the wing 10.A, then, for the relatively low ambient velocity $u_0$, the condition $(\Delta P_{B1} - \Delta P_{B2}) < 0$ is satisfied, wherein:
the resulting changes $\Delta P_{B1}$ and $\Delta P_{B2}$ of the static pressures, both are positive, if the contribution of the effective change $\overline{\Delta P_B}$ is dominant relative to $\widetilde{\Delta P}_{B1}$ and $\widetilde{\Delta P}_{B2}$;
the resulting changes $\Delta P_{B1}$ and $\Delta P_{B2}$ of the static pressures, both are negative, if the contributions $\widetilde{\Delta P}_{B1}$ and $\widetilde{\Delta P}_{B2}$ are dominant and the effective change $\overline{\Delta P_B}$ is minor; and the resulting change $\Delta P_B$, is negative and the resulting change $\Delta P_{B2}$ is positive, if the condition $|\widehat{\Delta P}_{B1}| > |\overline{\Delta P_B}| > |\widehat{\Delta P}_{B2}|$ is satisfied.

For the sake of concretization and without loss of generality, consider the case when $\Delta P_{B1} < 0$ and $\Delta P_{B2} > 0$. When, on the one hand, the portion $B_1$ 10.1 becoming the upper-side shaped boundary layer 10.3 is subjected to a sudden decrease in the resulting static pressure $\Delta P_{B1}$, it pulls-in both an upper-side portion 10.5 of the ambient air and the wing 10.A into the upper-side boundary layer 10.3, and, on the other hand, the portion $B_2$10.2 becoming the lower-side shaped boundary layer 10.4 is subjected to a sudden increase in the resulting static pressure $\Delta P_2$, it pushes-off both a lower-side portion 10.6 of the ambient air and the wing 10.A away from the lower-side shaped boundary layer 10.4. The resulting action on wing 10.A in unison is manifested as the lift effect characterized by the lift-force $F_L$ 10.F. In the assumption that the air portions $B_1$ 10.1 and $B_2$102 suddenly become the shaped boundary layers 10.3 and 10.4, correspondingly, wherein the shaped boundary layers are extremely thin, completely laminar, and ideally aligned with the wing sides' curvatures, as the pulling-in and pushing-off act to both the wing 10.A and ambient air in the same extent, i.e. not more than a half the difference $(\Delta P_{B1} - \Delta P_{B2})$ contributes to the lift, the lift-force $F_L$ 10.F acting on the wing 10.A is limited by the value $$\left[-\frac{1}{2} \times (\Delta P_{B1} - \Delta P_{B2})\right] \times A_{WING},$$

where $A_{WING}$ is the area of a projection of wing 10.A on a horizontal plane. The actual value of the lift-force $F_L$ 10.F is determined by the suddenness of the transformation of the air portions $B_1$ 10.1 and $B_2$ 102 into the upper-side and lower-side thin boundary layers 10.3 and 10.4, correspondingly. The suddenness is specified by the suddenness factor $C_S$. Namely, as the interaction between, on the one hand, the wing 10.A and, on the other hand, the refreshed and suddenly compressed or decompressed air portions within the shaped boundary layers 10.3 and 10.4 is relevant for the lift force $F_L$ 10.F origination, then, in the case when the relatively thin shaped boundary layers 10.3 and 10.4 (the thickness of which is velocity-dependent) are strictly-aligned to the relatively big airfoil surfaces of the wing 10.A, the velocity-dependent suddenness factor $C_S$ tends to $1 (C_S \to 1)$, and, the slower-refreshed and so thicker the boundary layers 10.3 and 10.4 and the weaker the alignment, the smaller the velocity-dependent suddenness factor $C_S$. Assuming an airfoil corpus moving with the velocity $u_0$, which remains lower than a critical velocity $u_4$ such when the lift-force $F_L$ 10.F is yet upward-directed, a simplified approximation for the velocity-dependent suddenness factor $C_S$ is given by the expression:

$$C_S = \frac{M}{M_*}, \quad M \leq M_*, \qquad \text{Eq. (1.1j)}$$

where M is M-velocity specified as the velocity measured in Mach numbers and $M_*$ is the specific M-velocity specified as equal to $\sqrt{(\gamma-1)/\gamma}$, where $\gamma$ is the adiabatic compressibility parameter of the air (again, $\gamma = 7/5$ is a good approximation for the air composed of diatomic molecules dominantly). Taking into account the suddenness factor $C_S$, the lift-force $F_L$ 10.F is specified as:

$$F_L = \left[-\frac{1}{2} C_S (\Delta P_{B1} - \Delta P_{B2})\right] \times A_{WING}. \qquad \text{Eq. (1.1k)}$$

The expression in the squired brackets in the right part of the equation Eq. (1.1 k) has the physical sense of the effective pressure difference $\Delta P_L$ providing the lift-force $F_L$ 10.F, i.e.

$$F_L = \Delta P_L \times A_{WING} \qquad \text{Eq. (1.1l)},$$

wherein the effective pressure difference $\Delta P_L$ is commonly written in the form:

$$\Delta P_L \approx C_L \times \rho_0 \frac{u_0^2}{2} \qquad \text{Eq. (1.1m)}$$

where $C_L$ is a so-called coefficient of lift that depends on the wing geometry and Reynolds Number. (For instance, for the classic asymmetric wing 10.A exposed to airflow at the zero attack angle, when the associated Reynolds Number is in the range between $5 \times 10^6$ and $10 \times 10^6$, the value 0.52 is an acceptable approximation of the coefficient of lift $C_L$.) Comparing the equations Eq. (1.1i), Eq. (1.1k), and Eq. (1.1m), the lift coefficient $C_L$ is interrelated with the suddenness factor $C_S$ as follows:

$$C_L = \frac{1}{2} C_S \frac{u_1^2 - u_2^2}{u_0^2}, \qquad \text{Eq. (1.1n)}$$

wherein the geometry-dependence is performed by the values of the boundary layers velocities $u_1$ and $u_2$, which, also depend on the suddenness factor $C_S$.

FIG. 1e Case (B) is a prior art schematic drawing of a geometrically symmetric airfoil profile of an airplane wing 10.B, symmetric relative to a horizontal plane when oriented horizontally in a sagittal plane. Comparison between the classic asymmetric airfoil profile of the airplane wing 10.A and geometrically symmetric airfoil profile of the airplane wing 10.B is further analyzed to clarify a contribution to the lift-force 10.F generated due to the Coanda-effect.

To move the wing 10.B with the mentioned certain relatively-low velocity $u_0$, an engine "ENGINE-B", which is not shown here, consumes a certain power to overcome the mentioned certain resistance of the ambient fluid. The two wing configurations: 10A and 10.B, characterized by equal cross-sectional areas and chords, are subjected to the same resistance against the headway motion. So, to move the wings 10.A and 10.B with the same velocity $u_0$, the engines: "ENGINE-A" and "ENGINE-B", correspondingly, consume the same power, burning the same amount of fuel. However, while wing 10.B is not subjected to a lift-force, wing 10.A is subjected to the lift-force, seemingly, given free of charge. Actually, the lift-force 10.F acting on wing 10.A is given due to the Coanda-effect at the expense of the heat energy of the ambient fluid, and so, from the point of view of the burned fuel, the lift-force 10.F is given free of charge indeed. Note that the phrase "given free of charge" does not mean "given from nothing". It is the well-known principle of commonly used airplanes. So (for the sake of simplicity, considering the zero attack angle), a very heavy airplane flies using a relatively economical engine providing for a headway motion and thereby triggering the Coanda-jet-effect originating the lift-force 10.F working at the expense of the heat energy of the ambient fluid, Airfoil Wing is not a Perpetuum Mobile Meanwhile, on the one hand, the above-expounded analysis, made from the point of view of the Energy Conservation Law, says that the term "given free of charge" does not mean "given from nothing" and so proves that the airfoil wing 10.A is not a Perpetuum Mobile of the first kind; on the other hand, it remains the frequently asked question if the airfoil wing 10.A is a Perpetuum Mobile of the second kind contravening to the Second Law of Thermodynamics because the heat energy of the ambient fluid becomes transformed into the useful lift-force without any additional contribution of energy as soon as we compare the wings 10.A of Case (A) and 10.B of Case (B).

For this matter, the applicant points out that:
1. The case of a wing, moving in a fluid, is the same as the case of moving fluid, flowing around the wing, according to Galilean relativity; and
2. Any portion of the moving fluid cannot be considered as an isolated system, at least because the moving portion of fluid inherently contacts with both: an adjacent upstream portion and an adjacent downstream portion of the ambient fluid, i.e. it is not an isolated system by definition.

Hence, the Second Law of Thermodynamics is not applicable to the moving portion of the fluid flowing around the wing, because the moving portion of the fluid is an open system from the point of view of the thermodynamics by definition, and so, the wing 10.A of Case (A) cannot be defined as the Perpetuum Mobile of the second kind as well.

When the attack angle is zero, an aircraft consumes power for headway forwarding against the frictional-dragging only, and the lift-force $F_L$ 10.F working for the keeping a height of flight (i.e. for the upward motion against the gravity) is originated at the expense of the ambient warmth due to the Coanda-jet-effect; the use of this phenomenon is one of the primary features of claimed embodiments of the present patent application;

Broken Boundary Layer

FIG. 1*e* Scheme (E) is a prior art schematic drawing extracted from D06 showing a widening boundary layer 1G.40 bordered, on the one side, by a seemingly-airfoil solid surface 1G.41 of a wing and, on the other side, by a streamline 1G.42. Portions of streamlines within the boundary layer 1G.40 are indicated by a set of arrows 1G.43. The dashed line 1G.44 divides the boundary layer 1G.40 between two portions: upstream, where the boundary layer is yet laminar, and downstream, where the turbulent vortex 1G.45 takes place. The separation point 1G.46 is the point on the upper side, where the boundary layer is completely separated from the surface, reducing lift drastically. This is known as stalling. There are broken or jumping all: the headway velocity, the static pressure, the absolute temperature, and the mass density nearby the separation point 1G.46.

Two prior art methods of boundary layer control are: first, Prandtl developed mechanisms to suck the boundary layer along the upper side of wings, thus maintaining the laminar flow and preventing separation and, second, others studied ways of blowing air into the boundary layer near the leading edge, to energize the boundary layer and prevent separation. One of the difficulties to implement the controlled sucking portions from and/or blowing portions into the boundary layer is that the boundary layer structure depends on the airflow velocity.

Further Features of Airfoil Wing
The inventor points out that:
To control a lift-force of an airfoil wing, one uses wings supplied with moving flaps that, as well as a non-zero attack angle, undesirably boosts turbulence and drag;

A well-known phenomenon of upper-side flux 10.3 adiabatic cooling at low-subsonic velocities is observed. Natural air is humid, and the local cooling, accompanied by the pressure reduction, acts, in particular, as a water condensation trigger. If the wind flows around a wing with an M-velocity equal to or higher than the Mach number (i.e. the speed of sound), a well-known phenomenon of shock sound-wave emission takes place. This shock sound-wave is not caused by wing vibration, but arises when a myriad of acoustic waves become in-phase superposed thereby forming the resonance resulting in the shock sound-wave; moreover, it becomes evident that the shock sound-wave is originated at the expense of the internal heat energy of air and so is accompanied by the air temperature shock decrease, provoking the process of vapor condensation into water-aerosols;

One could note that the effect of considerable amounts of water-vapor condensation into water-aerosols and sublimate into micro-flakes-of-snow, which are observed behind the high-speed aircraft's wings, occurs at flow speeds substantially Tower than the Mach number, i.e. it is not triggered by the mentioned phenomenon of shock sound-wave emission. In contrast to the prediction of the extra-decrease of static pressure and temperature at transonic and supersonic velocities only, on the one hand, an explanation of this phenomenon and, on the other hand, the phenomenon that air-fluxes flowing nearby around a body, when the body flies in air-environment with transonic, supersonic, and/or hypersonic velocities become warmer and extra-warmed, both are is expounded, for example, in A01, A02, and A03;

When flying with transonic and supersonic velocities, the warmed and extra-warmed portion of flow moving above a wing, having the classic airfoil profile 10.A oriented horizontally, results in a negative lift-force and so a non-zero attack angle undesirably boosting a drag is required to fly horizontally; and It is also well-known that, when flying with transonic and supersonic velocities, a wing, having the classic airfoil profile 10A oriented horizontally but knocked-over to have a convexity on the lower side of the wing, results in a positive lift-force.

Had one possessed a technique to control the flow velocity and static pressure within the boundary layer without inertia and without moving parts, it would become possible to suppress the undesired concomitant turbulence and, thereby, to improve the functionality of the wing substantially. The present patent application proposes a method for providing the laminarity within a boundary layer resulting in an increased lift-force and proposes solutions to overcome the problematic occurrence of turbulence and negative lift-force.

Point of Sail

The term "point of sail" is used to describe a sailing boat orientation relative to a prevalent direction of the ambient wind.

Prior art FIG. 2*a* is a schematic illustration of points of sail. A sailboat exposed to ambient headwind 18.0 in positions and orientations: 18.1, 18.3, 18.5, 18.6, 18.7, 18.9, 18.11, and 18.12 relative to the prevalent direction of ambient headwind 18.0 is shown schematically. The positions and orientations of the sailboat, i.e. the points of sail, are classified by groups, indicated by symbols "A", "B", "C", "D", and "E". Group "A" is the so-called "in irons" (into the wind) or "no-go zone", group "B" is so-called "close-hauled", group "C" is so-called "beam reach", group "D" is so-called "broad reach", and group "E" is so-called "running".

The sailboat is a well-known example, showing that a passive sail, playing a role of a trivial nozzle, enables to move the sailboat at least partially in the upstream direction against ambient headwind 18.0, for instance along a zigzag path. In other words, the passive sail exposed to ambient headwind 18.0 produces "a net jet-thrust" against the ambient headwind 18.0. In simple words, in fact, the ambient headwind 18.0 sucks the passive sail but not pushes off it. Shaded sector 18.2 corresponds to the "no-go zone", where the single passive sail, being in position and orientation 18.12 belonging to point of sail group "A", does not provide a net jet-thrust in the upstream direction against the ambient headwind 18.0.

Point of sail "B", called also "B"-point of sail, having the sailboat position and orientation 18.1, is shown also in enlarged view 18. Streamlines 18.13 show a windward wind flow aligned with the concave side of sail; streamlines 18.14 show a leeward wind flow subjected to the Coanda-effect and so moving along a curved trajectory adjoining the convex side of the elastic sail, self-adapted to pressures of the wind flows; a multiplicity of arrows 18.15 indicate "lift-forces", in this case, directed horizontally, caused by the difference between static pressures at the concave and convex sides of sail; and arrow 18.16 indicates a portion of wind accelerated convectively, i.e. at the expense of the internal heat energy of wind. The convectively accelerated wind portion 18.16 acts on the sailboat by reactive force 18.17 according to Newton's Third Law. Reactive force 18.17 is vectored in the upstream direction. While lift-forces 18.15 become compensated dominantly by a stabilizing reaction of the sailboat's keel, which is not shown here, the reactive force 18.17 defines the sailboat headway motion primarily. The effect of net jet-thrust against the ambient wind is a kind of jet-effect; i.e. it is the effect of convective acceleration of a wind portion flowing along a curved trajectory adjoining the convex side of passive sail in point of sail "B" due to the Coanda-jet-effect, and in turn, the accelerated wind portion causes the net jet-thrust, according to Newton's Third Law. To move against the wind, the sail, characterized by the pant of sail "B" and orientation 18.1, must extract from the air the internal heat power, associated with the arisen reactive force 18.17, higher than the mechanical power of the oncoming headwind 18.0 blowing the sail downstream away. In this case, one observes that the drag in the wide sense, determined by the cumulative resistance of the sailboat to the oncoming airflow due to: the sailboat non-zero frontal cross-sectional area plus the effect of so-called skin-friction and plus the effect of turbulence, is weaker than the seemingly "negative drag", determined by the jet-thrust.

The inventor takes note that, when tracing after a wind portion relative to a system of coordinates linked with the wind portion yet to be accelerated due to the Coanda-jet-effect operation, one interprets the mentioned wind portion local acceleration as a peculiar shock-like wave propagating downstream, backward relative to the headway motion of the sailboat.

For the purposes of the present patent application, the introduced term "peculiar shock-like wave" or "peculiar wave" should be understood as a fluid reaction originated by a fluid portion local acceleration in a prevalent direction, in contrast to the term "forced wave" that should be understood as fluid oscillation originated and determined by an action of an external periodically-alternating force.

In view of the foregoing description referring to prior art FIG. 2a, it will be evident to a person skilled in the art that two sailboats, both being positioned in "B"-point of sail, wherein one of the sailboats has the position and orientation 18.1 and the other sailboat has the position and orientation 18.11, when consolidated together and thereby aggregated as a whole, provide a condition for a resultant net jet-thrust applied to the aggregation, directed straight against the ambient headwind 18.0. In this case, the ambient headwind 18.0 just sucks the passive pair of sailboats.

The inventor points out and emphasizes that the phenomenon of net jet-thrust of sail in point of sail "B" occurs due to the self-acceleration of an airflow portion at the expense of the air portion's warmth. I.e., in other words, the net jet-thrust of sail in point of sail "B" occurs due to the Coanda-jet-effect.

In spite of the fact that the effect of net jet-thrust against the ambient wind is widely used in cruising on the water, the effect remains unused in the world industry.

There is, therefore, a need in the art for a method and apparatus to provide proper analysis and optimal design of a system, implementing the kind of jet-effect providing the net thrust in the upstream direction, for a controllable use in industry.

Flying Bird

For the purposes of the present patent application, the inventor points out to a flying bird, to take note that the jet-effect is not so exotic, to emphasize the jet-effect potential efficiency, and to make clear that the Coanda-jet-effect is one of the primary and quintessential aspects of the present patent application. The inventor points out that a flying bird makes waving motions rather than rowing or pushing-off motions by its wings. The waving can be interpreted as a booster of the Coanda-jet-effect as well as a source of forced elastic waves. The inventor points out to a flying bird, the wings waving of which is not so frequent but-nevertheless is enviably efficient. In particular for a pigeon, while the wings waving velocity relative to the bird body is between 1 and 2 m/sec only, the bird flying-acceleration in a horizontal direction up to seemingly-paradoxical high velocities, higher than 10 m/sec (actually, higher than 30 m/sec and even 40 m/sec), becomes reachable; —it confirms that the primary mechanism of the flying-acceleration is at least not the pushing-off in the direct sense.

For comparison, a flying relatively large bird, for instance, a golden eagle, and a running cheetah, both overcome the air drag and support the upward and downward mobility (wherein the cheetah's vertical mobility is defined by a ground relief and small jumps of the cheetah's center of mass only). For simplicity of the comparison, ignore the sidelong (leftward and rightward) mobility. The flying golden-eagle, "pushing-off" gaseous air (take note, the "pushing-off" is not intensively-frequent), overcomes the air drag and supports the upward and downward mobility much easier and moves in the horizontal direction much faster, than the running cheetah pushing-off a stationary surface, wherein pushing-off substantially more intensive-frequently providing for a velocity of paws relative to cheetah's body being equal to the velocity of a cheetah. At first glance, this fact looks like a confusingly-paradoxical mystery. However, it becomes easily-explainable, if not to ignore the triggered Coanda-jet-effect as for the lift-force as well as for the forward motion acceleration (analogously as the net jet-thrust in the aforementioned example with the sailboat in "B"-point of sail described with the reference to FIG. 2a). I.e. it becomes easily-explainable if the wing of a bird is interpreted as a sail oriented horizontally as "B"-point of sail to provide an upward-and-forward jet-thrust as seemingly "negative drag". As further examples:
- a flying snowy owl is extremely noiseless, i.e. it has an actually-airfoil wing and body as a whole to provide for the suppression of turbulences, and
- a bird-swift is capable of non-stop flying for a long time, measured in months and years, wherein the bird-swift, flying under its own power and wherein not-frequently waving, is capable of reaching a horizontal velocity of 47 m/sec (169 km/h).

In spite of the fact, that the efficiency of net jet-thrust of the flying bird is attractively high, the phenomenon remains unused in the world industry.

Furthermore, the style of a flock of cranes flying is well-known. The style combines the waving of wings when the flying is accelerating and the wings gliding when the flying is stabilized. This style prompts that:
- on the one hand, there are no turbulent vortices behind the gliding wings of the flying cranes, i.e. the wings of a crane are actually-airfoil, and so the previous gliding crane does not hinder but even helps the next gliding crane in a lift and jet-thrust; and
- on the other hand, there is an interference of omnidirectional waves generated by the waving wings of the cranes of the flock, thus, it is self-suggested the assumption that the flying cranes use constructive interference thereby helping each other in the waving-itself.

In spite of the fact that the cranes apply the cascaded multi-stage repeating and thereby reinforcing the Coanda-jet-effect for originating both: the lift-force and the net jet-thrust, over a long time, this technique remains unused in the world industry.

There is, therefore, a need in the art for a method and apparatus to provide proper analysis and optimal design of a system implementing the repeatedly reinforced Coanda-jet-effect of laminar moving fluid as well as the repeatedly reinforced constructive interference of waves in the fluid, both providing the scalable and controllable use of the acquired power in the industry.

The inventor also points out the capability of taking-off, for example, a pigeon, having a mass of 0.3 kG and span of wings of 0.5 m, when waving with the wings waving velocity relative to the bird body of between 1 and 2 m/sec only, can rise dominantly-vertically faster than 2 meters per second. The "pushing-off" from the gaseous air more efficiently than the pushing off from a hypothetical "fixed ladder" already looks like a confusingly-paradoxical mystery. Moreover, the inventor points out that:
- to raise the mass of the pigeon, the lift-force $F_L$ of wings must be greater than 3 N, i.e. $F_L > 3$ N;
- the lift-force of wings $F_L$ is interrelated with the wings area $A_{WINGS}$ given approximately as 0.08 m² and a difference in static and/or stagnation pressures $\Delta P_L$ in the air portions under and above the wings by the expression $F_L = A_{WINGS} \times \Delta P_L$.
- taking into account a classic specification of the $\Delta P_L$, the equation for the lift-force is: $F_L = 0.5 \times A_{WINGS} \times C_L \times \rho \times u_w^2$, where $\rho$ is the air mass density given as $\rho \approx 1.2$ kG/m³, $u_w$ is the velocity of an air portion relative to the wings, and $C_L$ is the coefficient of lift, which at most can reach the value 1.75 in the extremal case of airflow impacting a classic wing 10.A at the attack angle of 16° as illustrated in FIG. 1e Graph (C) and a value between 2.0 and 3.0 when it becomes a coefficient of drag in the extremal case of airflow striking a hemispherical concave surface (the value 1.75 is used for the coefficient of drag of a parachute). So, to reach the value for $F_L$ of 3 N, a pigeon must accelerate an air portion up to the velocity $u_w = \sqrt{2Fc/(A_{WINGS} \times C_L \times \rho)}$ estimated as at least 5 m/sec; it is much higher than the reachable velocity of the wings waving.

It looks like a mystery if not to take into account the thermoregulation of the warm-blooded bird providing for that the fuzz at the lower side of the bird's wing keeps air warmer than the air kept in the fuzz at the wing's upper side (because both dominant warming muscles: pectoralis and supracoracoideus, are located lower than the bird's wings) and that the frequent waving results in the origination of air boundary layers around the wings, wherein the fuzz also smooths surges in pressure gradients.

As the mechanism of the taking-off effect of warm-blooded birds is directly related to claims of the present patent application, a detailed explanation of the mechanism is expounded hereinafter in the sub-paragraph "Taking-off Of A Warm-blooded Bird".

Taking-Off of a Warm-Blooded Bird

When considering a wing of a bird, for the sake of simplicity and without loss of reasonability, reference is made again to the schematic profile of classic wing 10.A (FIG. 1e).

The thermodynamic equation Eq. (1.1b), when applied to the boundary layers around a wing of a bird, in particular, says that, in contrast to a "cold-blooded" wing of an airplane acting on the convergent-divergently shaped boundary layers by "passive" heating and cooling due to either: the effect of skin-friction, and/or the Coanda-effect, and/or the Venturi effect; the warm-blooded wing of bird causes active heating of the convergent-divergently shaped boundary layers in addition to the mentioned "passive" heating and cooling. In particular, as the wing's lower side is warmer than the wing's upper side, while the upper-side shaped boundary layer is subjected to the "passive" warming and cooling dominantly, the lower-side shaped boundary layer is kept heated by the warmed fuzz. This means that the lower portion of the airflow is subjected to forced sudden warming $\Delta T_F$ resulting in additional forced sudden compression $\Delta P_F$. The additional forced sudden compression $\Delta P_F$ is added to the mentioned difference $\Delta P_{B2}$, thereby, increasing the difference $|\Delta P_{B1} - \Delta P_{B2}|$ and, in turn, increasing the lift-force $F_L$. To estimate, how much the added forced sudden compression $\Delta P_F$ can contribute to the effect of taking-off of a pigeon, consider:
- the normal ambient air conditions: $T \approx 300K$, $P \approx 100,000$ Pa, and $\gamma = 7/5$;
- the wings of the pigeon having a chord of 16 cm and a total span of 50 cm; i.e. $A_{WING} = 0.08$ m²;
- the effective velocity $u_W$ of wings waving is given by 2 m/sec that corresponds to about 5 swayings per second; i.e. the suddenness factor is $C_S \approx 0.01$, and
- an exemplary value of the additional to ambient temperature difference: $\Delta T_F$ of (−9 C), is taken for the estimation, noting that $\Delta T_F$ is interrelated with the suddenly originated effective additional static pressure difference $\Delta P_F$ according to the equation Eq. (1.1b).

So, the ratio $|\Delta T_F|/T \approx 0.03$, the ratio $|\Delta P_F|/P \approx 0.03 \times (7/5)/(2/5) = 0.1$, the contribution to the suddenly originated additional static pressure difference is $|\Delta P_F|\approx 0.1\times 10^5$ Pa, and the contribution to the lift-force is specified as $$\Delta F_L = \frac{1}{2} \times C_S \times A_{WING} \times |\Delta P_F| \qquad \text{Eq. (1.1o)}$$

and estimated as approximately 4 N; it is sufficient to lift the mass 0.3 kG of the pigeon in the vertical direction with the acceleration of up to 3.3 m/sec². Thereby, the estimation shows that the forced sudden warming $\Delta T_F$ plays a decisive role in the taking-off of the pigeon.

Now, to estimate the efficiency of the temperature regulation of a warm-blooded wing to contribute to the effect of thrust, further consider as follows:

the frontal cross-sectional area of a pigeon including both the relatively thin wings and approximately elliptical body is $A_{FR}\approx 0.0025$ m²;

the overall surface area of the pigeon including two sides of wings and the approximately elliptical body is $A_{OV}\approx 0.45$ m²;

considering the warm-blooded bird capability of thermoregulation, an exemplary value of the additional temperature difference $\Delta T_{TH}$ between the "head" and rear part of the bird's body and wings is taken as (−5 C); i.e. the temperature is distributed such that the head of the bird is colder than the bird's rear part of the body; and the value of the forced sudden compression $\Delta P_{TH}$ caused by the additional temperature difference $\Delta T_{TH}$, estimated using the interrelation Eq. (1.1b) is:

$$\Delta P_{TH} = \left(\frac{-5}{300}\right)\times\left(\frac{7}{2}\right)\times 10^5 \approx -6{,}000 \text{ Pa.}$$

So, the contribution to the thrust $\Delta F_{TH}$ specified as $$\Delta F_{TH} = \frac{1}{2} \times C_S \times A_{FR} \times |\Delta P_{TH}| \qquad \text{Eq. (1.1p)}$$

is estimated as 1.5 N. The contribution to the thrust of 1.5 N is sufficient to accelerate the mass of the pigeon in the horizontal direction With the acceleration of up to 5 m/sec² and to overcome a velocity-dependent drag in the air when moving with the headway velocity $u_0$ of at least 33 m/sec that follows from the interrelation derived from the well-known equation for drag and skin-friction, namely $u_0=\{|\Delta F_{TH}|/[0.5\rho_0(C_d A_{FR}+C_f A_{OV})]\}^{1/2}$, where:

$C_f$ is the skin-friction coefficient, normally, given as about 0.045 for an airfoil wing that can be interpreted as the worst-case approximation for the body and wings of the pigeon, $C_d$ is the drag coefficient, normally, given as about 0.5 for a frontal convexly-rounded configuration of an airfoil body that, again, can be interpreted as the worst-case approximation for the body and Wings of the pigeon.

The estimation of $u_0 \geq 33$ m/sec was done assuming the minimal value of the suddenness factor $C_S$ estimated for waving wings, although the suddenness factor $C_S$ is higher when the bird moves with a higher velocity.

Flying Insects

FIG. 2*b* is an illustration of a honeybee 1J.0 as an exemplary insect capable of flying. In contrast to the bird's wings, the insect's wings are neither profiled nor warm-blooded. It is a well-known frequently asked question in relation to the possibility of insects flying. One pays attention that the size of the insects wings 1J.1 and the velocity of the insect's wings motion are far from sufficient for active lifting the mass of the insects. However, this becomes explainable if to take into account that, on the one hand, the insect's wings function as a ventilator blowing the insect's hairy corpus and, on the other hand, the phenomenon of in-flight and pre-flight thermoregulation of the insects corpus, as described, in particular, in D13 and D14. For instance, Japanese honeybee is capable of increasing their body temperature above 46° C., as described in D15.

In particular, consider the honeybee 1J.0 having an ellipsoidal-like hairy corpus having a mass of 0.1 g, length 1J.3 of 15 mm, cross-sectional diameter 1J.2 of 5 mm, and cross-sectional area in a frontal plane of about 20 mm². The honeybee 1J.0, having a pair of blade like wings 1J.4, each of which is 10 mm in length 1J.1 and up to 2.5 mm in width such that the area $A_{WINGS}$ of a pair of wings is at most of 25 mm², is capable of waving at a rate up to 250 blows per second, corresponding to the effective velocity $\overline{u_B}$ of the blade-like wings of approximately 2.5 m/sec, mystery-providing a much higher flying velocity $u_0$ up to 18 m/sec (65 km/h). Moreover, to provide the lift-force $F_{L,INSECT}\approx 0.001$ N for taking-off, the blade-like wings, seemingly, must blow the honeybee's body with the velocity $u_B$ (i.e. must move with the velocity $u_B$) defined as $\sqrt{2F_{L,INSECT}/(\beta C_L A_{WINGS})}$ and estimated as at least 6 m/sec; it is confusingly higher than the reachable effective velocity $\overline{u_B}$ of the wings waving.

The insects use their neither profiled nor warm-blooded wings as blades to blow their hairy corpus which (the corpus), in turn, plays the role of a thermoregulated wing proving the lift-force. Thus, when referring to equation Eq. (1.1o), the area $A_{WINGS}$ has the sense of an area $A_{INSECT}$ of the insect's corpus projection on a horizontal plane. For the considered case, the area $A_{INSECT}$ is estimated as 75 mm² and the effective velocity $\overline{u_B}$ of the blade-like wings of approximately 2.5 m/sec determines the suddenness factor $C_S$ of approximately 0.013. Considering the exemplary honeybee and referring to the equation Eq. (1.10), but now using the value $A_{INSECT}=75$ mm² and taking into account the capability of pro-flight thermoregulation, the lift-force is specified as:

$$\Delta F_{L,INSECT} = \frac{1}{2} \times C_S \times A_{INSECT} \times |\Delta P_{INSECT}| \qquad \text{Eq. (1.1q)}$$

It can be derived from the equation Eq. (1.1q) that, to provide the lift-force $F_{L,INSECT}\approx 0.001$ N for taking-off using the actual blade-like wings waving with the effective velocity of 2.5 m/sec, the insect must provide the static pressure difference $|\Delta P_{INSECT}|$ of approximately 2 kPa due to the temperature difference of about 1.7° C.; this and much bigger temperature differences correspond to the capability of the honeybee's thermoregulation.

It follows from the foregoing sub-paragraphs "Flying Bird" and "Flying Insects" that there is a need in the art for a method and apparatus to provide a design of a system implementing an increased lift-force allowing for controllable use of the increased lift-force in the industry.

The use of the controllable temperature difference between boundary layers to contribute to the lift-force is suggested in the present patent application.

FIG. 2*c* is a prior art schematic illustration of a wind turbine 17.1 built-in into cylinder 17.2 having real sidewalls and open butt-ends. A widened description of FIG. 2*c* may be referred to AU03, which (the widened description) is not narrated herein for brevity. Instead, the inventor points out that the sub-portion 17.41 of the fluid stream enters cylinder 17.2 with a certain headway-motion velocity, indicated by $u_{41}$, which is lower than the headway-motion velocity of sub-portion 17.42, indicated by $u_{42}$, which flows outside cylinder 17.2. The reason for the negative difference ($u_{41}$−$u_{42}$) is explained by the drag of blades of wind turbine 17.1, namely, as the blades are subjected to impact of flow 17.41, the blades retard the flow 17.41 by the same drag according to Newton's Third Law of motion. In such an application, the effect of flow retarding is undesired. There is, therefore, a need in the art for a method and apparatus to provide a design of an improved wind turbine where the undesired effect of flow retarding would be reduced and the desired effect of producing electric power would be boosted.

Sound as Complicated Movement in Molecular Fluid

In physics, an acoustic (elastic) wave is an oscillation accompanied by a transfer of energy that travels through a medium (for instance, the ambient fluid). Waves consist of oscillations or vibrations of particles (molecules), around almost fixed locations.

A forcedly accelerated membrane is a trivial aerodynamic device—a fluid pusher-off, capable of originating an elastic wave propagating in the ambient fluid. Wave motion transfers energy from one point to another, displacing particles of the transmission medium with little or no associated mass transport. From the point of view of the energy consumption by a source of the acoustic wave, the energy transmission is given free of charge; it is given at the expense of the heat energy of the ambient fluid as a result of the triggered waving jet-effect as described in A02 and A03. The wavefront propagates in accordance with the Huygens-Fresnel principle saying that every point, which a wave-front disturbance reaches, becomes a source of a secondary spherical wave, wherein the interference superposition of these secondary waves determines the form of the wave at any subsequent time.

In physics, sound (acoustic wave) in a fluid is interpreted as an oscillating change of the fluid's thermodynamic parameters, namely, the oscillating change of the static pressure P, mass density p, and absolute temperature T, wherein the thermodynamic parameters are interrelated according to the van der Waals law of fluid state in an adiabatic process. Wherein, the oscillating changes in the fluid's thermodynamic parameters are such to result in triggering of the jet-effect manifested as fluid motion in the form of the propagating acoustic wave.

For the sake of concretization and without loss of generality, consider:
the air as a particular case of the fluid, and
the sound propagating in the air as a particular case of the acoustic wave propagating in the fluid.

The associated with sound oscillating changes of the fluid's thermodynamic parameters along an axis x collinear with the direction of the sound propagation is expressed as:

$$\begin{cases} \delta P = \Delta P \times e^{-i(\omega t - \kappa x)} & \text{Eq. (1.2a)} \\ \delta \rho = \Delta \rho \times e^{-i(\omega t - \kappa x)} & \text{Eq. (1.2b)} \\ \delta T = \Delta T \times e^{-i(\omega t - \kappa x)} & \text{Eq. (1.2c)} \end{cases}$$

where:
$\delta P$, $\delta \rho$, $\delta T$ are the oscillating changes of the static pressure, the mass density, and the absolute temperature, correspondingly;
$\Delta P$, $\Delta \rho$, $\Delta T$ are amplitudes of the oscillating change of the static pressure, the mass density, and the absolute temperature, correspondingly;
$\omega$ is the cyclic frequency of the oscillating change;
$\kappa$ is the wavenumber interrelated with the cyclic frequency $\omega$ of the acoustic wave as $\kappa = \omega/u_s$, where $u_s$ is the phase velocity of the sound propagation in the fluid.

Taking into account the interrelations between the thermodynamic parameters in an adiabatic process described hereinabove in the sub-paragraph "Lift-Force Mechanism" referring to FIG. 1e Graph (C) by the equations Eqs. (1.1a) and (1.1b), the equations Eqs. (1.2a), (1.2b), and (1.2c) describing the oscillating changes of the fluid's thermodynamic parameters associated with the sound are rewritten as a system of equivalent equations as follows:

$$\begin{cases} \dfrac{\delta P}{P} = \dfrac{\Delta P}{P} \times \exp[-i(\omega t - \kappa x)] & \text{Eq. (1.3a)} \\ \dfrac{\delta \rho}{\rho} = \dfrac{1}{\gamma} \dfrac{\Delta P}{P} \times \exp[-i(\omega t - \kappa x)] & \text{Eq. (1.3b)} \\ \dfrac{\delta T}{T} = \dfrac{\gamma - 1}{\gamma} \dfrac{\Delta P}{P} \times \exp[-i(\omega t - \kappa x)] & \text{Eq. (1.3c)} \end{cases}$$

A human-hearer perceives the oscillating changes of the air static pressure as sound loudness; the air static pressure, absolute temperature, and mass density are measured by the so-called "SPL" (sound pressure level), "STL" (sound temperature level), and "SDL" (sound density level), correspondingly; and the sound loudness is measured also by "SIL" (sound intensity level) or "SWL" sound power level.

The SPL is measured in decibels (dB). It is equal to $20 \times \log_{10}$ of the ratio of the route mean square (RMS) of sound pressure to the reference of sound pressure that (the reference sound pressure) in the air is $2 \times 10^{-5}$ N/m² or 0.0002 Pa, in turn, corresponding to the reference acoustic wave power (the loudness as power) estimated approximately as $10^{-12}$ W. The characteristic SPL of speakers is defined for the distance of 1 m from the speaker. Normally, a range of the characteristic SPL for a speaker is between 0 to 80 dB that corresponds to changes in the static pressure in the range from 0.0002 Pa to 2 Pa and changes in the acoustic wave power in the range from $10^{-12}$ W to $10^{-4}$ W. Using the equation Eq. (1.3c), the reference sound temperature in the air is estimated as $5.4 \times 10^{-10}$K and the range of temperature changes for the speaker is estimated from $5.4 \times 10^{-10}$K to $5.4 \times 10^{-6}$K.

Sound (acoustic wave) is considered as a complicated movement of a molecular fluid, wherein the complicated movement is composed of:
The Brownian motion of the air molecules with the Brownian velocity, indicated by $u_{Brownian}$, which interrelates with the velocity of sound $u_{sound}$ as $U_{Brownian} = \sqrt{3/\gamma} \times u_{sound}$; $u_{sound} \approx 345$ m/sec and $u_{Brownian} \approx 500$ m/sec.
The oscillating motion of molecules with so-called "particle velocity", the amplitude of which is indicated by $u_{particle}$ and interrelated with the sound loudness; normally, in the air,
near an oscillating membrane which is a source of the sound, the particle velocity amplitude $u_{particle}$ is predetermined by the velocity of the oscillating membrane and is between 0.1 m/sec and 10 m/sec, while far from the oscillating membrane, where the sound front becomes substantially widened, the particle velocity amplitude $u_{particle}$ is very low: between $5 \times 10^{-8}$ m/sec and $5 \times 10^{-4}$ m/sec;

wherein the particle velocity relates to the mass of the oscillating air as a whole; note that, considering a local slow flow moving with the particle velocity, a widening of a frontal cross-sectional area is accompanied by a decrease in the amplitude of the particle velocity, according to the equation of continuity;

The specific conveying motion that is interrelated with the cascaded oscillating motion of particles moving with the "particle velocity" that [the "particle velocity"], in turn, is interrelated with the acoustic wave amplitude manifested as the sound loudness. The specific conveying motion is a kind of movement, which (in contrast to the oscillating motion of the air as a whole) is interpreted as a directional motion of a tiny portion of fluid mass that [the tiny portion of mass] determines the air mass density oscillating change only. The specific conveying motion can be interpreted as composed of two complementary alternating movements of positive and negative changes of air mass density, wherein both alternating movements are in the same direction (that is the direction of sound propagation) and, when in open space, with the M-velocity of 1 Mach. The so-called Umov-vector is a measure of the specific conveying motion of the tiny portion of the fluid mass. The SPL, characterizing the sound loudness, is interrelated with the so-called: "SVL" (sound particle velocity level). Thus, the oscillating (positive and negative) change in mass density along the direction of the wave propagation (again, which is interrelated with the sound loudness) is considered as the directional motion of the tiny mass, wherein the motion is with the mass density change conveying velocity $u_{convey}$ that is the same as the velocity of sound $u_{sound}$, i.e., when propagating in open space, M-velocity of 1 Mach; and The concomitant turbulent motion, as dis-laminarity of the mentioned oscillating and conveying components of the complicated movement of air, depends on both the shape of a horn and the acoustic wave amplitude (sound loudness);

wherein, in contrast to acoustic waves in open space where the turbulent component of fluid motion, inherently-accompanying the acoustic waves, causes the inevitable dissipation of the propagating acoustic waves manifested as a decrease of sound loudness, the turbulent component of fluid motion within a horn is pre-determined by restricted degrees of freedom, so, the horn, if elaborated, can provide for reduced concomitant turbulence accompanied by increased intensity of sound. In other words, the elaborated horn plays the role of a fluid pusher-off capable of transforming the kinetic power of the concomitant turbulence into the wave power accompanied by increased both the particle velocity amplitude $u_{particle}$ and the conveying velocity $u_{convey}$.

For the purposes of the present patent application, the term "heat energy in a broad sense" should be understood as the cumulative kinetic energy of both the Brownian motion of the air molecules and the concomitant turbulent motion.

When a sound is originated by an oscillating membrane of a classic source of acoustic waves rated by a power supplier, the net-efficiency, defined for the classic source of acoustic waves as the ratio of the power of sound to the supplied power, normally, is between 0.1% and 2%. The mentioned originated concomitant turbulence, originated due to sudden jumping changes of thermodynamic parameters and velocity of adjacent fluid portions, especially, near the edges of the moving membrane, is the dominant reason for:

such a low net-efficiency of sound launching and, vice-versa, detection (the introduced term "sound detection" should be understood as registration and/or recording the electric voltage and/or current induced in the electrical circuit due to sound impact); and that, when the sound is propagating in open space, the sound loudness measured in SPL is further decreasing exponentially with the propagation path increase; wherein the exponential decrease in SPL is stronger for the sound of higher frequencies.

I.e., in other words, 98% to 99.9% of the power consumed by a classic source of acoustic waves goes for the kinetic power of the undesired turbulent motion of the ambient fluid.

One way to reduce the undesired concomitant turbulence accompanying the originated sound is to reduce the ratio of the amplitude of motion to the area of an oscillating membrane and, thereby, to reduce the contribution of the sudden jumping changes of thermodynamic parameters and velocity of adjacent fluid portions to the concomitant turbulence. For example, it is the commonly used piezo-effect manifested as small deformations of a piezo plate originating an ultrasound. However, taking into account that the power of sound is proportional to squared both amplitude and frequency of oscillation, the way can provide for the audible sound of unpractically ultra-low power and has a practical sense to launch and detect the ultrasound only.

There is, therefore, a need in the art for a method and apparatus to provide an improved design of a source and detector of acoustic waves; wherein, in particular, a net-efficiency would be increased by suppression of originated concomitant turbulence in the ambient fluid.

Horn as Sound-Booster

To reduce the kinetic power of the concomitant turbulence and thereby to increase the net-efficiency of sound launching, one uses an elaborated nozzle as an aerodynamic apparatus capable of transforming the kinetic energy, in general, of fluid particles, and, in particular, of the concomitant turbulence into the wave power of the sound.

FIG. 3a, a prior art illustration of horns playing the role of a sound booster, is divided into three schematic drawings: case (A), case (B), and case (C) as follows: (Case (A), illustrating a megaphone-A 1n.A comprising a movable membrane 1n.A1, capable of a controlled oscillating motion originating a sound, and an exponentially-divergent horn 1n.A2 having an outlet area 1n.AA;

Case (B), illustrating a megaphone-B 1n.B comprising a movable membrane 1n.B1, capable of a controlled oscillating motion originating a sound, and a triple-folded exponentially-divergent horn formed by three cascaded sequentially scaled parts: 1n.B2, 1n.B3, and 1n.B4. The triple-folded exponentially-divergent horn as a whole has an outlet area 1n.BA which is the same as the outlet area 1n.AA; in another view, megaphone-B 1n.B differs from megaphone-A 1n.A by the triple-folded cumulative length of the exponentially-divergent nozzle. It is found that, while megaphone-A 1n.A increases the intensity of the originated sound on 10 dB, the megaphone-B 1n.B increases the intensity of the originated sound on 20 dB; and Case (C), illustrating a gramophone 1n.0 supplied by an exponentially-divergent nozzle 1n.C1 playing the role of the acoustic waveguide. Diameter $D_{ou}$ 1n.C2 of sound-outlet of the exponentially-divergent nozzle 1n.C1 is greater than the diameter $D_{in}$ of a narrow sound-inlet throat 1n.C3 by the factor $F_D$ that is much greater than 1, in some implementation, the factor $F_D$ is equal to 60. The factor $F_D$ equal to 60 corresponds to the area-variation ratio of the sound frontal-outlet cross-sectional area to the sound frontal-inlet cross-sectional area of 3,600. The exponentially-divergent nozzle 1n.C1 is destined to solve the problem to widen the frontal cross-sectional area of sound rather than to contribute, in general, to the heat in a broad sense, and, in particular, to the concomitant turbulence of fluid. When a sound is established, in addition to the mentioned complicated movement of fluid, a portion of air, that takes a place within the exponentially-divergent nozzle 1n.C1, is subjected to forward-and-backward oscillating longitudinal motion accompanied by substantial deformations and accelerations of the air portion. If to ignore the de Laval jet-effect, it is expected that the area-variation ratio of 3,600 is accompanied by the air velocity inverse ratio of the same order of value. When considering the fluid motion component moving with the conveying velocity $u_{convey}$, a change in cross-sectional area of longitudinally-moving change in fluid mass density triggers the de Laval jet-effect, as soon as the velocity $u_{convey}$ measured in Mach numbers is higher than the specific M-velocity, and, when considering the fluid motion component moving with the particle velocity $u_{particle}$ a local change in the cross-sectional area of forward-and-backward oscillating longitudinally moving fluid triggers the local Venturi effect. In any case for an elaborated horn, the jet-effect of a transformation of both:

the fluid heat energy, and the energy of the concomitant turbulence, into the energy of the fluid oscillating motion is manifested as sound boosting.

On the one hand, the advantage of the use of an elaborated horn as a sound booster self-suggests finding an optimal geometrical configuration of the elaborated horn, and, on the other hand, a disadvantage of the use of any horn as a sound booster is that a source of acoustic waves supplied by such a horn occupies an increased space.

The inventor points out that the set of equations Eqs. (1.3a), (1.3b), and (1.3c), described hereinabove in the subparagraph "Sound as Complicated Movement in Molecular Fluid", in fact, says that a sound can be generated by a forced inertialess varying of the temperature of a portion of the ambient fluid, and, as a result, the static pressure and mass density of the fluid portion will become varied as a derivation according to the interrelations Eqs. (1.3a), (1.3b), and (1.3c). I.e., in other words, the mentioned subparagraph says that, hypothetically, it is possible to manipulate the temperature of a portion of fluid such that to result in triggering of the jet-effect manifested as the fluid motion in the form of the propagating acoustic wave. Had one possessed a technique to change the temperature of the ambient fluid portion without inertia and without moving parts, it would become possible to create sound with no creation of the undesired concomitant turbulence and, thereby, to increase the efficiency of a source of sound substantially. On the other hand, had one possessed a technique to detect the temperature changes of the ambient fluid portion without inertia and without moving parts, it would become possible to avoid undesired concomitant turbulence and so to increase the efficiency of a sound detector substantially. There is, therefore, a need in the art for a method and apparatus to provide an improved design of a compact source and detector of acoustic waves; wherein, in particular, a net-efficiency would be increased by suppression of originated concomitant turbulence in the ambient fluid.

External Ear as Sound Booster

FIG. 3b comprises a schematic drawing of a sectional profile of a human ear in a sagittal plane. External ear 1L.0 of humans comprises a pinna and ear canal. The pinna, destined to be exposed to an incoming sound, comprises a funnel characterized by an outer-inlet cross-section 1L.1, and the ear canal, destined for conveying the sound to eardrum 1L.6, comprises an ear canal inlet cross-section 1L.2 such that the pinna funnel outer-inlet cross-sectional area is greater than the ear canal inlet cross-sectional area by the factor $F_{12}$ of, approximately, 5.5. The ear canal is a tunnel for sound, further characterized by:

an after-inlet widened cross-section 1L.3, the cross-sectional area of that is greater than the cross-sectional area of the ear canal inlet cross-section 1L.2 by the factor $F_{32}$ of at least 1.1, a narrow throat cross-section 1L.4, the cross-sectional area of that is smaller than the cross-sectional area of the ear canal after-inlet widened cross-section 1L.3 by the factor $F_{34}$ of, approximately, 3; moreover, the cross-sectional area of the ear canal inlet cross-section 1L.2 is greater than the cross-sectional area of the narrow throat cross-section 1L.4 by the factor $F_{14}$ of approximately 2.7; and a wide outlet cross-section 1L.5 adjacent to the eardrum 1L.6, the cross-sectional area of that [1L.5 or 1L.6] is greater than the cross-sectional area of the ear canal narrow throat cross-section 1L4 by the factor $F_{54}$ of, approximately, 5.5.

The inventor points out the primary set of conditions satisfied for the shape of external ear 1L.1 as follows:

the factor $F_{12} \approx 5.5$ is much greater than the ratio of 1 Mach to the specific M-velocity, i.e. $F_{12} > 1/M_*$, $F_{32} > 1$, $F_{34} > F_{32}$, $F_{14} > 1$, and $F_{54>1}/M$ which (the set of conditions) will be further commented hereinbelow in sub-paragraph "Two-Staae Convercent-Divergent Jet-Nozzle" referring to FIG. 6c and in sub-paragraph "Phonendoscone and Sound Booster" referring to FIG. 7a cases (B) and (C), where it will be shown that the external ear, shaped to provide the mentioned set of satisfied conditions, functions as an aerodynamic apparatus pulling-in and pushing-off portions of fluid (i.e. a fluid pusher-off) which is capable of sound loudness boosting wherein the aerodynamic apparatus—the fluid pusher-off can be further amended.

There is, therefore, a need in the art for a method and apparatus to provide proper analysis and optimal design of a convergent-divergent nozzle to implement applications appropriate for use in industry for efficient boosting the sound based on enhanced jet-effects accompanied, in general, with reduced heat energy in a broad sense, and, in particular, with suppressed concomitant turbulence.

Thermoelectric Devices

A well-known thermoelectric effect is an aspect of claims of the present patent application, FIG. 4a is a prior art schematic illustration of a thermocouple 1o.0. The thermocouple 1o.0 is an electrical device consisting of two dissimilar electrical conductors: 1o.1 (for instance, Nickel-Chromium) and 1o.2 (for instance, Aluminum-Chrommium), forming an electrical junction 1o.3. When the junction 1o.3 is submerged in an ambient fluid having a certain temperature (for instance, the absolute temperature of 573K or 300 C), the thermocouple 1o.0 produces a temperature-dependent voltage V 1o.4 (for instance, 12.2 mV) between the two dissimilar electrical conductors 1o.1 and 1o.2. Thus, the thermocouple 1o.0 inertialessly originates a self-transformation of the absolute temperature into the electrical voltage V 1o.4. In D12, the author (Karpen), testing several systems providing the thermocouple effect: the voltage self-generation solely due to the presence of contacting mutually-repelling materials, points out that there is no any chemical reaction between the phases in contact, i.e. there is no process which would be stopped in the future. At the first glance, a system, comprising the thermocouple 1o.0 and an electrical circuit powered by the induced voltage, seems like a closed system, where one seemingly confusingly-paradoxically observes a local decrease in entropy, i.e. that the charging of the electrical circuit occurs at the expense of own temperature, but not a temperature difference. However, in reality, the system is inherently characterized by the junction 1o.3 of mutually-repelling materials contacting with the ambient fluid (i.e. the system is open from the point of view of thermodynamics), and the electric power is acquired at the expense of the ambient heat that is allowed for an open system. Thereby, the system, open from the point of view of thermodynamics, is neither a Perpetuum Mobile of the first kind nor a Perpetuum Mobile of the second kind. The thermocouple is an inherent attribute of a thermoelectric element providing for either Seebeck effect or the Peltier effect, both assuming an amplifying the thermocouple effect accompanied with acquired useful energy when either a temperature gradient between the ends of two dissimilar mutually-repelling electrical conductors is provided to induce an electromotive force (emf) or, vice-versa, forcedly established emf results in temperature separation, correspondingly, as described hereinafter.

For the purpose of the present patent application the terms "thermocouple" and "thermoelectric (TE) couple" and are reserved for the thermocouple 1o.0 that, in contrast to a TE element 1.0 described hereinafter referring to FIG. 4b, provides inertialess interrelation between the absolute temperature of the junction 1o.3 [but not a temperature difference] and the temperature-dependent voltage 1o.4 (or a derivative current in a closed electric circuit).

The term "thermoelectric device" should be understood in a broad sense including (a) an electric heater consuming electric power and radiating Jole heat which (the electric heater) is interpreted as a trivial thermoelectric device wherein the temperature increase due to the Joule heating effect is time-dependent (the longer the time, the higher the temperature), (b) a thermocouple which, in addition to the capability to radiate the Jole heat, is capable of inertialessly-inducing a temperature-dependent voltage bias and so is capable of functioning as a detector of temperature changes, and (c) a thermoelectric (TE) element described hereinbelow referring to FIG. 4b, which (the TE element) is further capable of transmitting heat from one side to another side of the device and so is capable of inertialessly-controlling of a temperature difference between the two sides of the device.

FIG. 4b, divided into three parts:
Case (A) REFRIGERATION MODE,
Case (A) TIME CHARACTERISTIC, and
Case (B) POWER GENERATION MODE,
is a prior art illustration of a THERMOELECTRIC ELEMENT 1.0, called also a thermoelectric (TE) module, and its exemplary time characteristic, where numerals, which have the letter "A", belong to Case (A) and numerals, which have the letter "B", belong to Case (B).

The TE module 1.0, as in particular described in D01, comprises a TE element 1.0A or 1.0B, in turn, composed of:
an n-type (negative thermopower and electron carriers) 1.1A or 1.1B semiconductor material, and
a p-type (positive thermopower and hole carriers) 1.2A or 1.2B semiconductor material, both inter-connected through highly electro-conductive (normally, made from copper) contact pads, on the one hand, 1.3A or 1.3B, and, on the other hand, a pair of pads: 1.41A and 1.42A, or 1.41B and 1.42B. Ceramic buses, on the one hand, 1.7A and 1.7B, or, on the other hand, 15A, and 15.B are usually made of aluminum oxide.

FIG. 4b Case (A) REFRIGERATION MODE illustrates the Peltier effect, which is the basis for many modern-day thermoelectric refrigeration devices, and FIG. 4b Case (B) POWER GENERATION MODE illustrates the Seebeck effect, which is the basis for TE power generation devices; both devices are with no moving parts. The refrigeration and power generation, both can be accomplished using the same TE module 1.0.

In Case (A) REFRIGERATION MODE, thermoelectric energy conversion utilizes the heat using the Peltier-Seebeck Thermoelectric Element 1.0A, wherein, due to the Peltier effect, when an electric current, generated by a source 1.6A of direct current (DC) electromotive force (emf), circulates through the Peltier-Seebeck Thermoelectric Element 1.0A where the DC direction is indicated by arrow 1.8A, the temperature difference between the bus ACTIVE COOLING 1.7A and the bus HEAT REACTOR 1.5A is originated such that the bus ACTIVE COOLING 1.7A becomes colder than the bus HEAT REACTOR 1.5A and so the ambient heat, first, becomes absorbed on the cold side 1.7A (i.e. on the bus ACTIVE COOLING), then, transferred through (or pumped by) the thermoelectric materials 1.1A and 1.2A to the bus HEAT REACTOR 1.5A, and, further, rejected at the sink (the bus HEAT REACTOR) 1.5A. Thereby, the cold side 1.7A providing a refrigeration capability. In other words, the cold side 1.7A, when becoming colder than the ambient fluid, extracts additional heat 1.91 from the ambient fluid and the TE element conveys and contributes the additional heat to the rejected heat 1.92A. In practice, to function efficiently, a powerful ventilator 1.9A is used to provide that the heat, accumulated at the bus HEAT REJECTOR 1.5A, transmitting away from the bus HEAT REACTOR 1.5A for thermostating the bus HEAT REJECTOR 1.5A and so providing for cooling the bus ACTIVE COOLING making it colder than the ambient fluid. Normally, an airflow made by the powerful ventilator is slower than 10 m/sec. The presence of the ventilator 1.9A reduces the advantage of the absence of moving parts. If, instead of the source 1.6A of DC emf, to use a source of the DC emf of opposite polarity originating a DC in the opposite direction relative to the DC direction 1.8A, the heat transfer becomes in the opposite direction as well.

In Case (B) POWER GENERATION MODE, the thermoelectric energy conversion occurs due to a passive Peltier-Seebeck thermoelectric element 1.0B that utilizes the temperature difference ΔT between a heat source 1.7B and heat sink 1.5B. Namely, a DC emf is generated due to the Seebeck effect when the passive Peltier-Seebeck thermoelectric element 1.0B utilizes the overabundant heat 1.92B entrapped by a heat source 1.7B (for instance, the heat source is powered by sunlight) while the heat passes through a thermoelectric materials 1.1B and 1.2B, and, further, is dissipated at the heat sink 1.5B being colder than the heat source 1.7B; the DC emf is manifested as a voltage bias induced at the pair of pads 1.41B and 1.42B and applied to an electrical load 1.6B accompanied by DC the direction of which is indicated by arrow 1.8B. If the load resistor 1.6B is replaced with a voltmeter, the circuit functions as a temperature-sensing thermocouple. The advantages of TE solid-state energy conversion are compactness, quietness (no moving parts), and localized heating or cooling. However, speaking stricter, in practice, to function efficiently, a powerful ventilator 1.9B is used to provide that the heat, accumulated at the bus HEAT SINK 1.56, transmitting away from the bus HEAT SINK 1.58 for thermostating the bus HEAT SINK 1.5B and so making the bus HEAT SOURCE as functioning for absorbing the ambient heat. The presence of ventilator 1.9B reduces the advantage of the absence of moving parts. If to use a source of coldness instead of the heat source 1.7B and to use a cold sink instead of the heat sink 1.56, the originated DC emf will be manifested as a DC in the opposite direction relative to the DC direction 1.8B.

Considering a thermoelectric element, the phenomena of:
the Seebeck effect triggered by the temperature difference resulting in:
the expected heat transfer from a hotter side to a colder side, and
the seemingly-unexpected origination of electric current bringing electric power given free of charge in a certain sense, i.e. at the expense of the ambient heat,
and
the Peltier effect triggered by the electric current resulting in:
the expected consumption of electric power, for instance, for Joule heating, and
the seemingly-unexpected decrease in entropy manifested as heat transfer from one side becoming colder to another side becoming hotter, wherein the decrease in entropy is given free of charge in a certain sense, i.e., again, at the expense of the ambient heat,
both are the property of thermoelectric materials contacted with the ambient fluid.

The basic interrelations between the physical characteristics of the Seebeck effect and the Peltier effect are expounded in D02. In particular, the current density J is directly-proportional to the temperature difference ΔT between conductive contacts, on the one hand, 1.3A or 1.38, and, on the one hand, the pads: 1.41A and 1.42A or the pads: 1.418 and 1.426, correspondingly. Namely, the Seebeck effect generates an electromotive force, leading to the equation:

$$J = \sigma(-\Delta V - S\Delta T) \quad \text{Eq. (1.4a)},$$

where: σ is the effective electric conductivity of the thermoelectric module as a whole;
ΔV is the voltage bias between the pads 1.418 and 1.426;
ΔT is the mentioned temperature difference; and
S is the Seebeck coefficient, a property of the used material.

Peltier elements are thermoelectric components capable of pumping heat from one end of the device to the other end based on the direction of current, wherein the originated temperature is interrelated with the current according to the equation Eq. (1.4a) just rewritten as:

$$\Delta T = \frac{(-\Delta V - J/\sigma)}{S}. \quad \text{Eq. (1.4b)}$$

The interrelations Eqs. (1.4a) and (1.4b), both being forms of the Joule law for an electric circuit comprising emf, quantify the phenomena of the Seebeck effect and the Peltier effect, correspondingly, in the assumption of a hypothetically ideal contact with the ambient fluid providing for accumulated heat removing away inertialessly, where the value (−SΔT) determines the emf of the electric circuit. In the case of the Seebeck effect described by the equation Eq. (1.4a), when the two sides of the TE element are subjected to a forced temperature difference, the heat transfer from the hot side to the cold side accompanied by the origination of the acquired DC emf looks seemingly contradicting to both the Energy Conservation Law and the Second Law of Thermodynamics, if to ignore that the DC emf of the TE element, as an open thermodynamic system, is triggered by the temperature difference and acquired at the expense of the ambient heat, i.e., from the point of view of the forced temperature difference, the DC emf is given free of charge (i.e. at the expense of the ambient heat) or, speaking stricter, is given due to the heat entering via a cold side and removing away from a hot side. In the case of the Peltier effect described by the equation Eq. (1.4b), when the two sides of the TE element are subjected to a forced DC emf, a Joule heat dissipation, in particular, seemingly-confusingly accompanied by the temperature separation and so in the decrease in the entropy of a nearby fluid portion, looks like contradicting to both the Energy Conservation Law and the Second Law of Thermodynamics, if to ignore that the work for the temperature separation around the TE element (which is an open thermodynamic system) is triggered by the electric current and acquired at the expense of the ambient heat, i.e., from the point of view of the forced DC emf, the temperature separation is given free of charge (i.e. at the expense of the ambient heat) or, speaking stricter, is given due to the heat entering via the cold side and removing away from the hot side.

The thermoelectric element is neither:
a Perpetuum Mobile of the first kind as the energy balance is satisfied when either:
the acquired DC emf is from the ambient heat; it is triggered by the temperature difference, or
the acquired temperature separation is at the expense of the ambient heat; it is triggered by DC emf,
nor
a Perpetuum Mobile of the second kind when is capable of decreasing the local entropy when either:
the heat transfer is triggered by the temperature difference and accompanied by the acquired DC emf manifested as the origination of the Joule heating effect, or
the acquired temperature separation triggered by the DC emf and accompanied by the work of DC emf manifested as the origination of the Joule heating effect, as it is an open (but not isolated) system as the system inherently contacting with the ambient fluid wherein it is inherently assumed that the heat removing away.

In relation to the time-invariance, the interrelation Eq. (1.4a) between the temperature difference ΔT as a reason and the current density J as an originated effect as well as the interrelation Eq. (1.4b) between the current density J as a reason and the temperature difference ΔT as an originated effect, both are time-invariant, i.e. the equations Eqs. (1.4a) and (1.4b) are equations of state interrelating the temperature difference and the current density at any time moment. In practice, the time-invariance of the equations Eqs. (1.4a) and (1.4b) is restricted by thermo-conductivity and thickness of the used thermo-conductive buses and an inertial ventilator functioning for the heat removing away. The inertial ventilator, in particular, results in another parasitic effect determined by that the temperature difference triggers the inertial heat transfer from the hot side to the cold side through the thermoelectric material that reduces the efficiency of both the Seebeck effect and the Peltier effect. The combination of all the effects results in that, in reality, the Peltier effect is manifested not as a suddenly arisen temperature difference ΔT but as a growing temperature difference gradually reaching the value ΔT of saturation after a certain time. The lower the inertness of the desired heat removing away, the higher the efficiency of the TE element.

Case (A) TIME CHARACTERISTIC comprises a graph 1.80A extracted from 003. The graph 1.80A illustrates a time characteristic of an exemplary single-stage thermoelectric cooler. The exemplary thermoelectric cooler produces a maximal temperature difference of about 51° C. between its hot and cold sides [Typically, the reachable temperature difference ΔT, dependent on a value of DC 1.8A and a quality of heat rejector 1.5A, is 70° C.]. An issue with performance is a direct consequence of one of their advantages: being small. The TE modules can be constructed ranging in size from approximately 2.5 to 50 mm with square shape and, if using either the so-called direct copper bond technology or the so-called active solder process, 2.5-5 mm in height, and if using Nano-technologies, 0.5-1 mm in height as described, for example, in D04. This means that:

the hot side and the cool side will be very close to each other (a few millimeters away), making it easier for the heat to go back to the cool side, and harder to insulate the hot and cool side from each other; and a common 40 mm×40 mm can generate 60 W or more, that is, 4 W/cm² or more, requiring a powerful radiator to move the heat away.

The net-efficiency of the TE element depends on used thermoelectric material, a relevant property of which is characterized by the Seebeck coefficient and on the functionality of the powerful ventilator to remove the parasitic heat away from the cold side. From the point of view of the energy:

the Peltier effect and the Seebeck effect, both given free of charge in a certain sense (if to exclude the power consumption by the powerful ventilator) due to a non-zero value σ×S, and the energy consumption, in particular, goes for the parasitic Joule heating occurring due to the limited value σ.

In real refrigeration applications, thermoelectric junctions have about 10-15% net-efficiency. Due to this low efficiency, thermoelectric cooling is generally used in environments where the solid-state nature (no moving parts), low maintenance, compact size, and orientation insensitivity outweigh pure efficiency.

Had one possess a technology to implement and use the Seebeck-Peltier effect without a powerful ventilator, the net-efficiency would depend on the values σ and S characterizing the used thermoelectric material only, and a higher net-efficiency as the ratio of the power provided due to the Seebeck-Peltier effect given free of charge in the certain sense to the power consumed to trigger the Seebeck-Peltier. There is, therefore, a need in the art for a method and apparatus, when applied to a system appropriate for use in industry, to provide such an embodiment of the Peltier effect and/or the Seebeck effect that, on the one hand, would not require powerful ventilation and, on the other hand, would provide for a high net-efficiency and explicit relevance of all the mentioned possible advantages.

The curve 1.81A shows that the temperature difference ΔT of 48° C. is reached in 240 sec, i.e. the average temperature rate is 0.2 C/sec. However, considering the first 20 seconds, the local temperature rate is 0.25 C/sec which is indicated by the dotted line 1.82A. Further, referring to the mentioned in D04 TE modules made using Nano-technologies, the estimated local temperature rate is 1.25 C/sec which is indicated by the dashed line 1.83A. This, in particular, means that a very small temperature change, for instance, ranged from $5.4 \times 10^{-10}$ K to $5.4 \times 10^{-6}$ K can be reached for a short time ranged from $4.4 \times 10^{-6}$ sec to $4.4 \times 10^{-10}$ sec, correspondingly. This estimation takes into account the parasitic inertia due to a normally used ventilator for transmitting the accumulated heat away. Looking ahead, for disclosed systems related to acoustic waves such that there will neither significant temperature differences nor accumulated heat in the disclosed systems, this estimation will be used as a reference for the worst-case estimations with a spare reserve. The fact that a small temperature change can be reached for an extremely short time is one of the primary features that is used in the present patent application.

Furthermore, assuming a hypothetic possibility of extra-fast removing the accumulated heat away, the local temperature rate becomes dependent on the used material for the thermoconductive buses 1.3A and 1.5A in Case (A), and 1.3B and 1.5B in Case (B). For example, the thermoconductivity of aluminum oxide is between 28 and 35 $Wm^{-1}K^{-1}$, the thermoconductivity of copper is 384.1 $Wm^{-1}K^{-1}$, and the thermoconductivity of natural diamond is yet higher between 895 and 1350 $Wm^{-1}K^{-1}$. Referring to the commonly used copper pads 1.3A and 1.41A and aluminum oxide buses 1.7A and 1.5A, the estimated local temperature rate is about $3 \times 10^4$ C/sec, i.e. the buses 1.7A, 1.3A, 1.41A, and 1.5A, each of 0.5 mm thickness, are almost inertialess indeed. Looking ahead, this estimation will be a reference for the estimation of applications related to extra-fast cooled surfaces. The possibility to reduce the reaction time of the TE module would allow for a specific use of the TE module to control a local temperature immediately without a significant delay, however, if the necessity of a powerful ventilator is avoided. The present patent application discloses such use of a TE module.

An advanced Peltier device comprises a multiplicity of TE elements which are electrically connected by conductive (for instance, copper) bridges in series as shown hereinafter in FIGS. 4c and 4d. Ceramic plates, usually made of aluminum oxide, are used to thermally bond the conductive bridges which are electrically separated each from other.

Reference is now made to FIG. 4c, divided between two parts: Case (A) and Case (B), illustrating schematically a prior art TE multi-module device 1Q.0 comprising an array of TE elements; wherein the numerals, which have the letter "A", belong to Case (A) and the numerals, which have the letter "B", belong to Case (B). The TE multi-module device 1Q.0 is built up of an array of the TE elements 1Q.0A1 or 1Q.0B1, which are arranged electrically in series and thermally in parallel to manifest thermal properties in unison. From the point of view of functioning, the use of TE multi-module device 1Q.0 is considered in two cases:

Case (A) where the TE multi-module device 1Q.0A comprises a source 1Q.6A of DC emf and an in-line cascade of several TE elements 1Q.0A1 [shown three] that, from the electric point of view, are connected into a sequential electrical circuit and, from the constructive point of view, have a common bus of ACTIVE COOLING becoming colder and a common bus of HEAT REACTOR becoming warmer when the source 1Q.6A of DC emf originates a voltage bias applied to the end pads: 1Q.41A and 1Q.42A, and an electric CURRENT indicated by arrow 1Q.8A;

Case (B) where the TE multi-module device 1Q.0B comprises an electrical load 1Q.6B and an in-line cascade of several TE elements 1Q.0B1 [shown three] that, from the electric point of view, are connected into a sequential electrical circuit and, from the constructive point of view, have a common bus of HEAT SOURCE exposed to the overabundant ambient warmth and a common bus of HEAT SINK being colder than the bus of HEAT SOURCE; wherein, as a result, the sequentially connected TE elements 1Q.0B provide for the cumulative electromotive force (emf) manifested as:
a voltage bias induced between the end pads: 141B and 1.42B, and applied to the electrical load 1Q.6B, and
an induced electric CURRENT indicated by arrow 1Q.8B.

FIG. 4d is a prior art schematic illustration of an exemplary planar arrangement 1R.0A of a multiplicity of thermoelectric elements (modules) 1R.0A1 that (the planar arrangement 1R.0A) is a quintessential component of a multi-layer TE multi-module device. Again, from the electric point of view, the TE elements 1R.0A1 are connected each to another in a boustrophedon trajectory, thereby, forming a sequential electrical circuit and, from the constructive point of view, the TE elements 1R.0A1 have contacts pads 1R.3A at the cold side and contacts pads 1R.4A at the warm side. There is but not shown both:
a common bus of ACTIVE COOLING above the contacts pads 1R.3A, and
a common bus of HEAT REACTOR under the contacts pads 1R.4A.

When the source 1R.6A of DC emf originates both:
a voltage bias applied to the end pads: 1R.41A and 1R.42A, and
an electric CURRENT indicated by arrow 1R.8A,
the common bus of ACTIVE COOLING (again, that is not shown here) becomes colder and the common bus of HEAT REACTOR (that is not shown here) becomes warmer.

Reference is now made to FIG. 4e, divided between two parts: Case (A) and Case (B), illustrating schematically a prior art multi-layer TE multi-module device 1t.0 comprising a matrix of TE elements aggregated in layers one above another multi-stage repeatedly; wherein the numerals having the letter "A" belong to Case (A) and the numerals having the letter "B" belong to Case (B). The multi-layer TE multi-module device 1t.0 is built up of a matrix of the elements 1t.0A1 or 1t.0B1, which are arranged, on the one hand, electrically in series along a boustrophedon trajectory and, on the other hand, in layers spatially cascaded one above another to cascade manifestations of the thermal properties multi-stage repeatedly in unison.

From the point of view of functioning, the use of multi-layer TE multi-module device 1t0 is considered in two cases:

Case (A) where the multi-layer TE multi-module device 1t0A comprises a source 1t6A of DC emf and a matrix of several TE elements 1t.0A1 [shown 9]. When the source 1t6A of DC emf originates a voltage bias applied to the end pads: 1t.41A and 1t.42A, and an electric CURRENT indicated by arrow 1t.8A, the TE elements 1t.0A1:
from the electric point of view, are connected into a sequential electrical circuit along a boustrophedon trajectory, and,
from the constructive point of view, have common EXTERNAL AND INTERNAL ACTIVE COOLING BUSES becoming colder and common EXTERNAL AND INTERNAL HEAT REJECTION BUSES becoming warmer, wherein the common INTERNAL ACTIVE COOLING BUSES and the common INTERNAL HEAT REJECTION BUSES are arranged adjacently, thereby, in the final analysis, to transmit the warmth from the common EXTERNAL ACTIVE COOLING BUS to the common EXTERNAL HEAT REJECTION BUS;

and

Case (B) where the multi-layer TE multi-module device 1t.0B comprises an electrical load 1t6B and a matrix of several TE elements 1t0B1 [shown 9]. From the electric point of view, the TE elements 1t.0B1 are connected into a sequential electrical circuit along a boustrophedon trajectory. From the constructive point of view, the TE elements 1t.0B1 have:
a common EXTERNAL HEAT SOURCE BUS exposed to the overabundant ambient warmth,
adjacently arranged INTERNAL HEAT SINK BUSES and INTERNAL HEAT SOURCE BUSES, and
a common EXTERNAL HEAT SINK BUS being colder than the common EXTERNAL HEAT SOURCE BUS.

As a result, the multi-layer matrix 1t.0B of TE elements 1t0B1 provides for the cumulative electromotive force (emf) manifested as:
a voltage bias induced between the end pads: 1t.41B and 1t.42B, and applied to the electrical load 1t.6B, and
an induced electric CURRENT indicated by arrow 1t8B.

As a sound propagating in the fluid is accompanied by oscillating changes: $\delta P$, $\delta \rho$, and $\delta T$, of thermodynamic parameters: the static pressure, mass density, and absolute temperature, correspondingly, of the fluid portions wherein the interrelation between the changes is inertialess, a controller of a source of the sound should be if not inertialess then at least almost inertialess to provide the desired frequency of oscillating changes. A thermoelectric device: either a thermocouple or a thermoelectric (TE) element, but rather than an electric heater, provides the desired requirement.

SUMMARY OF THE INVENTION

Unity and Novelty of the Invention

The unity and novelty of the invention are in a method and modified aerodynamic apparatuses: fluid pushers-off and/or fluid motion-sensors, which are geometrically shaped and supplied with built-in thermoelectric devices having sensor-controllers; wherein the thermoelectric devices are controlled by the sensor-controllers to provide for the spatial distribution of the temperature-dependent static pressure in ambient fluid around the modified aerodynamic apparatuses to result in pulling-in and/or pushing-off and/or motion detection of a portion of the ambient fluid; furthermore, the modified aerodynamic apparatuses are designed to operate in such a way as to exclude the necessity of a powerful ventilator, wherein the presence of the thermoelectric devices provides for improved and new functional properties of the fluid pushers-off and fluid motion-sensors.

Primary Basic Features of the Present Invention

The claims define the invention.

One of the primary features of the present invention is a method for:
- extra-fast removing of accumulated heat from a space adjacent to a thermoelectric device without a powerful ventilator,
- using thermoelectric elements, inertialess manipulation of the temperature difference between components of the modified aerodynamic apparatus—the fluid pusher-off;
- using thermoelectric elements, inertialess detection of a temperature difference between portions of ambient fluid moving adjacent to the modified aerodynamic apparatus—the fluid motion-sensor; and
- providing the improved and new functional properties of the modified aerodynamic apparatuses such that the modified aerodynamic apparatuses supplied with thermoelectric elements becoming functioning either as:
  - a highly-efficient source of acoustic waves (a fluid pusher-off as a motionless loudspeaker),
  - a highly-efficient detector of acoustic waves (a fluid motion-sensor as a motionless microphone),
  - a wireless charger based on ultrasound,
  - a modified convergent-divergent nozzle adapted to an acceleration of laminar flow,
  - a modified convergent-divergent nozzle adapted to an acceleration of a tiny portion of the fluid and thereby to boost a sound,
  - an airfoil wing capable of controlling a lift-force and thrust; and
  - an airfoil corpus which, when blown, contributes to lift-force and thrust.

In particular:
(In the matter of the modified convergent-divergent nozzle supplied with built-in a multiplicity of thermoelectric elements, the thermoelectric elements aggregated into a surface matrix a side of which has a thermoconductive bus aligned with a smoothly shaped tunnel to provide for triggering the Joule heating effect, the Seebeck effect, and the Peltier effect altogether allowing for controllably distributed temperature along the tunnel such to adapt a geometrical configuration of the tunnel to a velocity of fluid flow entering the tunnel, wherein the tunnel having a varying cross-sectional area characterized by a cross-sectional area profile function $A(x)$ of x interrelated with functions $u(x)$ and $T(x)$ of x representing profiles of the fluid flow's headway velocity and absolute temperature, correspondingly, along the tunnel length, wherein the multiplicity of the thermoelectric elements providing for a degree of freedom to interrelate the functions $A(x)$, $u(x)$, and $T(x)$ by the condition of flow continuity Eq. (6.0) expressed as:

$$A(x) = \frac{A_* \sqrt{(\gamma-1)RT(x)}}{u(x)} \left( \frac{2}{\gamma+1} + \frac{(u(x))^2}{(\gamma+1)RT(x)} \right)^{\frac{\gamma+1}{2(\gamma-1)}},$$

where $A_*$ is a constant, $\gamma$ is an adiabatic compressibility parameter of the fluid flow, and R is a specific gas constant characterizing the fluid, wherein the functions $u(x)$ and $T(x)$ both are gradually-smoothed monotonic, wherein:

the gradually-smoothed monotonic function of the absolute temperature $T(x)$ is determined by:
- an absolute temperature $T_{in}$ of the fluid flow at the open inlet,
- temperature change $\delta T_0(x)$ interrelated with adiabatic compression-expansion occurred due to an adiabatic action of the Coanda-jet-effect, and/or the Venturi effect, and/or the de Laval jet-effect, all, in turn, determined by a curvature of the stationary geometrical configuration of the tunnel, and
- forcedly established temperature contribution $\delta T_1(x)$ to the absolute temperature $T(x)$ along the boundary layers subjected to controllable heating and/or cooling action of the thermoelectric device, such that $$T(x) = T_{in} + \delta T_0(x) + \delta T_1(x),$$

and the gradually-smoothed monotonic function of the headway velocity $u(x)$ is determined by the velocity $u_{in}$ of the fluid flow at the open inlet, convective acceleration resulting in a velocity gradient along the tunnel length as the fluid flow is subjected to the adiabatic Coanda-jet-effect, and/or the Venturi effect, and/or the de Laval jet-effect, and controllable acceleration occurred due to controllable heating and/or cooling action of the thermoelectric devices.

thereby, the modified convergent-divergent nozzle is applicable to convey:
- in general, laminar flow to solve the problem of originated turbulence, and
- in particular, tiny portions of the fluid associated with the propagation of an acoustic wave to solve the problem of sound power dissipation;

note that:
- the degree of freedom $\delta T_1(x)$ to manipulate with the function $T(x)$ allows to adapt a tunnel having a smooth shape to a wide range of velocities of incoming fluid flow entering the tunnel; and
- the relatively fast fluid flow provides for conditions allowing to exclude using a powerful ventilator;

In the matter of a thermoelectric device functioning as the highly-efficient source of the acoustic waves (loudspeaker), on the one hand, the controlled temperature difference between two opposite sides of the thermoelectric device and, on the other hand, the controlled temperature distribution along a divergent horn of the loudspeaker, both allow for efficient generation of acoustic waves accompanied by suppressed concomitant turbulence in the ambient fluid nearby the source of the acoustic waves; wherein the generation of acoustic waves is accompanied by a reincarnation of the heat radiated from a side of the thermoelectric device into the wave power which is removed away from the thermoelectric device by the originated acoustic waves propagating with the velocity of sound.

In the matter of a thermoelectric device functioning as the highly-efficient detector and/or booster of acoustic waves, on the one hand, the controlled temperature difference between two opposite sides of the thermoelectric device, and, on the other hand, the controlled temperature distribution along a two-stage convergent-divergent phonendoscope, both allow for efficient detection and/or boosting of acoustic waves; and In the matter of the airfoil body: wing or capsule, supplied with built-in thermoelectric devices, the thermoelectric devices, aggregated into a surface matrix a side of which forms or at least is adjacently-aligned with a smoothly shaped surface of the airfoil body to control distributed temperature difference between opposite sides (for instance, upper and lower) of the airfoil body, provides for the desired distribution of static pressures in boundary layers adjacent the airfoil body thereby resulting in controllable lift-force and thrust.

Principal Objects

Accordingly, it is a principal object of the present invention to overcome the limitations of existing methods and apparatuses for controlling the operation of aerodynamic devices such as wings and corpus of a flying vehicle, convergent-divergent nozzles, loudspeakers, and detectors of acoustic waves, all of a highly-efficient functionality.

BRIEF DESCRIPTION OF THE DRAWINGS

To understand the invention and to see how it may be carried out in practice, a preferred embodiment will now be described, by way of a non-limiting example only, referring to the accompanying drawings, in the drawings:

Of prior arts:

FIG. 1a is a schematic drawing of the convergent-divergent Venturi tube;

FIG. 1b is a schematic view of the convergent-divergent de Laval nozzle;

FIG. 1c is a schematic illustration graphics of gas velocity, static pressure, and temperature distributions within the de Laval convergent-divergent jet-nozzle;

FIG. 1d is a schematic drawing of a body blown by an airflow portion;

FIG. 1e is a schematic drawing of a classic prior art asymmetrical and mirror-symmetrical profiles of an airplane wing;

FIG. 2a is a schematic illustration of points of sail;

FIG. 2b is an illustration of a honeybee as an exemplary insect capable of flying;

FIG. 2c is a schematic illustration of a wind turbine, built-in into a cylinder;

FIG. 3a, composed of three parts: Case (A), Case (B), and Case (C), comprises prior art schematic drawings of megaphones and a gramophone, each supplied by a horn;

FIG. 3b is a schematic drawing of a human ear profile in a sagittal plane;

FIG. 4a is a schematic drawing of a thermocouple;

FIG. 4b is a schematic drawing of a thermoelectric element;

FIG. 4c is a schematic drawing of a thermoelectric multi-module device;

FIG. 4d is an exemplary planar arrangement of thermoelectric elements;

FIG. 4e is a schematic drawing of a thermoelectric multi-module device; and

Figure 5A:
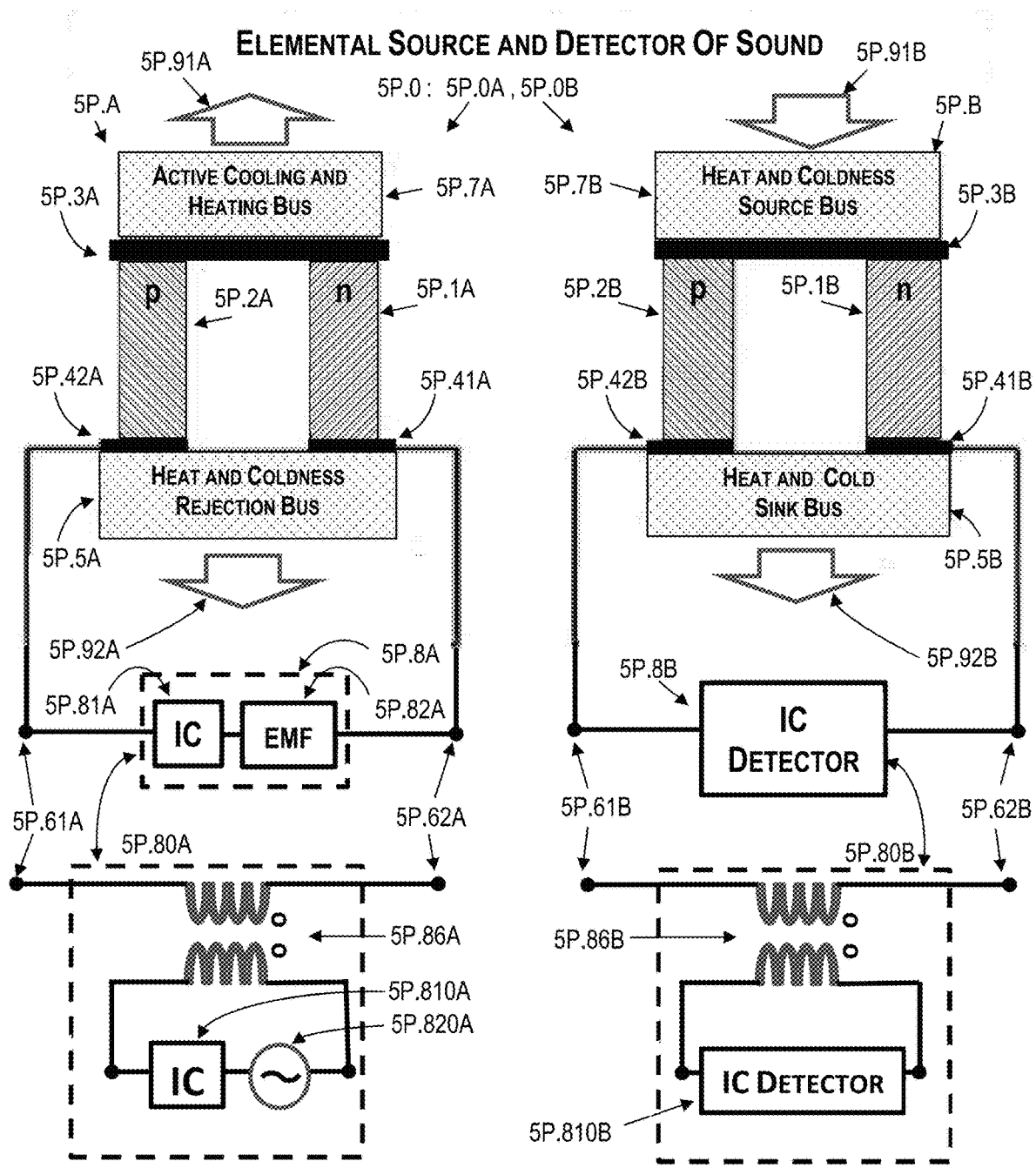
Figure 5C:
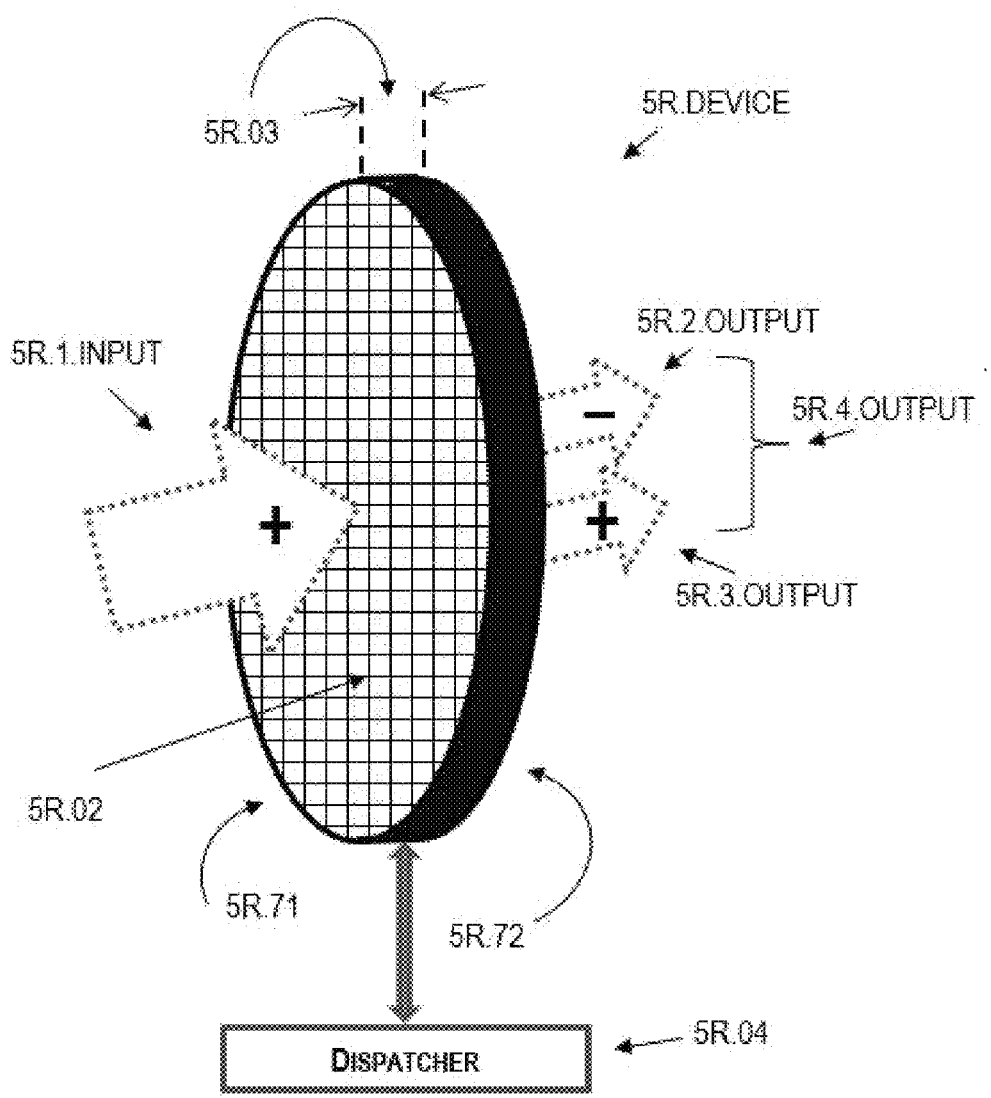
Figure 5D:
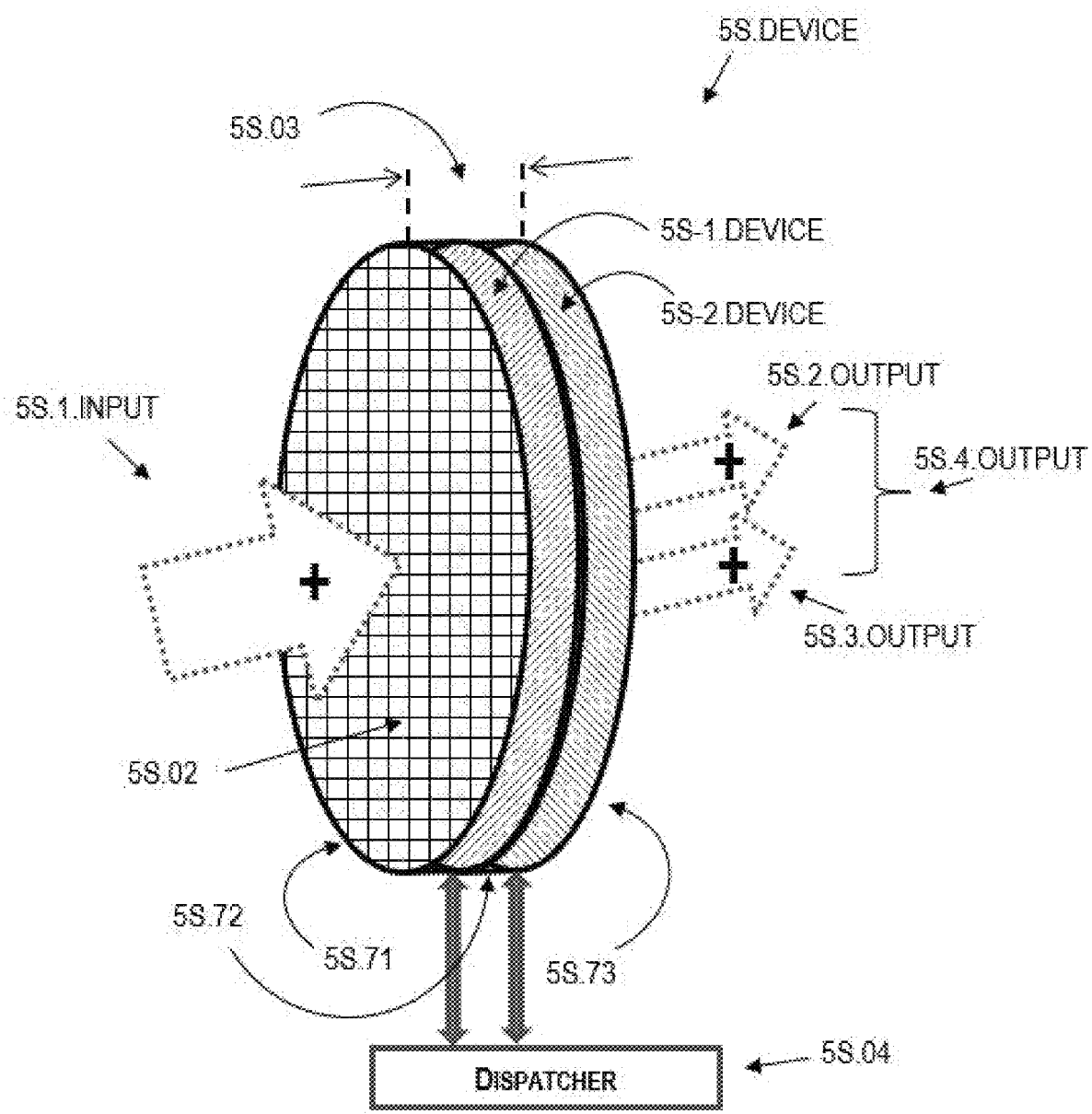
Figure 5E:
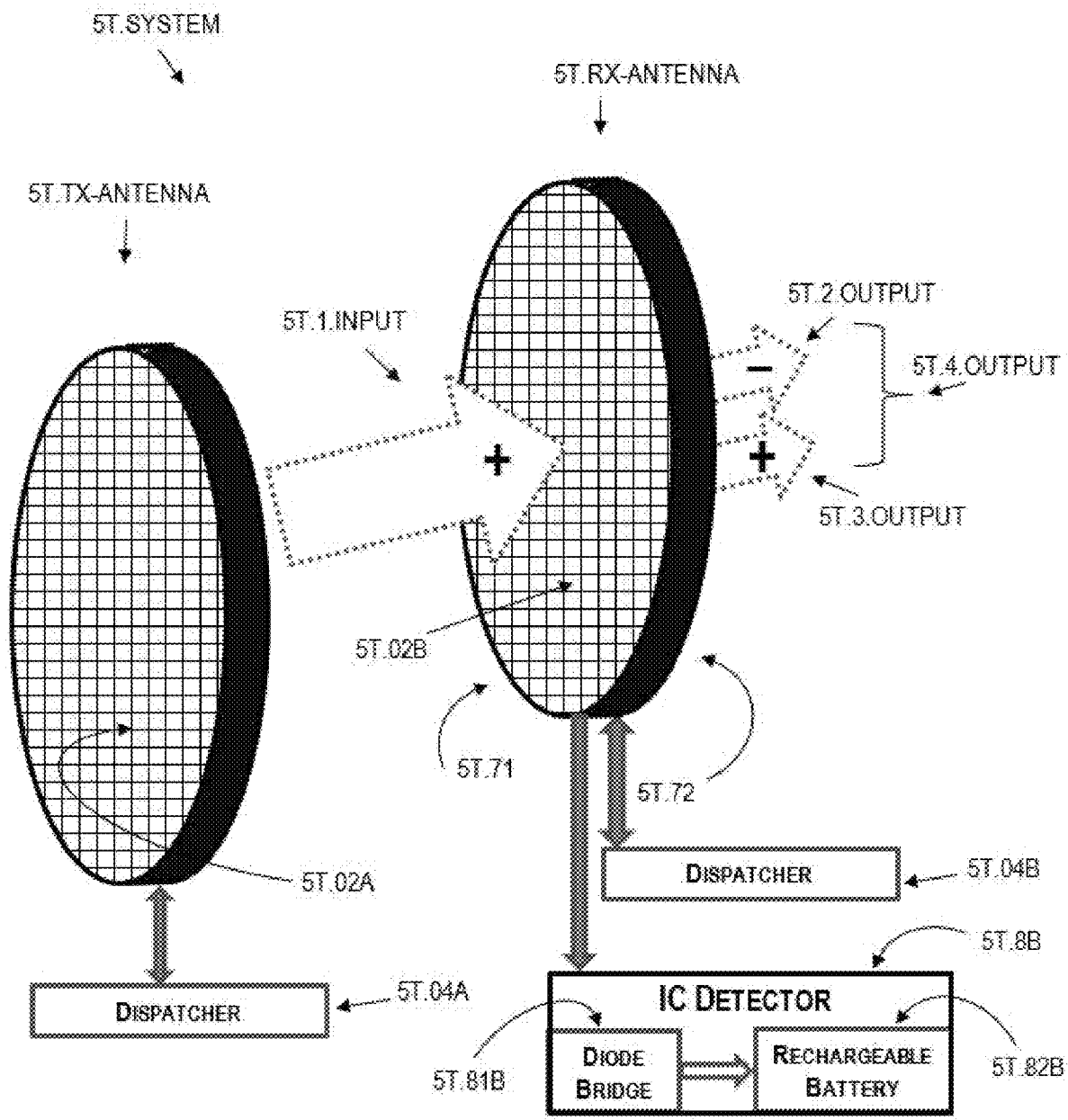
Figure 6C:
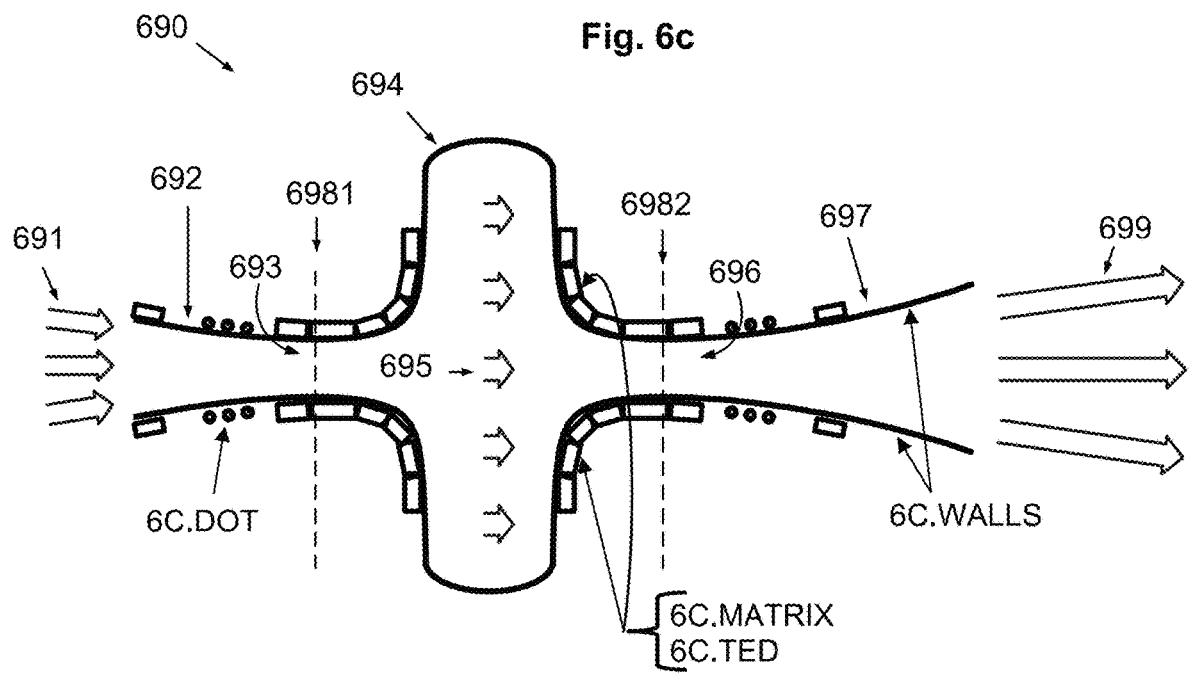
Figure 7:
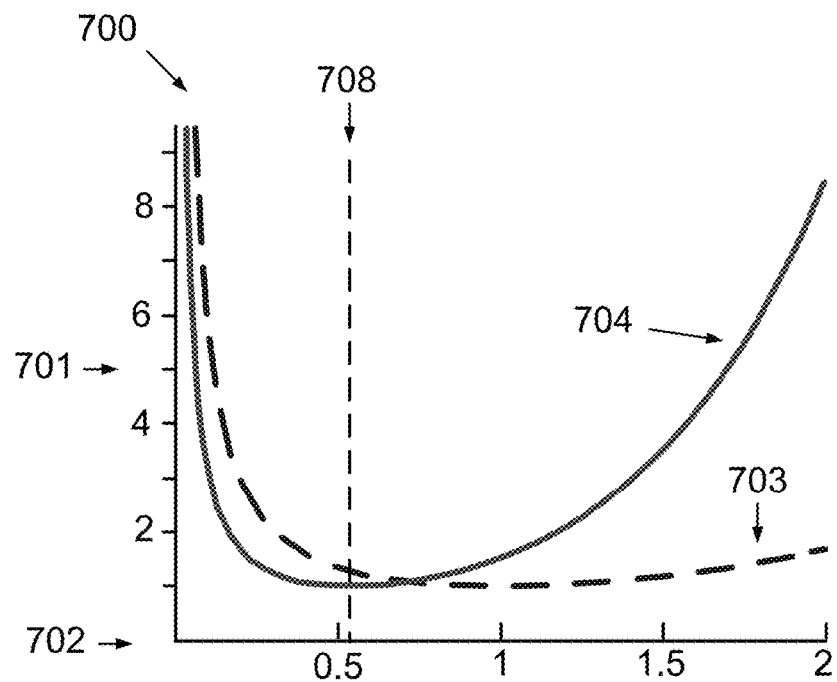
Figure 7C:
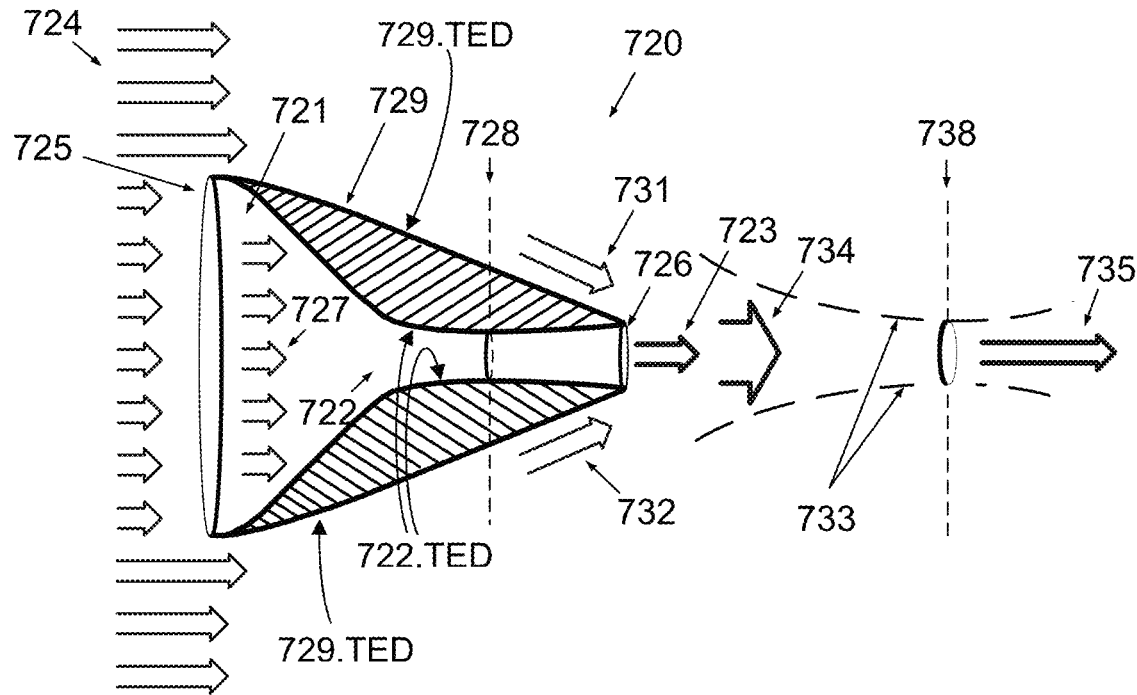
Figure 7D:
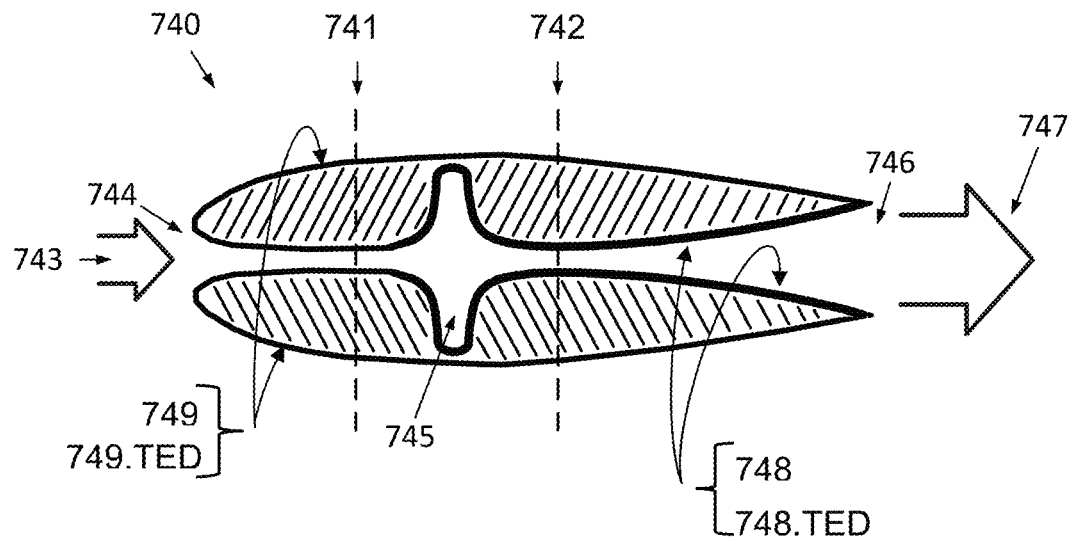
Figure 8A:
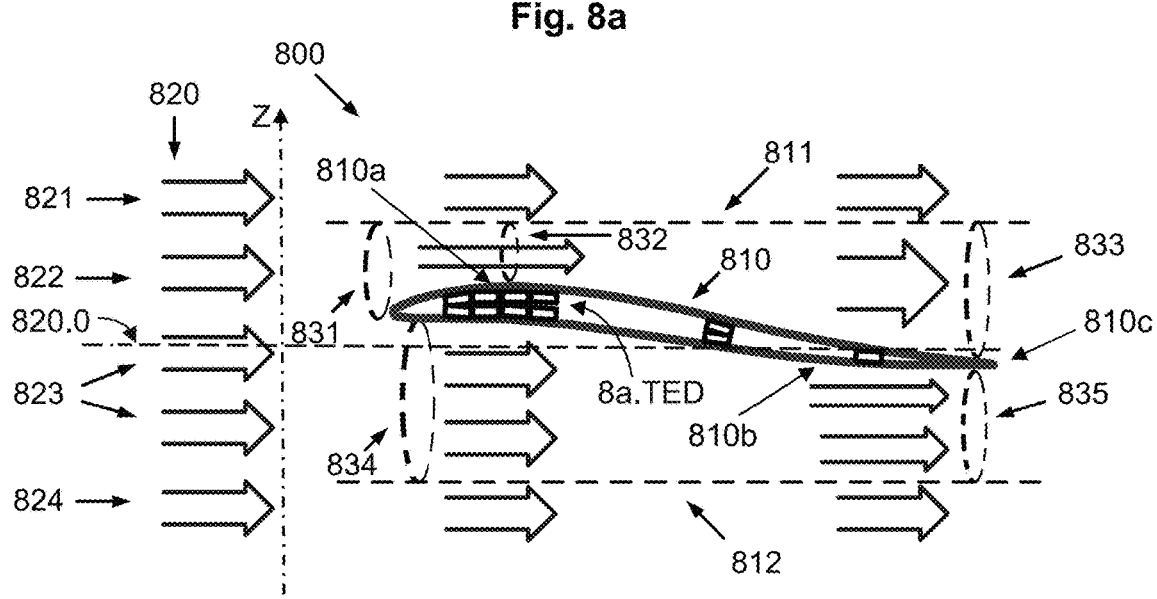
Figure 8B:
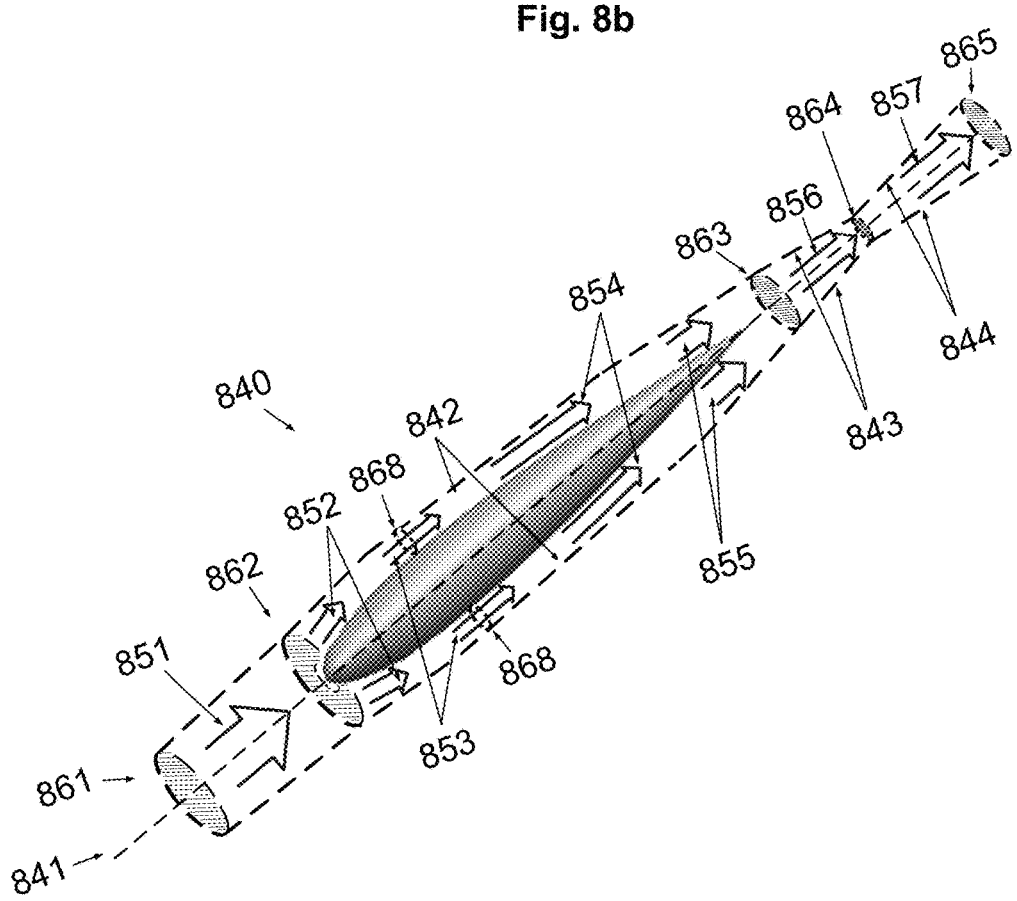
Figure 9A:
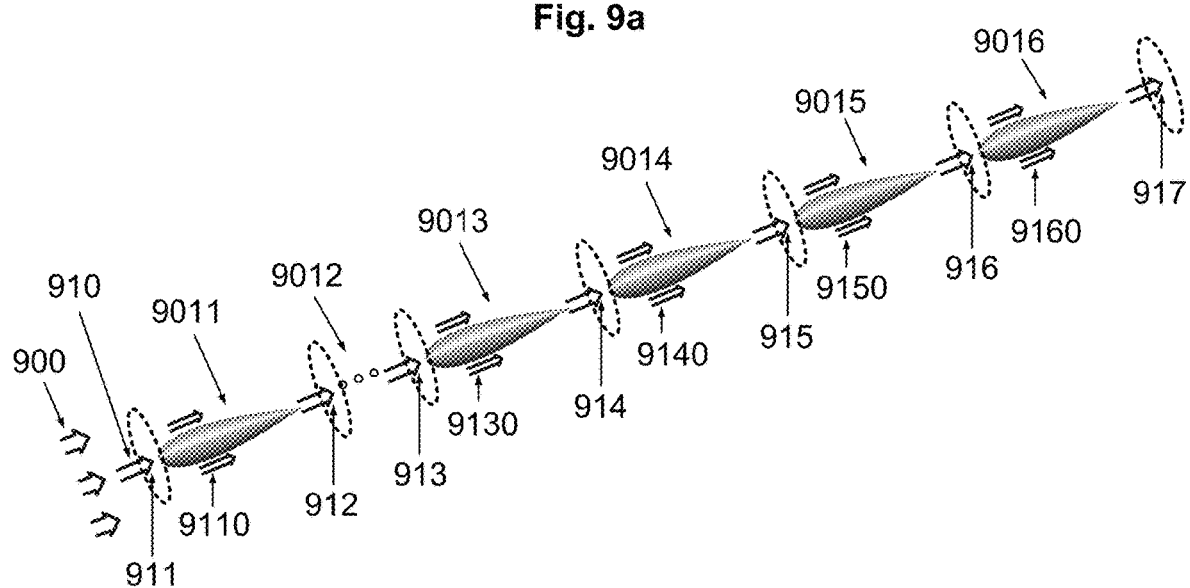
Figure 9B:
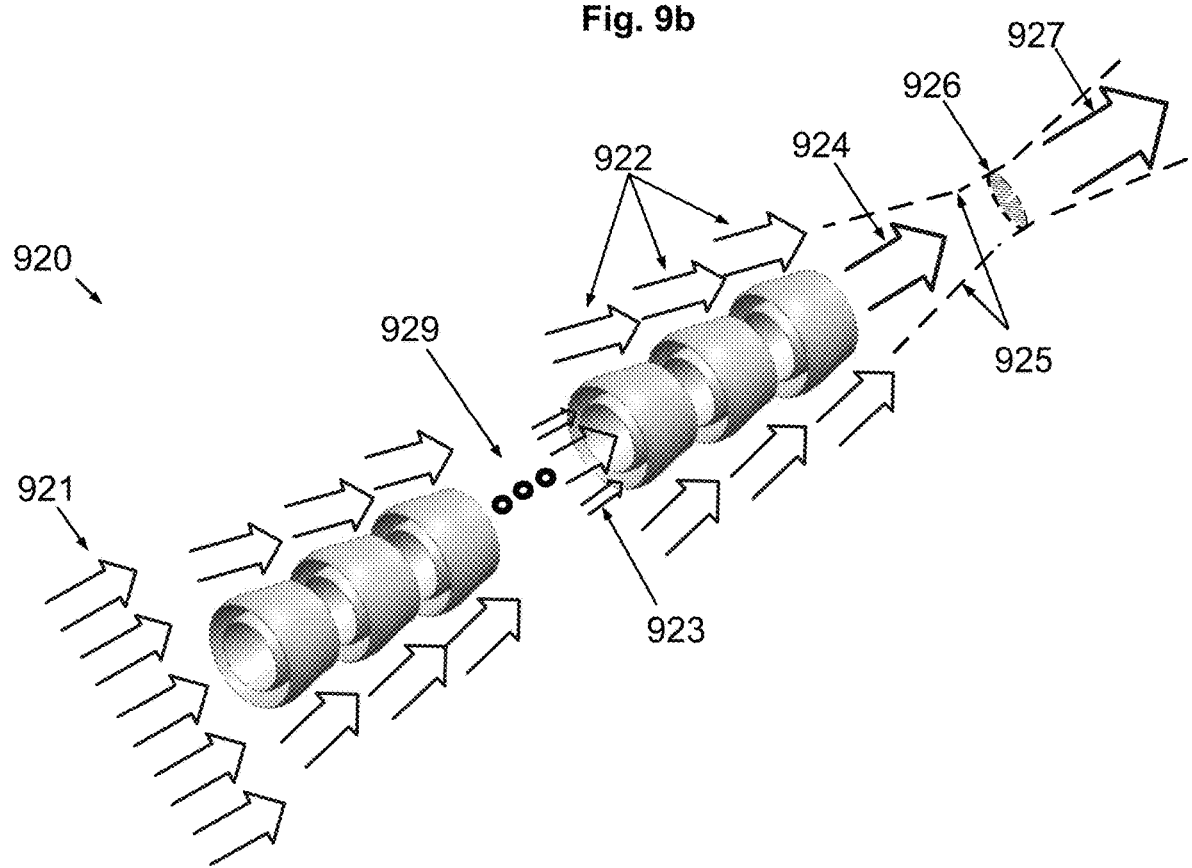
Figure 9C:
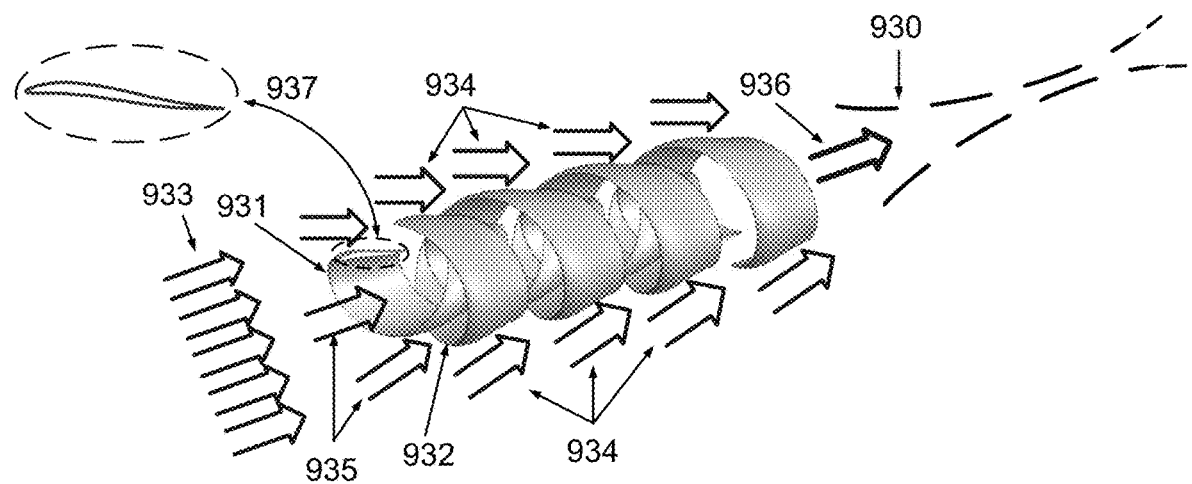
Figure 9D:
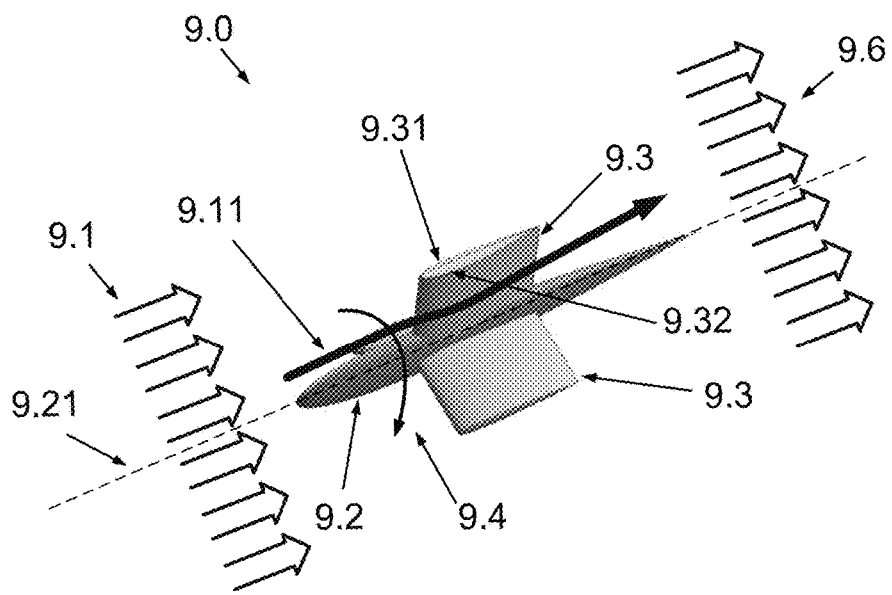
Figure 9E:
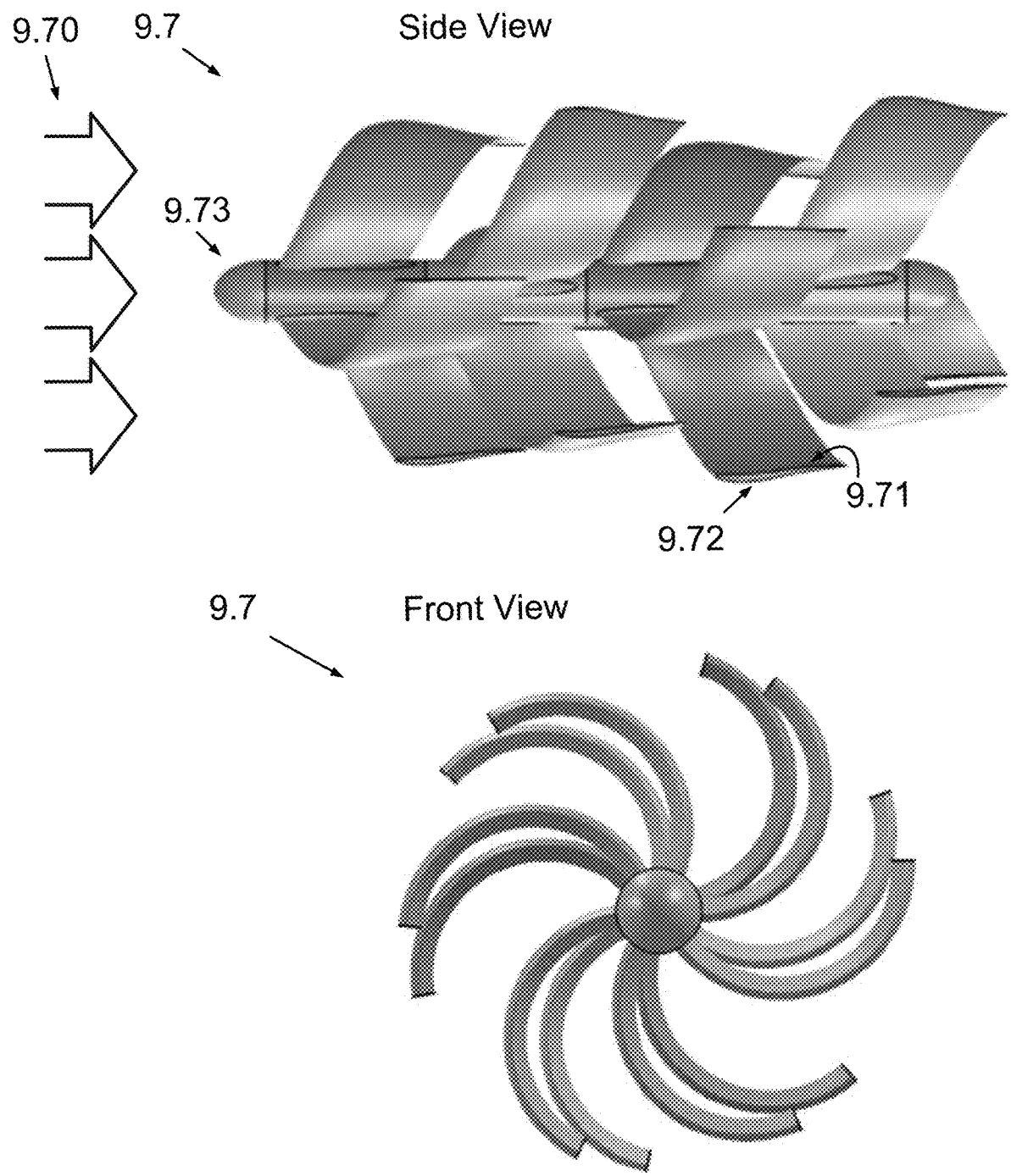
Figure 9F:
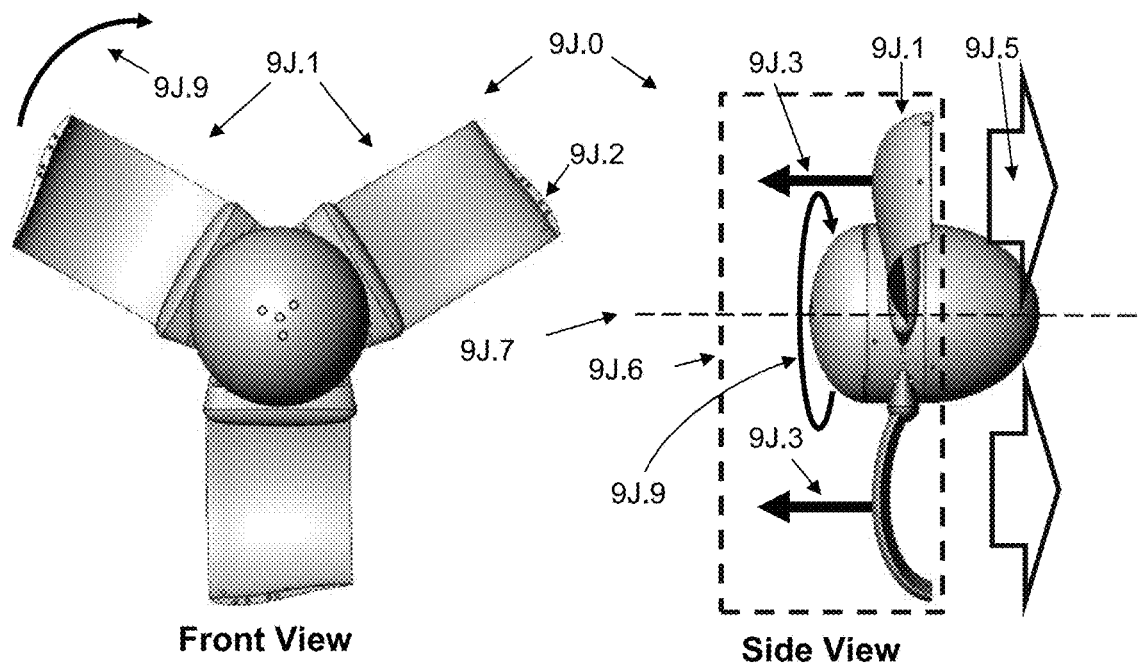
Figure 9G:
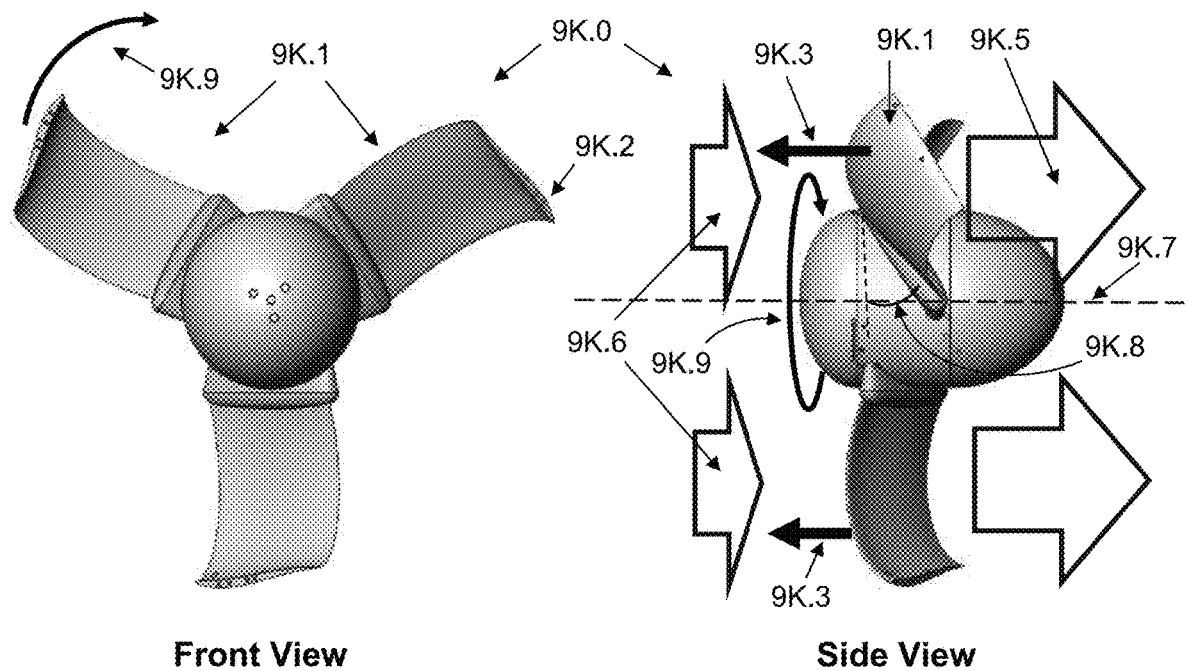
Figure 9H:
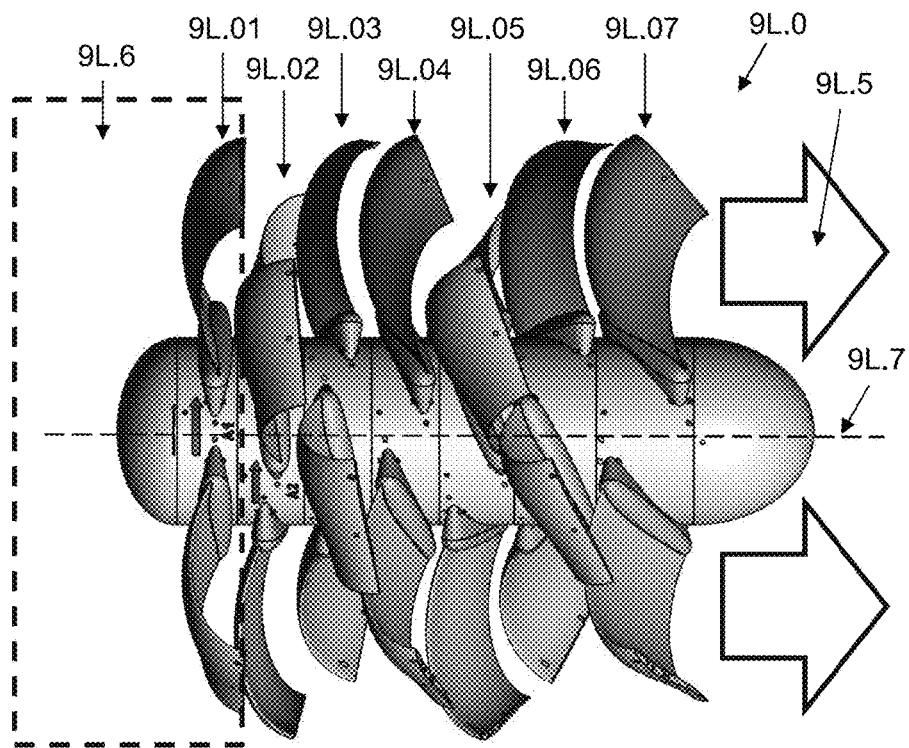
Figure 9I:
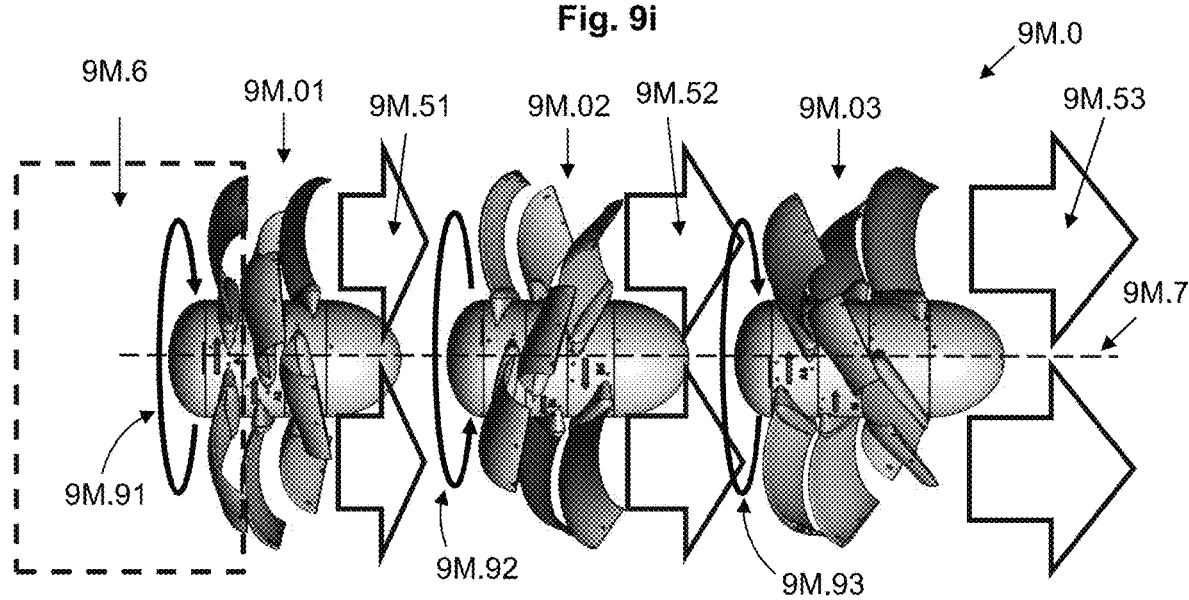
Figure 9J:
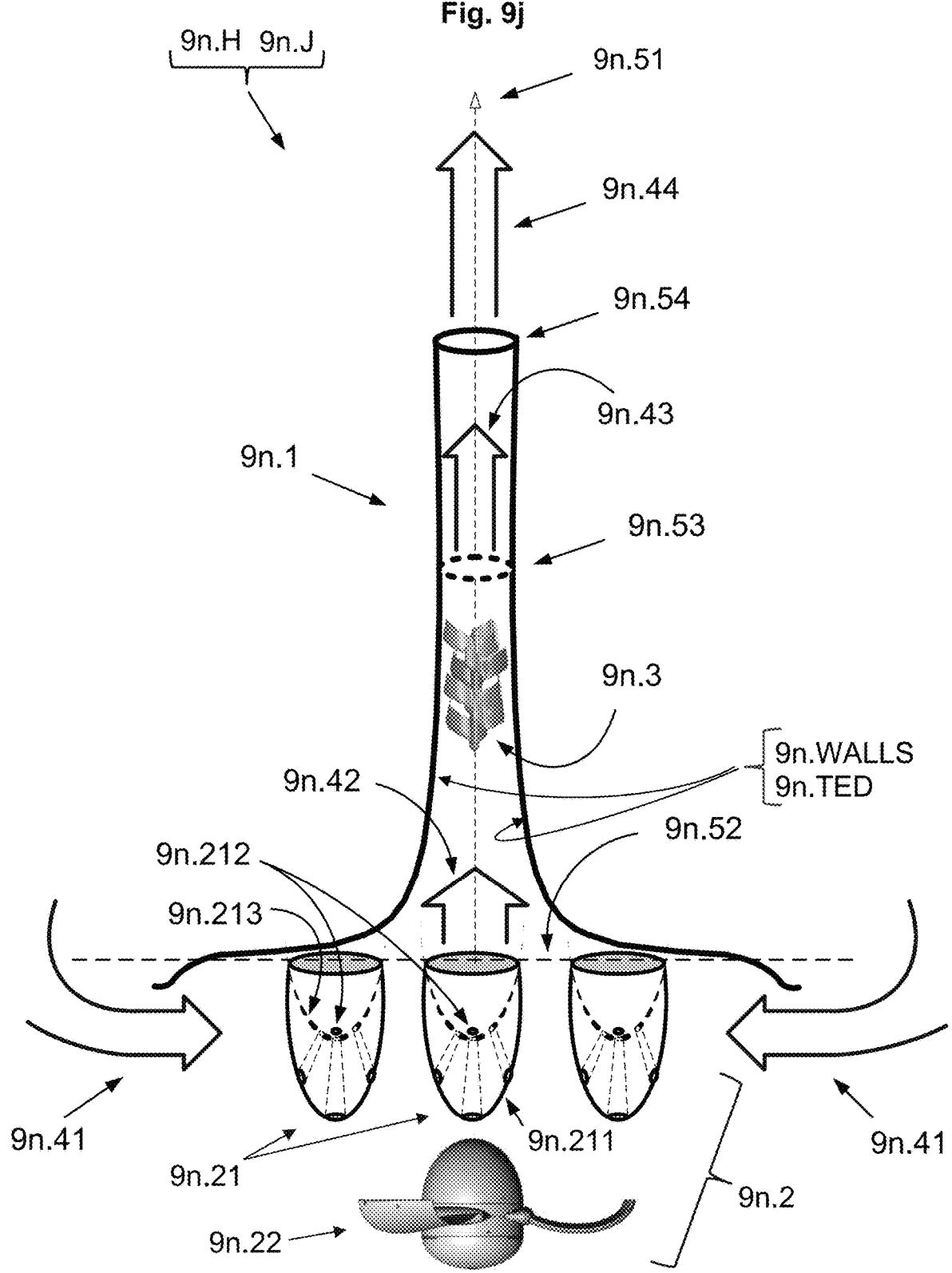

Of embodiments, constructed according to the principles of the present invention:

FIG. 5a is a schematic illustration of an elemental source and detector of sound;

FIG. 5b is a schematic illustration of a matrix of elemental sources and detectors of sound;

FIG. 5c is a schematic illustration of a multi-module thermoelectric device;

FIG. 5d is a schematic illustration of a two-stage sound amplifier;

FIG. 5e is a schematic illustration of a communication system;

FIG. 6a is a schematic illustration of an optimized convergent-divergent jet-nozzle;

FIG. 6b is a schematic illustration of an optimized inverse convergent-divergent nozzle;

FIG. 6c is a schematic illustration of a two-stage convergent-divergent jet-nozzle;

FIG. 7 shows comparative graphs of the dependencies of the nozzle extension ratio vs. the airflow M-velocity, calculated by the classical and suggested models;

FIG. 7a, composed of three parts: case (A), case (B), and case (C), comprises schematic illustrations of sound boosters where: case (A) is a horn for a gramophone, case (B) is a phonendoscope, and case (C) is a hearing aid;

FIG. 7b is a schematic illustration of a compressor supplied by an optimized convergent-divergent jet-nozzle;

FIG. 7c is a schematic sectional view of a flying capsule;

FIG. 7d is a schematic sectional view of a flying capsule;

FIG. 8 is a schematic illustration of a symmetrical wing supplied with a TE device;

FIG. 8a is a schematic illustration of an actually-airfoil wing blown by the wind;

FIG. 8b is a schematic illustration of a flying airfoil body;

FIG. 8c is a schematic illustration of flying airfoil bodies;

FIG. 8d is a schematic illustration of two-stage airfoil wings;

FIG. 9a is a schematic illustration of a sequential cascade of airfoil bodies;

FIG. 9b is a schematic illustration of an in-line cascade of rings having airfoil walls;

FIG. 9c is a schematic illustration of two Archimedean screws having airfoil walls;

FIG. 9d is a schematic drawing of an improved wind-turbine;

FIG. 9e is a schematic side and front views of an improved wind-turbine;

FIG. 9f is a schematic illustration of a jet-ventilator;

FIG. 9g is a schematic illustration of a jet-propeller;

FIG. 9h is a schematic illustration of a multi-module jet-ventilator;

FIG. 9i is a schematic illustration of cascaded multi-module jet-propellers; and FIG. 9j is a schematic illustration of a jet-transformer.

Figure 9K:
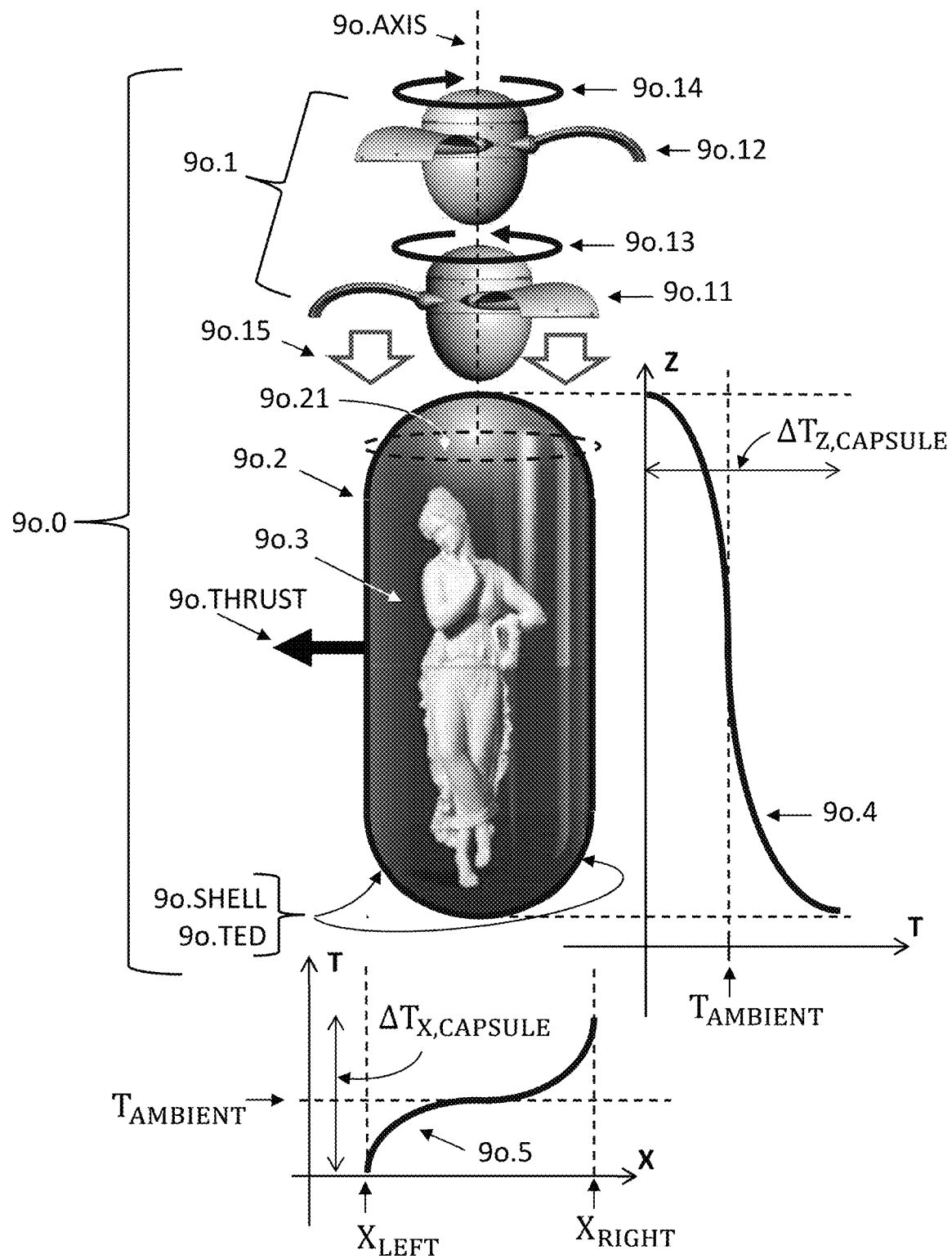

FIG. 9k is a schematic illustration of a levitating apparatus.

All the above and other characteristics and advantages of the invention will be further understood through the following illustrative and non-limitative description of preferred embodiments thereof.

DETAILED DESCRIPTION OF PREFERRED EMBODIMENTS

The principles and operation of a method and an apparatus according to the present invention may be better understood referring to the drawings and the accompanying description, it being understood that these drawings are given for illustrative purposes only and are not meant to be limiting.

Preface

The jet-effect occurring in moving fluid can be manifested as:
- the Venturi effect and the de Laval jet-effect resulting in either:
  - convective self-acceleration accompanied by self-cooling, or
  - self-retarding accompanying by self-warming, when a portion of the headway moving fluid is subjected to a reshaping;
- the Coanda-effect resulting in both:
  - lift-force acting on a profiled wing, and
  - thrust-force acting on a sail oriented as so-called "B-Point of Sail";
  when a convexly-curved surface is tangentially blown by a headwind; and
- the waving jet-effect resulting in both:
  - acoustic wave (audible sound or ultrasound) origination, and
  - conveying of a tiny portion of fluid transmitting wave energy away along the direction of the acoustic wave propagation;
  when a portion of the fluid is subjected to oscillating change in static pressure;

wherein these are manifestations of the jet-effect defined as an effect of transformation of the heat power into the kinetic power of fluid motion as a whole and, vice-versa, an effect of transformation of the kinetic power of fluid motion as a whole into the heat power. Further, the DETAILED DESCRIPTION OF THE PREFERRED EMBODIMENTS is divided between two paragraphs: "Conceptual Idea" and "Embodiments", each having sub-paragraphs.

Conceptual Idea

Prerequisites:
On the one hand, an inertialess controller is required; namely, in general, as a fluid flow acceleration is accompanied by varying thermodynamic parameters of portions of the fluid wherein the interrelation between the varying thermodynamic parameters is inertialess, control of the fluid flow should be if not inertialess then at least almost inertialess to provide the desired control of the thermodynamic parameters efficiently; and, in particular,
- as the Coanda-effect, that manifested by pulling-in the fluid portions forming a boundary layer and causing a lift-force, is accompanied by changes in thermodynamic parameters of the fluid portions wherein the interrelation between the changes is inertialess, a controller of the changes should be if not inertialess then at least almost inertialess to provide the desired boundary layer and lift-force;
- as the Venturi effect and the de Laval effect, both accompanied by the fluid portions' reshaping and inertialessly interrelated changes in thermodynamic parameters, again, a controller of the changes should be if not inertialess then at least almost inertialess to provide the desired thermodynamic parameters meeting the conditions of flow laminarity;
- as the upward-vectored lift-force is the property of the ambient-adjacent boundary layer, likewise, a controller of the changes in the thermodynamic properties of the ambient-adjacent boundary layer should be if not inertialess then at least almost inertialess to provide the desired property of the ambient-adjacent boundary layer; and
- as a sword propagating in the fluid is accompanied by oscillating changes: $\delta P$, $\delta \rho$, and $\delta T$, of thermodynamic parameters: the static pressure, mass density, and absolute temperature, correspondingly, of the fluid portions wherein the interrelation between the changes is inertialess, alike, a controller of a source of the sound should be if not inertialess then at least almost inertialess to provide the desired frequency of oscillating changes; and On the other hand, an almost inertialess thermoelectric device having no moving parts can be used: namely, considering a thermoelectric (TE) device based on the Peltier effect, the almost inertialess interrelation between the current density J and the temperature difference $\Delta T$, at least when removing the accumulated heat away is extra-fast and/or when the desired temperature difference $\Delta T$ is extremely small, makes using the TE device (optionally made using Nano-technologies from a thermoelectric material of high quality) promising, in general, to control the changes of the thermodynamic parameters of the moving fluid, and, in particular, to:
- create and control the lift-force; wherein, taking into attention that the TE device does not have moving parts, the using of the TE device allows to create and control the lift-force without the creation of undesired turbulence, and thereby, to create and control the lift-force much more efficiently than using wings supplied with moving flaps;
- create and control laminarity of a flow within a convergent-divergent nozzle: either a Venturi pipe or a de Laval tube; wherein, taking into attention that the TE device does not have moving parts, the using of the TE device allows smoothing the distributed static pressure to suppress so-called Mach waves and thereby to control the laminarity; and
- create, detect, and suppress the acoustic waves; wherein, as the TE device does not have moving parts, the using of the TE device allows creating the acoustic waves without the creation of undesired turbulence, and thereby, to launch and detect the acoustic waves (sound or ultrasound) much more efficiently than using classical speakers and microphones, correspondingly, which are supplied with a moving membrane.

Essence of Concept

Thus, the conceptual idea of the present invention is in the use of a thermoelectric device to:
- control gradients of thermodynamic parameters of flow along a convergent-divergent nozzle: either a Venturi pipe or a de Laval tube;
- create a pressure difference between the upper and lower sides of an airfoil body (for instance, a wing) to originate and control lift-force;
- create a pressure difference between anterior and tail parts of an airfoil body to originate and control thrust;
- create the oscillating changes: $\delta P$, $\delta \rho$, and $\delta T$, of thermodynamic parameters: the static pressure, mass density, and absolute temperature, correspondingly, of a portion of the fluid, to pull-in and push-off the fluid portion, and, thereby, to create acoustic waves much more efficiently than using a standard speaker having a moving membrane; and, vice-versa,
- detect and/or suppress the oscillating changes: $\delta P$, $\delta \rho$, and $\delta T$, of thermodynamic parameters: the static pressure, mass density, and absolute temperature, correspondingly, of a portion of the fluid, and thereby to detect and/or suppress the acoustic waves much more efficiently than using a standard microphone having a moving membrane.

The conceptual idea, being one of the primary features of the present invention, lies in the basis of the disclosed method and aerodynamic apparatuses (fluid pushers-off and fluid motion-sensors) for the creation and controlling of lift-force and thrust and for the creation and detection of sound.

Embodiments

Elemental TE Device as Source of Sound

FIG. 5a is a schematic illustration of an elemental acoustic thermoelectric device 5P.0, capable of functioning in two controllable modes: "A", to originate temperature difference between two buses 5P.7A and 5P.5A using the Peltier effect and, "B", vice versa, to detect the temperature difference between two buses 5P.7B and 5P.5B using the Seebeck effect.

The mode "A" is a case of forced controlling the temperature and thereby the static pressure of a portion of the ambient fluid, wherein the changes in temperature and static pressure are mutually-interrelated according to the equations Eq. (1.16) and Eq. (1.3c). The mode of forced-varying temperature assumes that the varying of the temperature and thereby the static pressure of the portion of the ambient fluid is periodically alternating, i.e. increasing and decreasing the static pressure that, in turn, indicates to generating an elastic (acoustic) wave propagating in the ambient fluid. The mode "A" is concretized as Case (A) SOUND LAUNCHING MODE. The feature is that the acoustic wave permanently transmits the wave energy away from the source in the direction of the Umov-vector collinear with the direction of the acoustic wave propagation. Thus, the elemental acoustic thermoelectric device 5P.0 operating in the mode "A" becomes interpreted as an aerodynamic apparatus—a fluid pusher-off, which is pulling-in and pushing-off a portion of the fluid and, thereby, is capable of triggering the conveying motion of a tiny portion of the ambient fluid (the conveying motion associated with the acoustic wave propagation), wherein the necessity of a powerful ventilator is excluded.

The mode "B" is a case of detecting the periodically alternating temperature changes of a portion of the ambient fluid. Again, the varying static pressure of the portion of the ambient fluid is interpreted as an indication of the presence of an elastic wave. So, the elemental acoustic thermoelectric device 5P.0 operating in the mode "B" becomes interpreted as an aerodynamic apparatus—a fluid motion-sensor, and the mode "B" is concretized as Case (B) SOUND DETECTION MODE.

Thus, the elemental acoustic thermoelectric device 5P.0, called an ELEMENTAL SOURCE AND DETECTOR OF SOUND, constructed according to the principles of the present invention, is an aerodynamic apparatus: a fluid pusher-off and/or a fluid motion-sensor, capable of operation in the two modes: Case (A) SOUND LAUNCHING MODE and Case (B) SOUND DETECTION MODE, as either an ELEMENTAL SOURCE OF SOUND 5P.0A or an ELEMENTAL DETECTOR OF SOUND 5P.0B, correspondingly.

From the point of view of construction, the two cases: Case (A) SOUND LAUNCHING MODE and Case (B) SOUND DETECTION MODE, differ as follows:

In the Case (A) SOUND LAUNCHING MODE, an ELEMENTAL SOURCE OF SOUND 5P.0A comprises a TE element 5P.A supplied with an individual controller 5P.8A connected between the connection points 5P.61A and 5P.62A and comprising an integrated circuit (IC) 5P.81A and a manipulatable source of emf 5P.82A, wherein two opposite sides of the TE element 5P.A comprise, on the one side, an ACTIVE COOLING AND HEATING BUS 5P.7A and, on the other side, a HEAT AND COLDNESS REJECTION BUS 5P.5A, both merged in the ambient fluid and wherein the manipulations in the polarity of the source of emf 5P.82A are periodically oscillating such that the originated oscillating temperature differences between the two opposite sides interrelated with whereby originated oscillating pressure differences are regarded as indicators of the presence of an acoustic wave propagating and transmitting the heat energy away from the ELEMENTAL SOURCE OF SOUND 5P.0A as the wave energy, and hence preventing the heat accumulation near the ELEMENTAL SOURCE OF SOUND 5P.0A;

and

In the Case (B) SOUND DETECTION MODE, an ELEMENTAL DETECTOR OF SOUND 5P.08 comprises a TE element 5P.B supplied with an individual controller IC DETECTOR 5P.8B comprising an integrated circuit (IC) and a detector of an induced varying electric current [for instance, alternating current (AC)] originated by the TE element 5P.B when a HEAT AND COLDNESS SOURCE BUS 5P.7B is exposed to ambient fluid and subjected to impacting acoustic wave characterized by varying heating and cooling of a tiny portion of the ambient fluid adjacent the HEAT AND COLDNESS SOURCE Bus 5P.7B, wherein the varying heating and cooling are manifested as periodically oscillating pressure and temperature, wherein, as the acoustic wave prevents the heat accumulation near the ELEMENTAL DETECTOR OF SOUND 5P.0B, one does not need in forcible thermostating the ELEMENTAL DETECTOR OF SOUND 5P.0B;

The inventor points out, again, that, the thermoelectric elements: 5P.A and 5P.B, as well as the thermoelectric elements 1.0 (1.0A and 1.0B) described hereinabove in THE BACKGROUND OF THE INVENTION referring to FIG. 4b, are characterized by the time-invariant interrelation between the current density J and the temperature difference ΔT. On the other hand, the time-invariance allows implementing the elemental acoustic thermoelectric devices 5P.0: an ELEMENTAL SOURCE OF SOUND 5P.0A and ELEMENTAL DETECTOR OF SOUND 5P.0B, such that:

in the Case (A) SOUND LAUNCHING MODE, the ELEMENTAL SOURCE OF SOUND 5P.0A functioning in the SOUND LAUNCHING MODE differs from TE element 1.0A (FIG. 4b Case (A) REFRIGERATION MODE) functioning in the REFRIGERATION MODE p and normally supplied with the ventilator 1.9A by that the source 1.6A of DC emf and the ventilator 1.9A, altogether are now replaced by an individual controller 5P.8A having the integrated circuit IC 5P.81A and the manipulatable source of emf 5P.82A controlled by the integrated circuit IC 5P.81A such that the manipulatable source of emf 5P.82A is capable of generating an alternating emf of a frequency f in the range of frequencies of the audible sound and ultrasound, i.e. from 20 Hz and lower to 20 kHz and higher; wherein, optionally, the individual controller 5P.8A can be implemented as a block 5P.80A of an electric scheme supplied by a transformer as 5P.86A of the alternating current and voltage that (the transformer 5P.86A), on the one hand, is connected to the metallic electrical contact pads 5P.41A and 5P.42A of an n-type (negative thermopower and electron carriers) semiconductor material 5P.1A and of a p-type (positive thermopower and hole carriers) semiconductor material 5P.2A, correspondingly, and on the other hand, is connected to the generator of alternating current and voltage 5P.820A, which is manipulatable by an individual integrated circuit IC 5P.810A, to separate the AC generated by the generator 5P.820A and the AC induced in the circuit of the TE element 5P.A; wherein, referring to exemplary TE modules, made using Nano-technologies, characterized by the estimated local temperature rate is 1.25 C/sec the estimated local temperature rate is 1.25 C/sec as described hereinabove in THE BACKGROUND OF THE INVENTION referring to FIG. 4b Case (A) TIME CHARACTERISTIC and citing D04, the estimations of reachable SPL for audible sound are as follows:

when 20 Hz sound is required, half of the time-period allowing for the temperature oscillation is $0.5 \times \tau_{20Hz} = 0.025$ sec and the reachable amplitude of the temperature difference is approximately 0.03K that corresponds to SPL=SDL=STL level of 155 dB;

when 20 kHz sound is required, half of the time-period allowing for the temperature oscillation is $0.5 \times \tau_{20kHz} = 2.5 \times 10^{-5}$ sec and the reachable amplitude of the temperature difference is, approximately, $3 \times 10^{-5}$ K that corresponds to SPL=SDL=STL level of 95 dB;

The investor points out that the estimation is the worst-case estimation made with a spare reserve because the generated sound transmits the heat and coolness away with the velocity of sound in the ambient fluid, i.e., on the one hand, one does not need to use a ventilator for the heat removing (note, the gusty-choppy operating ventilator would not allow to generate so precise temperature differences), and, on the other hand, the not accumulated heat provides for desired inertialess of the thermoelectric element functioning. In other words, the SPL, much higher than the worst-case estimated 95 dB, is reachable. Thus, in any case, the reachable SPL is much higher than the usually used SPL between 0 to 80 dB, and so the ELEMENTAL SOURCE OF SOUND 5P.0A is capable to launch acoustic waves as audible sound 5P.91A and 5P.92A, launched from the ACTIVE COOLING AND HEATING BUS 5P.A and the HEAT AND COLDNESS REJECTION BUS 5P.5A, correspondingly, wherein the launched acoustic waves 5P.92A differ from the launches acoustic waves 5P.91A in phase on 180°. It further will be evident for a commonly educated person that the alternating current generated by the generator 5P.820A results in the origination and radiation of an electromagnetic wave characterized by the frequency f of the current alternation; and in the Case (B) SOUND DETECTION MODE, the ELEMENTAL DETECTOR OF SOUND 5P.0B functioning in the SOUND DETECTION MODE differs from TE element 1.0B functioning in the POWER GENERATION MODE and normally supplied with the ventilator 1.9B by that the load 1.6B (FIG. 4b Case (B) POWER GENERATION MODE) and the ventilator 1.9B, altogether are now replaced by an individual integrated circuit IC DETECTOR 5P.8B capable of detection AC originated by acoustic wave 5P.91B impacting the HEAT AND COLDNESS SOURCE BUS 5P.7B which, as a result, becomes subjected to alternating heating and cooling accompanying by the origination of alternating electric current. Again, optionally, the connection of the individual integrated circuit IC DETECTOR 5P.8B to the TE element 5P.B can be implemented using a transformer 5P.86B of the induced alternating electric current and voltage wherein the transformer 5P.86B:

on the one hand, is connected to the metallic electrical contact pads 5P.41B and 5P.42B of an n-type (negative thermopower and electron carriers) semiconductor material 5P.1B and a p-type (positive thermopower and hole carriers) semiconductor material 5P.2B, correspondingly, and on the other hand, is connected to the individual integrated circuit IC DETECTOR 5P.810B, to separate the AC generated by the TE element 5P.B and the AC induced in the individual integrated circuit IC DETECTOR 5P.80B. It further will be evident for a commonly educated person that the induced alternating electric current originated in the thermoelectric element 5P.B, on the one hand, can be registered and/or recorded by any classic method, and on the other hand, results in the origination and radiation of an electromagnetic wave characterized by the frequency f of the induced current alternation that, in turn, can be detected using an RE receiving antenna.

As a consequence, from the point of view of functioning, the two cases: (A) and (B), differ as follows:

In Case (A) SOUND LAUNCHING MODE, an ELEMENTAL SOURCE OF SOUND 5P.0A is capable of operation in a SOUND LAUNCHING MODE providing for audible sound and ultrasound launching; and, vice-versa, and In Case (B) SOUND DETECTION MODE, an ELEMENTAL DETECTOR OF SOUND δP.0B is capable of functioning in a SOUND DETECTION MODE providing for audible sound and ultrasound detection.

In view of the foregoing description referring to FIG. 5a, it will be evident for a commonly educated person that:

In Relation to Accompanying Electro-Magnetic Waves,

When operating in the sound launching mode, the ELEMENTAL SOURCE OF SOUND 5P.0A radiates electromagnetic waves of the same frequency as the frequency of the launched acoustic waves; in other words, the metallic electrical contact pad 5P.3A of the ELEMENTAL SOURCE OF SOUND 5P.0A operates as a transmitting antenna of electromagnetic waves, If the ELEMENTAL SOURCE AND DETECTOR OF SOUND 5P.0 is exposed to an electromagnetic wave of a certain frequency in the range between 20 Hz and 20 kHz (or higher), then the metallic electrical contact pad 5P.3A, as a receiving antenna detecting the electromagnetic wave, plays the role of the generator of alternating electric current or voltage 5P.820A providing the emf resulting in the generation of an acoustic wave (audible or ultrasound) of the same certain frequency; and If the ELEMENTAL DETECTOR OF SOUND 5P.0B is exposed to an acoustic wave of a certain frequency, the metallic electrical contact pad 5P.3B radiates an electromagnetic wave of the same certain frequency and so plays the role of a transmitting antenna allowing to detect the presence of sound using a sensor of electromagnetic waves wirelessly;

In Relation to the Reversibility of the Elemental Source and Detector of Sound,

If the manipulatable source of emf 5P.82A is shunted and the integrated circuit IC 5P.81A provides for the functionality of the individual integrated circuit IC DETECTOR 5P.8B, the ELEMENTAL SOURCE OF SOUND 5P.0A can be adapted to function as the ELEMENTAL DETECTOR OF SOUND 5P.0B in the Case (B) SOUND DETECTION MODE. This allows using the TE element 5P.A for operation as both:
- a source of sound when functioning in the sound launching mode, and
- a detector of sound when functioning in the sound detection mode; and In Relation to Phase-Inverter, In the detection mode, the opposite sides HEAT AND COLDNESS SOURCE BUS 5P.7B and HEAT AND COLD SINK BUS 5P.5B, both become heated and cooled alternatingly with the frequency f equal to the frequency of the impacting sound, wherein the phase of the temperature changes adjacent to the HEAT AND COLD SINK BUS 5P.5B differs from the phase of the temperature changes adjacent the HEAT AND COLDNESS SOURCE BUS 5P.7B on 180°. This, in particular, means that the TE element 5P.B functions as a phase-inverter which receives the acoustic wave 5P.91B impacting the HEAT AND COLDNESS SOURCE BUS 5P.7B and launches the acoustic wave 5P.92B propagating away from the HEAT AND COLD SINK BUS 5P.5B, wherein the phase of the launched acoustic wave 5P.92B differs from the phase of the received acoustic wave 5P.91B on 180°. It will be evident for a commonly educated person, that if now the individual integrated circuit IC DETECTOR 5P.8B is supplied by an amplifier providing for increasing an induced electric current, the TE element 5P.B becomes capable of functioning as an amplifier of acoustic waves which receives the acoustic wave 5P.91B impacting the HEAT AND COLDNESS SOURCE BUS 5P.7B and launches the amplified acoustic wave 5P.92B propagating away from the HEAT AND COLD SINK BUS 5P.5B, wherein the phase of the launched acoustic wave 5P.92B differs from the phase of the received acoustic wave 5P.91B on 180°.

Multi-Module Matrix Device

FIG. 5b, composed of two parts: (A) and (B), is a schematic illustration of components of a multi-module thermoelectric device.

The inventor points out, that, taking into account the foregoing description of THE BACKGROUND OF THE INVENTION referring to FIGS. 1b and 1c, it will be evident for a commonly educated person that a MULTI-MODULE SOURCE AND DETECTOR OF SOUND is feasible by aggregating a multiplicity of the ELEMENTAL SOURCES OF SOUND 5P.0A and ELEMENTAL DETECTORS OF SOUND 5P.0B such that the ELEMENTAL SOURCES OF SOUND 5P.0A and ELEMENTAL DETECTORS OF SOUND 5P.0B are connected into a sequential electric scheme and arranged to create and detect, correspondingly, the changes of the thermodynamic parameters of the ambient fluid in unison.

In view of the foregoing description of the elemental acoustic thermoelectric devices 5P.0, capable of functioning in two controllable modes: "A", to originate temperature difference between two buses 5P.7A and 5P.5A using the Peltier effect and, "B", vice versa, to detect the temperature difference between two buses 5P.7B and 5P.5B using the Seebeck effect, it will be evident to a commonly educated person that the elemental acoustic thermoelectric device 5P.0 can be utilized as a combined both a microphone and speaker being placed at the same location and functioning simultaneously. This advantage over a prior art device for sound or ultrasound generation of A05 provides additional degrees of freedom to implement useful, compact, and efficient devices.

Moreover, an arrangement of the ELEMENTAL SOURCES OF SOUND 5P.0A and ELEMENTAL DETECTORS OF SOUND 5P.0B can be more sophisticated.

FIG. 5b (A) is a schematic isometry illustration of a fragment of planar arrangement 5Q.MATRIX of elemental thermoelectric elements 5Q.01, arranged in a plane (X, Y) in a system of coordinates (X, Y, Z) 5Q.0 and electrically mutually isolated.

FIG. 5b (B) is a schematic illustration of a cross-sectional cut of a multi-module thermoelectric device 5Q.DEVICE, called MATRIX SOURCE AND/OR DETECTOR OF SOUND, constructed according to the principles of the present invention.

The device MATRIX SOURCE AND/OR DETECTOR OF SOUND 5Q.DEVICE is composed of a multiplicity of $N=N_x \times N_y$ elemental TE devices 5Q.02, where $N_x$ and $N_y$ are numbers of the TE devices 5Q.02 arranged along the axes X and Y, correspondingly. Each of the N elemental TE devices 5Q.02 is similar to the elemental TE device 5P.0 functioning as an ELEMENTAL SOURCE AND/OR DETECTOR OF SOUND as described hereinabove in the subparagraph "In Relation To Phase-Inverter" referring to FIG. 5a. The $N_x \times N_y$ elemental TE devices 5Q.02 are arranged in a plane (X, Y) in a system of coordinates (X, Y, Z) 5Q.0, electrically mutually isolated, and have individual thermo-conductive buses, i.e. each of the $N_x \times N_y$ elemental TE devices 5Q.02 has individual both controller 5Q.08 and thermo-conductive bus 5Q.05 to be controlled individually. Each of the controllers 5Q.08 comprises an individual integrated circuit IC 5Q.81, a manipulatable source of emf (for instance, a generator of alternating electric current and voltage) 5Q.82, and, optionally, transformers 5Q.86 as described hereinabove referring to FIG. 5a. For the sake of simplicity of the schematic illustration:
- An arrangement along the axis X is shown only; and
- Points 5Q.03 symbolize that each of the numbers $N_x$ and $N_y$ can be much greater than shown.

Wherein:
- Each of the $N_x \times N_y$ elemental TE devices 5Q.02 is the ELEMENTAL SOURCE OR DETECTOR OF SOUND 2P.0A or 2P.0B described hereinabove with the reference to FIG. 5a Case (A) SOUND LAUNCHING MODE or FIG. 5a Case (B) SOUND DETECTION MODE, correspondingly; and
- Each of the $N_x \times N_y$ individual integrated circuits IC 5Q.81, is individually controlled by a common controller-dispatcher 5Q.04.

In the launching mode, elemental acoustic waves, launched by the individually controlled $N_x \times N_y$ ELEMENTAL SOURCES OF SOUND 5Q.02 of the device MATRIX SOURCE AND/OR DETECTOR OF SOUND 5Q.DEVICE can differ in amplitude, phase, frequency, and delay, all controlled by the common controller-dispatcher 5Q.04. Thereby, the desired spatial interference map associated with the resulting acoustic wave composed of the elemental acoustic waves is feasible. Namely, a well-known technique "phased array" can be applied to the elemental acoustic waves when using the matrix of the multiplicity of $N_x \times N_y$ ELEMENTAL SOURCES OF SOUND 5Q.02. In contrast to the prior art device for sound or ultrasound generation of A05, the multi-module thermoelectric device 5Q.DEVICE, each of the individual TE devices 5Q.02 of which is capable of functioning in two modes: launching elastic waves and detecting temperature changes, is characterized by a degree of freedom to apply the phased array principle providing for additional specific properties of the multi-module thermoelectric device 5Q.DEVICE, one of which is in control of spatial and temporal distributions of thermodynamic parameters of the ambient fluid portions adjacent to the individual thereto-conductive buses 5Q.05.

Another useful property of the device MATRIX SOURCE AND/OR DETECTOR OF SOUND 5Q.DEVICE is that the loudness of the resulting launched sound can be controlled by the quantity of operating ELEMENTAL SOURCES OF SOUND 5Q.02. In practice, the device MATRIX SOURCE AND/OR DETECTORS OF SOUND 5Q.DEVICE comprising the big number $N_x \times N_y$ of ELEMENTAL SOURCES OF SOUND 5Q.02 provides for a big number of degrees of freedom for manipulation with characteristics of the elemental acoustic waves to create the desired waveform of the resulting launched acoustic wave. The big number of degrees of freedom allows for the coding, directing, and focusing of the resulting launched acoustic wave, wherein the device MATRIX SOURCE AND/OR DETECTORS OF SOUND 5Q.DEVICE remains relatively compact as not requiring big horns and is efficient comparing with classic speakers as not having moving components and so not originating concomitant turbulence.

In the detection mode, the $N_x \times N_y$ ELEMENTAL DETECTORS OF SOUND 5Q.02 of the device MATRIX SOURCE AND/OR DETECTOR OF SOUND 5Q.DEVICE are capable to detect a reached beam of elemental acoustic waves and release $N_x \times N_y$ associated elemental electrical signals and the common controller-dispatcher 5Q.04 is capable to superpose the released $N_x \times N_y$ elemental electrical signals. If the beam brings coded information due to that the $N_x \times N_y$ elemental acoustic waves differ in amplitude and/or phase and/or frequency and/or delay, then the $N_x \times N_y$ ELEMENTAL DETECTORS OF SOUND 5Q.02 release $N_x \times N_Y$ different associated elemental electrical signals. Further, using the common controller-dispatcher 5Q.04 capable to superpose the released $N_x \times N_y$ elemental electrical signals using a decoding algorithm, a decoding of the coded information becomes feasible.

In view of the foregoing description referring to FIG. 5a and FIGS. 2b (A) and (B) in combination with FIG. 1c, it will be evident for a commonly educated person that a three-dimensional matrix of a multiplicity of $N_x \times N_y \times N_z$ elemental TE devices 5Q.02, where $N_z$ is the number of the ELEMENTAL SOURCES OF SOUND 50.01 arranged along the axis Z in a manner shown in FIG. 1c, can be implemented to increase the reachable amplitude of the oscillating temperature difference δT using a smaller amplitude of the oscillating current density J when the elemental TE devices 50.02 function to launch acoustic waves.

Diversity of Uses for Multi-Module Matrix Devices

Thus, when the elemental acoustic thermoelectric devices 5P.0 are aggregated into a matrix thereby forming the matrix device 5Q.DEVICE, it becomes possible a broad diversity of uses such as an acoustic wave phase inverter or optimal detector of sound, a sound amplifier, a phased array acoustic wireless charger, a suppressor of turbulence in a jet-nozzle, a suppressor of turbulence in a flow boundary layer, and a lift-and-thrust force booster, each of which will be described hereinbelow referring to FIGS. 5c, 5d, 5e, 6a, 7c, and 8, correspondingly.

Detector of Sound

FIG. 5c is a schematic illustration of a multi-module thermoelectric device 5R.DEVICE, comprising a matrix of a multiplicity of N ELEMENTAL DETECTORS OF SOUND 5R.02, each of which comprises an individual integrated circuit controller as described hereinbefore referring to FIG. 5a, and a common controller-dispatcher 5R.04 capable to control the N ELEMENTAL DETECTORS OF SOUND 5R.02 individually by amplifying, and/or delays, and/or phase-shifting, and/or summing the associated induced individual electric currents. The multi-module thermoelectric device 5R.DEVICE has an overall shape of a plate having two sides: 5R.71 and 5R.72. When the side 5871 is exposed to an acoustic beam 5R.1.INPUT, a secondary acoustic wave 5R.2.OUTPUT is radiated from the side 5R.72 due to the Seebeck effect and the Peltier effect as a contribution to the resulting acoustic beam 5R.4.OUTPUT, as described hereinabove in the subparagraph "In Relation To Phase-Inverter" referring to FIG. 5a considering an alone ELEMENTAL SOURCE AND DETECTOR OF SOUND 5P.0. The two acoustic beams: 5R.1.INPUT and the secondary acoustic wave 5R.2.OUTPUT, are marked by opposite signs: "+" and "−", correspondingly, symbolizing the 180° phase-difference between the fronts of the two acoustic beams: 5R1.INPUT and the secondary acoustic wave 5R.2.OUTPUT, adjacent to the two sides: 5R.71 and 5R.72, correspondingly.

It will be evident to a commonly educated person that the acoustic beam 5R.1.INPUT acts on the side 5R.71 the thermoelectric device 5R.DEVICE not only due to the oscillating changes in temperature but also mechanically impacting the side 5R.71 of the thermoelectric device 5R.DEVICE due to the oscillating changes in static pressure. The mechanic impacts partially transmit the acoustic beam 5R.1.INPUT through the thermoelectric device 5R.DEVICE without the phase-inversion, thereby, resulting in the portion 5R.3.OUTPUT of the acoustic beam 5R.1.INPUT, which (the portion) is passed through the thermoelectric device 5R.DEVICE as a contribution 5R3.OUTPUT to the resulting acoustic beam 5R.4.OUTPUT and radiated from the side 5R.72. As soon as the front of the contribution 5R.3.OUTPUT is not subjected to the phase-inversion and the velocity of acoustic waves in the solid material of the thermoelectric device 5R.DEVICE is much higher than the velocity of the acoustic waves in the air, the phase of the contribution 5R.3.OUTPUT radiated from the side 5R.72 is almost the same as the phase of the acoustic beam 5R.1.INPUT and so is reasonably indicated by sign "+". If the common controller-dispatcher 5R.04 of the thermoelectric device 5R.DEVICE provides for amplifying the induced current to trigger the Peltier effect originated in unison with the triggered by the impacting acoustic beam 5R.1 INPUT Seebeck effect, and, thereby, to amplify the secondary acoustic wave 5R.2.OUTPUT exceeding the acoustic beam portion contribution 5R.3.OUTPUT, the thermoelectric device 5R.DEVICE is interpreted as a phase-inverter.

Optimized Detector of Sound

If the common controller-dispatcher 5R.04 of the thermoelectric device 5R.DEVICE comprises a so-called negative feedback loop to provide for that the two contributions:

the secondary acoustic wave 5R.2.OUTPUT, and the portion 5R.3.OUTPUT of the acoustic beam 5R.1.INPUT which (the portion) passed through the thermoelectric device 5R.DEVICE, having the mutually opposite phases are such that the resulting electric current in the thermoelectric devices 5R.02 is zero, in turn, providing that the resulting acoustic beam 5R.4.OUTPUT has a zero amplitude, then the wave energy, brought by the acoustic beam 5R.1 INPUT, and the electric energy, consumed by both a multiplicity of individual integrated circuit controllers and the common controller-dispatcher 5R.04, altogether are transformed into the Joule heat and radiation of an electromagnetic wave which is accompanying the induced alternating current originated in the thermoelectric device 5R.DEVICE. This also means that there are suppressed waves reflected from the side 5R.71. Thus, the device 5R.DEVICE is adapted to function as a detector of sound or a silencer, optimized to maximize the net-efficiency of sound detection.

Two-Stage Sound Amplifier

FIG. 5d is a schematic illustration of a two-stage sound amplifier 5S.DEVICE, constructed according to the principles of the present invention as a multi-module thermoelectric device, representing a cascade of two mutually electrically-separated thermoelectric devices: 5S-1.DEVICE and 5S-2.DEVICE, each of which is similar to the thermoelectric device 5R.DEVICE described hereinabove referring to FIG. 5c. The thermoelectric device 5S.DEVICE comprises a multiplicity of 2 N ELEMENTAL DETECTORS OF SOUND 5S.02, each of which comprises an individual controller similar to the individual controller 5P.8A described hereinbefore referring to FIG. 5a, and a common controller-dispatcher 5S.04 capable to control the 2N ELEMENTAL DETECTORS OF SOUND individually by amplifying, and/or delays, and/or phase-shifting, and/or summing the induced individual electric currents.

When the side 5S.71 is exposed to an impacting acoustic beam 5S.1.INPUT, the inner side 5S.72 is cooled and heated in anti-phase relative to the heating and cooling side 5S.71. Further, a secondary acoustic wave 5S.2.OUTPUT is radiated from the side 5S.73 due to the Peltier effect as a contribution to the resulting acoustic beam 5S.4.OUTPUT. The two acoustic beams: impacting 5S.1.INPUT and the secondary acoustic wave 5S.2.OUTPUT, are marked by the same sign: "+", symbolizing the zero phase difference between the fronts of the two acoustic beams: impacting 5S.1.INPUT and the secondary acoustic wave 5S.2.OUTPUT, adjacent to the two sides: 5S.71 and 5S.73, correspondingly.

Again, it will be evident to a commonly educated person that the impacting acoustic beam 5S.1.INPUT acts on the side 5S.71 of the thermoelectric device 5S.DEVICE not only due to the oscillating changes in temperature but also mechanically impacting the side 5S.71 of the thermoelectric device 5S.DEVICE due to the oscillating changes in static pressure. The mechanic impacts partially transmit the impacting acoustic beam 5S.1.INPUT through the thermoelectric device 5S.DEVICE without the phase-inversion, thereby, resulting in a contribution 5S.3.OUTPUT to the resulting acoustic beam 5S.4.OUTPUT radiated from the side 5S.73. As soon as the front of the contribution 5S.3.OUTPUT is not subjected to the phase-inversion and the wavelength of an acoustic wave in a solid material of the thermoelectric device 5S.DEVICE is much greater than the thickness 5S.03 of the thermoelectric device 5S.DEVICE, the phase of the contribution 5S.3.OUTPUT radiated from the side 5S.73 is almost the same as the phase of the impacting acoustic beam 5S.1.INPUT and so is reasonably indicated by sign "+" as well. The two contributions: 5S.2.OUTPUT and 5S.3.OUTPUT, are in-phase, hence, in this case, the thermoelectric device 5S.DEVICE is adapted to function as a two-stage sound amplifier, optimized to maximize the net-efficiency of sound boosting. As both the Seebeck effect and the Peltier effect are triggered in the thermoelectric device 5S.DEVICE, the resulting sound-amplifying partially occurs at the expense of the ambient heat.

It will be evident for a commonly educated person that a phonendoscope and hearing aid, both can be supplied with the two-stage sound amplifier embodied as the thermoelectric device 5S.DEVICE.

Acoustic Wireless Charger

FIG. 5e is a schematic illustration of a communication system 5T.SYSTEM, constructed according to the present invention. The communication system 5T.SYSTEM comprises:

- a multi-module thermoelectric device 5T.TX-ANTENNA, having a matrix composed of a multiplicity of N ELEMENTAL SOURCES OF SOUND 5T.02A functioning in the SOUND LAUNCHING MODE and a common controller-dispatcher 5T.04A, and
- a multi-module thermoelectric device 5T.RX-ANTENNA, composed of a matrix composed of a multiplicity Of N ELEMENTAL DETECTORS OF SOUND 5T.02B functioning in the SOUND DETECTION MODE and a common controller-dispatcher 5T.04B.

While the common controller-dispatcher 5T.04A provides for an implementation of the technique phased array applied to the matrix of the multiplicity of N ELEMENTAL SOURCES OF SOUND 5T.02A to form an acoustic beam 5T.1.INPUT directed to the multi-module thermoelectric device 5T.RX-ANTENNA, the common controller-dispatcher 5T.04B provides for the operation of the sound detecting multi-module thermoelectric device 5T.RX-ANTENNA similar to the operation of the multi-module thermoelectric device 5R.DEVICE described hereinabove in subparagraph "Optimized Detector Of Sound" referring to FIG. 5c, namely, such that the two contributions 5T.2.OUTPUT and 5T.3.OUTPUT (both analogous to the aforementioned two contributions 5R.2.OUTPUT and 5R.3.OUTPUT) having the mutually opposite phases, such that the resulting acoustic beam 5T.4.OUTPUT has zero amplitude (analogously to the aforementioned resulting acoustic beam 5R.4.OUTPUT). The IC DETECTOR 5T.8B is similar to the IC DETECTOR 5P.8B (FIG. 5a) but is now specified as having a DIODE BRIDGE 5T.81B and a RECHARGEABLE BATTERY 5T.81B. An induced alternating electric current generated in the IC DETECTOR 5T.8B moves through the DIODE BRIDGE 5T.81B and charges the RECHARGEABLE BATTERY 5T.81B, thereby, cumulating the electric energy, which is acquired from the wave energy of the detected acoustic beam 5T.1.INPUT. Thus, the communication system 5T.SYSTEM represents an acoustic wireless charger.

To estimate the practical feasibility of the acoustic wireless charger, consider the multi-module thermoelectric device 5T.TX-ANTENNA having a linear size of several times greater than 1 mm and the acoustic beam 5S.1.INPUT which is composed of acoustic waves at the ultrasound frequency of 340 kHz. In this case, the wavelength of the ultrasound is estimated as 1 mm; and half of the time-period allowing for the temperature oscillation is $0.5 \times \tau_{340\ kHz} \approx 1.5 \times 10^{-6}$ sec and the reachable amplitude of the temperature difference is, approximately, of $1.8 \times 10^{-6}$ K that corresponds to SPL=SDL=STL level of 70 dB.

The phased array technique is applicable to the wavelength of 1 mm, as the linear size of the multi-module thermoelectric device 5T.TX-ANTENNA is assumed of several times greater than 1 mm. Normally, the net-efficiency of the electrical scheme of the IC DETECTOR 5T.8B is higher than 50%. Taking into account that the wave power is proportional to squired frequency; if the charging energy is further destined to generate a 2 kHz sound, a reachable SPL of the 2 kHz sound is about 109 dB. The estimation shows that the acoustic wireless charger can be sufficiently efficient when charging the multi-module thermoelectric device 5T.RX-ANTENNA wirelessly from 1 m distance using the 340 kHz ultrasound.

In view of the foregoing description referring to FIGS. 5a, 5b, 5c, 5d, and 5e, it will be evident for a person skilled in the art that, if the multi-module thermoelectric device 5T.RX-ANTENNA operates in a passive mode without the functioning of the dispatcher 51.048, then the magnitudes of the contributions 5T.2.OUTPUT and 5T.3.OUTPUT, both are neither controlled nor optimized and so a non-zero resulting acoustic beam 5T.3.OUTPUT determines a reduced net-efficiency of the acoustic wireless charger.

Convercent-Divergent Jet-Nozzle

FIG. 6*a*, composed of two parts: (A) Shape and (B) Graph, is a schematic illustration of a modified convergent-divergent jet-nozzle.

FIG. 6*a* (A) Shape shows schematically a sectional view of the modified convergent-divergent jet-nozzle 610 in a sagittal plane. The modified convergent-divergent jet-nozzle 610 having a shaped tunnel is applied to accelerate a laminarly flowing compressed and hot compressible-expandable fluid 611. In contrast to the prior art convergent-divergent nozzles, which are passively adapted to only certainly-given velocity and thermodynamic parameters (and are not adapted to arbitrary velocity and thermodynamic parameters) of an incoming fluid flow to provide for a laminar flow as described hereinabove in subparagraph "De Laval Effect" referring to FIG. 1*b*, the modified convergent-divergent jet-nozzle 610, constructed according to an exemplary embodiment of the present invention, allows for the implementation of either the enhanced Venturi effect or the enhanced de Laval jet-effect, each providing a laminar acceleration of fluid flow 611 for a wide range of velocities $u_{in}$ and thermodynamic parameters: the static pressure $P_{in}$, absolute temperature $T_{in}$, and mass density $\rho_{in}$, of entering fluid flow 611 at an open inlet 617. The shaped tunnel of the modified convergent-divergent jet-nozzle 610 has opposite walls 6A.WALLS, which are either formed by or at least supplied with a surface matrix 6A.MATRIX of densely-arranged elemental thermoelectric devices 6A.TED. The triplet of dots 6A.* DOT symbolizes that the elemental thermoelectric devices 6A.TED are arranged unbrokenly. The surface matrix 6A.MATRIX is analogous to the planar matrix 5Q.MATRIX of elemental thermoelectric devices 5Q.02 described hereinabove referring to FIG. 5*b*, but now is aligned to the opposite walls 6A.WALLS's shape. The opposite walls 6A.WALLS are shaped, for the sake of concretization and without loss of generality, axis-symmetrically around an imaginary sagittal x-axis 615, as a convergent funnel 612 comprising an open inlet 617 having a cross-sectional area $A_{in}$ and diameter $D_{in}$, narrow throat 613 comprising point 618 of the narrowest cross-section cross-sectional area $A_{th}$ and diameter $D_{th}$, and divergent exhaust tailpipe 614 having an open outlet 619 having a cross-sectional area $A_0$ and diameter $D_0$. When moving through the smoothly shaped tunnel having controllably heated and/or cooled walls, the fluid stream 611 becomes subjected, on the one hand, to change in cross-sectional area and, on the other hand, to forcedly established temperature distributed due to controllably functioning densely-arranged elemental thermoelectric devices 6A.TED. The linear sizes: $D_{in}$, $D_{th}$, $D_{ou}$ may differ from associated linear sizes of the mentioned prior art passively adapted convergent-divergent nozzle, passively adapted to only certainly-given velocity and thermodynamic parameters of the incoming fluid flow 611, on a thickness of a boundary layer nearby the opposite walls 6A.WALLS. Thus, the thickness of the boundary layer near each of the walls 6A.WALLS plays the role of a tolerance allowing for a degree of freedom to manipulate with the forcedly establishing of the temperature using the thermoelectric devices 6A.TED. The surface matrix 6A.MATRIX of the thermoelectric devices 6A.TED provides for controllably distributed temperature along the sagittal axis 615 having a distance parameter x. The varying cross-sectional area of the smoothly shaped tunnel is characterized by a cross-sectional area profile function A(x) of x interrelated with functions u(x) and T(x) of x representing profiles of the fluid flow's headway velocity and absolute temperature, correspondingly, along the tunnel length, wherein the thermoelectric devices 6A.TED providing for a degree of freedom to interrelate the functions A(x), u(x), and T(x) by a condition of flow continuity expressed as:

$$A(x) = \frac{A_* \sqrt{(\gamma-1)RT(x)}}{u(x)} \left( \frac{2}{\gamma+1} + \frac{(u(x))^2}{(\gamma+1)RT(x)} \right)^{\frac{\gamma+1}{2(\gamma-1)}}, \quad \text{Eq. 6.0}$$

where $A_*$ is a constant, $\gamma$ is an adiabatic compressibility parameter of the flowing fluid, and R is a specific gas constant characterizing the fluid flow, wherein the functions u(x) and T(x) both are gradually-smoothed monotonic, wherein:

the gradually-smoothed monotonic function of the absolute temperature T(x) is determined by:
the absolute temperature $T_{in}$ the fluid flow at the open inlet;
the temperature change $\delta T_0(x)$ interrelated with adiabatic compression-expansion occurred due to an adiabatic action of the Coanda-effect, in turn, determined by a curvature of the stationary geometrical configuration of the tunnel; and
forcedly established temperature contribution $\delta T_1(x)$ to the absolute temperature T(x) along the boundary layers subjected to controllable heating and/or cooling action of the thermoelectric devices 6A.TED,
such that $T(x)=T_{in}+\delta T_0(x)+\delta T_1(x)$, and
the gradually-smoothed monotonic function of the headway velocity u(x) is determined by the certain headway velocity $u_{in}$ of the fluid flow 611 at the open inlet, convective headway acceleration resulting in a velocity gradient along the tunnel length as the fluid flow 611 is subjected to the adiabatic Coanda-effect, and controllable headway acceleration occurred due to controllable heating and/or cooling action of the thermoelectric devices 6A.TED.

The condition of flow continuity Eq. (6.0) is correct as for relatively slow motions corresponding to low M-velocities, lower than the specific M-velocity $M_*=\sqrt{(\gamma-1)/\gamma}$ as well as for relatively fast motions corresponding to high M-velocities, higher than the specific M-velocity.

The constant $A_*$ is a characteristic cross-sectional area defined for a certain fluid; the characteristic cross-sectional area $A_*$ is a hypothetically-minimal reachable by a portion of the fluid when the portion of the fluid is convectively accelerated in an adiabatic process, according to the equation of continuity. Considering the case:

when the minimal cross-sectional area $A_{th}$ of the narrow throat is greater than the hypothetically-minimal reachable constant $A_*$, there are no critical condition points within the tunnel and the convergent-divergent nozzle 610 plays the role of a Venturi pipe providing for the Venturi effect; and when the minimal cross-sectional area $A_{th}$ of the narrow throat is lesser than or equal to the hypothetically-minimal reachable constant $A_*$ ($A_{th} \leq A_*$), the flowing fluid 611, being subjected to a convective acceleration in an adiabatic process and crossing the minimal cross-sectional area $A_{th}$ of the narrow throat 613, is capable of reaching at most the specific M-velocity $M_*=$ $\sqrt{(\gamma-1)/\gamma}$ (which is a characteristic of the fluid as well) and so the convergent-divergent nozzle 610 plays the role of a de Laval jet-nozzle providing for the de Laval jet-effect; wherein the condition $A_{th}<A_*$ contradicts the condition of flow continuity (6.0) and thereby the de Laval jet-effect is not optimized on the criterion of laminar motion of the fluid flow 611.

Considering the case, when the modified convergent-divergent jet-nozzle 610 is destined to trigger the enhanced de Laval jet-effect recognized by a laminar motion of the fluid flow 611, the narrow throat 613 should be narrow sufficient such that the minimal cross-sectional area $A_{th}$ is the hypothetically-reachable minimal cross-sectional area $A_*$ providing the "critical condition" point 618 where the temperature-dependent M-velocity gradually reaches the value of the specific M-velocity $M_*=\sqrt{(\gamma-1)/\gamma}$. In practice, to provide the strict condition $A_{th}=A_*$ using a passively adapted convergent-divergent nozzle is almost impossible. The surface matrix 6A.MATRIX of the densely-arranged elemental thermoelectric devices 6A.TED allows for such a control of the temperature contribution $\delta T_1(x)$ that the resulting gradually-smoothed monotonic function of the absolute temperature $T(x)=T_{in}+\delta T_0(x)+\delta T_1(x)$ satisfies the condition Eq. (6.0).

The degree of freedom to manipulate with the function $T(x)$ via the function $\delta T_1(x)$ to satisfy the condition of flow continuity Eq. (6.0) provides for that the combined action on the fluid stream 611 provides for gradually-smoothed monotonic changes preventing jumps of the fluid stream headway velocity $u(x)$ and all of the thermodynamic parameters of the fluid: the static pressure $P(x)$, the absolute temperature $T(x)$, and the mass density $\rho(x)$, thereby, providing the following beneficial features:
  smoothing (or, preferred, linearizing) of the fluid stream headway velocity, providing suppression of the undesired flow turbulence;
  smoothing (or, preferred, linearizing) of the fluid stream static pressure, providing suppression of the undesired Mach waves and, thereby, suppression of nearby body vibrations;
  smoothing (or, preferred, linearizing) of the fluid stream mass density, providing suppression of the undesired flow disturbances accompanied by shock waves;
  smoothing of the flowing fluid absolute temperature, providing suppression of adjacent surface tensions; and
  smoothing (or, preferred, linearizing) of the flowing fluid M-velocity, providing a trade-off of suppressions of undesired all: the turbulence, vibrations, shock and Mach waves, and surface tensions.

The relatively fast fluid flow 611 provides for conditions allowing to exclude using a powerful ventilator, normally, accompanying thermoelectric devices.

FIG. 6a (B) Graph, in conjunction with FIG. 6a (A) Shape, is a schematic graphic illustration of the distribution of the flowing fluid 611's four mutually-scaled parameters: headway velocity 620.u, static pressure 630.P, absolute temperature 640.T, and M-velocity 650.M along the length of nozzle 610, constructed according to the principles of a preferred embodiment of the present invention to provide a linear function of M-velocity 650.M of the flowing fluid. The narrowest cross-section of the narrow throat 613 provides the "critical condition" point 618. Compressed and hot fluid 611 flows through the narrow throat 613, where the velocity picks up 621 such that M-velocity 650.M reaches the specific M-velocity $M_*=\sqrt{(\gamma-1)/\gamma}$ at the critical condition point 618. Ahead of the critical condition point 618, the pressure and temperature fall, correspondingly 631 and 641. Hot flowing fluid 611 crosses the critical condition point 618 and enters the widening stage of the narrow throat 613 and further divergent exhaust tailpipe 614 having an open outlet. Flowing fluid 611 expands there, and this expansion is optimized such that the extra-increase of velocity 622 is substantially smoothed; and the pressure and temperature extra-decrease, 632 and 642, correspondingly, are substantially smoothed as well, in contrast to that at the critical condition point 180 associated with the classic prior art rocket nozzle 100 of FIGS. 1b, 1c. The smoothed change of static pressure 630.P provides suppression of unwanted in general, acoustic waves, and, in particular, Mach waves. In practice, the suppression of Mach waves provides suppression of undesired vibrations that, in particular, especially important for fast accelerating vehicles.

It will be evident for a person skilled in the art that:
  If, in a particular case, the geometrical configuration of the shaped tunnel is such that, for a certain velocity $u_{in}$ of a fluid stream 611 at the inlet 617 and certain thermodynamic parameters, the condition of flow continuity Eq. (6.0) is satisfied without the forcedly establishing temperature distribution, then the condition of flow continuity (6.0) reverts into the prior art equation Eq. (1.a) described hereinabove in the subparagraph "De Laval Effect" referring to FIG. 1b;
  If, in general, the geometrical configuration of the shaped tunnel is gradually-smoothed or, in a particular case, the geometrical configuration of the shaped tunnel is trivial cylindrical, wherein, in any case, the linear size of the narrow throat (for instance, the diameter $D_{th}$) is of the same order of value as the thickness of the boundary layer near each of the walls 6A.WALLS, and if the fluid flow having the absolute temperature $T_{in}$ corresponding to the left point of the curve 640.T enters the tunnel with velocity $u_{in}$ corresponding to the left point of the curve 620.u, then a forcedly established temperature profile along the shaped tunnel corresponding to the curve 640.T provides for:
    the fluid stream static pressure decrease corresponding to the curve 630.P,
    the fluid stream velocity increase corresponding to the curve 620.u, and
    the fluid stream M-velocity linear increase corresponding to the curve 650.M; and
  In practice, if a substantial acceleration is desired, hardly, it is preferred to use the mentioned
  trivial cylindrical geometrical configuration assuming $\delta T_0(x)=0$ and provide the desired temperature distribution $T(x)$ using the forcedly established temperature $\delta T_0(x)$ only, but it is preferred to use at least an almost adapted geometrical configuration already providing the temperature distribution $T_{in}+\delta T_0(x)$ and use the degree of freedom to compensate for a lack of temperature distribution $\delta T_1(x)$ using the densely-arranged elemental thermoelectric devices 6A.TED.

A convergent-divergent jet-nozzle, constructed applying the condition of flow continuity Eq. (6.0) accompanied by the satisfying condition of the smoothed thermodynamic parameters of the flowing fluid 611 according to an exemplary embodiment of the present invention, allows the use of the enhanced de Laval jet-effect to accelerate incoming compressed and hot airstream 611 moving with low M-velocities to obtain outflowing accelerated and cooled jet-stream 616, reaching high M-velocities [i.e. M-velocities, higher than the specific M-velocity $M_*=\sqrt{(\gamma-1)/\gamma}$], in particular, high-subsonic velocities.

In view of the foregoing description referring to FIG. 6a, it will be evident to a person skilled in the art that one can use different criteria of the gradualness of u(x), T(x), P(x), ρ(x), and M(x), for different preferred optimizations of the convergent-divergent shape of a tunnel. Namely, the conditions, providing laminarity of the airstream motion, are:

if suppression of disturbances, which are capable of growing into turbulence, is the most preferred, then u(x) should be given as the linear function $u(x) = \bar{u}(x) = u_* + \alpha_u(x - x_*)$, where x is the x-coordinate at x-axis 615, and $\alpha_M$ is a positive constant defining a scale factor and having a sense of constant gradient of velocity spatial distribution, i.e. $\alpha_u = \partial \bar{u}(x)/\partial x$, and the function $\delta T_1(x)$ should be established such that the function $T(x) = T_{in} + \delta T_0(x) + \delta T_1(x)$ would satisfy to the condition of flow continuity Eq. (6.0); wherein because the higher the velocity of the moving stream 611 the shorter the possible response time of the TE devices 6A.TED: up to $2.5 \times 10^{-5}$ sec and shorter (as described hereinabove referring to FIG. 5a), the TE devices occupying a path of 5 mm are capable of preventing a local temperature jump, and so preventing an origination of a turbulent vortex bigger than 5 mm in a boundary layer moving with the velocity of 200 m/sec, and a hypersonic laminar flow (for instance, of 3500 m/sec) can be controlled in a long tunnel;

if suppression of Mach waves and body vibrations are the most preferred, then the function $\delta T_1(x)$ should be established such that the temperature-dependent function $M(x) = u(x)/\sqrt{\gamma R \times [T_{in} + \delta T_0(x) + \delta T_1(x)]}$ becomes given as the function $M(x) = \sqrt{2\{[P_0/\bar{P}(x)]^{(\gamma-1)/\gamma} - 1\}/\gamma}$, where $\bar{P}(x)$ is a linear function of the static pressure vs. x-coordinate: $\bar{P}(x) = P_* + \alpha_p(x - x_*)$, $P_*$ is the static pressure of the flowing fluid at the critical condition point $x_*$, and $\alpha_p = \partial \bar{P}(x)/\partial x$ is a constant gradient of the static pressure distributed along the x-axis within a specially shaped tunnel;

if the suppression of temperature jumps is the most preferred, then the function $\delta T_1(x)$ should be established such that the function $[T_{in} + \delta T_0(x) + \delta T_1(x)]$ is a linear function $\bar{T}(x)$ of the fluid temperature vs. x-coordinate: $\bar{T}(x) = T_* + \alpha_T(x - x_*)$, $T_*$ is the temperature of the flowing fluid at the critical condition point $x_*$, and $\alpha_T = \partial \bar{T}(x)/\partial x$ is a constant gradient of the fluid temperature distributed along the x-axis within a specially shaped tunnel;

if suppression of shock waves is the most preferred, then the function $\delta T_1(x)$ should be established such that the temperature-dependent function $M(x) = u(x)/\sqrt{\gamma R \times [T_{in} + \delta T_0(x) + \delta T_1(x)]}$ becomes given as the function $M(x) = \sqrt{2\{[\rho_0 \bar{\rho}(x)]^{(\gamma-1)} - 1\}/\gamma}$, where $\bar{\rho}(x)$ is a linear function of the fluid mass density vs. x-coordinate: $\bar{\rho}(x) = \rho_* + \alpha_\rho(x - x_*)$, $\rho_*$ is the mass density of said flowing fluid at the critical condition point $x_*$, and $\alpha_\rho = \partial \bar{\rho}(x)/\partial x$ is a constant gradient of the fluid mass density distributed along the x-axis within a specially shaped tunnel; and if a trade-off between all the mentioned suppressions is preferred; then the function $\delta T_1(x)$ should be established such that the temperature-dependent function $M(x) = u(x)/\sqrt{\gamma R \times [T_{in} + \delta T_0(x) + \delta T_1(x)]}$ becomes a linear function $\bar{M}(x) = M(x) = M_* + \alpha_M(x - x_*)$, where x is the x-coordinate at x-axis 615, and $\alpha_M$ is a positive constant defining a scale factor and having a sense of constant gradient of M-velocity spatial distribution, i.e. $\alpha_M = \partial \bar{M}(x)/\partial x$.

It will become further evident for a person, who has studied the present invention, that it is possible to compose a multi-stage nozzle composed of N nozzles each of which satisfies the condition of flow continuity Eq. (6.0); wherein the N nozzles, enumerated from 1 to N, are united together to join the N tunnels associated with the N nozzles, correspondingly, such that each of the N tunnels is a fragment of a resulting unbroken tunnel formed thereby as a whole; an n-th fragment, where n is an integer between 1 and N: $1 \leq n \leq N$, has the varying cross-sectional area characterized by a cross-sectional area profile function $A_n(x)$ of x expressed as an individual condition of flow continuity:

$$A_n(x) = \frac{A_{*n}\sqrt{(\gamma - 1)RT_n(x)}}{u_n(x)} \left( \frac{2}{\gamma + 1} + \frac{(u_n(x))^2}{(\gamma + 1)RT_n(x)} \right)^{\frac{\gamma + 1}{2(\gamma - 1)}}$$

where $A_{*n}$ is n-th constant, and the functions $u_n(x)$ and $T_n(x)$ are representing profiles of the fluid flow's headway velocity and absolute temperature, correspondingly, along the n-th fragment of the resulting unbroken tunnel length; the resulting unbroken tunnel as a whole is either converging, or divergent, or convergent-divergent, or two-stage convergent-divergent; or multi-stage convergent-divergent; wherein piecewise-monotonic profile functions u(x), P(x), ρ(x), T(x), and M(x), composed of associated gradually-smoothed monotonic profile functions concatenated together, all remain gradually-smoothed along the resulting unbroken tunnel as a whole, thereby, the multi-stage nozzle is applicable to convey:

in general, laminar flow to solve the problem of originated turbulence, and in particular, tiny portions of the fluid associated with an acoustic wave propagating within and along the tunnel to solve the problem of sound power dissipation.

Further, for the purposes of the present invention, the term "airfoil" or "actually-airfoil" should be understood as related to a wall shape and as specifying a convergent-divergent shape of a flow portion's streamlines aligned to the airfoil wall, wherein, in contrast to a seemingly-airfoil shape, the convergent-divergent shape calls for the condition of flow continuity Eq. (6.0) and at least one of the aforementioned conditions for the functions u(x) and T(x), thereby, providing laminarity of the flow portion motion.

In view of the foregoing description referring to FIG. 6a, it will be evident to a person skilled in the art that:

Ina more general case, when imaginary sagittal axis 615 is oriented at least partially in the vertical direction in the Earth's gravitational field, the condition of laminar flow should be corrected becoming different from the condition of flow continuity Eq. (6.0) by a component depending on the gravitational acceleration g, namely:

$$\frac{A}{A_*} = \frac{M_*}{M} \left( \frac{1 + \frac{\gamma}{2}M^2 + \frac{g\Delta h}{RT}}{1 + \frac{\gamma}{2}M_*^2} \right)^{\frac{\gamma + 1}{2(\gamma - 1)}} \quad \text{Eq. (6.0a)}$$

where Δh is a change of the flow effective height with respect to the critical condition point. It will be further evident to a person skilled in the art that, when the considered temperatures and M-velocities are sufficiently high to provide for the conditions: $g\Delta h/RT \ll 1$ and $g\Delta h/RT \ll \gamma M^2/2$ to be satisfied, the use of the condition of flow continuity in the form of Eq. (6.0) becomes justified;

Taking into account molecular interactions for flowing liquid or plasma, for which changes of the partial deep-stagnation pressure-a $\delta P_a$ become at least noticeably distributed in space, the generalized adiabatic compressibility parameter $\gamma$ in the condition of flow continuity Eq. (6.0) is not a constant but varies with the changes of the partial deep-stagnation pressure-a $\delta P_n$;

If the flowing molecular fluid is an ionized gas, i.e. plasma, controlled by an external magnetic field, then the specifically shaped walls 6A.WALLS of the tunnel can be imaginary, formed by streamlines of the flowing plasma subjected to and controlled by an action of the magnetic field;

When the shape of the tunnel is not completely optimized on one of the mentioned criteria either:
smoothing of the flowing fluid velocity, or
smoothing of the flowing fluid M-velocity, or
smoothing of the flowing fluid static pressure, or
smoothing of the flowing fluid temperature, or
smoothing of the flowing fluid mass density,
at least because the tunnel shape must be adapted to the initial velocity and thermodynamic parameters of the laminarly flowing hot-and-compressed compressible-expandable fluid 611, any of the desired optimizations is reachable by controlling the elemental TE devices 6A.TED of the surface matrix 6A.MATRIX while the densely-arranged elemental TE devices 6A.TED are capable of providing for the desired temperature at the locations corresponding to the elemental TE devices 6A.TED Peltier effect. Moreover, the forcedly established desired distributed temperature prevents the "separation-points" [like 1G.46 of FIG. 1e Scheme (D)] of breaking or jumping of all: the headway velocity, the static pressure, the absolute temperature, and the mass density nearby the tunnel walls 6A.WALLS. The feasibility of such a control is supported by the property of flowing fluid moving adjacent to an airfoil wall described hereinabove referring to FIG. 1e Graph (D). Namely, on the one hand, a tiny portion of the flow, moving adjacent to a solid surface, can be heated or cooled by the solid surface when getting the temperature of the solid surface and, on the other hand, a big portion of the flow, moving farther from the solid surface, is capable of removing of excess heat or reverting the reduced portion of the heat, correspondingly; wherein, on the one hand, the faster flow the faster heat-transmitting, and, on the other hand, the tiny portion always has the temperature of the solid surface. In other words, it is possible to optimize the fluid stream within the shaped tunnel by changing the temperature of the fluid stream using the Peltier effect originated by the surface matrix 6A.MATRIX of the elemental TE devices 6A.TED built-in into the specifically shaped walls 6A.WALLS of the tunnel;

As the surface matrix 6A.MATRIX of the elemental TE devices 6A.TED, built-in into the specifically shaped walls 6A.WALLS of the tunnel, is capable to transform the temperature differences between:
on the one hand, the inner side of the specifically shaped walls 6A.WALLS which contacts with the fluid stream 611 within the tunnel, and
on the other hand, the outer side of the tunnel, which contacts with the ambient fluid, into electricity due to the Seebeck effect, it becomes possible to optimize the shape of the tunnel such that to take into account the change in temperature caused due to pumping out the heat energy of the fluid stream 611 to produce the controllably consumed electric power; wherein the optimization is such that to maintain the laminarity of the fluid stream 611 within the tunnel and, thereby, to provide efficient functionality of the elemental TE devices 6A.TED use;

and

The parameter $\gamma$ is varying when the chemical composition of the flowing fluid is changing.

De Laval Retarding-Effect

FIG. 6b, composed of two parts: (A) Shape and (B) Graph, is a schematic illustration of an inverse convergent-divergent jet-nozzle.

FIG. 6b (A) Shape illustrates a sectional view of the inverse convergent-divergent jet-nozzle 650 in a sagittal plane. Convergent-divergent jet-nozzle 650, constructed according to the principles of a preferred embodiment of the present invention, as inverse de Laval nozzle, applied to retard a fast fluid-flow 651, streaming with a high M-velocity $M_{651}$, higher than the specific M-velocity $M_* = \sqrt{(\gamma-1)/\gamma}$. Convergent-divergent jet-nozzle 650 has the sectional shape mirror-symmetrically congruent to the sectional shape of the modified convergent-divergent jet-nozzle 610, shown in FIG. 6a (A) Shape, and oriented to oncoming fluid-flow 651 in the back direction. Namely, the shaped tunnel of the inverse convergent-divergent jet-nozzle 650 has opposite walls 6B.WALLS, which are either formed by or at least supplied with a surface matrix 6B.MATRIX of densely-arranged elemental thermoelectric devices 6B.TED. The triplet of dots 6B.DOT symbolizes that the elemental thermoelectric devices 6B.TED are arranged unbrokenly. A convergent funnel 652 having open inlet is as inverse divergent exhaust tailpipe 614 (FIG. 6a (A) Shape), narrow throat 653 comprises point 658 of the narrowest cross-section, and divergent exhaust tailpipe 654 is as inverse convergent funnel 612. Convergent funnel 652, narrow throat 653, and divergent exhaust tailpipe 654 have not real separation features between them. For the purpose of the present patent application narrow throat 653 is specified as a fragment of the inner tunnel having imaginary inlet 6531 and outlet 6532, wherein the term "principal interval" of x-axis has a sense as corresponding to the interval occupied by the specifically shaped tunnel, i.e. at least comprising narrow throat 653.

FIG. 6b (Graph), in conjunction with FIG. 6b (A) Shape, is a schematic graphic illustration of the distribution of the fluid 651's three parameters: headway velocity 660.u, static pressure 670.P, and temperature 680.T along the length of nozzle 650 calculated according to the condition of flow continuity Eq. (6.0) to provide a linear decrease in M-velocity of the flow. The linear function of M-velocity is not shown here.

The narrowest cross-section of the throat 653 provides the "critical condition" point 658, triggering the inverse de Laval jet-effect, according to the condition of flow continuity Eq. (6.0), that is observed as an effect of flow slowing, when the flow moves along convergent funnel 652, and further slowing, when the flow moves through the divergent stage of convergent-divergent jet-nozzle 650 downstream-behind the critical condition point 658. For the purposes of the present patent application, the term "de Laval retarding-effect" is introduced as relating to the inverse de Laval jet-effect. Fast fluid-flow 651 moves along convergent funnel 652, where, ahead of the critical condition point 658 of narrow throat 653, the velocity falls 661, and the pressure and temperature pick up, correspondingly 671 and 681. The velocity falls 661 such that M-velocity $M_{663}$, corresponding to marker 663, reaches the specific M-velocity $M_*=\sqrt{(\gamma-1)/\gamma}$ at the critical condition point 658. Fluid-flow 651 exits throat 653 and enters the widening divergent exhaust tailpipe 654, where fluid-flow 651 is subjected to an increase of cross-sectional area, and this action is optimized such that the decrease of M-velocity 662 is accompanied by a substantially smoothed increase of the pressure and temperature, 672 and 682, correspondingly. Slow hot-and-compressed fluid at position 656 outflows from wide exhaust tailpipe 654. Again, the smoothed change of static pressure 670.P provides suppression of unwanted Mach waves. In practice, the suppression of Mach waves provides suppression of undesired vibrations that, in particular, especially important for a fast decelerating flying vehicle.

In view of the foregoing description referring to FIG. 6b, it will be evident to a person skilled in the art that, on the one hand, to trigger the de Laval retarding-effect the high M-velocity $M_{651}$ must be low sufficient to reach the specific M-velocity M, while slowing in convergent funnel 652 and the convergent stage of throat 653. On the other hand, taking into account that, in practice, for the case wherein fluid-flow 651 is an airflow, the M-velocity is distributed in the direction normal to an adjacent surface such that decreases almost down to zero at the surfaces of convergent-divergent jet-nozzle 650's walls 6B.WALLS. Thus, a certain portion of fast fluid-flow 651 at the critical condition point 658 moves with the effective M-velocity equal to the specific M-velocity $M_*$ and is subjected to a convergent-divergent reshaping and to forcedly established distributed temperature in throat 653, thereby, the conditions for the de Laval retarding-effect triggering is satisfied for any high M-velocity $M_{651}$, higher than the specific M-velocity $M_*$.

In view of the foregoing description referring to FIGS. 6a and 6b, the de Laval jet-effect and the de Laval retarding-effect, both observed in the case of a converging flow, are specified as the following. The de Laval jet-effect is specified as an effect of a convergent flow portion convective acceleration, occurring, when the convergent flow portion moves with M-velocities lower than the specific M-velocity upstream-afore the critical condition point, reaches the specific M-velocity at the critical condition point, and moves with M-velocities higher than the specific M-velocity downstream-behind the critical condition point; and the de Laval retarding-effect is specified as an effect of a convergent flow portion warming and slowing, occurring, when the convergent flow portion moves with M-velocities higher than the specific M-velocity upstream-afore the critical condition point, reaches the specific M-velocity at the critical condition point, and moves with M-velocities lower than the specific M-velocity downstream-behind the critical condition point.

For the purposes of the present patent application, the terms "Venturi M-velocity", "de Laval M-velocity", "de Laval low M-velocity", and "de Laval high M-velocity" should be understood as the following:

- a Venturi M-velocity is defined as an M-velocity, lower than the specific M-velocity $M_*$ and low sufficient to cross a narrow throat with said M-velocity, lower than the specific M-velocity $M_*$;
- a de Laval low M-velocity is defined as an M-velocity lower than the specific M-velocity $M_*$ and high sufficient to reach the specific M-velocity $M_*$ at the critical condition point $x_*$;
- a de Laval high M-velocity is defined as an M-velocity higher than the specific M-velocity $M_*$ and low sufficient to reach the specific M-velocity $M_*$ at the critical condition point $x_*$; and
- a de Laval M-velocity is at least one of the de Laval low M-velocity and the de Laval high M-velocity.

In view of the foregoing description referring to FIG. 6b, it will be evident to a person skilled in the art that one can optimize the specifically shaped tunnel of convergent-divergent jet-nozzle 650 providing such conformity of the cross-sectional area of the open inlet and the forcedly established temperature distribution with the de Laval high M-velocity of flowing fluid crossing the open inlet, that the flowing fluid M-velocity is substantially smooth at the entering the open inlet. Furthermore, one can control the cross-sectional area of the open inlet and the forcedly established temperature distribution, according to the condition of flow continuity Eq. (6.0), providing conformity of the thermodynamic conditions at the open inlet with the variable M-velocity of the entering flowing fluid. This may become important, for example, to suppress vibrations of a fast slowing vehicle.

Two-Stacie Convergent-Divergent Jet-Nozzle

FIG. 6c is a schematic illustration of a two-stage convergent-divergent jet-nozzle 690 exposed to an incoming fast fluid flow 691, streaming with a high M-velocity $M_{691}$, higher than the specific M-velocity $M_*=\sqrt{(\gamma-1)/\gamma}$, i.e. with a de Laval high M-velocity. Two-stage convergent-divergent jet-nozzle 690 comprises an inner tunnel, constructed according to the principles of a preferred embodiment of the present invention, having opposite walls 6C.WALLS, which are either formed by or at least supplied with a surface matrix 6C.MATRIX of densely-arranged elemental thermoelectric devices 6C.TED. The triplet of dots 6C.DOT symbolizes that the elemental thermoelectric devices 6C.TED are arranged unbrokenly. The inner tunnel comprises the first and second convergent-divergent stages, separated by a divergent-convergent (widened) reservoir (cavity) 694. The first convergent-divergent stage performs the first-stage convergent inlet-funnel 692 gradually turning into the first-stage narrow convergent-divergent throat 693 having a local narrowest cross-section providing the first critical condition point 6981 and having an inverse-funnel shaped pipe leading to the widened reservoir 694. The second convergent-divergent stage comprises the second-stage narrow throat 696, having a local narrowest cross-section providing the second critical condition point 6982, and the second-stage divergent exhaust tailpipe 697.

Incoming fast fluid-flow 691 is gradually slowing down, becoming warmer and more thickened and compressed as moving along the first convergent-divergent stage to the widened reservoir 694. Then, slow hot-and-compressed fluid 695 further movies through the second convergent-divergent stage. The fluid flow is accelerating as moving through throat 696, where exceeds the specific M-velocity $M_*=\sqrt{(\gamma-1)/\gamma}$ downstream-behind the second critical condition point 6982.

The first and second convergent-divergent stages of the inner tunnel are characterized by cross-sectional area profile functions $A_1(x)$ and $A_2(x)$ of distance parameter x, such that:

$$A_1(x) = \frac{A_{*1}\sqrt{(\gamma-1)RT_1(x)}}{u_1(x)}\left(\frac{2}{\gamma+1}+\frac{(u_1(x))^2}{(\gamma+1)RT_1(x)}\right)^{\frac{\gamma+1}{2(\gamma-1)}} \quad \text{Eq. (6.1)}$$

$$A_2(x) = \frac{A_{*2}\sqrt{(\gamma-1)RT_2(x)}}{u_2(x)}\left(\frac{2}{\gamma+1}+\frac{(u_2(x))^2}{(\gamma+1)RT_2(x)}\right)^{\frac{\gamma+1}{2(\gamma-1)}} \quad \text{Eq. (6.2)}$$

where $A_{*1}$ and $A_{*2}$ are the minimal cross-sectional areas of the first-stage narrow throat 693 and the second-stage narrow throat 696, correspondingly, and the functions, on the one hand, $u_1(x)$ and $T_1(x)$ and, on the other hand, $u_2(x)$ and $T_2(x)$ $u_2(x)$ are representing profiles of the fluid flow headway velocities and absolute temperatures in the first and second convergent-divergent stages, correspondingly, along the inner tunnel length. The equations Eq. (6.1) and Eq. (6.2) are particular cases of the condition of flow continuity Eq. (6.0) described hereinbefore with references to FIGS. 6a and 6b, correspondingly. The cross-sectional area profile $A_{ca}(x)$ of the widened reservoir 694 is such that a function $A(x)$, which is composed of sequentially concatenated cross-sectional area profile functions $A_1(x)$, $A_{ca}(x)$, and $A_2(x)$, is smooth.

Jetstream 699, outflowing through divergent exhaust tailpipe 697, is faster and colder than slow hot-and-compressed fluid 695, yet to be entered into the second convergent-divergent stage, as described hereinbefore tracing after incoming compressed and hot airstream 611 with reference to FIGS. 6a and 6b. Fast outflowing jetstream 699 has a cross-section wider than incoming fast fluid-flow 691 at the input of convergent inlet-funnel 692. So, the M-velocity $M_{699}$ of fast outflowing jetstream 699 is higher than the M-velocity $M_{691}$ of fast fluid-flow 691, according to the condition of flow continuity Eqs. (6.1) and (6.2).

Thereby, two-stage convergent-divergent jet-nozzle 690 operates as a jet-booster based on the enhanced de Laval jet-effect launching outflowing jetstream 699, which is faster than the fast fluid-flow 691 incoming with the de Laval high M-velocity $M_{691}$, i.e. higher than the specific M-velocity $M_*=\sqrt{(\gamma-1)/\gamma}$. This is one more teaching of the present invention.

In view of the foregoing description referring to FIGS. 6a, 6b, and 6c in combination with the foregoing description referring to FIGS. 5a and 5b, it will be evident to a person skilled in the art that, if a tunnel is preliminary optimized for a certain fluid, laminarly flowing within the tunnel with certain distributions of velocity and thermodynamic parameters, but, actually, the fluid is characterized by other thermodynamic parameters and enters the tunnel with another velocity, it remains possible to optimize the fluid stream within the shaped tunnel by forced establishing the temperature distribution of the fluid stream using the Peltier effect originated by a surface matrix of densely arranged elemental TE devices built-in into the walls of the tunnel.

Optimal Implementation of Convergent-Divergent Jet-Nozzle

FIG. 7 shows comparative graphs 700 for the dependencies of the nozzle tunnel extension ratio vs. the airflow M-velocity in an adiabatic process, calculated, on the one hand, using the classical model described, in particular, in D11 and, on the other hand, suggested in prior arts A01, A02, and A03 equation Eq. (1.a), namely, curves 703 and 704 correspondingly; wherein the vertical axis 701 is the ratio $A/A_*$, and the horizontal axis 702 is the airflow M-velocity in an adiabatic process measured in temperature-dependent Mach numbers. The dashed curve 703 is the convergent-divergent cross-sectional area ratio $A/A_*$ profile vs. the airflow M-velocity, calculated using classical equations derived from the Euler equations of fluid motion. The solid curve 704 is the convergent-divergent cross-sectional area ratio $A/A_*$ profile vs. the airflow M-velocity of an adiabatic motion, calculated using the prior art equation Eq. (1.a) derived from the specified equations of fluid motion in an adiabatic process described in A01, A02, and A03. The critical condition point 708 corresponds to the specific M-velocity $M_*=\sqrt{(\gamma-1)/\gamma}$ 0.5345. Comparative graphs 700 show that one needs in a substantially extra-widened nozzle tunnel 704 to reach the airflow M-velocities substantially higher than 1 Mach.

One of the primary ideas of the present invention is that the desired improved dependence 704 is reachable using an arbitrary smoothly shaped tunnel if the temperature distribution along the tunnel's walls is forcedly controlled to satisfy the condition of flow continuity Eq. (6.0).

Therefore, a convergent-divergent jet-nozzle, constructed according to an exemplary embodiment of the present invention, allows for a controllably-increased efficiency of the jet-effect for use at high-subsonic, transonic, supersonic, and hypersonic velocities that can be applied to rocket nozzle design.

Taking into account The Bernoulli Theorem written in the form via M-velocity:

$$\frac{T_0}{T} = \left(\frac{P_0}{P}\right)^{\frac{\gamma-1}{\gamma}} = \left(\frac{\rho_0}{\rho}\right)^{\gamma-1} = 1 + M^2\frac{\gamma}{2}, \quad \text{Eq. (7.1)}$$

where $P_0$, $\rho_0$, and $T_0$ are so-called stagnation thermodynamic parameters: the static pressure, the mass density, and the absolute temperature, and M is the M-velocity, one can derive conditions for the stagnation thermodynamic parameters and the thermodynamic parameters of the fluid flow: $P_e$, $\rho_e$, and $T_e$ are so-called stagnation thermodynamic parameters: the static pressure, the mass density, and the absolute temperature, all at the exhaust-nozzle outlet to design an improved convergent-divergent nozzle to originate the enhanced de Laval effect. The exhaust-nozzle outlet M-velocity $M_e$ is bonded with the ratios $P_0/P_e$ and $T_0/T_e$ as follows:

$$M_e = \sqrt{\frac{2}{\gamma}}\sqrt{\left(\frac{P_0}{P_e}\right)^{\frac{\gamma-1}{\gamma}}-1} \quad \text{Eq. (7.1a)}$$

$$\frac{P_0}{P_e} = \left(\frac{2+\gamma M_e^2}{2}\right)^{\frac{\gamma}{\gamma-1}} \quad \text{Eq. (7.1b)}$$

$$\frac{T_0}{T_e} = \left(\frac{2+\gamma M_e^2}{2}\right) \quad \text{Eq. (7.1c)}$$

$$\frac{\rho_0}{\rho_e} = \left(\frac{2+\gamma M_e^2}{2}\right)^{\frac{1}{\gamma-1}} \quad \text{Eq. (7.1d)}$$

In contrast to a frequently used condition, saying that both: the de Laval jet-effect and the velocity of sound are reachable when the ratio $P_0/P_e$ is of 1.893, equation Eq. (7.1b) shows that, on the one hand, to obtain the de Laval jet-effect [i.e. condition $M_e>M_*$] for air using a nozzle tunnel having an optimal convergent-divergent shape, one must provide the ratio $P_0/P_*$ at least of 1.893, and, on the other hand, to accelerate an air portion up to the velocity of sound [i.e. $M_e=1$], one must provide the ratio $P_0/P_e$ at least of 6.406. Equation Eq. (7.1c) says that, on the one hand, to obtain the de Laval jet-effect for air utilizing a nozzle tunnel having an optimal convergent-divergent shape, one must provide the ratio $T_0/T_*$ at least of 1.2; and, on the other hand, to accelerate an air portion up to the velocity of sound, one must provide the ratio $T_0/T_e$ at least of 1.7. So, the principle condition either $1.893 < P_0/P_e < 6.406$ or/and $1.2 < T_0/T_e < 1.7$ can provide the de Laval jet-effect occurring without the phenomenon of shock sound-wave emission that is one of the primary principles of the present invention. Thus, a convergent-divergent jet-nozzle tunnel, constructed according to an exemplary embodiment of the present invention and exploited in accordance with the principle conditions, allows for an optimal implementation and efficient use of an enhanced jet-effect at de Laval M-velocities.

Use of Optimal Convergent-Divergent Jet-Nozzle

In view of the foregoing description referring to FIGS. 6a, 6b, and 6c in combination with the description of sub-paragraphs "Horn as Sound-Booster" referring to prior art FIG. 3a and "External Ear as Sound Booster" referring to prior art FIG. 3b, it will be evident to a person skilled in the art that:

an optimized at least one of converging, divergent, convergent-divergent, and two-stage convergent-divergent nozzle can play the role of an enhanced acoustic waveguide capable to:
  reduce a turbulent component of fluid motion accompanying acoustic waves and causing dissipation of a propagating sound; and
  amplify the intensity of acoustic waves at the expense of both the heat energy and the turbulence of fluid and so to boost the loudness of sound;
and
the exponentially-divergent horn n.C1 of gramophone 1n.C (FIG. 3a) functions as the divergent exhaust tailpipe 614 of the convergent-divergent nozzle 610 (FIG. 6a), but not optimized according to the condition of flow continuity Eq. (6.0) yet.

Optimized Horn for Gramophone

FIG. 7a case (A) shows schematically a divergent horn 7a.A, submerged in a molecular fluid (for the sake of concretization, the molecular fluid is air) and exposed to a portion of sound 7a.A0 entering an open inlet 7a.A1 and outflowing from the open outlet 7a.A2 of the divergent horn 7a.A. The specific conveying motion of the air mass density is interpreted as composed of two complementary alternating movements of positive and negative changes of air mass density, wherein both alternating movements are in the same direction (that is the direction of sound propagation) and, when in open space or at the open inlet 7a.A1, with the M-velocity of 1 Mach. The specific conveying motion of the air mass density is subjected to influence within the divergent horn 7a.A. The cross-sectional area of the divergent horn 7a.A varies along the divergent horn 7a.A length, i.e. along a sagittal axis 7a.A5, in accordance with the condition of flow continuity Eq. (6.0) such that to provide substantially laminar motion of the positive and negative changes of air mass density within the divergent horn 7a.A due to the enhanced de Laval jet-effect applied to the moving positive and negative changes of air mass density, moving with the high M-velocity, higher than the specific M-velocity. In particular, when the open sound-inlet has a cross-sectional area $A_{1,1}$, the cross-sectional area profile $A(x)$ is a divergent cross-sectional area profile function $A_{ho}(x)$ expressed as:

$$A_{horn}(x) = \frac{A_{in}\sqrt{\gamma RT(x)}}{u(x)} \left( \frac{2RT(x) + u^2(x)}{(2+\gamma)RT(x)} \right)^{\frac{\gamma+1}{2(\gamma-1)}},$$

where $\gamma$ is an adiabatic compressibility parameter of the fluid and $u(x)$ is a monotonically-increasing gradually-smooth function of x representing a profile of the sound propagation velocity, i.e. a conveying velocity of the fluid tiny portion moving within and through the divergent horn (the fluid tiny portion is the mentioned interpretation of the positive and negative changes of air mass density associated with the propagating sound).

The enhanced de Laval jet-effect, in particular, results in extra-acceleration of the laminar motion of the positive and negative changes of air mass density within the divergent horn 7a.A at the expense of the air heat understood in the wide sense including the concomitant turbulence inherently accompanying the sound. Thus, the portion of sound 7a.A0 becomes boosted due to the enhanced de Laval jet-effect.

In practice, sometimes, not optimized functioning of the divergent horn 7a.A occurs at least because of other portions 7a.A6 and 7a.A7 of ambient sound enter the divergent horn 7a.A through the sidewalls of the divergent horn 7a.A. To prevent the undesired reason, the divergent horn 7a.A is further supplied with a matrix TE device 7a.A4 covering the surface of the divergent horn 7a.A. The matrix TE device 7a.A4, when functioning like the multi-module thermoelectric device 5R.DEVICE comprising a matrix of a multiplicity of N ELEMENTAL DETECTORS OF SOUND 5R.02 which results in the zero 5R.4.OUTPUT as described hereinabove referring to FIG. 5c, is capable to isolate the entered portion 7a.A0 from the interfering portions 7a.A6 and 7a.A7.

It will be evident for a person, who has studied the present invention, that the ELEMENTAL SOURCE OF SOUND 5P.0A described hereinabove referring to FIG. 5a Case (A), can play the role of a source of the sound 7a.A0, and so the ELEMENTAL SOURCE OF SOUND 5P.0A supplied with the divergent horn 7a.A performs an efficiently functioning megaphone.

Phonendoscope and Sound Booster

FIG. 7a cases (B) and (C) are schematic illustrations of two-stage convergent-divergent nozzles 7a.B and 7a.C, destined for amplifying the intensity of an entering portion of sound 7a.B0 and 7a.C0, correspondingly. The enhanced phonendoscope 7a.B and sound booster 7a.C, both constructed according to the principles of the present invention, comprise common configurational elaborated features, and while the two-stage convergent-divergent nozzle 7a.B is configured to be used as an enhanced phonendoscope 7a.B, the two-stage convergent-divergent nozzle 7a.0 is configured to have a corpus 7a.C1 ergonomically adapted to a human's ear canal, thereby, allowing to be used as a sound booster 7a.0 ergonomically adapted to a human's ear 7a EAR. The mentioned common configurational elaborated features are related to optimized inner canals of the nozzles 7a.B and 7a.0 which are the optimized two-stage convergent-divergent tunnels 7a.B2 and 7a.C2, having:

an open sound-inlet 7a.B5 and 7a.C5 of the cross-sectional area $A_{IN}$,
an open sound-outlet 7a.B6 and 7a.C6 of the cross-sectional area $A_{OU}$, and
shaped portions of varying cross-sections as follows:
  a convergent funnel 7a.B41 and 7a.C41,
  a first-stage narrow throat 7a.B42 and 7a.C42 having a local minimal cross-sectional area $A_{th1}$, a divergent-convergent (widened) cavity 7a.B43 and 7a.C43 having a local maximal cross-sectional area $A_{ca}$, a second-stage narrow throat 7a.B44 and 7a.C44 having a local minimal cross-sectional area $A_{th2}$, wherein $A_{th2}$ at most equal to $A_{th1}$, and divergent funnel 7a.B45 and 7a.C45, having an open sound-outlet 7a.B6 and 7a.C6, correspondingly.

Sound 7a.C0, when entering the open inlet 7a.C5, becomes subjected to the action of the optimized convergent-divergent tunnel 7a.C2 such that, first, when the sound 7a.C0 propagates through convergent funnel 7a.C41, the sound intensity becomes, on the one hand, decreased because the mass density change conveying with the velocity of sound becomes subjected to retarding due to the de Laval retarding effect applied to the mass density change moving with the high velocity, higher than the specific M-velocity, and on the other hand, increased due to:

z superposition of spatially distributed portions of sound becoming concentrated and joint in-phase, thereby, resulting in constructive interference, transformation of the internal heat energy of fluid into the acquired power of sound, as a manifestation of the Venturi effect, applied to longitudinal oscillation motion with the particle velocity, and suppression of concomitant turbulence, power of which, in the final analysis, becomes transformed into the acquired power of sound, as a phenomenon accompanying the Venturi effect applied to longitudinal oscillation motion with the particle velocity;

and second, interrelations between the cross-sectional areas $A_{in}$, $A_{th1}$, $A_{ca}$, $A_{th2}$ and $A_{ou}$ satisfying conditions as follows:

(a)

$$\frac{A_{in}}{A_{th1}} \geq \sqrt{\left(\frac{\gamma-1}{\gamma}\right)\left(\frac{2+\gamma}{\gamma+1}\right)^{\frac{\gamma+1}{(\gamma-1)}}},$$

so, when the sound propagates through the first-stage narrow throat 7a.C42, the sound intensity is predetermined by the conveying velocity $u_{convey}$ and particle velocity $u_{particle}$, wherein the local conveying M-velocity is of $M_* = \sqrt{(\gamma-1)/\gamma}$ when crossing the narrowest cross-section within the first-stage narrow throat 7a.C42;

(b) $A_{ca}/A_{th1} > 1$ so, when the sound propagates through widened cavity 7a.C43, the local conveying M-velocity becomes lower than the specific M-velocity $M_*$, due to the de Laval retarding effect;

(c) $A_{ca} > A_{ch2}$, so, when the sound propagates through the second-stage narrow throat 7a.C44, the local conveying M-velocity reaches the specific M-velocity $M_*$, due to the de Laval jet-effect;

(d) $A_{th1} \geq A_{th2}$, and (e)

$$\frac{A_{ou}}{A_{th2}} > \sqrt{\left(\frac{\gamma-1}{\gamma}\right)\left(\frac{2+\gamma}{\gamma+1}\right)^{\frac{\gamma+1}{(\gamma-1)}}},$$

so, when the sound propagates further through divergent funnel 7a.C45, the sound intensity becomes increased because the mass density change conveying with the varying velocity of sound becomes subjected to extra-acceleration due to the enhanced de Laval jet-effect, optimized to suppress turbulent component of the complicated movement of fluid when conveying the sound and applied to the mass density change moving with the high velocity, higher than the specific M-velocity; this effect of sound boosting is similar to that which occurs when using a classic gramophone supplied with an exponentially-divergent horn as described hereinabove in THE BACKGROUND OF THE INVENTION referring to prior art FIG. 3a, but now the divergent funnel configuration is optimized according to the condition of flow continuity Eqs. (6.1) and (6.2), namely, the cross-sectional area profile smooth function A(x) is composed of sequentially concatenated cross-sectional area profile functions $A_1(x)$, $A_{ca}(x)$, and $A_2(x)$, wherein:

$A_1(x)$ is cross-sectional area profile function of the first convergent-divergent fragment, which provides for the enhanced de Laval retarding-effect resulting in deceleration of the fluid tiny portion moving laminarly, $A_2(x)$ is cross-sectional area profile function of the second convergent-divergent fragment, which provides for the enhanced de Laval jet-effect resulting in acceleration of the fluid tiny portion moving laminarly, and the cross-sectional area profile functions $A_1(x)$ and $A_2(x)$ are given by the equations expressed as:

$$\begin{cases} A_1(x) = \frac{A_{th1}\sqrt{(\gamma-1)RT_1(x)}}{u_1(x)}\left(\frac{2RT_1(x)+u_1^2(x)}{(\gamma+1)RT_1(x)}\right)^{\frac{\gamma+1}{2(\gamma-1)}}, \\ A_2(x) = \frac{A_{th2}\sqrt{(\gamma-1)RT_2(x)}}{u_2(x)}\left(\frac{2RT_2(x)+u_2^2(x)}{(\gamma+1)RT_2(x)}\right)^{\frac{\gamma+1}{2(\gamma-1)}}, \end{cases}$$

where:

$A_{th1}$ and $A_{th2}$ are local minimal cross-sectional areas of narrow throats of the first and second convergent-divergent fragments, correspondingly;

$u_1(x)$ is a monotonically-decreasing gradually-smooth function of x, representing the conveying velocity $u_{convey}$ within the first convergent-divergent fragment, $T_1(x)$ is a monotonically-increasing gradually-smooth function of x, representing the temperature of the fluid within the first convergent-divergent fragment, $u_2(x)$ is a monotonically-increasing gradually-smooth function of x, representing the conveying velocity $u_{convey}$ within the second convergent-divergent fragment, $T_1(x)$ is a monotonically-decreasing gradually-smooth function of x, representing the temperature of the fluid within the first convergent-divergent fragment, $A_{ca}(x)$ is cross-sectional area profile function of the divergent-convergent cavity defined between $x_{b,i}$ and $x_{a,2}$ such that providing for the enhanced Venturi effect as a gradually-smooth function $u_{ca}(x)$ of x, representing a velocity profile of the tiny portion of the fluid moving in the divergent-convergent cavity between the first and second narrow throats, is such that an associated M-velocity function $M_{ca}(x)$, remains lower than the specific M-velocity $M_* = \sqrt{(\gamma-1)/\gamma}$; and $u_1(x)$, $u_{ca}(x)$, and $U_2(x)$ are such that, when sequentially-concatenated, as a whole form a gradually-smooth function u(x) of x, representing a velocity profile of the fluid tiny portion moving within and through the two-stage convergent-divergent nozzle's through-hole tunnel-waveguide;

thereby, the conditions altogether providing for that, a portion of the propagating sound, entering the open sound-inlet, propagating through the two-stage convergent-divergent tunnel, and becoming launched from the open sound-outlet, becomes characterized by an increased Umov-vector and so has an amplified loudness.

In view of the foregoing description of the sub-paragraphs "Optimized Horn For Grammophone" referring to FIG. 7a case (A) and "Phonendoscope and Sound Booster" referring to FIG. 7a cases (B) and (C) in combination with the description of sub-paragraphs: "Sound as Complicated Movement in Molecular Fluid" referring to prior art FIG. 3a and "External Ear as Sound Booster" referring to prior art FIG. 3b, it becomes evident to a person who has studied the present patent application that, conceptually:

The external ear 1L.0 (FIG. 3b) functions as the described passive sound booster 7a.C, but not optimized for suppression of concomitant turbulences according to the condition Eq. (6.0) yet;

An optimized two-stage convergent-divergent nozzle, optimized for suppression of concomitant turbulences according to the condition of flow continuity Eq. (6.0), can be adapted to a diversity of applications as a wave-guiding and sound-amplifying nozzle for detectors or launchers of sound, for instance:

the optimized two-stage convergent-divergent nozzle 7a.B can be utilized as a phonendoscope; and the optimized two-stage convergent-divergent nozzle 7a.0 can be miniaturized to become adapted to the size of a human's ear canal and play a role of a passive sound booster utilized for amplifying the loudness of a portion of ambient sound; and An optimized divergent horn, optimized for widening a front of sound accompanied by suppression of concomitant turbulences according to the condition of flow continuity Eq. (6.0), can be scaled to play the role of an enhanced generalized gramophone utilized for boosting a sound launched by a source of acoustic waves.

It will be also evident for a person, who has studied the present invention, that each of the two-stage convergent-divergent nozzles 7a.B and 7a.C, when supplied with the two-stage sound amplifier 5S.DEVICE described hereinabove referring to FIG. 5d, can play the role of an efficiently functioning hearing aid.

Compressor Supplied by Convergent-Divergent Jet-Nozzle

FIG. 7b, having two parts: Case (A) and Case (B), is a schematic illustration of a pressure-transformer 710.P and a heat-transformer 710.H, correspondingly, both constructed according to the principles of the present invention, to accelerate a compressed and heated air portion.

In pressure-transformer 710.P, the optimized convergent-divergent jet-nozzle 710 with the critical condition point 718 comprises a reservoir 712 where an air portion 711 is compressed and thereby heated due to a piston 714. As it was described hereinabove referring to FIG. 7, to trigger the enhanced de Laval jet-effect, one needs either to compress air portion 711 up to the static pressure $P_0=1.893 \times P_a$, where $P_a$ is the ambient pressure (for instance, $P_a=1$ bar), or, alternatively, to heat the air portion 711 up to the absolute temperature $T_0=1.2 \times T_a$, where $T_a$ is the ambient temperature (for instance, $T_a=298$ K), wherein the static pressure $P_0$ and increased temperature $T_0$ are interrelated. In this case, if the divergent portion 710 of the optimized de Laval nozzle has the outlet cross-sectional area wider than the cross-sectional area at the critical condition point 718 by the factor $1/M_* = \sqrt{\gamma/(\gamma-1)}$, the M-velocity of the outflowing stream 713 is about 1 Mach. To compress air portion 711 up to pressure $P_0=1.893$ bar one needs to consume the energy $E_0$ estimated as $(P_0-P_a)V_0$, where $V_0$ is the volume of the gas reservoir 712. For $V_0=1$ m$^3$, the energy $E_0$ is estimated as $E_0 \approx 0.9 \times 10^5$ J=90 kJ. The volume $V_0$ is composed of approximately n $(P_0/P_a) \times 1000/22.4 = 286$ moles of gas. When air portion 711 is accelerated and expanded in de Laval-like nozzle 710, it acquires kinetic energy at the expense of thermodynamically related pressure and temperature decrease; wherein the pressure decreases from $P_0$ to $P_a$ and the temperature decreases from $T_0$ to $T_a$. Again, consider the air portion 711 acceleration in hypothetically optimal convergent-divergent jet-nozzle 710 such that the velocity of the outflowing stream 713 is almost as the speed of sound, i.e. the exhaust M-velocity is of $M_e$ 1, i.e. such that $T_0/T_e=1.7$ and $(T_0-T_e) = T_0(1-1/1.7) = 0.412T_0$, where $T_a$ is the absolute temperature of the cold outflowing stream 713 wherein the temperature difference $(T_0-T_a) = 0.412T_0$ is estimated as 123 C. In this case, the acquired kinetic energy equals $K=n \times (T_0-T_e)R$ that is estimated as:

$$K = n \times 0.412 T_0 R \approx 286 \times 0.412 \times 298 \times 278 \approx 9{,}761{,}674 \text{ J} = 9{,}762 \text{ kJ}.$$

This estimation shows that, taking into account a 15% net-efficiency of an engine pushing the piston 714, the triggered acquired kinetic energy K may exceed the triggering consumed energy $E_0$ at least at subsonic velocities by the factor of about 16 times. The acquired kinetic energy can be applied to a vehicle motion or to an engine for electricity generation with positive net-efficiency. On the other hand, the acquiring of kinetic energy is accompanied by the air temperature decrease, therefore, such a convergent-divergent jet-nozzle can be applied to cooling of a vehicle engine as well as be used either for electricity harvesting by means of a Peltier element operating as a thermoelectric generator and/or as an effective condenser of vapor to water.

In heat-transformer 710.H, the optimized convergent-divergent jet-nozzle 710.B, optionally, unbrokenly covered with a multiplicity of thermoelectric devices 717.B similar to the surface matrix 6A.MATRIX of densely-arranged elemental thermoelectric devices 6A.TED described hereinabove referring to FIG. 6a, has the outlet cross-sectional area wider than the cross-sectional area at the critical condition point 718.B by the factor $1/M_* = \sqrt{\gamma/(\gamma-1)}$ and supplied with a reservoir 712.B, a wall of which is covered with another multiplicity of thermoelectric devices 714.B and has a multiplicity of relatively long and narrow through-hole pipes 715.6. Shape of the through-hole pipes 715.8 is not optimized for a laminar motion of flow neither if entering the reservoir 712.B nor if outlawing back to ambient space.

Inner air portions 711.6 and outer air portions 716.6, both are subjected to the functioning of the multiplicity of thermoelectric devices 714.B such that, on the one hand, the inner air portions 711.B are heated and thereby compressed and, on the other hand, the outer air portions 716.B are cooled and thereby thickened. When the absolute temperature $T_0$ of the inner portions 711.6 is kept equal $1.2 \times T_a$ [i.e. $T_0=357.6$K, i.e. $\Delta T=(T_0-T_a)=59.6$ C that, normally, is reachable by a thermoelectric device], the condition for triggering the enhanced de Laval jet-effect becomes satisfied. The optional covering with the multiplicity of thermoelectric devices 717.6 is for controlling the temperature distribution dependent on the velocity of the inner portions 711.6, which (the velocity) in turn, is determined by the functioning of the multiplicity of thermoelectric devices 714.8; the controlling is to provide laminarity of flow 719.6 within the optimized convergent-divergent jet-nozzle 710.6. Points 718.13 symbolize that the thermoelectric devices 717.8 cover the optimized convergent-divergent jet-nozzle 710.6 unbrokenly. The asymmetry of conditions that, on the one hand, the temperature distribution along the relatively long pipes 715.B is not optimized for a laminar motion of the flow, and on the other hand, the tunnel 710.8 is optimized for a laminar motion of the flow, causes a tendency of the inner air portions 711.8 to move directionally through the optimized convergent-divergent jet-nozzle 710.6. As a result, the reservoir 712.8 is permanently filled with the fresh outer portions 716.6 via the through-hole pipes 715.6 such that the velocity of the outflowing stream 713.8 is almost as the speed of sound. Optionally, the pipes 715.6 can be fulfilled as valvular conduits (Testa valves) to increase the efficacy of the jet-nozzle 710.6.

Again, $T_0/T_a=1.7$ and $(T_0-T_e)=T_0(1-1/1.7)=0.412T_0$, where $T_a$ is the absolute temperature of the cold outflowing stream 713.8 wherein the temperature difference $(T_0-T_a)=0.412T_0$ is estimated as 123 C. In this case, the acquired kinetic energy equals $K=n\times(T_0-T_e)R$ that is estimated as:

$$K=n\times0.412T_0R\approx286\times0.412\times298\times278\approx9,761,674 \text{ J}=9,762 \text{ kJ}.$$

Taking into account a 15% net-efficiency of the multiplicity of the thermoelectric device, the triggered acquired kinetic energy K may exceed the triggering consumed energy $E_0$ at least at subsonic velocities by the factor of about 16 times. As the flow 719.B within the optimized convergent-divergent jet-nozzle 710.B becomes colder than the ambient fluid, the multiplicity of thermoelectric devices 717.B can be also used for harvesting of electricity.

In view of the foregoing description referring to FIG. 7b Case (B), it will be evident to a person skilled in the art that, instead of Peltier elements (thermoelectric devices 714.B), any kind of electric heater (i.e. a thermoelectric device in the broad sense) can be used to increase the temperature of the inner air portions 711.B, because the inertness of temperature difference controlling is not critical for a steady-established and relatively slow intake of air portions 711.B.

Flying Capsule as Dragging-Jet Engine

FIG. 7c is a schematic sectional view of a flying capsule corpus 720 in a sagittal plane. Capsule corpus 720, constructed according to the principles of the present invention, has an outer airfoil side 729 covered with a surface matrix thermoelectric device 729.TED and inner walls, which are formed by another surface matrix thermoelectric device 722.TED, in turn, forming a through-hole corridor having:
an inner converging reservoir 721 as a dragging compressor having an open inlet 725 exposed to ambient wind 724, and further
a hypothetically optimal convergent-divergent tunnel 722 with a narrow throat comprising a critical condition point 728 and divergent exhaust tailpipe having an open outlet 726 of area $A_e$.

The velocity of ambient air 724 relative to capsule 720 is $u_a$ which is substantially lower than the critical condition velocity u, corresponding to the specific M-velocity $M_*=\sqrt{(\gamma-1)/\gamma}$. The wind portion 727 enters the inner converging reservoir 721 with a velocity equal to $u_{in}$. The area $A_{in}$ of inlet 725 is substantially wider than the area $A_*$ of the throat's cross-section at the critical condition point 728 such that air portion 727 crosses the area $A_*$ at the critical condition point 728 with the maximal reachable M-velocity equal to the specific M-velocity $M_*=\sqrt{(\gamma-1)/\gamma}$, and so the enhanced de Laval jet-effect is expected in the divergent exhaust tailpipe having outlet 726, where the velocity of outflowing jetstream 723 reaches a value $u_{723}$ higher than the velocity $u_*$ corresponding to the critical condition point 728. In an exemplary embodiment of the present invention, an optimal shape of tunnel 722 and forcibly established temperature distribution along the inner walls using the surface matrix thermoelectric device 722.TED, both provide that the value $u_{723}$ is lower than the speed of sound $u_{sound}$. Outflowing jetstream 723 brings the kinetic power acquired at the expense of the flows warmth. The acquired kinetic power of outflowing jetstream 723 may be high as or even become higher than the power consumed to compensate drag, defined by a drag coefficient corresponding to a concave shape of the inner converging reservoir 721, and thereby to maintain the flying velocity $u_a$ of capsule 720. Capsule 720 is interpreted as a motionless dragging jet engine.

Outer airfoil side 729 of capsule corpus 720 provides laminar-like flowing of wind outer sub-portions 731 and 732, moving adjacent to outer airfoil side 729 and being subjected to both: forcibly established temperature distribution using the surface matrix thermoelectric device 729.TED and the Coanda-effect operation and, thereby, attracted to the nearby surfaces of outer airfoil side 729. Outflowing jetstream 723 having the decreased static pressure sucks outer sub-portions 731 and 732. The cumulative confluence of sub-portions 731, 732, and 723 constitutes the cumulative jetstream 734, associated with the airfoil corpus of capsule 720. In general, the formed cumulative jetstream 734, composed of sub-portions 731, 732, and 723, is turbulent; however, in an optimal case, the turbulence can be suppressed substantially. For simplicity, consider a case of a laminar-like cumulative jetstream 734, "bordered" by streamlines 733. On the one hand, the velocities of outer sub-portions 731 and 732, being lower than the critical condition velocity $u_*$, are increasing as the attracted outer sub-portions enter the space of cumulative jetstream 734, where the velocities increase is accompanied by a constriction of outer sub-portions 731 and 732, in accordance with the condition of flow continuity Eq. (6.0). On the other hand, at outlet 726, the velocity of inner sub-portion 723 is of value $U_{723}$ higher than the critical condition velocity $u_*$. According to the condition of flow continuity Eq. (6.0), the velocity of inner sub-portion 723 is decreasing as the sub-portion enters the space of cumulative jetstream 734, where inner sub-portion 723 is constricting as well. If the case is optimized such that both constrictions are identical, cumulative jetstream 734 is expected to be laminar-like indeed. Bordering streamlines 733 constitute an imaginary convergent-divergent jet-nozzle comprising a narrow throat having the minimal cross-sectional area at the outer critical condition point 738, where the effective M-velocity of cumulative jetstream 734 reaches the specific value $M_*=\sqrt{(\gamma-1)/\gamma}$. If, upstream-afore the outer critical condition point 738, the effective M-velocity of cumulative jetstream 734 is lower than the specific M-velocity $M_*$, then the M-velocity of cumulative jetstream 734 is increasing as cumulative jetstream 734 moves such that outflowing divergent portion 735 has M-velocity higher than $M_*$ downstream-behind the outer critical condition point 738; and vice versa, if, upstream-afore the outer critical condition point 738, the effective M-velocity of cumulative jetstream 734 is higher than the specific M-velocity $M_*$, then the M-velocity of cumulative jetstream 734 is decreasing as cumulative jetstream 734 moves such that outflowing divergent portion 735 has the M-velocity lower than the specific M-velocity $M_*$.

In view of the foregoing description referring to FIG. 7c, it will be evident to a person skilled in the art that:

The shape of tunnel 722 and the forcibly established temperature distribution along the inner walls using the surface matrix thermoelectric device 722.TED, both can be adapted to the velocity $u_a$ of ambient air 724 and optimized to provide that the velocity value $u_{723}$ of outflowing jetstream 723 becomes higher than the speed of sound $u_{sound}$. As well, it will be evident to a person skilled in the art that the shape of tunnel 722 and outer airfoil side 729 of capsule 720 and forcibly established temperature distribution along the inner walls using the surface matrix thermoelectric device 729.TED, both can be optimized to provide that outflowing divergent portion 735 has increasing M-velocity reaching values higher than the specific M-velocity $M_*$;

Supplying a flying vehicle or helicopter's propeller blades by nozzles similar to capsule 720 operating as a jet-booster, one could save fuel consumption substantially and even provide a stable motion against a drag and skin-friction resistance entirely with no fuel burning at all. As well, it will be evident to a person skilled in the art that this is not a so-called "Perpetuum mobile", but the use of ambient fluid heat to produce useful motion, strongly according to the Energy Conservation Law. Furthermore, point out that an even number of such jet-boosters, attached to the even number of blades of a helicopter's propeller, result in stabilization of the effective velocities of incoming and outflowing jetstreams associated with the jet-boosters. The predictably equalized velocities enable easier controllable lift-forces when the helicopter is flying speedily;

The described airfoil capsule can be stationarily exposed to oncoming wind (either natural or artificial) and thereby become applicable to efficient harvesting of electricity providing a positive net-efficiency; and One can further aggregate the open outlet of a specifically shaped convergent-divergent tunnel with an engine using the enhanced jet-effect providing an extra-accelerated and extra-cooled jetstream outflowing through the open outlet; wherein the engine is either a jet-engine, and/or a turbo-jet engine, and/or a motor applied to a vehicle, and/or a generator of electricity, and/or a cooler, and/or a Peltier element operating as a thermoelectric generator, and/or vapor-into-water condenser.

FIG. 7d is a schematic sectional view of a flying capsule 740, constructed according to the principles of the present invention. Flying capsule 740's profile in a sagittal plane has an airfoil outer contour and a contour of a specifically shaped two-stage inner tunnel. Similar to the flying capsule 720 illustrated hereinbefore referring to FIG. 7c, inner and outer walls 748 and 749 of capsule 740s tunnel and outer shell are supplied with forcedly controllable surface matrix thermoelectric devices 748.TED and 749.TED, correspondingly. In contrast to flying capsule 720 illustrated hereinbefore referring to FIG. 7c, capsule 740 flies with a de Laval high M-velocity, i.e. higher than the specific M-velocity $M_* = \sqrt{(\gamma-1)/\gamma}$, and the two-stage inner tunnel is shaped similar to the tunnel of two-stage convergent-divergent jet-nozzle 690, described above referring to FIG. 6c. Namely, the two-stage inner tunnel comprises two narrow throats providing for two associated critical condition points 741 and 742. The oncoming fast flow 743 enters the open inlet 744 of the inner tunnel with a de Laval high M-velocity $M_{743}$, higher than the specific M-velocity $M_*$. Then flow 743 is gradually slowing down, becoming warmer and more compressed as moving to critical condition point 741 where reaching the specific M-velocity $M_*$, further, is gradually extra-slowing, extra-warming and extra-compressing as moving to reservoir 745, according to the condition of flow continuity Eq. (6.0), further, is gradually accelerating, cooling, and becoming decompressed as moving to critical condition point 742 where again reaching the specific M-velocity $M_*$, and further, is gradually extra-accelerating, extra-cooling, and extra-decompressing as moving to outlet 746, as described hereinbefore with references to FIGS. 6a, 6b, and 6c. The cross-section of outlet 746 is wider than the cross-section of inlet 744, thereby providing for that capsule 740 operates as a jet-booster launching a widened and cooled outflowing jetstream 747 with a high M-velocity, higher than the de Laval high M-velocity of oncoming fast flow 743.

In view of the foregoing description referring to FIGS. 7c and 7d, it will be evident for a person skilled in the art that one can use the surface matrix thermoelectric devices to provide for at least one of:

Adapting to the de Laval high M-velocity $M_{743}$ of the oncoming fast flow 743 and controlling the laminarity of both: the flow 473 moving within the specifically shaped two-stage inner tunnel and outer portions of the ambient-adjacent flow; and Harvesting electricity from originated temperature differences.

Modified Symmetrical Wink

FIG. 8, a schematic illustration of a symmetrical wing 8.00 supplied with a multi-layer TE device 8.20, is composed of three sub-drawings:

FIG. 8 (A) is a schematic drawing of a sectional profile of a modified symmetrical wing 8.00 in a sagittal plane (X, Z) in a system of coordinates (X, Y, Z);

FIG. 8 (B) is a profile of temperature difference function $\Delta T(x)$ between two opposite surfaces: upper-side 8.01 and lower-side 8.02 along the X-axis in a system of coordinates (X, $\Delta T$); and FIG. 8 (C) is a profile of temperature difference function $\Delta T(z)$ between two opposite butt-ends: anterior and tail, along the Z-axis in a system of coordinates ($\Delta T$, Z).

The modified wing 8.00, mirror-symmetrical relative to the horizontal plane (X, Y), having a cross-sectional thickness 8.$\Delta Z$, is oriented to meet the oncoming fluid flow 8.10 at the zero attack angle. The oncoming fluid flow 8.10, when flowing around the modified symmetrical wing 8.00, becomes divided into two portions:

upper-side 8.11, forming the upper-side boundary layer 8.31 moving nearby the upper-side surface 8.01 and having thickness 8.41; and lower-side 8.12, forming the upper-side boundary layer 8.32 moving nearby the lower-side surface 8.02 and having thickness 8.42;

each of which is subjected to the action of the Coanda-effect. If the upper-side 8.01 and lower-side 8.02 surfaces of the modified symmetrical wing 8.00 are made from the same material and have the same temperature, the two portions: upper-side 8.11 and lower-side 8.12, of fluid flow, both are subjected to the mirror-symmetrically acting Coanda-effect such that the lift-force is zero and only the Archimedes' upward-vectored force 8.LIFT acts on the modified symmetrical wing 800 against the downward attracting gravitational force. Normally, the effective mass density of the modified symmetrical wing 800 is much greater than the mass density of the natural air, and if the ambient fluid is the natural air, then the Archimedes' upward-vectored force is much weaker than the downward attracting gravitational force. Speaking strictly, the two boundary layers 8.31 and 8.32 differ in thermodynamic parameters: the static pressure, mass density, and absolute temperature, as the boundary layers 8.31 and 8.32, both characterized by the mass density and subjected to gravitational downward attraction, occupy spaces differing in height above the world Oceanus level. The seemingly-insignificant difference in the static pressures is a reason for Archimedes' upward-vectored force.

The modified symmetrical wing 800 is modified by that the upper-side 8.01 and lower-side 8.02 surfaces are mutually-contacted through the multi-layer TE device 8.20, which is similar to the multi-layer TE multi-module device 1t.0 comprising a matrix of TE elements aggregated in layers one above another multi-stage repeatedly as described hereinabove referring to prior art FIG. 4e. The multi-layer TE device 8.20 comprises:
- the upper-side layer composed of unbrokenly arranged anterior TE devices 8.21, withers TE devices 8.23, and tail TE devices 8.25, all having an upper side forming the upper-side surface 8.01 of the modified symmetrical wing 8.00, and
- the lower-side layer composed of unbrokenly arranged anterior TE devices 8.22, withers TE devices 8.24, and tail TE devices 8.26, all having a lower side forming the lower-side surface 8.02 of the modified symmetrical wing 8.00, wherein points 8.27 and 8.28 symbolize that TE devices are arranged unbrokenly.

The multi-layer TE device 8.20, when controlled by a controller, provides for an additional temperature difference 8ΔT(x) (additional to the seemingly-insignificant temperature difference) between the upper-side 8.01 and lower-side 8.02 surfaces along the X-axis.

The profile of the modified symmetrical wing 8.00 is airfoil in a certain sense only. When the ambient velocity is in a certain range of velocities, the stalling effect, accompanied by broken or jumping all: the headway velocity, the static pressure, the absolute temperature, and the mass density, occurs nearby the separation point 1G.46 resulting in reducing lift-force drastically, as described hereinabove in the subparagraph: "Broken Boundary Layer" referring to FIG. 1e Scheme (E).

The inventor points out that all parameters: the headway velocity, the static pressure, the absolute temperature, and the mass density, are interrelated according to laws of gas state and laws of aerodynamics, and so controlling of at least one of the parameters allows to control all the other parameters. In particular, to suppress the uncontrolled stalling effect, the use of the multi-layer TE device 8.20 controlled by a controller allows for providing a forcibly established specific temperature distribution along the upper-side 8.01 and lower-side 8.02 contours of the modified symmetrical wing 8.00 profile. The forcibly established specific temperature distribution along the upper-side 8.01 and lower-side 8.02 contours is such to provide the mentioned thermodynamic conditions for laminar flowing in the boundary layers 8.31 and 8.32, correspondingly, each of which becomes an optimized convergent-divergent nozzle, completely optimized on one of the mentioned criteria either:
- smoothing of the flowing fluid M-velocity, or
- smoothing of the flowing fluid static pressure, or
- smoothing of the flowing fluid absolute temperature, or
- smoothing of the flowing fluid mass density, as described hereinabove in the subparagraph "Convergent-Divergent Jet-Nozzle" referring to FIG. 6a. Thus, it is preferred to use a specifically distributed additional temperature difference 8ΔT(x), distributed along the contours 8.01 and 8.02. An exemplary distribution of the additional temperature difference 8.ΔT(x) is optimized to provide laminar motions of portions 8.11 and 8.12 accompanied by gradual changes in M-velocities dependent on the cross-sectional area of the boundary layers 8.31 and 8.32, correspondingly, according to the condition of flow continuity Eq. (6.0), adapted to the M-velocity of oncoming flow 8.10 equal to 0.35 Mach and effective thicknesses 8.41 and 8.42, both equal to 3.7 cm. The specifically distributed additional temperature difference 8ΔT(x), having a zone downstream behind the TE devices 8.25 and 8.26 where the temperature differences 8.12 are reversed in sign, is such that, downstream behind the sharp butt-end 8.03 of the modified symmetrical wing 8.00, the velocities of the upper-side 8.11 and lower-side 8.12 portions gradually become the same and the temperatures of both upper-side 8.11 and lower-side 8.12 portions become gradually reverted to the temperature of the ambient fluid. This condition is necessary to prevent or at least to suppress turbulence downstream behind the sharp butt-end 8.03 thereby making the modified symmetrical wing 8.00 actually-airfoil.

Considering an action of the multi-layer TE device 8.20 making the upper-side surface 8.01 colder than the lower-side surface 8.02, when fresh portions of fluid are suddenly transformed into the upper-side and lower-side boundary layers, the additional effective temperature difference 8.ΔT (eff) equal to $\overline{\Delta T}$ causes suddenly originated effective temperature differences between fluid portions, i.e.:
- $\overline{\Delta T}_1$ between the upper-side portion of the ambient fluid and a tiny portion within the refreshed upper-side boundary layer 8.31,
- $\overline{\Delta T}_2$ between a tiny portion within the refreshed upper-side boundary layer 8.31 and a tiny portion within the refreshed lower-side boundary layer 8.32,
- $\overline{\Delta T}_3$ between a tiny portion within the refreshed lower-side boundary layer 8.32 and the refreshed lower-side portion of the ambient fluid, wherein the condition: $\overline{\Delta T}_2 = -(\overline{\Delta T}_1 + \overline{\Delta T}_3)$ says that the ambient fluid outside the boundary layers remains in normal thermodynamic conditions. There are extremely low velocities of airflow in close proximity above the upper-side solid surface 8.01 and under the lower-side solid surface 8.02 as described hereinabove in the subparagraph: "Boundary-layer" referring to FIG. 1e Graph (D). Hence, the condition $\overline{\Delta T}_2 \leq \overline{\Delta T}$ (again, $\overline{\Delta T}$ is the additional effective temperature difference 8.ΔT(eff) between the upper-side and lower-side surfaces: 8.01 and 8.02) is satisfied also when the wing 8.00 moves. When the refreshed boundary layers are relatively thin and well-aligned with the airfoil surfaces, the approximation $\overline{\Delta T}_2 \cong \overline{\Delta T}$ becomes justified. The higher the ambient velocity, the thinner the refreshed boundary layers, and the more appropriate the interrelation $\overline{\Delta T}_2 \cong \overline{\Delta T}$. Further, for concretization, the relatively thin and well-aligned boundary layers flowing with high-subsonic velocities are assumed. Considering fresh incoming portions of the boundary layers, the suddenly originated additional effective temperature differences $\overline{\Delta T}_1$, $\overline{\Delta T}_2$, and $\overline{\Delta T}_3$ are interrelated with the suddenly originated additional effective static pressure differences, additional to the seemingly-insignificant static pressure difference associated with Archimedes' upward-vectored force. Namely, the suddenly originated $\overline{\Delta T_1}$, $\overline{\Delta T_2}$, and $\overline{\Delta T_3}$ are interrelated with the suddenly originated additional effective static pressure differences of $\overline{\Delta P_1}$ between the upper-side portion of the ambient fluid and a tiny portion within the refreshed upper-side boundary layer 8.31, $\overline{\Delta P_2}$ between a tiny portion within the refreshed upper-side boundary layer 8.31 and a tiny portion within the refreshed lower-side boundary layer 8.32, $\overline{\Delta P_3}$ between a tiny portion within the refreshed lower-side boundary layer 8.32 and the refreshed lower-side portion of the ambient fluid, correspondingly. The resulting suddenly originated negative additional effective pressure difference $\overline{\Delta P_2}$ interrelates with the suddenly originated positive additional effective pressure differences: $\overline{\Delta P_1}$ and $\overline{\Delta P_3}$, wherein:

the suddenly originated positive additional effective pressure difference $\overline{\Delta P_1}$ results in downward pulling-in the upper-side portion of the ambient fluid and upward pulling-in the modified symmetrical wing 8.00 into the refreshed upper-side boundary layer 8.31, and the suddenly originated positive additional effective pressure difference $\overline{\Delta P_3}$ results in downward pushing-off the lower-side portion of the ambient fluid and upward pushing-off the modified wing symmetrical 8.00 away from the refreshed lower-side boundary layer 8.32, thereby, both contributing to the upward-vectored force 8.LIFT applied to the modified symmetrical wing 8.00 in unison, wherein the condition: $\overline{\Delta P_2}=-(\overline{\Delta P_1}+\overline{\Delta P_3})$ says that the ambient fluid outside the boundary layers remains in normal thermodynamic conditions, Thus, the suddenly originated additional positive effective pressure difference $(-\overline{\Delta P_2})=(\overline{\Delta P_1}+\overline{\Delta P_3})$ works for both:

downward shifting the upper-side and lower-side portions of the ambient fluid, and a positive contribution $\Delta F_{LIFT}$ to the upward-vectored force 8.LIFT, in the same extent, i.e. not more than half the sum $(\overline{\Delta P_1}+\overline{\Delta P_3})$ contributes to the lift. Moreover, as the contribution to the lift works if the additional effective static pressure differences are originated between two fresh portions of air just suddenly, a velocity-dependent suddenness factor $C_S$ determines the value of the positive contribution $\Delta F_{LIFT}$ to the upward-vectored force 8.LIFT. Namely, as the interaction between, on the one hand, the wing and, on the other hand, the refreshed and suddenly heated or cooled boundary layers is relevant only, then, when the relatively thin boundary layers (the thickness of which is velocity-dependent) are strictly-aligned to the relatively big airfoil surfaces of the modified symmetrical wing 8.00, the velocity-dependent suddenness factor $C_S$ tends to 1 ($C_S\to 1$), and, the slower-refreshed and so thicker the boundary layer and the weaker the alignment, the smaller the velocity-dependent suddenness factor C. Assuming an airfoil corpus, a simplified approximation for the velocity-dependent suddenness factor $C_S$ defined hereinabove by the equitation Eq. (1.1j) is further specified for higher M-velocities by the expression:

$$C_S = \begin{cases} M/M_*, & M \leq M_* \\ \exp(1-M/M_*), & M > M_* \end{cases} \quad \text{Eq. (8.0a)}$$

where M is M-velocity and $M_*$ is the specific M-velocity. The approximation Eq. (8.0a) makes physical sense: the greater the difference $|1-M/M_*|$, the lower the suddenness factor, which is manifested as a thicker boundary layer. Thus, the positive contribution $\Delta F_{LIFT}$ is defined as:

$$\Delta F_{LIFT}=\frac{1}{2}\times C_S \times A_{(X,Y)}\times(-\overline{\Delta P_2}), \quad \text{Eq. (8.0b)}$$

where $A_{(X,Y)}$ is the area of a projection of the upper-side surface 8.01 (or the lower-side surface 8.02) of the modified symmetrical wing 8.00 in a horizontal plane (X, Y). As the high-subsonic velocity range is assumed, the approximation $C_S=1$ is used for the estimation of the concept's practicality for industrial use [For comparison, in the case of wings waving by a pigeon to result in the effect of the bird taking-off dominantly-vertically (the case is highlighted hereinabove in the subparagraph "Flying Bird" referring to FIG. 2a), the suddenness factor $C_S$ is estimated as about 0.01 that gives $\Delta F_{LIFT}$ of approximately 3.5 N obtained by the waving that explains the effect of the bird taking off dominantly-vertically so efficiently]. To evaluate the concept's practicality for industrial use, an exemplary positive contribution $\Delta F_{LIFT}$ to the upward-vectored force 8.LIFT is estimated referring to the specifically distributed additional temperature difference 8.ΔT(x) considering:

the normal ambient air conditions: T≈300K, P≈100,000 Pa, and γ=7/5;

the wing 8.00 having a chord of 2 m and a span of 10 m; i.e. $A_{(X,Y)}$=20 m$^2$; and the normally reachable value of the additional temperature difference 8.T1 using TE devices is −75 C, and taking into account that it is preferred to use the specifically distributed additional temperature difference 8.ΔT(x), distributed on the upper-side 8.01 and lower-side 8.02 surfaces along the X-axis, the suddenly originated effective difference of $\overline{\Delta T_2}=\overline{\Delta T}$=−30 C is taken for the estimation, noting that $\overline{\Delta T_2}$ is interrelated with the suddenly originated effective additional static pressure difference $\overline{\Delta P_2}$ according to equation Eq. (1.1b) described hereinabove in the subparagraph "Lift-Force Mechanism" referring to FIG. 10.

Thereby, the values are quantified as follows: $C_S$=1, the ratio $(-\overline{\Delta T_2})/T\approx 0.1$, the ratio $(-\overline{\Delta P_2})/P\approx 0.1\times(7/5)/(2/5)=0.35$, the suddenly originated additional static pressure difference is $(-\overline{\Delta P_2})=(\overline{\Delta P_1}+\overline{\Delta P_3})\approx 0.35\times 10^5$ Pa, and the contribution $\Delta F_{LIFT}$ 8.LIFT to the upward-vectored force is $$\Delta F_{LIFT}=\frac{1}{2}\times C_S\times A_{(X,Y)}\times(-\overline{\Delta P_2})\approx 0.35\times 10^6 N \quad \text{Eq. (8.0c)}$$

that is sufficient to support a mass of 35 ton fast-moving horizontally in the air.

In view of the foregoing description referring to FIGS. 8 (A) and (B), it will evident for a person skilled in the art that the modified symmetrical wing 8.00 has advantages as follows:

it becomes relevant to use an increased upward-vectored force, increased by the contribution $\overline{\Delta F}_{LIFT}$, to contribute to the lift-force;

it is possible to use the zero attack angle only or at least dominantly but not to use flaps to control lift-force;

it becomes possible to control flow laminarity within the upper-side and lower-side boundary layers;

it becomes solved the problem of arising a negative lift-force at M-velocities higher than the specific M-velocity; and it becomes possible to imitate an actually-airfoil wing by suppression turbulence downstream behind the modified symmetrical wing.

Further, the controlled multi-layer TE device 8.20 allows for the controllable creation of an additionally distributed temperature difference 8.$\Delta T(z)$ between the anterior and tail butt-ends of the modified symmetrical wing 800. For the sake of concretization, the shown additional distributed temperature difference 8.$\Delta T(z)$ is negative such that the additionally distributed temperature difference 8.$\Delta T(z)$ providing the negative effective temperature difference $\Delta T_{FORE\text{-}TAIL}$ between the anterior and tail butt-ends. Analogously and in contrast to the origination of the positive contribution to the lift-force 8.LIFT by the added upward-vectored force $\Delta F_{LIFT}$, a contribution to the thrust 8.THRUST by the added positive thrust $\Delta F_{THRUST}$ is provided due to the added negative effective temperature difference $\Delta T_{HEAD\text{-}TAIL}$ interrelated with the added negative effective static pressure difference $\Delta P_{HEAD\_TAIL}$. Namely, analogously to the specification of the force $\Delta F_{LIFT}$, the force $\Delta F_{THRUST}$ is specified as:

$$\Delta F_{THRUST} = -\tfrac{1}{2} \times C_u \times \Delta P_{HEAD\text{-}TAIL} \times A_{(Y,Z)} \quad \text{Eq. (8.0d),}$$

where $A_{(Y,Z)}$ is the cross-sectional area in a frontal plane (Y, Z). To estimate the practicality of the concept, an exemplary positive contribution $\Delta F_{THRUST}$ to thrust 8.THRUST is estimated referring to the added negative effective temperature difference $\Delta T_{FORE\text{-}TAIL}$ considering:

the value of cross-sectional thickness 8.$\Delta Z$ of the modified symmetrical wing 8.00 equal to 0.2 m and a span of 10 m; i.e. $A_{(Y,Z)} = 2 \text{ m}^2$; and the value of the negative effective temperature difference $\Delta T_{HEAD\text{-}TAIL}$ using TE devices of $-60$ C, i.e. the ratio $(-\Delta T_{HEAD\text{-}TAIL})/T \approx 0.2$; so, referring to the equation Eq. (1.1b) described hereinabove in the subparagraph "Sound as Complicated Movement in Molecular Fluid" prefacing the reference to FIG. 3$a$, the ratio $(-\Delta P_{HEAD\text{-}TAIL})/P \approx 0.7$, and $(-\Delta P_{HEAD\text{-}TAIL}) \approx 0.7 \times 10^5$ Pa. Thereby, the force $\Delta F_{THRUST}$ is estimated as $(1/2) \times (0.7 \times 10^5 \text{ Pa}) \times (2 \text{ m}^2) = 0.7 \times 10^5$ N that is sufficient to overcome a velocity-dependent drag in the air when moving with the headway velocity $u_0$ of the high-subsonic velocity range, that can be confirmed referring to the condition derived from the well-known drag and skin-friction equation as follows:

$$u_0 = \{|\Delta F_{THRUST}|/[0.5 \times \rho_{AIR} \times (C_d \times A_{(Y,Z)} + C_f \times A_{(X,Y)})]\}^{1/2} \quad \text{Eq. (8.0e),}$$

where: $A_{(Y,Z)} = 2 \text{ m}^2$, $A_{(X,Y)} = 20 \text{ m}^2$, $C_f$ is the skin-friction coefficient, normally, given as about 0.045 for an airfoil wing, $C_d$ is the drag coefficient, normally, given as about 0.5 for a frontal convexly-rounded configuration of an actually-airfoil wing, and $\rho_{AIR}$ is the mass density of the air, normally, given as about 1.18 kg/m$^3$, i.e. $u_0 \approx 250$ m/sec.

In view of the foregoing description of the subparagraph "Modified Symmetrical Wing" referring to FIG. 8, it becomes evident for a commonly educated person that, using the surface matrix thermoelectric devices as an enhanced distributor of static pressure, a spatial function of temperature differences $\Delta T(x, z)$ within boundary layers can be enforced to provide for temperature asymmetry of a geometrically symmetrical wing to control lift-force and thrust, and, in particular, flying capsules 720 and 740 described hereinabove in the subparagraph "Flying Capsule as Dragging-Jet Engine" referring to FIGS. 7$c$ and 7$d$, both can have an optimized controlled thrust and controlled lift-force.

Shaped Wing as a Convergent-Divergent Jet-Nozzle

FIG. 8$a$ is a schematic visualization 800 of an oncoming wind portion 820, without loss of generality, moving horizontally and flowing around actually-airfoil biconvex wing 810, supplied with a multi-layer TE device 8$a$.TED. Oncoming wind portion 820 comprises airflow sub-portions 821, 822, 823, and 824 flowing around actually-airfoil biconvex wing 810, having a side-view sectional profile, constructed according to the principles of the present invention. The side-view sectional profile determines a sagittal axis 820.0. The upper side of actually-airfoil biconvex wing 810 comprises:

(a) a forward part meeting upper-side sub-portion 822 having imaginary cross-section 831;

(b) a withers 810$a$ defined as the highest point on the upper side of the airfoil profile convexity, where sliding sub-portion 822 has imaginary narrowed cross-section 832; and (c) a rearward part, attracting and, thereby, redirecting the mass-center of the upper-side sliding sub-portion 822 backward-downward, where sliding sub-portion 822 has imaginary widened cross-section 833.

The upper and lower sides of the actually-airfoil biconvex wing 810, each having a convexity: 810$a$ and 810$b$, correspondingly, join together forming a sharp trailing end 810$c$.

When airflow sub-portions 821, 822, 823, and 824 are flowing around actually-airfoil wing 810, the streamlines [not shown here] of sub-portions 822 and 823, flowing near actually-airfoil biconvex wing 810, are curving in alignment with the airfoil-profile, the streamlines [not shown here] of portions 821 and 824, flowing farther from actually-airfoil biconvex wing 810, keep substantially straight trajectories aligned with imaginary horizontal lines 811 and 812 (collinear with the sagittal axis 820.0) correspondingly above and under actually-airfoil wing 810. Actually-airfoil biconvex wing 810's surface material properties, porosity, and structure are elaborated according to the principles of the present invention such that air sub-portions 822 and 823 are subjected to the Coanda-effect, defined by the partial pressure-c $\delta P_4$, rather than to the skin-friction resistance, occurring in an imaginary boundary layer and being quantified by the difference $(a_w - a - \delta a)$, where $a$ and $a_w$ are the van der Waals parameters characterizing the fluid and attraction between the fluid and an adjacent wall, correspondingly, and $\delta a$ is the van der Waals parameter characterizing the partial deep-stagnation pressure-a $\delta P_4$. Imaginary lines 811 and 812 can be considered as imaginary walls, thereby, together with the airfoil-profile forming imaginary nozzles. The upper-side imaginary nozzle comprises imaginary cross-sections 831, 832, and 833, and the lower-side imaginary nozzle comprises imaginary cross-sections 834 and 835. Cross-section 831 is wider than cross-section 832 and cross-section 832 is narrower than cross-section 833, thereby, the upper-side imaginary nozzle has a convergent-divergent shape, and sliding sub-portion 822 represents a convergent-divergent jetstream while flowing through cross-sections 831, 832, and 833. Cross-section 834 is wider than cross-section 835, so the lower-side imaginary nozzle has a converging shape.

The orientation of the sharp trailing end 810$c$ collinear with the sagittal axis 820.0 predetermines the direction of motion tendency of the outflowing sub-portions 822 and 823, which are going off from the sharp trailing end and joining downstream behind the cross-sections 833 and 835, correspondingly. For the purposes of the present invention, an angle between the sagittal axis 820.0 collinear with the direction of motion tendency of the lower-side outflowing sub-portion 823 and the horizontal direction defines an angle of attack (called also an attack angle). The definition of the attack angle is in conformance with the definition of the attack angle specified hereinabove in the subparagraph "Airfoil Wing (definition of attack angle)" of THE BACKGROUND OF THE INVENTION for a classic wing associated with a fuselage of airplane. Here is the zero attack angle in the shown schematic visualization 800. The zero attack angle provides for minimized impact by the oncoming flow and a generation of the lift-force due to the Coanda-effect only or at least dominantly.

Consider a case, when actually-airfoil biconvex wing 810 flies with a certain de Laval low M-velocity $M_{810}$ that is lower than the specific M-velocity $M_*\approx 0.5345$ Mach$\approx$664 km/h, but such that sliding sub-portion 822, moving through the upper-side imaginary nozzle, reaches the specific M-velocity $M_*$ when passes through the narrowest cross-section 832. So, the de Laval-like jet-effect arising is expected above actually-airfoil wing 810, i.e. within the upper-side imaginary convergent-divergent jet-nozzle. This is accompanied by the static pressure decrease and extra-decrease, as described hereinabove with the reference to FIG. 6a (B) Graph, and thereby results in the lift-effect, becoming stronger. The narrowest cross-section 832 linear size, i.e. thickness δ of a boundary layer, dependent on both a so-called "characteristic size" $L_*$ and the so-called Reynolds Number Re, can be estimated using, for example, approximation by Prandtl: $\delta = 0.37 \times L_*/Re^{0.2}$, where $L_*$ has the sense of a chord of an airfoil wing. As well, the thickness a of the boundary layer can be specified experimentally for a kind of body corpus. In view of the foregoing description referring to FIG. 6a and FIG. 8a, it will be evident to a person skilled in the art that, interpreting the narrowest cross-section 832's linear size as the thickness of the boundary layer, one can apply the condition of flow continuity Eq. (6.0) to design an improved profile of the wing.

In view of the foregoing description referring to FIG. 8a, it will be evident to a person skilled in the art that the described de Laval-like jet-effect is similar to the classical de Laval jet-effect, but arising in an optimized convergent-divergent tunnel having imaginary walls formed by streamlines of a flow. Namely, the specifically shaped convergent-divergent tunnel comprises two opposite walls; wherein one of the two opposite walls is constructed from a solid material and another of the two opposite walls is imaginary and formed by streamlines of the flowing fluid subjected to the Coanda-effect operation.

Further, it will be evident to a person skilled in the art that considering the case, when actually-airfoil biconvex wing 810 flying with a certain Venturi M-velocity $M_{810}$,
which (the Venturi M-velocity $M_{810}$) is lower than the specific M-velocity $M_* = \sqrt{(\gamma-1)/\gamma} \approx 0.5345$ Mach$\approx$664 km/h and such that, when sliding sub-portion 822 moves through the upper-side imaginary nozzle and passes through the narrowest cross-section 832, the maximally accelerated M-velocity remains lower than the specific M-velocity $M_*$, the condition of flow continuity Eq. (6.0) allows designing an improved profile of the wing optimized to meet flow, oncoming with the Venturi M-velocity $M_{810}$. While a gradual change in static pressure within boundary layers adjacent to the upper-side and lower-side surfaces of the actually-airfoil biconvex wing 810 is the primary condition for the suppression of undesired turbulences nearby the wing surfaces, one of the primary criteria of the optimization is also to provide minimized differences between velocity-vectors and static pressures of the outflowing sub-portions 822 and 823 as the primary condition for suppression of undesired turbulences downstream behind the sharp trailing end 810c. While the curvatures of the upper-side and lower-side surfaces should provide gradual changes of the static pressures and M-velocities, the sharpness of the sharp trailing end 810c should provide the dominantly horizontal direction of motion tendency of both outflowing sub-portions 822 and 823.

Thus, a method for a wing profile design, based on the condition of flow continuity Eq. (6.0) according to an exemplary embodiment of the present invention, allows optimizing the wing airfoil shape to reach the best efficiency of the lift-effect as a result of the Coandajet-effect accompanied by enhanced at least one of the Venturi effect and de Laval jet-effect occurring above and under the wing. The inventor notes that the profile of the actually-airfoil biconvex wing 810, designed and optimized using the condition of flow continuity Eq. (6.0), has a shape similar to a shape of a birdwing rather than to the shape of the classic wing of the airplane.

The actually-airfoil biconvex wing 810, while designed and optimized using the condition of flow continuity Eq. (6.0) applied to the overall geometrical configuration only, is actually-airfoil in a certain sense when considering the mentioned certain M-velocity $M_{810}$. To provide optimized conditions for a wide range of velocities, the actually-airfoil biconvex wing 810, is further supplied with the multi-layer TE device 8a.TED built-in between the upper-side and lower-side surfaces of the actually-airfoil biconvex wing 810. The multi-layer TE device 8a.TED comprises:

an upper side forming the upper-side surface of the actually-airfoil biconvex wing 810, and a lower side forming the lower-side surface of the actually-airfoil biconvex wing 810.

The multi-layer TE device 8a.TED, when controlled by a controller, provides for additional forcibly established temperature difference, additional to the temperature difference between the upper-side and lower-side surfaces along the sagittal axis 820.0 determined by the Coanda-effect accompanied by at least one of the Venturi effect and the de Laval effect. The forcibly established temperature difference ($\Delta T_0(x) + \Delta T(x)$) distributed along the sagittal axis 820.0, where:

$\Delta T_0(x)$ is the distributed original temperature difference between the upper-side and lower-side boundary layers specified when designing the overall geometrical configuration of the actually-airfoil biconvex wing 810 considering the mentioned certain M-velocity $M_{810}$ and the derivative distribution $M_{810}(x)$ along the sagittal axis 820.0, and $\Delta T(x)$ is the additional forcibly established distribution of the temperature difference, provides for adaptation of the overall shape of the actually-airfoil biconvex wing 810 to an arbitrary velocity $u_{B4}$ of the oncoming wind portion 820. For this purpose, the forcibly established distribution of the temperature difference ($\Delta T_0(x) + \Delta T(x)$) is defined as:

$$(\Delta T_0(x) + \Delta T(x)) = \frac{1}{\gamma R} \times \left[\frac{u_{8a}}{M_{810}(x)}\right]^2.$$

The Coanda-Effect Operation Providing an Imaginary Convergent-Divergent Nozzle

FIG. 8b is a schematic illustration of a flying airfoil body 840 having the shape of an elongated drop. For simplicity and without loss of reasoning, the shape is axis-symmetrical around the longitudinal axis 841. The airfoil body 840 comprises:
- a forward part meeting oncoming flow portion 851;
- a "withers", defined as the highest point on the upper side of the airfoil profile, where sliding sub-portion 853 has an imaginary narrowed cross-section 868, and
- a rearward part.

When an oncoming air portion 851, originally having a cross-sectional area 861, is running at the forward part of flying body 840, it is subjected to the Coanda-effect operation resulting in air portion 851 reshaping, and thereby forming an ambient-adjoining convergent-divergent jetstream, comprising sliding sub-portions: 852 being convergent, 853 being narrow and having imaginary narrowed cross-section 868 of the minimal cross-sectional area, 854 being divergent, and 855 becoming convergent due to the Coanda-effect attraction. Body 840's surface material properties, porosity, and structure are implemented according to the principles of the present invention, thereby providing that air portion 851 is subjected to the Coanda-effect, defined by the partial pressure-c $\delta P_c$, rather than to the skin-friction resistance, occurring in an imaginary boundary layer and being quantified by the difference $(a_w-a-\delta a)$. Furthermore, sliding sub-portions 855, join together, forming the resulting cumulative air portion 856. Oncoming air portion 851 and all the mentioned derivative sub-portions move within space "bordered" by imaginary walls marked by dashed contours 842. The imaginary walls 842 together with the airfoil surface of body 840 constitute an imaginary tunnel. The tunnel's cross-section gradually constricts from the inlet cross-section 862 to the narrowest cross-section 868 and then gradually widens up to the outlet cross-section 863. I.e. sliding sub-portions 852 are shrinking while reaching the withers of airfoil body 840, where the cross-sections 868 of sub-portions 853 become minimal. Then, behind the withers, the cross-sections of sub-portions 854 and 855 are widening as moving.

Sliding sub-portions 855, being under the subjection of the Coanda-effect operation, turn aside in alignment with the slippery surfaces of airfoil body 840's rearward part and join together, forming the resulting air portion 856. It results in a convergence of resulting air portion 856, i.e. in that, cross-section 864, located farther downstream, becomes narrower than cross-section 863 located immediately behind airfoil body 840, and opposite streamline-fragments 843 form an imaginary convergent funnel. Furthermore, opposite streamline-fragments 844, which are bordering flow portion 857, constitute an imaginary divergent stage of a tunnel downstream-behind the narrowest cross-section 864. The converging opposite streamline-fragments 843 and divergent opposite streamline-fragments 844 together constitute the imaginary convergent-divergent tunnel, and, correspondingly, portions 856 and 857 together constitute an outflowing convergent-divergent jetstream.

As the shape of the imaginary convergent-divergent tunnel comprising streamlines 843-844 and cross-sections 863, 864, and 865 is a derivation of the Coanda-effect operation nearby the solid surfaces of the airfoil body 840, the airfoil body 840 is supplied with a matrix TE device (which is not shown here), built-in within the airfoil body 840's corpus and in close proximity under the solid surfaces to control the surface temperature and thereby to control the Coanda-effect and laminarity of the streamlines 842-843-844.

Jet-Booster Based on the Venturi Effect

First, consider a case, when airfoil body 840 flies with a Venturi M-velocity, i.e. with a low M-velocity, lower than the specific M-velocity $M_*=\sqrt{(\gamma-1)/\gamma}\approx 0.5345$ Mach, and low sufficient to provide that M-velocity $M_{868}$ of accelerated sliding sub-portions 853, passing cross-sections 868 over the withers, and M-velocity $M_{864}$ of accelerated sub-portions 856, passing through the narrowest cross-section 864, both remain lower than the specific M-velocity $M_*$, i.e. $M_{868}<M_*$ and $M_{864}<M_*$. In this case, the narrowest cross-section 864 of outflowing air portion 856 is narrower than the original cross-section 861 of oncoming air portion 851, and the M-velocities $M_{361}$, $M_{863}$, $M_{864}$, $M_{865}$, and $M_{363}$, where the indices correspond to markers of associated cross-sections, satisfy the following conditions:

$M_{661}<M_{868}<M_*$,
$M_{863}<M_{868}<M_*$,
$M_{863}<M_{864}<M_*$,
$M_{661}<M_{864}<M_*$, and
$M_{865}<M_{864}<M_*$.

Thus, body 840 operates as a jet-booster basing on the Venturi effect occurring in the imaginary tunnel adjacent to body 840's surfaces.

A practical application of the phenomenon that, under certain conditions, outflowing portion 856, moving through the narrowest cross-section 864, has a velocity higher than the velocity of oncoming portion 851 is one of the primary teachings of the present invention.

Jet-Boosters Based on the De Laval-Like Jet-Effect

Secondly, consider a case, when airfoil body 840 flies relatively slowly, such that sliding sub-portions 853 passes cross-sectional areas 868 with an M-velocity that remains lower than the specific M-velocity, i.e. $M_{853}<M_*$, but high sufficient to provide that the increased M-velocity of portion 856 is higher than the M-velocity of sub-portions 853 and reaches the specific M-velocity $M_*=\sqrt{(\gamma-1)/\gamma}$ at the critical condition point 864. In this case, M-velocity $M_{863}$ is the de Laval low velocity and the de Laval-like jet-effect is triggered, resulting in that the M-velocity of the divergent flow portion 857 exceeds the specific M-velocity $M_*$. In this case, the M-velocities $M_{861}$, $M_{863}$, $M_{864}$, $M_{865}$, and $M_{368}$ satisfy the following conditions:

$M_{861}<M_{868}<M_*$,
$M_{863}<M_{868}<M_*$,
$M_{663}<M_{864}=M_*$,
$M_{861}<M_{864}=M_*$, and
$M_{865}>M_{864}=M_*$.

So, body 840 operates as a jet-booster basing on the de Laval-like jet-effect occurring in the imaginary tunnel downstream-behind airfoil body 840. Thereby, the Coanda-jet-effect operation forcedly forms convergent-divergent laminar-like streamlines downstream-behind airfoil body 840, wherein the static pressure is distributed gradually along the convergent-divergent laminar-like streamlines that provides an optimized extension of air portion 857 resulting in the enhanced de Laval-like jet-effect accompanied by extra-cooling and extra-acceleration of air portion 857. This is one more teaching of the present invention.

A practical application of the phenomenon that, under certain conditions, outflowing portion 857 has an M-velocity higher than the specific M-velocity is one of the primary teachings of the present invention.

It will be evident to a person skilled in the art that the enhanced jet-effect results in an optimized reactive thrust-force applied to airfoil body 840.

Thirdly, consider a case, when airfoil body 840's shape is optimized using the condition of flow continuity Eq. (6.0) basing on an estimated linear size of cross-section 868, and when airfoil body 840 flies with a de Laval low M-velocity $M_{851}$, i.e. lower than the specific M-velocity $M_*=\sqrt{(\gamma-1)/\gamma}\approx 0.5345$ Mach, but high sufficient to provide that M-velocity of sliding sub-portions 853 reaches the value of the specific M-velocity, i.e. $M_{868}=M_*$ at the critical condition point 868. Thereby, the enhanced de Laval-like jet-effect occurs downstream-behind the withers, providing that $M_*<M_{854}<M_{855}$, where the indexes correspond to associated sliding air sub-portions. In this case, according to the condition of flow continuity Eq. (6.0), shrinking portion 856, moving with a de Laval high M-velocity, is slowing down, becoming warmer and more compressed, as moving on the way to the critical condition point associated with cross-section 864. The de Laval-like retarding-effect occurs downstream-behind cross-section 864 resulting in portion 857 expanding and further slowing down, warming, and compressing while reaching cross-section 865, The M-velocities $M_{861}$, $M_{863}$, $M_{864}$, $M_{865}$, and $M_{868}$ satisfy the following conditions:

$M_{861}<M_{868}=M_*$,
$M_{863}>M_{868}=M_*$,
$M_{863}>M_{864}=M_*$,
$M_{861}<M_{864}=M_*$, and
$M_{865}<M_{864}=M_*$.

So, in the final analysis, body 840 operates as a jet-booster, triggering both the de Laval-like jet-effect and the de Laval-like retarding-effect.

Fourthly, consider a case, when airfoil body 840's shape is optimized using the condition of flow continuity Eq. (6.0) basing on an estimated linear size of cross-section 868, and when airfoil body 840 flies with a de Laval high M-velocity, i.e. higher than the specific M-velocity $M_*=\sqrt{(\gamma-1)/\gamma}\approx 0.5345$ Mach. According to the condition of flow continuity Eq. (6.0), the de Laval-like retarding-effect occurs in the imaginary convergent-divergent tunnel formed by streamlines 842. Namely, shrinking air portions 852 are slowing down, becoming warmer and more compressed, as moving on the way to withers such that the M-velocity of the narrowest sliding sub-portions 853 reaches the specific M-velocity, i.e. $M_{868}=M_*$ at the critical condition point 868; and further, portions 854 continue to slow down while expanding downstream-behind the withers. Relatively slowly moving sliding sub-portions 855, now having a de Laval low M-velocity, join downstream-behind cross-section 863, thereby, providing for resulting shrinking portion 856 acceleration, accompanied by a decrease of temperature and static pressure, while reaching again the specific M-velocity $M_*$ at the narrowest cross-section 864. The de Laval-like jet-effect occurs downstream-behind cross-section 864 resulting in expanding portion 857 further acceleration accompanied by a deeper decrease of temperature and static pressure on the way to cross-section 865. So, the M-velocities $M_{861}$, $M_{863}$, $M_{864}$, $M_{865}$, and $M_{868}$ satisfy the following conditions:

$M_{861}>M_{868}=M_*$,
$M_{863}<M_{868}=M_*$,
$M_{663}<M_{864}=M_*$,
$M_{861}>M_{864}=M_*$, and
$M_{865}>M_{864}=M_*$.

Again, in the final analysis, body 840 operates as a jet-booster, triggering both the de Laval-like retarding-effect and the de Laval-like jet-effect.

In view of the foregoing description referring to FIGS. 6a, 7a, 7b, 7c, 8a, and 8b, it will be evident to a person skilled in the art that:

a method for an airfoil body shape design, based on the condition of flow continuity Eq. (6.0) according to an exemplary embodiment of the present invention, allows, modifying the overall geometry of the body, to optimize the efficiency of the enhanced jet-effect occurring outside of the body;

the described convergent-divergent jet-nozzles can be applicable to many apparatuses using mechanical and heat energy provided by either a flowing gas or liquid;

triggering and controlling the desired de Laval-like jet-effect can be provided by manipulating by the oncoming wind de Laval M-velocity. As the M-velocity is temperature-dependent, one can heat or cool air portions flowing within a specifically shaped tunnel, in particular, in an imaginary tunnel around a flying body;

reaching and controlling the desired de Laval-like jet-effect can be provided by manipulating by the value of specific M-velocity, depending on the generalized adiabatic compressibility parameter $\gamma$. For example, one can inject a gas composed of multi-atomic particles into a tunnel, in particular, into an imaginary tunnel around a flying body. As well, it will be evident to a person skilled in the art that, for example, micro-flakes-of-snow could play the role of such multi-atomic particles. Another technique to change the generalized adiabatic compressibility parameter $\gamma$ and thereby to control the specific M-velocity is to ionize the flow, moving through the tunnel; and the described convergent-divergent jet-nozzles can be applicable to many apparatuses using mechanical and heat energy, provided by flowing gas or liquid.

Two-Stage Operation of the Coanda-Set-Effect

FIG. 8c is divided into two parts: Case (A) and Case (B).

FIG. 8c Case (A) is a schematic illustration of flying airfoil bodies 850 and 860, arranged such that the withers of airfoil bodies 860 follow downstream-behind the withers of body 850. For simplicity and without loss of reasoning, each airfoil body 850 and 860 has the shape of an elongated drop 840 described above referring to FIG. 8b. All reference numerals 841, 861, 851, 862, 852, 868, 853, 842, and 854 are the same as described referring to FIG. 8b.

Consider a case, when flying airfoil bodies 850 and 860 meet oncoming portion 851 with a de Laval high M-velocity $M_{851}$, higher than the specific M-velocity $M_*=\sqrt{(\gamma-1)/\gamma}\approx 0.5345$ Mach. According to the condition of flow continuity Eq. (6.0), sub-portions 852 of flowing fluid (for instance and without loss of generality, the flowing fluid is airflow) are slowing down as constricting on the way to the withers of body 850, such that M-velocity of the narrowest sliding sub-portions 853 reach the specific M-velocity, i.e. $M_{853}=M_*$ at the critical condition point 868. The de Laval-like retarding-effect occurs downstream-behind the withers. It provides the condition $M_*>M_{854}$, where index "854" corresponds to air sub-portions 854. So, airfoil bodies 860 meet oncoming sub-portions 854 flowing slower than with the specific M-velocity $M_*=\sqrt{(\gamma-1)/\gamma}$, but high sufficient to provide the critical condition near their [bodies 860's] withers. Again, according to the condition of flow continuity Eq. (6.0), air sub-portions 859 have an M-velocity $M_{859}$ higher than the specific M-velocity $M_*$. Thus, flying airfoil bodies 850 and 860 meet the upstream air portions, and leave the downstream air portions, flowing faster than with the specific M-velocity $M_*=\sqrt{(\gamma-1)/\gamma}$. Furthermore, a cumulative cross-section of air sub-portions 859, wider than cross-section 861 of oncoming portion 851, means that the M-velocity $M_{859}$ is higher than the high M-velocity $M_{851}$ of oncoming portion 851. In this case, the Coanda-jet-effect two-stage operation accelerates a portion of ambient airflow that originally moves faster than with the specific M-velocity $M_*$. Thus, in contrast to the case when a body, having a not-optimized shape, flies in an air-environment with transonic, and/or supersonic, and/or hypersonic velocities, flying airfoil body 850, operating in tandem with each flying airfoil body 860, moving downstream behind the withers of airfoil body 850, results in a specific effect of acceleration and cooling air portion 851, oncoming faster than with the specific M-velocity $M_*$. This is one other primary teaching of the present invention.

FIG. 8c Case (B) is a schematic illustration of a sectional cut of flying actually-airfoil wings 850.B and 860.B in a sagittal plane. The flying actually-airfoil wings 850.B and 860.B are arranged to meet and act on an oncoming portion 851.8 of flowing fluid sequentially (for instance and without loss of generality, the flowing fluid is airflow). In view of the foregoing description referring to FIG. 8c Case (A), it becomes evident that, in particular, considering a tandem 880.B of two airfoil bodies consolidated as a whole embodied in the form of actually-airfoil wings 8502 and 860.B (for instance, each of which similar to that described hereinabove referring to FIG. 8a) will provide the described specific effect of acceleration and cooling of the airflow portion 851.B originally oncoming faster than with the specific M-velocity $M_*$, The tandem 880.B comprises all the features of the flying airfoil bodies 850 and 860 of Case (A), and, in contrast to Case (A), the two airfoil bodies, namely, the two actually-airfoil wings 850.8 and 860.8, have an asymmetry relative to the horizontal plane 841.8.

The reference numerals are as follows:
- 851.B is an oncoming flow portion yet to be subjected to an action of the tandem 880.B of two actually-airfoil wings 850.8 and 860.B consolidated as a whole;
- 852.61 and 852.B2 are sub-portions of the oncoming flow portion 851.B in positions where, when running on the first met local convexity 869.61 and 869.B2, correspondingly, subjected to convergence above and under the tandem 880.8;
- 868.B1 and 868.B2 are narrowed cross-sections of the locally-minimal cross-sectional areas, correspondingly, above and under the first met local convexity: 869.61 and 869.62, of the tandem 880.6;
- 853.61 and 853.B2 are sub-portions of the oncoming flow portion 851.B in positions where, when flowing adjacent to the first met local convexity: 869.81 and 869.22, correspondingly, subjected to narrowing to have narrowed cross-sections 868.61 and 868.82 of the locally-minimal cross-sectional areas, correspondingly, above and under the first met local convexity: 869.81 and 869.82, of the tandem 880.8;
- 854.81 and 854.82 are sub-portions of the oncoming flow portion 851.8 in positions where, when passing the first met local convexity: 869.81 and 869.82, correspondingly, subjected to divergence above and under the tandem 880.8;
- 852.83 and 852.84 are sub-portions of the oncoming flow portion 851.B in positions where, when running on the second met local convexity: 869.83 and 869.84, correspondingly, subjected to convergence above and under the tandem 880.8;
- 868.83 and 868.84 are narrowed cross-sections of the locally-minimal cross-sectional areas, correspondingly, above and under the second met local convexity: 869.83 and 869.64, of the tandem 880.8; and
- 854.83 and 854.64 are sub-portions of the oncoming flow portion 851.8 in positions where, when passing the second met local convexity: 869.83 and 869.64, correspondingly, subjected to divergence above and under the tandem 880.8.

The profiles of the two actually-airfoil wings 850.6 and 860.8 are elaborated to meet the oncoming flow portion 851.6 originally oncoming faster than with the specific M-velocity $M_*$ such that the two boundary layers composed of the sub-portions, flowing above and under the tandem 880.8, correspondingly, both, when subjected to action by the tandem 880.8, become subjected to a two-stage convergence-divergence accompanying first, by the triggered de Laval retarding-effect and then by the triggered de Laval jet-effect. Borders of the two boundary layers are schematically marked by double-dot dashed lines 842.81 and 842.82 symbolizing imaginary, in general, curved surfaces formed by streamlines bordering the portion 581.8 above and under the tandem 880.8, correspondingly; without loss of generality, the surfaces are indicated as being almost plane and separating, on the one hand, the two two-stage convergent-divergent boundary layers composed of sub-portions of the portion 581.B, which are substantially deforming as moving along the tandem 880.B, and, on the other hand, portions of the ambient flowing fluid which remain relatively weakly deformed. The triggering of the de Laval retarding-effects occurs when the retarding of sub-portions 852.61 and 852.B$_2$ are such that the sub-portions 853.61 and 853.82 cross the narrowed cross-sections 868.61 and 868.62 of the locally-minimal cross-sectional areas, correspondingly, with the specific M-velocity $M_*$; and the triggering of the de Laval jet-effects occurs when the acceleration of sub-portions 852.B3 and 852.B4 are such that the sub-portions 853.B3 and 853.64 cross the narrowed cross-sections 868.B3 and 868.84 of the locally-minimal cross-sectional areas, correspondingly, again, with the specific M-velocity $M_*$.

The asymmetry of the tandem 880.B relative to the horizontal plane 841.B causes that:
- on the one hand, as soon as the upper-side outlet sub-portion 854.83 is wider than the upper-side inlet sub-portion 852.61, integrally, the upper-side sub-portion becomes accelerated, as it is described hereinabove in the sub-paragraph "Two-Stage Convergent-Divergent Jet-Nozzle" referring to FIG. 6c; and
- on the other hand, since the lower-side outlet sub-portion 854.84 is narrower than the lower-side inlet sub-portion 852.B2, integrally, the lower-side sub-portion remains retarded.

Such an action of the tandem 8802 on the sub-portions of the relatively fast oncoming flow portion 851.B, which (the action) is imbalanced relative to the horizontal plane 841.B, originates a resulting upwardly-vectored lift-force cumulatively acting on the tandem 880.8, that is also one of the primary teachings of the present invention.

FIG. 8d is a schematic illustration of two-stage airfoil wings, constructed according to the principles of the present invention: (A) a two-stage wing 870 having a side-view sectional double-humped airfoil profile 871, and (B) a two-stage wing 8d having a side-view sectional classical airfoil profile and modified by supplying with the multi-layer TE device 8d.TED.

In FIG. 8d (A), the orientation of the double-humped airfoil profile 871 determines a sagittal axis 871.0, in turn, oriented horizontally. The two-stage double-humped airfoil wing 870 comprises two withers: forward 872 and rear 873, separated by concavity 874. The lift-force force originated by the profile is analyzed, considering the flying M-velocity which is higher than the specific M-velocity $M_* = \sqrt{(\gamma-1)/\gamma} \approx 0.5345$ Mach, i.e. when the lift-force, originated by a classical wing 10.A described hereinabove the subparagraph "Airfoil Wing (definition of attack angle)" referring to FIG. 1e Case (A), is negative.

An oncoming flow portion 875 runs at the double-humped airfoil wing 870, becomes a boundary layer moving adjacent to the upper-side surface of the double-humped airfoil wing 870 under an imaginary surface, which, in a sagittal sectional plane, is indicated by a double-dot dashed line 871.1 symbolizing an imaginary, in general, the curved surface formed by streamlines bordering the portion 875 above the double-humped airfoil wing 870, and passes positions: 801, 802, 803, 804, 805, 806, 807, 808, and 809 sequentially with associated M-velocities: $M_{801}$, $M_{802}$, $M_{803}$, $M_{804}$, $M_{905}$, $M_{806}$, $M_{807}$, $M_{808}$, and $M_{909}$, correspondingly. The double-humped airfoil profile 871 provides for the Coanda-jet-effect two-stage operation: upstream-afore and downstream-after concavity 874. At position 801, flow portion 875, having the de Laval high M-velocity $M_{801}$, is yet to be subjected to the Coanda-jet-effect operation over wing 870's profiled surfaces. The double-humped airfoil profile 871 causes that the cross-sectional area of portion 875 is varying as portion 875 moves over wing 870 as the boundary layer under the imaginary surface 871.1. So, portion 875 shrinks at position 802 while upping over the forward part, has the first local minimum of cross-section area at position 803 above the forward withers 872, expands at position 804 while downing into concavity 874, reaches the local maximum of cross-section area at position 805 when passing concavity 874, shrinks again at position 806 on the way to the rear withers 873, gets the second local minimal value of cross-section area at position 807 above the rear withers, and expands at positions 808 and 809. Thus, there are two convergent-divergent portions of the boundary layer moving adjacent to the upper-side surface of the double-humped airfoil wing 870:

first, upstream relative to concavity 874, comprising positions 802, 803, 804, and 805 when flowing over the forward withers 872, and second, downstream relative to concavity 874, comprising positions 805, 806, 807, 808, and 809 when flowing over the rear withers 873.

Each of the two convergent-divergent portions of the boundary layer is elaborated according to the condition of flow continuity Eq. (6.0) providing for gradually smooth changes of M-velocity to suppress undesired turbulences.

According to the condition of flow continuity Eq. (6.0), portion 875, as the boundary layer moving under the imaginary surface 871.1, is subjected to the de Laval-like jet-effect and the de Laval-like retarding-effect such that:

at position 802, the flow convergence is accompanied by the de Laval-like retarding-effect resulting in compressing and warming of flow portion 875 and a decrease of M-velocity, i.e. $M_{801} > M_{602}$;

at position 803, the first critical condition point, where the varying value of flow portion 875s cross-sectional area has the first local minimum, provides for that the M-velocity of flow portion 875 reaches the specific M-velocity $M_*$, so, $M_{801} > M_{802} > M_{803} = M_*$, i.e. the critical condition of the de Laval-like retarding-effect triggering is satisfied;

at position 804, the flow divergence is accompanied by further compressing and warming of flow portion 875 and a decrease of M-velocity lower than the specific M-velocity $M_*$, i.e. $M_* > M_{804}$;

at position 805 above concavity 874, the M-velocity $M_{80s}$ is minimal, thereby, providing the condition: $M_{801} > M_{82} > M_{803} = M_* > M_{804} > M_{905}$;

at position 806, the flow convergence is accompanied by cooling of flow portion 875, a decrease of static pressure, and an increase of M-velocity, i.e. $M_{805} < M_{806}$;

at position 807, the second critical condition point, where the varying value of the flow portion 875's cross-sectional area has the second local minimum, is designed to provide for that the M-velocity of flow portion 875 reaches the specific M-velocity $M_*$, i.e. the condition $M_{805} < M_{806} < M_{807} = M_*$ triggering the de Laval-like jet-effect is satisfied; and so, at positions 808 and 809, the flow divergence is accompanied by further cooling of flow portion 875, a decrease of static pressure, and an increase of M-velocity, i.e. $M_{805} < M_{806} < M_{807} = M_* < M_{808} < M_{809}$.

Depending on profile 871, the M-velocity $M_{809}$ of flow portion 875 at downstream position 809, may exceed the high M-velocity $M_{601}$ of flow portion 875 at upstream position 801, so, wing 870 can be used as a jet-booster based on the de Laval-like jet-effect, operating at high velocities.

In general, the use of a double-humped airfoil profile of a wing flying with the de Laval high M-velocities, in order to provide for the desired jet-effect, is yet one of the teachings of the present invention.

In view of the foregoing description referring to FIG. 8d (A), it will be evident to a person skilled in the art that the effect of high M-velocity acceleration by the Coanda-jet-effect two-stage operation is applicable, for example, to high-speed aircraft design. One of the primary advantages of a double-humped airfoil wing is that, in contrast to a classic wing, the double-humped airfoil wing 870 being stationary (not-variably) configured-and-oriented has a positive lift-force as for low M-velocities and for high M-velocities.

In view of the foregoing descriptions referring to FIGS. 8a, 8c, and 8d (A), it will be also evident to a person skilled in the art that a pair of actually-airfoil wings (i.e. having sharp trailing ends adapted to provide laminarity of air sub-portions outflowing downstream behind the sharp trailing ends), being arranged in-line along a sagittal axis one downstream behind the other and combined as a whole being stationary (not-variably) configured-and-oriented, can function similar to a double-humped airfoil wing 870 to provide a positive lift-force as for low M-velocities as well as for high M-velocities. Thus, the tandem 880.B of two airfoil bodies embodied in the form of actually-airfoil wings 850.B and 860.B consolidated as a whole (FIG. 8c Case (B)) can be interpreted as a broken double-humped airfoil wing.

In view of the foregoing descriptions referring to FIGS. 6c, 7d, 8c, and 8d (A), it will be evident to a person skilled in the art that, considering a body, flying in air-environment with transonic, and/or supersonic, and/or hypersonic velocities, i.e. with high M-velocities higher than the specific M-velocity $M_* = \sqrt{(\gamma-1)/\gamma}$, in contrast to a case, wherein a body having an arbitrary shape is decelerating when air-fluxes, which flow nearby around the body, become warmer and extra-warmed, a specifically-shaped body, having a double-humped airfoil profile providing for the two-stage operation of the Coanda-jet-effect, is accelerating, and air-fluxes, which flow nearby around the accelerating specifically-shaped body, become cooled and extra-cooled.

In FIG. 8d (B), it is shown a schematic drawing of a modified airfoil wing 8d, supplied with the multi-layer TE device 8d.TED built-in between the upper-side and lower-side surfaces of the modified airfoil wing 8d. The modified airfoil wing 8d has a side-view sectional classical airfoil profile, the orientation of which determines a sagittal axis 8d.0 oriented horizontally. For the purpose of the comparison between two wings: the double-humped airfoil wing 810 and the modified airfoil wing 8d, when the flying M-velocity is higher than the specific M-velocity $M_*=\sqrt{(\gamma-1)/\gamma}$ 0.5345 Mach;

an oncoming flow portion 8d.5 runs at the modified airfoil wing 8d, becomes a boundary layer moving adjacent to the upper-side surface of the airfoil wing 870 under an imaginary surface, which, in a sagittal sectional plane, is indicated by a double-dot dashed line 8d.1 symbolizing an imaginary, in general, the curved surface formed by streamlines bordering the portion 8d.5 above the airfoil wing 8d, and passes positions: 8d.1, 8d.2, 8d.3, 8d.4, 8d.5, 8d.6, 8d.7, 8d.8, and 8d.9 sequentially with associated M-velocities: $M_{D1}$, $M_{D2}$, $M_{D3}$, $M_{D4}$, $M_{D5}$, $M_{D6}$, $M_{D7}$, $M_{D8}$, and $M_{D9}$, correspondingly. The temperature distribution along the upper-side surface is forcibly controlled by the multi-layer TE device 8d.TED such that as the flow moves nearby above the modified airfoil wing 8d:

when crossing the positions 8d.02, 8d.03, and 8d.04, the temperature is gradually increasing thereby imitating the flow convergence and divergence when moving within a de Laval tube similar to the case when the flow moves nearby above the double-humped airfoil wing 870 crossing the positions 802, 803, and 804, correspondingly; and after reaching the position 8d.05 and further, when crossing the positions 8d.06, 8d.07, 8d.08, and 8d.09, the temperature is gradually decreasing thereby imitating the flow convergence and divergence when moving within a de Laval tube similar to the case when the flow moves nearby above the double-humped airfoil wing 870 crossing the positions 806, 807, 808, and 809, correspondingly.

An advantage of the modified airfoil wing 8d over the double-humped airfoil wing 870 is that the modified airfoil wing 8d provides for all the useful properties of the double-humped airfoil wing 870 in a wide range of velocities, wherein all the useful properties are controllably improved using degrees of freedom of the multi-layer TE device 8d.TED. While the overall geometry of the double-humped airfoil wing 870 is optimized to be adapted to the certain M-velocity $M_{875}$ of oncoming flow 875, the modified airfoil wing 8d is capable to be optimally adapted to an arbitrary M-velocity $M_{8d.5}$ of oncoming flow portion 8d.5. For this purpose, the forcibly established distribution of the temperature difference $\Delta T_{8d}(x)$ between the upper-side and lower-side boundary layers around the modified airfoil wing 8d is defined as:

$$\Delta T_{8d}(x) = \Delta T_{870}(x) \times \left[\frac{M_{8d.5}}{M_{875}}\right]^2,$$

where $\Delta T_{870}(x)$ is the distributed original temperature difference between the upper-side and lower-side boundary layers specified when designing the overall geometrical configuration of the double-humped airfoil wing 870 considering the mentioned certain M-velocity $M_{875}$ of oncoming flow 875.

Cascaded Jet-Boosters

FIG. 9a is a schematic illustration of a sequential cascade of in-line arranged airfoil bodies 9011, 9013, 9014, 9015, and 9016, each in the shape of an elongated drop, exposed to oncoming wind 900 having the ambient M-velocity substantially lower than the specific M-velocity $M_*=\sqrt{(\gamma-1)/\gamma}$. The shape and forcedly distributed temperature of the elongated drops is optimized using the condition of flow continuity Eq. (6.0) basing on a specified thickness of a boundary layer over convex withers, as described hereinabove referring to FIGS. 8a and 8b. Points 9012 symbolize that the sequence of airfoil bodies may be much longer than shown. For simplicity, oncoming wind 900 is laminar. Trace a moving-small-portion 910 of ambient oncoming wind 900 passing positions 911, 9110, 912, 913, 9130, 914, 9140, 915, 9150, 916, 9160, and 917, considering a case when moving-small-portion 910 is subjected to the Coanda-jet-effect in an adiabatic process, defined by the partial pressure-c $\delta P_c$, rather than affected by the skin-friction resistance, quantified by the difference $(a_w-a-\delta a)$. Moving-small-portion 910 at position 911 is yet to be subjected to the Coanda jet-effect operation. I.e. at least the forward airfoil body 9011 meets moving-small-portion 910 with M-velocity, lower than the specific M-velocity $M_*=\sqrt{(\gamma-1)/\gamma}$, and so body 9011 operates as a jet-booster based on the Venturi effect occurring in the adiabatic process in an imaginary tunnel adjacent to body 9011, as described above referring to FIG. 8b. Further, moving-small-portion 910 is subjected to a cascaded operation of the Coanda jet-effect in the adiabatic process by in-line arranged airfoil bodies 9011, 9013, 9014, 9015, and 9016, each of which operates as an elemental jet-booster, while meeting moving-small-portion 910 with M-velocity, lower than the specific M-velocity $M_*=\sqrt{(\gamma-1)/\gamma}$. The cascaded operation of the Coanda-jet-effect results in aligning of the Brownian random motion of moving-small-portion 910's molecules with the surfaces of in-line arranged airfoil bodies 9011, 9013, 9014, 9015, and 9016, that is observed as an increase of the effective velocity of moving-small-portion 910, accompanied by moving-small-portion 910 temperature decrease, as moving-small-portion 910 sequentially passes positions 9110, 9130, 9140, 9150, and 9160, where flowing as ambient-adjoining convergent-divergent jetstreams. Thus, this results in an increase of moving-small-portion 910's kinetic energy at the expense of moving-small-portion 910's internal heat energy. Consider certain identical cross-sectional areas at positions 911, 912, 913, 914, 915, 916, and 917, marked by dashed ellipses, such that the Coanda-jet-effect operation influence is still perceptible within the marked areas. Considering flow velocities much lower than the specific M-velocity $M_*=\sqrt{(\gamma-1)/\gamma}$, the effective velocity of flow crossing the marked areas at positions 911, 912, 913, 914, 915, 916, and 917 increases exponentially as the flow moves along the sequential cascade of in-line arranged airfoil bodies 9011-9016. For example, if the Coanda-jet-effect operation of each of airfoil bodies 9011-9016 in the adiabatic process provides an increase of the effective velocity of a flow portion, crossing the associated marked area, on 2%, then after 35 airfoil bodies 9011-9016 the effective velocity of the wind portion, crossing the marked area, is twice as high as the velocity of oncoming wind 900 yet to be subjected to the Coanda-jet-effect multi-stage cascaded operation. Consider a case, when the M-velocity $M_{9130}$ of moving-small-portion 910, flowing as an ambient-adjoining convergent-divergent jetstream nearby the withers of airfoil body 9013, reaches the specific M-velocity $M_*=\sqrt{(\gamma-1)/\gamma}$ at position 9130. Triggering of the de Laval-like jet-effect causes the M-velocity $M_{914}$ at position 914 to become higher than the specific M-velocity $M_*$. The moving-small-portion 910 becomes cooled between positions 913 and 9130 and becomes extra-cooled between positions 9130 and 914. Running at airfoil body 9014, moving-small-portion 910 is subjected to the de Laval-like retarding-effect, such that the portion's M-velocity decreases down to the specific M-velocity $M_*=\sqrt{(\gamma-1)/\gamma}$ at position 9140 nearby the withers of airfoil body 9014, and becomes lower than the specific M-velocity $M_*$ at position 915. The moving-small-portion 910 becomes warmer between positions 914 and 9140 and becomes extra-warmed between positions 9140 and 915. Then moving-small-portion 910 is subjected to the de Laval-like jet-effect and the M-velocity increases again. Thus, when the sequence of airfoil bodies 9011-9016 is sufficiently long, the effective M-velocity of moving-small-portion 910 reaches the value of the specific M-velocity $M_*=\sqrt{(\gamma-1)/\gamma}$ nearby the withers of airfoil bodies and varies around the value between the airfoil bodies. This is yet one more of the teachings of the present invention.

In view of the foregoing description referring to FIG. 9a, it will be evident to a person skilled in the art that:
- in a more general case, when oncoming wind 900 is turbulent, such that moving-small-portion 910 comprises whirling groups of molecules, the Coanda-jet-effect multi-stage cascaded operation results in aligning also of the turbulent motion of the whirling groups of molecules with the surfaces of in-line arranged airfoil bodies 9011, 9013, 9014, 9015, and 9016, that is observed as an increase of the effective velocity of moving-small-portion 910, accompanied by moving-small-portion 910's inner turbulence decrease, as moving-small-portion 910, flowing as ambient-adjoining convergent-divergent jetstreams nearby around the withers of airfoil bodies 9011,9013, 9014, 9015, and 9016, sequentially passes positions 9110, 9130, 9140, 9150, and 9160, correspondingly. Thus, this results in an increase of moving-small-portion 910's kinetic energy also at the expense of moving-small-portion 910's inner turbulent energy;
- the effect of M-velocity acceleration and stabilization by a multi-stage cascaded operation of the Coanda-jet-effect thereby reinforced multi-repeatedly is applicable, for example, to a high-speed long-train design;
- the effect of M-velocity stabilization is applicable, for example, to a flying train-like object, in particular, supplied with wings, which are not shown here, providing for a lift-force;
- an arrangement of airfoil bodies 9011, 9013, 9014, 9015, and 9016 along a smoothly curved locus, instead of the in-line arrangement, can be implemented; and
- the stabilized temperature difference between the extra-cooled airflow portions subjected to the triggered de Laval-like jet-effect and the extra-warmed airflow portions subjected to the triggered de Laval-like retarding-effect can be used to power a Peltier-element operating as a thermoelectric generator producing electricity.

Reference is now made again to FIG. 9a, wherein now, all the in-line arranged airfoil bodies 9011, 9013, 9014, 9015, and 9016 are made from a conductive material, for simplicity, from a hypothetic super-conductor, wherein the sequence is exposed to electric flux 900. In view of the foregoing description referring to prior art FIG. 1f, the inventor points out that the effective electric flux crossing the marked areas at positions 911, 912, 913, 914, 915, 916, and 917 is self-increasing exponentially as flowing along the sequential cascade of in-line arranged airfoil conductive bodies 9011 to 9016 due to the electromagnetic jet-effect.

FIG. 9b is a schematic illustration of a sequential multi-stage cascade of outer and nested airfoil rings 920, exposed to oncoming wind 921. Outer and nested airfoil rings 920 are formed by coiled-up walls having an actually-airfoil wing profile and forcedly distributed temperature, similar, for example, to that of actually-airfoil wing 810, shown schematically in FIG. 8a. Thereby, outer and nested airfoil rings 920 have shapes of streamlined converging nozzles. The actually-airfoil wing profiles and forcedly distributed temperature are optimized using the condition of flow continuity Eq. (6.0) basing on the specified thickness of a boundary layer over convex withers, as described hereinabove with the references to FIG. 8a. Points 929 symbolize that the sequence of outer and nested airfoil rings 920 may be much longer than shown. Airflow portions 922, flowing as ambient-adjoining convergent-divergent jetstreams, sliding outside of the sequential multi-stage cascade of outer rings 920, as well as wind portions 923, flowing and impacting inside of outer and nested airfoil rings 920, are subjected to the Coanda-jet-effect operation. Again, consider a case when airflow portions 922 and 923 are subjected to the Coanda-effect operation rather than to skin-friction resistance, thereby providing that each pair of outer and nested airfoil rings 920 operates as an elemental jet-booster. Airflow portions 922 and 923 join a cumulative outflow 924, wherein the Coanda-effect provides streamlines 925 forming an imaginary convergent-divergent nozzle downstream-behind the sequential multi-stage cascade of outer and nested airfoil rings 920. A sufficiently long multi-stage cascade of outer and nested airfoil rings 920 provides that the M-velocity of resulting cumulative outflow 924 reaches the specific M-velocity $M_*=\sqrt{(\gamma-1)/\gamma}$ at the minimal cross-section 926 of the imaginary convergent-divergent nozzle and the de Laval-like jet-effect is triggered downstream-behind the minimal cross-section 926. Airflow portion 927 is expanded adiabatically; therefore, it is extra-cooled and extra-accelerated. A prolonged multi-stage cascade of outer and nested airfoil rings 920 may enable the M-velocity of airflow portions 922 to reach the specific M-velocity $M_*$ nearby the withers of airfoil outer rings 920. In this case, airflow portions 922 become subjected to the de Laval-like jet-effect, such that the effective M-velocity of airflow portions 922 is stabilized, as described hereinbefore referring to FIG. 9a, considering a sequential multi-stage cascade of in-line arranged airfoil bodies, each having the shape of an elongated drop.

FIG. 9c is a schematic illustration of a modified sequential multi-stage cascade of the outer and nested airfoil rings 920 of FIG. 9b into a pair of unbroken spirals shaped as the Archimedean screws 931 and 932 by helical coiling-up walls having airfoil profile 937 and forcedly distributed temperature, for example, similar to described above referring to FIG. 8a. Airfoil profile 937, also shown separately above and to the left in an enlarged scale, and forcedly distributed temperature, both are optimized using the condition of flow continuity Eq. (6.0) basing on the specified thickness of a boundary layer over convex withers, as described hereinabove with the reference to FIG. 8a, and taking into account an M-velocity range used for the spirals 931 and 932.

Oncoming airflow portion 933 is yet to be subjected to the Coanda-jet-effect operation. Both: the sliding outside air sub-portions 934 flowing around and the inside impacting air sub-portions 935 flowing through the pair of spirals 931 and 932, are subjected to the Coanda-jet-effect operation, resulting in a converging flow when convergent flow sub-portions 934 and 935 laminarly join a resulting cumulative outflow 936. I.e. a fragment [for instance, one coil] of the pair of spirals 931 and 932 operates as an elemental jet-booster, and a longer fragment of converging spirals 931 and 932 provides higher acceleration of the airflow. Again, the Coanda-jet-effect provides streamlines 930 forming an imaginary convergent-divergent jet-nozzle downstream-behind the airfoil construction.

Moreover, the two spirals 931 and 932 have counter helical screwing rotations, namely: clockwise and inverse-clockwise, thereby providing a spatially varying cross-sectional area of gaps between the walls of the two spirals 931 and 932. The spatially varying cross-sectional area of the gaps provides a Venturi effect for velocities lower than the specific M-velocity $M_*=\sqrt{(\gamma-1)/\gamma}$ and the de Laval-like jet-effect for velocities providing for reaching the specific M-velocity $M_*=\sqrt{(\gamma-1)/\gamma}$ at the critical condition point where the variable cross-sectional area of gaps becomes minimal. Sufficiently long converging spirals 931 and 932 provide acceleration of the airflow and stabilization of the effective velocity at the value of the specific M-velocity $M_*=\sqrt{(\gamma-1)/\gamma}$ analogous to the cases described above with references to FIGS. 9a and 9b.

In view of the foregoing description of FIGS. 9a, 9b, and 9c, it will be evident to a person skilled in the art that:

One can implement many alterations, re-combinations, and modifications of elemental jet-boosters, taught herein, without departing from the spirit of the disclosure that can be generalized as the following. A sufficiently long aggregation of elemental jet-boosters provides acceleration of an airflow portion, reaching the specific M-velocity $M_*=\sqrt{(\gamma-1)/\gamma}$, thereby triggering alternating the de Laval-like jet-effect and the de Laval-like retarding-effect, resulting in a stable alternation of the airflow portion effective M-velocity above and below the specific M-velocity $M_*=\sqrt{(\gamma-1)/\gamma}$ between the elemental jet-boosters; and The cumulative useful kinetic-power, including both: the originally brought kinetic-power and the acquired kinetic-power, provided by a multiplicity of elemental jet-boosters, aggregated into an adiabatic converging system, depends on the quality and quantity of the elemental jet-boosters and how the elemental jet-boosters are arranged and exploited. Moreover, it will be evident to a person skilled in the art that a sequential in-line multi-stage cascading of the elemental jet-boosters has a special sense.

For example, consider an aggregation comprising N elemental jet-boosters exposed to an ambient flow and oriented such that each elemental jet-booster provides an increase of the effective velocity of the flow portion moving through a certain effective cross-sectional area, by a factor F, wherein F>1, and for simplicity and without loss of the explanation generality, consider a case of sufficiently low velocity of the ambient flow and assume that it is the same factor, independently of the elemental jet-boosters arrangement and exploitation. As well, for simplicity, consider the case, when the M-velocities of accelerated flow remain lower than the specific M-velocity $M_*=\sqrt{(\gamma-1)/\gamma}$, thereby, justifying neglecting the flow's mass density change in further approximate estimations. As the kinetic-power of a flow portion moving through a certain cross-sectional area is directly proportional to the cross-sectional area and proportional to the third power of the flow portion velocity, each elemental jet-booster, when operating separately, launches a jetstream having the solitary useful kinetic-power, indicated by $W_1$, proportional to the third power of the factor F, expressed by $W_1=W_0\times F^3$, where $W_0$ is the originally brought ambient useful kinetic-power associated with the effective cross-sectional area of one elemental jet-booster.

The solitary acquired kinetic-power $\Delta W_1$ is defined by the difference between the solitary useful kinetic-power $W_1$ and the originally brought ambient useful kinetic-power $W_0$, namely, $\Delta W_1=W_0\times(F^3-1)$; and so the aggregation, comprising N such elemental jet-boosters and thereby accelerating the flow portions, moving through N effective cross-sectional areas, results in the cumulative useful kinetic-power: indicated by $W_{parallel}$, equal to $W_{parallel}=N\times W_1=N\times W_0\times F^3$, wherein the cumulatively acquired kinetic-power $\Delta W_{parallel}$ is defined as:

$$\Delta W_{parallel}=N\times\Delta W_1=N\times W_0\times(F^3-1),$$

in the case, when the elemental jet-boosters operate independently, that occurs,
if the elemental jet-boosters are arranged in parallel, or
if the elemental jet-boosters are arranged sequentially, but operating in a not adiabatic process, allowing for the solitary useful kinetic-power $W_1$ to be consumed in parallel within or behind each elemental jet-booster and restored afore each next elemental jet-booster;

or, alternatively,
indicated by $W_{sequential}$, equal to $W_{sequential}=W_0\times(F^3)^N$, wherein the cumulatively acquired kinetic-power $\Delta W_{sequential}$ is defined as:

$$\Delta W_{sequential}=W_0\times[(F^3)^N-N],$$

in the case, when the elemental jet-boosters are arranged sequentially operating in the adiabatic process, and the consumption of the cumulative useful kinetic-power is allowed behind the downstream-end of the last elemental jet-booster only.

In an exemplary practical case, the effective velocity increase factor equals F=1.097. Then the following conditions become satisfied:
the condition $W_{sequential}<W_{parallel}$ is satisfied for $N\leq 8$;
the condition $W_{sequential}>W_{parallel}$ is satisfied for $N\geq 9$;
the condition $W_{sequential}>2W_{parallel}$ is satisfied for $N\geq 13$;
the condition $W_{sequential}>3W_{parallel}$ is satisfied for $N\geq 15$; and
the condition $W_{sequential}>4W_{parallel}$ is satisfied for $N\geq 16$.

In view of the foregoing description of FIGS. 9a, 9b, and 9c, one of the primary teachings is that an artificial wind can be used for the profitable harvesting of electricity. For example, one can:

use a big-front ventilator [or group of ventilators], having 50%-net-efficiency, i.e. consuming electric-power $W_{consumed}$ and creating an originally incoming artificial airflow, bringing kinetic-ewer $W_{income}=0.5\times W_{consumed}$, wherein the originally incoming artificial airflow has the front area $A_{income}$ of 4 times bigger than the effective cross-sectional area of an elemental jet-booster and has the effective velocity $U_{income}$;

implement a sequential multi-stage cascade, comprising N=15 elemental jet-boosters, each of which is characterized by the effective velocity increase factor F=1.097, such that altogether making an outflowing artificial jetstream, having the velocity $u_{jetstream}=u_{income}\times F^N [F^N=1.097^{15}\approx 4]$ and having the resulting effective frontal cross-sectional area $A_{jetstream}$, decreased approximately 4 times relative to the area $A_{income}$ of originally incoming airflow [$A_{income}/A_{jetstream}=F^N 4$]. Thus, the outflowing artificial jetstream brings the resulting useful kinetic-power $W_{jetstream}$, estimated as:

$$W_{jetstream}=[(u_{jetstream}/u_{income})^3\times(A_{jetstream}/A_{income})]\times W_{income}, \text{i.e.}$$

$$W_{jetstream}=[4^3/4]\times W_{income}=[16]\times 0.5\times W_{consumed}=8\times W_{consumed};$$

and
use a wind-turbine, producing electricity with 50%-net-efficiency, thereby, harvesting the useful electric-power $W_{useful}$ of 4 times higher than the consumed elect is-power $W_{consumed}$, namely, $$W_{useful}=0.5\times W_{jetstream}=0.5\times(8\times W_{consumed})=4\times W_{consumed}$$

Wherein, the profit becomes greater than estimated, when the de Laval-like jet-effect is triggered. Thereby, in view of the foregoing description referring to FIGS. 9a, 9b, and 9c, it will be evident to a person skilled in the art that profitable harvesting of electricity, using a jet-effect created by a multi-stage cascaded operation of the Coanda-jet-effect thereby reinforced multi-repeatedly, is feasible, for example, attaching sequentially arranged elemental jet-boosters to a sufficiently-long moving vehicle and using a wind-turbine, arranged behind the downstream-end of the last elemental jet-booster.

In view of the foregoing description referring to FIGS. 9a, 9b, and 9c, the inventor points out that, when reaching the stabilized effective velocity equal to the value of the specific M-velocity $M_*=\sqrt{(\gamma-1)/\gamma}$, the periodical local extra-acceleration and extra-retarding generate a forced extra-intensive elemental acoustic wave, wherein the distance between each two neighbor withers equals half of the wavelength of the forced extra-intensive elemental acoustic wave. Furthermore, the forced extra-intensive elemental acoustic waves are superposed in-phase thereby constituting the resulting extra-intensive acoustic wave as constructive interference. It will be evident to a person skilled in the art that the arrangement of airfoil bodies, either:

9011, 9013, 9014, 9015, and 9016 as shown in FIG. 9a; or a multi-stage cascade of outer and nested airfoil rings 920 as shown in FIG. 9b; or a pair of unbroken spirals shaped as the Archimedean screws 931 and 932 by helical coiling-up walls having airfoil profile 937, as shown in FIG. 9c, subjected to the generalized jet-effect (namely, the Coanda-jet-effect, the de Laval-like jet-effect, the de Laval-like retarding effect, and the enhanced waving jet-effect) and supplied by an acoustic detector capable of detection of the resulting extra-intensive acoustic wave power, can play a role of an electricity generator that, in the final analysis, produces the electric power at the expense of the warmth of the air.

Jet-Turbine as Improved Wind-Turbine

FIG. 9d is a schematic drawing of a jet-rotor of modified improved wind-turbine, called also a jet-turbine, 9.0, constructed according to the principles of the present invention to operate under relatively fast airflow 9.1 for producing the electric power at the expense of the warmth of relatively fast airflow 9.1.

Modified improved wind-turbine or jet-turbine 9.0 comprises:

axle 9.2 oriented along sagittal axis 9.21 codirected with fast airflow 9.1, identical asymmetrical biconvex actually-airfoil blades 9.3, attached to axle 9.2; and an engine, which is not shown here, having a stator and rotatable shaft; the engine is capable of transforming the power of the forced mechanic rotational motion 9.4 of axle 9.2 into electric power.

The primary feature, making the jet-turbine 9.0 practically implementable and extremely efficient, is the specifically configured and so specifically functioning biconvex actually-airfoil blades 9.3. Namely, in contrast to standard wind-turbines having standardly shaped blades configured to be subjected to impacting by an incoming airflow that, in particular, results in the airflow turbulence, retarding, and warming, the jet-turbine 9.0 has asymmetrical biconvex wing like actually-airfoil blades 9.3:

having opposite convex sides 9.31 and 9.32 with withers differing in convexity, and being oriented along and so adapted to the incoming fast airflow jetstream 9.11 headway motion.

Thereby configured and oriented blades provide the zero attack angle:

to exclude or at least to minimize the impact by the incoming fast airflow jetstream 9.11, but to provide an interaction with the fast airflow jetstream 9.11 by the Coanda-jet-effect only, thereby resulting in acceleration and cooling of outflowing jetstream 9.6 and resulting in lift-forces, acting on identical biconvex actually-airfoil blades 9.3 and being imbalanced because of the aligned asymmetry of the identical biconvex airfoil blades.

In this case, the axle 9.2 rotational motion, shown by the curved arrow having numeral 9.4, is caused by the cumulative resulting lift-force. Take note again, that the Coanda jet-effect is triggered by the airflow kinetic-power and is actually powered at the expense of the airflow warmth but not at the expense of the incoming fast airflow jetstream 9.11 kinetic-power; contrariwise, the kinetic-power of outflowing jetstream 9.6 is increased or at least not decreased with respect to the oncoming fast airflow 9.1. Thus, in contrast to the standard wind-turbines, the proposed improved wind-turbine 9.0 is specifically characterized:

by the mechanism of operation, that is the Coanda jet-effect but not the impact; and by the power source of an operation, that is the warmth but not the kinetic power of airflow.

Also, in contrast to a kind of the standard wind-turbines having wing-like blades moving around a vertical axis, the proposed jet-turbine 9.0 is specifically characterized by the excluding of varying poorly-streamlined positions of the wing-like blades. As well, in contrast to the standard wind-turbines, the productivity of the proposed jet-turbine 9.0 is defined by the area of the biconvex airfoil blades rather than by a so-called "swept area", namely, the produced electric power due to the Coanda-effect is specified as proportional to the biconvex airfoil blades area, i.e. the productivity can be increased substantially for a given swept area.

In view of the foregoing description referring to FIG. 9d, it will be evident to a person skilled in the art that jet-turbine 9.0 comprising:

the biconvex airfoil blades, having a wing-like sectional contour with a longer so-called chord of wing, and/or an increased quantity of the biconvex airfoil blades, both circumstances provide for enforcing of the desired Coanda-jet-effect. As well, it is self-suggested a sequential in-line arrangement of a multiplicity of jet-turbines 9.0 one downstream after another (optionally, alternatingly differing in asymmetry to become forcedly rotated alternatingly clockwise and inverse-clockwise, correspondingly), each separately and all together efficiently operating within the given swept area.

Moreover, at least one of the profiles 9.31 and 9.32 is implemented to provide the enhanced de Laval jet-effect, when the incoming fast airflow jetstream 9.11 is flowing with a de Laval M-velocity and so a portion of jetstream 9.11 is reaching the specific M-velocity nearby the withers of the asymmetrical biconvex actually-airfoil blades 9.3. In this case, the extra-efficiency of the modified improved wind-turbine is expected.

Furthermore, optionally, sides 9.31 and 9.32 differ in shape such that one of the sides has one convex withers and the opposite side has a double-humped airfoil profile providing for the two-stage operation of the Coanda-jet-effect as described hereinabove with the reference to FIG. 8*d*. Such asymmetrical blades, when exposed to oncoming fast airflow 9.1 moving with a high M-velocity, higher than the specific M-velocity, become subjected, on the one hand, to the de Laval retarding effect, and on the other hand, to the enhanced de Laval jet-effect. This provides for extra-increased lift-forces acting in unison and in the same direction of rotation and so rotating axle 9.2. In this case, the extra-efficiency of the modified improved wind-turbine is expected in a wide range of velocities.

FIG. 9*e* is a schematic drawing comprising the side-view and front view of a jet-rotor of jet-turbine 9.7, constructed according to the principles of the present invention to operate under relatively fast airflow 9.70 for producing the electric power at the expense of the warmth of relatively fast airflow 9.70. An engine of the jet-turbine, which (the engine) having a stator and rotatable shaft, is not shown here, Axle 9.73, collinear with sagittal axis 9.74, is oriented to be codirected with the headway motion of the relatively fast airflow 9.70. In relation to all the principal features, the jet-turbine 9.7 is similar to the jet-turbine 9.0, described hereinabove referring to FIG. 9*d*, but now, referring to the aforementioned optional diversity of the implementation of the principal features, the biconvex actually-airfoil blades, which have opposite at least partially convex sides 9.71 and 9.72 with withers differing in convexity, are further curved and screwed to optimize a suppression of turbulence as well as are cascaded one downstream after another to provide a multi-stage repeated operation of the Coanda-jet-effect thereby contributing to the desired cumulative lift-force to rotate axle 9.73.

In view of the foregoing description referring to FIGS. 9*d* and 9*e*, it will be evident to a person skilled in the art that jet-turbine 9.0 or 9.7, when attached to a flying aircraft, is capable of efficient harvesting of the electric power from the ambient air warmth.

Furthermore, in view of the description expound hereinabove with references to FIGS. 5*l*, 5*j*, 5*k*, 9*a*, 9*b*, and 9*c*, the inventor points out that the mentioned multiplicity of jet-turbines 9.0 or 9.7, arranged sequentially one downstream after another [not shown here], results in the generation of acoustic waves accompanied by extraction of the internal heat energy of ambient air in favor for the wave power due to the enhanced waving jet-effect. Thus, a system, comprising the arrangement and a detector of the acquired wave power, has an additional degree of freedom to increase the efficacy of the production of electricity.

In view of the foregoing description referring to FIGS. 9*d* and 9*e* in combination with the foregoing description of subparagraphs "Point of Sail" and "Flying Bird", both with the reference to prior art FIG. 2*a*, it will be evident to a person skilled in the art that the construction of jet-turbine 9.7, when having a controllable speed of the axle 9.73 rotation adapted to the velocity of oncoming airflow 9.70 to keep the airflow remaining laminar, provides a controllable net jet-thrust against the oncoming airflow 9.70 and so becomes applicable as a kind of jet-engine for a controllable and substantially noiseless flying.

Furthermore, in view of the foregoing description referring to FIGS. 9*d* and 9*e*, it will be evident to a person skilled in the art that jet-rotor 9.7 having relatively massive actually-airfoil wings, when being attached to a body moving in a fluid and being capable of free rotation around the sagittal axis 9.74 due to the self-originated lift-forces acting on all the massive wings in unison and in the same direction of rotation, creates the gyroscopic effect that is defined as a tendency of the moving body to maintain a steady direction collinear with the sagittal axis 9.74 being the axis of the massive wings rotation and is manifested as a resistance to gusty fluctuations of motion of the ambient fluid, wherein the energy to generate the desired gyroscopic effect improving ballistic properties of the moving body is harvested from the ambient fluid warmth due to the Coanda-jet-effect.

Jet-Ventilator and Jet-Propeller

FIG. 9*f* is a schematic drawing of a modified improved ventilator, called also a jet-ventilator, 9J.0, constructed according to the principles of the present invention to create a headway laminarly moving flow. The jet-ventilator 9J.0 comprises a jet-rotor, which also is marked by numeral 9J.0, and a motor, which is not shown here, having a stator and rotatable shaft. The motor, being powered by either a burned fuel or electrical power, forcedly rotates the rotatable shaft and, thereby, the jet-rotor 9J.0.

One of the specifics of the jet-ventilator 9J.0 is that blades 9J.1, having a profile 9J.2 similar to the profile of actually-airfoil biconvex wing 810 described hereinabove referring to FIG. 8*a*, are configured to be actually-airfoil and, when rotating, oriented to run over air portions 9J.6 (yet to be subjected to a motion) under the zero attack angle and to act on the air portions 9J.6 due to the Coanda-effect only. As the air portions 9J.6, when subjected to the Coanda-effect, originate lift-force 9J.3 acting on the blades 9J.1, the blades 9J.1 push-off the air portions 9J.6 in the opposite direction collinear to sagittal axis 9J.7 according to Newton's Third Law. Thereby, headway-forwarding air portions become a headway-forwarding laminar no-whirling outflow 9J.5 created by the jet-ventilator 9J.0. As the used blades 9J.1 are actually-airfoil, relatively low power consumption can provide a relatively fast rotation 9J.9 of the blades 9J.1, wherein the velocity of the fast rotation 9J.9 is in conformance with an optimal configuration 9J.2 of the actually-airfoil blades 9J.1. Since the desired acceleration of the outflow occurs due to the Coanda-effect only, the method of accelerating the outflow allows for significantly reducing energy consumption compared with the classical technique based on the impact of the blades. It will be evident for a commonly educated person, that the concept of jet-ventilator 9J.0 is applicable to any fluid either gas or liquid. A disadvantage of the technique to create the laminar no-whirling flow 9J.5 is that the relatively fast rotation 9J.9 of the blades 9J.1 produces relatively slow laminar no-whirling flow 9J.5.

FIG. 9*g* is a schematic drawing of jet-propeller 9K.0, constructed according to the principles of the present invention. The jet-propeller 9K.0 comprises a jet-rotor, which also is marked by numeral 9K.0, and a motor, which is not shown here, having a stator and rotatable shaft. The motor, being powered by either a burned fuel or electrical power, forcedly rotates the rotatable shaft and, thereby, the jet-rotor 9K.0. As the function difference between jet-propeller 9K.0 and jet-ventilator 9J.0 is that, while the jet-rotor of jet-ventilator 9J.0 acts to initially motionless air portions 9J.6, the jet-rotor of jet-propeller 9K.0 acts to airflow 9K.6 oncoming to blades with a certain velocity; so, the primary constructive difference between jet-propeller 9K.0 and jet-ventilator 9J.0 is in the orientation of blades. Namely, blades 9K.1 of jet-propeller 9K.0 are turned on a certain angle 9K.8, called also pitch, such that, when rotating with a certain rate 9K.9, to run over oncoming airflow 9K.6 under the zero attack angle and to act on oncoming airflow 9K.6 due to the Coanda-effect only. As the lift-force 9K.3 acting on wings 9K.1 has a component directed collinearly to sagittal axis 9K.7 against the direction of the oncoming airflow 9K.6, the oncoming airflow 9K.6 becomes subjected to acceleration according to Newton's Third Law, thereby forming, resulting headway-forwarding outflow 9K.5. As the certain velocity of oncoming airflow 9K.6, the certain rate of blades 9K.1 rotation 9K.9, and the certain angle 9K.8 of blades 9K.1 orientation, all are interrelated, one can adapt the blades 9K.1 rotation rate 9K.9 and angle of orientation 9K.8 to the oncoming flow velocity 9K.6 to provide the zero attack angle to act on oncoming airflow 9K.6 due to the Coanda-effect only. When all the parameters are matched, the resulting headway-forwarding outflow 9K.5 accelerated by jet-propeller 9K.0 is laminar and no-whirling.

In view of the foregoing description referring to FIGS. 9f and 9g, it becomes evident, that:
- jet-propeller 9K.0 can comprise a variable pitch being capable of being adapted to the velocity of oncoming flow and rotation rate;
- jet-ventilator 9J.0 can be interpreted as a particular case of jet-propeller 9K.0, the pitch of which is adapted to initially stationary fluid;
- jet-ventilator 9J.0, pitch 9J.8 of which providing the zero attack angle of meeting stationary portions of air, and jet-propeller 9K.0, pitch 9K.8 of which being adapted to the velocity of airflow 9J.5 created by jet-ventilator 9J.0, can be arranged in-line: the jet-propeller after the jet-ventilator, thereby forming a system that as a whole performs an improved jet-ventilator providing for boosted outflow; and
- since the blades of jet-propeller 9K.0, when moving, meet the ambient fluid at the zero attack angle and so, on the one hand, consume power to overcome a minimized drag and, on the other hand, produce the useful-beneficial power of accelerated outflow at the expense of ambient warmth due to the Coanda-jet-effect, a net-efficiency higher than 100% becomes reachable.

Reference is now made to FIG. 9h. FIG. 9h is a schematic illustration of a multi-module jet-ventilator 9L.0, constructed according to the principles of the present invention to create a boosted headway-forwarding laminar no-whirling 9L.5. The multi-module jet-ventilator 9L.0 comprises a tuple of modules 9L.01 to 9L.07 attached to a common shaft. Each of the modules 9L.01 to 9L.07 is characterized by an individual pitch, wherein:
- The "zero" pitch of the first module 9L.01 provides for that, when the rotating blades of the first module 9L.01 run over the originally stationary portion of air 9L.6 at the zero attack angle, the first module 9L.01 functions as jet-ventilator 9J.0 described hereinabove referring to FIG. 9f;
- A relatively small pitch of the second module 9L.02 provides for that, when the rotating blades of the first module 9L.02 run over portions of a relatively slow flow originated by the first module 9L.01 at the zero attack angle, i.e. the second module 9L.02 functions as jet-ventilator 9K.0 adapted to a certain oncoming flow as described hereinabove referring to FIG. 9g;
- The individual pitch of each next module: 9L.03 to 9L.07, provides for that, when the rotating blades of the next module: 9L.03 to 9L.07 run over portions of a flow originated the previous module: 9L.02 to 9L.06, correspondingly, at the zero attack angle, i.e. all each of the modules 9L.03 to 9L.07 functions as jet-ventilator 9K.0 adapted to an associated oncoming flow as described hereinabove referring to FIG. 9g.

As a result of all the modules 9L.01 to 9L.07 operation as a whole, the resulting headway-forwarding laminar no-whirling outflow 9L.5 becomes accelerated reaching a relatively high velocity vectored collinearly to sagittal axis 9L.7.

FIG. 9i is a schematic illustration of a cascade 9M.0 of multi-module jet-ventilator 9M.01 and two multi-module propellers 9M.02 and 9M.03 aggregated along the common sagittal axis 9M.7. The cascade 9M.0 is constructed according to the principles of the present invention, wherein the multi-module jet-ventilator 9L.0 and multi-module propellers 9M.02 and 9M.03, each comprises a tuple of modules attached to a common shaft. The multi-module jet-ventilator 9M.01 acts on an initially stationary portion of fluid 9M.6 and creates outflow 9M.51, which, in turn, becomes oncoming flow 9M.51 blowing the multi-module jet-propeller 9M.02. The multi-module jet-propeller 9M.02 acts on the oncoming flow 9M.51 and creates outflow 9M.52, which, in turn, becomes oncoming flow 9M.52 blowing the multi-module jet-propeller 9M.03. The multi-module jet-propeller 9M.03 acts on the oncoming flow 9M.52 and creates the resulting outflow 9M.53. Without loss of generality, the tuple of the multi-module jet-ventilator 9M.01 is a triplet of modules attached to a common shaft. As well, again, without loss of generality, a tuple of each of jet-propellers 9M.02 and 9M.03 is a triplet of modules attached to a common shaft. Each of the mentioned modules comprises three sets of blades, wherein each of the sets is characterized by an individual pitch. The pitches of modules and rates of rotations 9M.91, 9M.92, and 9M.93 are chosen such that all the blades run over portions of oncoming flow at the zero attack angle.

Optionally, blades of jet-propeller 9M.02 are configured for rotations 9M.91 and 9M.92 in mutually-opposite directions: clockwise and contrary-clockwise, correspondingly. The alternating directions of the rotations of in-line arranged jet-rotors are preferred to compensate for the unwanted whirling of flow. Although the unwanted whirling is purposely suppressed by excluding or at least minimizing the impact by blades, it (the unwanted whirling) can be originated due to other effects such as skin-friction between the flow and blades as well as jet-thrust described hereinabove in subparagraphs "Point of Sail" and "Flying Bird", both with the reference to prior art FIG. 2a.

Heat-Turbine and Jet-Transformer

FIG. 9j is a schematic illustration of a concept to transform ambient warmth into electricity. The concept is embodied as a heat-turbine 9n.H and jet-transformer 9n.J comprising:
- a laminar flow maker 9n.2, in turn, comprising at least one of
  - a shaped heater 9n.21, conceptually, having a geometry of convex-concave corpus having airfoil outer walls 9n.211 and paraboloidal inner wall 9n.213 and being supplied by a point heater 9n.212 located in the focus of the paraboloidal inner wall 9n.213;
  - a shaped jet-ventilator 9n.22, conceptually, embodied as a multi-module jet-ventilator described hereinabove in the subparagraph Jet-Ventilator and Jet-Propeller referring to FIGS. 9f, 9g, 9h, and 9i [here, for simplicity of the drawing, a one-module jet-ventilator 9n.22 is shown];
- a specifically shaped pipe 9n.1 having the optimized convergent-divergent inner tunnel, described hereinabove in sub-paragraph "Convergent-Divergent Jet-Nozzle" with reference to FIG. 6a; namely, the convergent-divergent inner tunnel, elevated above the ground to allow for the ambient air $9n.41$ entering the optimized convergent-divergent inner tunnel, comprises forcedly controllable thermoelectric devices $9n.\text{TED}$ built-in into walls $9n.\text{WALLS}$ such that the geometry of the tunnel, temperature distribution along the tunnel, and velocity of the upward laminar flow become interrelated according to the condition of flow continuity Eq. (6.0); and at least one jet-turbine $9n.3$, designed as the jet-turbine $9.7$ described hereinabove referring to FIG. $9e$;

all, constructed according to the principles of the present invention.

The Case when the Shaped Heater $9n.21$ is Used in the Heat-Turbine $9n.\text{H}$ The specifically shaped pipe $9n.1$ is upward-oriented. The point heater $9n.212$ supplies the heat energy to a fluid portion adjacent to the focus of the parabolically-concave surface $9n.213$ of the shaped heater $9n.21$'s convex-concave corpus, thereby, on the one hand, to trigger the Archimedes' upward-vectored force lifting the heated fluid portion and, on the other hand, to align the airflow $9n.42$ upward along the vertical axis $9n.51$ which is a sagittal axis, for the case. The upward airflow $9n.42$ is relatively slow and substantially-laminar. The optimized convergent-divergent inner tunnel of the specifically shaped pipe $9n.1$, supplied with forcedly controllable thermoelectric devices $9n.\text{TED}$ built-in into walls $9n.\text{WALLS}$, is designed according to the condition of flow continuity Eq. (6.0) to provide for substantial suppression of jumps of the air thermodynamic parameters and, thereby, to provide for the substantial acceleration of the airflow $9n.42$, laminarly and so noseless streaming upward. So, the heating triggers the upward motion of air, and, in turn, the fluid motion itself triggers the convective acceleration as the airflow moves through the narrowing cross-section of the optimized convergent-divergent inner tunnel. Considering:

the temperature above the exhaust $9n.54$ equal $T_e$ that is lower than the temperature $T_a$ of the ambient air; the condition $T_a = T_a$ is for the worst-case estimation;

the temperature near the level $9n.52$ equal $T_0$, and the temperature near the narrow throat $9n.53$ equal $T_*$, equation (7.1c), described hereinabove referring to FIG. $7a$, says that:

to obtain the enhanced de Laval jet-effect for air utilizing the optimized convergent-divergent inner, one must provide the ratio $T_0/T_*$ at least of 1.2; and to provide that the temperature $T_e$ of outflowing stream $9n.44$ above the exhaust $9n.54$ become equal to the temperature of ambient air, to accelerate an air portion up to the velocity of sound, one must provide the ratio $T_0/T_e$ at least of 1.7.

Hence, providing the heating of air near the level $9n.52$ up to about the temperature 234° C. only, the condition of the enhanced de Laval jet-effect becomes satisfied, in turn, providing that the relatively low heat power, supplied by point heaters $9n.212$, triggers the enhanced de Laval jet-effect transforming the warmth of the moving airflow into the acquired kinetic power of the airflow.

The energy $E_0$, necessary for warming 1 cube meter of air from the temperature 25° C. up to the temperature 234° C., is estimated as $E_0 = \rho V C_V (T_0 - T_a)$, where V is the volume of 1 cube meter, $\rho$ is the air mass density, $\rho \approx 1.2$ kg/m$^3$, $C_V$, is the air heat capacity, $C_V \approx 0.72$ kJ/(kg·K), thereby, $E_0$ 1.2× 1×0.72×(234−25) 180 kJ.

As the mentioned assumed condition allows to accelerate the airflow portion $9n.54$ up to the specific M-velocity $M_* = \sqrt{(\gamma-1)/\gamma}$ near the narrow throat $9n.53$ and to accelerate the airflow portion $9n.54$ up to almost the speed of sound (i.e. the exhaust M-velocity is of $M_e \approx 1$), then, an exemplary estimation is as follows:

the acquired kinetic energy, $K_e$, of the outflowing airflow portion $9n.54$, which (the acquired kinetic energy $K_e$) is specified as the difference between bringing heat energies, equals $K_e \approx n \times (T_0 - T_e) \times R$, where n is number of moles in the considered 1 cube meter of air, $n \approx 44.64$, and R is the specific gas constant, approximated for the air by R=287 J/(kg·K), i.e. $K_e \approx 44.64 \times 209 \times 287 \approx 2,677$ kJ, that, in turn, says that the acquired kinetic energy $K_e$ may exceed the consumed energy $E_0$ at least at subsonic velocities by the factor of 15; and the acquired kinetic energy, $K_*$, of the airflow portion $9n.54$, when crossing the narrow throat, equals $K_* \approx n \times (T_0 - T_*) \times R \approx 764$ kJ, thereby showing that the acquired kinetic energy $K_*$ may exceed the consumed energy $E_0$ by the factor of 4.24.

It will be evident to a commonly educated person that, if not to use the optimized convergent-divergent inner tunnel, designed according to the condition of flow continuity Eq. (6.0), the mentioned effective conversion of the airflow heat energy into the airflow kinetic energy is impossible because of originated turbulences and Mach waves, both accompanied by noise and energy dissipation back to the air warmth.

The jet-turbine $9n.3$ meets the upping laminar airflow and provides for the production of electricity neither retarding the upward airflow and nor distorting the upward airflow laminarity as described hereinabove referring to FIGS. $9d$ and $9e$. The inventor points out again that the improved wind-turbine $9n.3$ harvests electric power at the expense of the airflow warmth but not from the airflow kinetic power, wherein the increased kinetic power of the airflow plays the role of a boosted trigger of the lift-force rotating the improved wind-turbine. Moreover, optionally, in-line arranged several jet-turbines $9n.3$ provide for a multi-stage repeatedly harvesting of electricity from the same airflow portion.

It will be evident to a person who has studied the present invention that both the outer convex wall $9n.211$ and the inner wall $9n.213$ can be supplied with built-in matrix thermoelectric devices to control the laminarity of the entering heated flow $9n.42$.

The Case when the Shaped Jet-Ventilator $9n.22$ is Used in Jet-Transformer $9n.\text{J}$ The substantially-laminar airflow $9n.42$ enters the specifically shaped pipe $9n.1$ with a certain velocity $u_{in}$. The optimized convergent-divergent inner tunnel of the specifically shaped pipe $9n.1$, supplied with forcedly controllable thermoelectric devices $9n.\text{TED}$ built-in into walls $9n.\text{WALLS}$, is designed according to the condition of flow continuity Eq. (6.0) such to be adapted to the velocity u, to result in the substantial acceleration of the airflow $9n.42$, laminarly and so noseless streaming along the optimized convergent-divergent inner tunnel; wherein, in this case, the orientation of the sagittal axis $9n.51$ is not obligatory upward.

Levitating Apparatus Imitating Effects of Taking-Off of Bird and Insect

FIG. $9k$ is a schematic illustration of a levitating apparatus $9o.0$ comprising:

a shaped propeller $9o.1$, conceptually, embodied as a multi-module jet-ventilator [here, for simplicity of the drawing, a pair of counter-rotating one-module jet-ventilators is shown; the rotations are indicated by the circle arrows $9o.13$ and $9o.14$] described hereinabove in the subparagraph Jet-Ventilator and Jet-Propeller referring to FIGS. 9f, 9g, 9h, and 9i; and a capsule 9o.2 having a dominantly-airfoil overall shape and being optionally scaled to fit a person [a sculpture 9o.3 is shown instead of the person].

The wings 9o.11 and 9o.12 of the shaped propeller 9o.1 are supplied with thermoelectric devices as described hereinabove in subparagraphs "Modified Symmetrical Wing" and "Shaped Wing as a Convergent-Divergent Jet-Nozzle" referring to FIGS. 8 and 8a such that providing the effective temperature difference $\Delta T_{WING}$ between the upper and lower sides of the wings 9o.11 and 9o.12. Shell 9o.SHELL of the capsule 9o.2 is supplied with a matrix thermoelectric device 9o.TED such that the temperature of the shell 9o.SHELL's outer side is forcedly controlled to be gradually distributed along the axis Z providing the integral temperature difference $\Delta T_{Z,CAPSULE}$ around the ambient temperature $T_{AMBIENT}$. The gradually smoothed curve 9o.4 is in coordinates (T, Z), where the axis-T indicates the temperature. When the wings 9o.11 and 9o.12 are rotating around the vertical axis 9o.AXIS:

while the wings 9o.11 and 9o.12 are subjected to:
the lift-force $F_{LIFT}$, that is a measure of the lift-effect of a "cold-blooded" wing, i.e. is provided by the airfoil geometry of the wings 9o.11 and 9o.12, and
the positive contribution $\Delta F_{BIRD}$ to the upward-vectored force, wherein the originated effect of the contribution $\Delta F_{BIRD}$ imitates the effect of taking-off of a bird;

the capsule 9o.2 is subjected to blowing by fresh portions of air triggering the positive contribution $\Delta F_{INSECT}$ to the upward-vectored force, wherein the originated effect of the contribution $\Delta F_{INSECT}$ imitates the effect of taking-off of an insect.

To evaluate the practicality of the flying apparatus 9o.0 for industrial use, exemplary positive contributions $\Delta F_{BIRD}$ and $\Delta F_{INSECT}$ to the upward-vectored force are estimated considering:

the normal ambient air conditions: $T = T_{AMBIENT} \approx 300K$, $P = P_{AMBIENT} \approx 100,000$ Pa, $\rho = \rho_{AMBIENT} \approx 1.2$ kg/m$^3$, and $\gamma = 7/5$;

an exemplary version of the shaped propeller 9o.1 performing a two-module ventilator having two triplets of wings 9o.11 (i.e. 6 wings);

each of the wings 9o.11 has a chord of 0.25 m and a span of 0.5 m; i.e. the total area of the wings is $A_{WINGS} = 6 \times 0.25 \times 0.5 = 0.75$ m$^2$;

the effective temperature difference between the upper and lower sides of the wings is $\Delta T_{WING} = -30$ C;

the refreshed air portions on the upper and lower sides of the wings are subjected to suddenly originated effective difference in static pressures along the axis Z, indicated by $\Delta P_{WING}$, interrelated with $\Delta T_{WING}$ according to equation Eq. (1.1b) described hereinabove in the subparagraph "Sound as Complicated Movement in Molecular Fluid" prefacing the reference to FIG. 3a, namely, the ratio $(-\Delta T_{WING})/T \approx 0.1$, the ratio $(-\Delta P_{WING})/P \approx 0.1 \times (7/5)/(2/5) = 0.35$, and so the suddenly originated effective additional static pressure difference is $(-\Delta P_{WING}) \approx 0.35 \times 10^5$ Pa;

the velocity-dependent suddenness factor, indicated by $C_{WING}$, for calculation of the $\Delta F_{BIRD}$ is given by 0.1 as corresponding to the effective velocity $u_{WING}$ of the wings rotation 9o.12 as fast as 20 m/sec;

the cross-sectional area 9o.21 of a projection of the capsule 9o.2, $A_{(X,Y),CAPSULE}$, in a horizontal plane is given by 0.8 m$^2$;

the integral temperature difference, $\Delta T_{Z,CAPSULE}$, is given by $-30$ C;

the refreshed air portions, when flowing around the capsule 9o.2, are subjected to suddenly originated effective difference in static pressures along the axis Z, indicated by $\Delta P_{Z,CAPSULE}$, interrelated with $\Delta T_{Z,CAPSULE}$ as follows: the ratio $(-\Delta T_{Z,CAPSULE})/T \approx 0.1$, the ratio $(-\Delta P_{Z,CAPSULE})/P \approx 0.1 \times (7/5)/(2/5) = 0.35$, and so the suddenly originated additional static pressure difference is $(-\Delta P_{Z,CAPSULE})$ $0.35 \times 10^5$ Pa; and the velocity-dependent suddenness factor, indicated by $C_{CAPSULE}$, for calculation of the $\Delta F_{INSECT}$ is given by 0.027 as corresponding to the velocity $U_{BLOW}$ of a flow 9o.15 when blowing the capsule 9o.2 given by 5 m/sec.

Thus, the originated forces are estimated as follows:

the lift-force $F_{LIFT}$ provided by the geometry of the six wings 9o.11, wherein the geometry is characterized by the coefficient of lift $C_L$ exemplary given by 0.5, is estimated as:

$$F_{LIFT} = 0.5 \times \rho \times A_{WINGS} \times C_L \times u_{WING}^2 \approx 90N;$$

the contribution $\Delta F_{BIRD}$ to the upward-vectored force, which ($\Delta F_{BIRD}$) is a measure of the imitated effect of taking-off of a bird, is:

$$\Delta F_{BIRD} = (\frac{1}{2}) \times C_{WING} \times A_{WINGS} \times (-\Delta P_{WING}) \approx 1,427N;$$

the contribution $\Delta F_{INSECT}$ to the upward-vectored force, which ($\Delta F_{INSECT}$) is a measure of the imitated effect of taking-off of an insect, is:

$$\Delta F_{INSECT} = (\frac{1}{2}) \times C_{CAPSULE} \times A_{(X,Y),CAPSULE} \times (-\Delta P_{Z,CAPSULE}) \approx 385N;$$

and, thereby, the accumulated contribution to the upward-vectored force is estimated as $(F_{LIFT} + \Delta F_{BIRD} + \Delta F_{INSECT}) \approx 1,839$ N that is sufficient to raise a mass of 184 kg.

Wherein, concerning power consumption:

to rotate the shaped propeller 9o.1 having wings 9o.11 and 9o.12 oriented to meet the ambient air portions at the zero attack angle dominantly, minimal power consumption is required for overcoming the minimal drag of wings only; and to support the required temperature differences, $\Delta T_{WING}$ and $\Delta T_{CAPSULE}$, a 15% net-efficiency of standard Peltier elements determines the required power consumption.

Further, the matrix thermoelectric device 9o.TED is capable of providing for controlled distribution of the shell 9o.SHELL's temperature along the axis X. The gradually smoothed curve 9o.5 is in coordinates (X, T), where:

axis X indicates the horizontal direction;

the maximal frontal cross-sectional area of the capsule 9o.2, indicated by $A_{(Y,Z),CAPSULE}$, is given by 2 m$^2$;

the integral temperature difference between the coordinates $X_{LEFT}$ and $X_{RIGHT}$ of the capsule 9o2 location, indicated by $\Delta T_{X,CAPSULE}$ is given by 30 C; and the refreshed air portions, when flowing around the capsule 90.2, are subjected to suddenly originated effective difference in static pressures along the axis X, indicated by $\Delta P_{X,CAPSULE}$, interrelated with $\Delta T_{X,CAPSULE}$ as follows: the ratio $(\Delta T_{X,CAPSULE})/T \approx 0.1$, the ratio $(\Delta P_{X,CAPSULE})/P \approx 0.1 \times (7/5)/(2/5) = 0.35$, and so the suddenly originated additional static pressure difference is $\Delta P_{X,CAPSULE} \approx 0.35 \times 10^5$ Pa.

Thus, the possible thrust 9o.THRUST for a sideward motion is:

$$\Delta F_{X,THRUST}=(\tfrac{1}{2})\times C_{CAPSULE}\times A_{(Y,Z),CAPSULE}\times(-\Delta P_{Z,CAPSULE})\approx 950N$$

that allows moving the mentioned mass of 184 kg with an acceleration of about 5 m/sec$^2$ in a horizontal direction. The controllable difference between the speeds of counter rotations 9o.13 and 9o.14 provides a controlled rotation of the capsule 9o.2 around the axis 9o.AXIS.

In view of the foregoing description referring to FIGS. 9j and 9k, it will be evident to a person skilled in the art that:

the levitating apparatus 9o.0 can be further supplied with at least one of the heat-transformer 710.H and the jet-transformer 9n.J having the shaped jet-ventilator 9n.22 and oriented such that the sagittal axis 9n.51 is directed downward and/or sideward;

Instead of Peltier elements (thermoelectric devices 9o.TED), any kind of electric heater and/or cooler (i.e. a thermoelectric device in the broad sense) can be used to control the temperature distribution over the shell 9o.SHELL's, because the inertness of temperature

The invention claimed is:

1. A nozzle [610,650] exposed to fluid flow, the nozzle having a geometrically configured corpus having:
   a shaped tunnel within the geometrically configured corpus, wherein the shaped tunnel has solid inner walls forming a cross-sectional profile specially adapted to a headway velocity and thermodynamic parameters of the fluid flow; and
   an acoustic thermoelectric device built-in within the solid inner walls; the acoustic thermoelectric device is capable of forcedly establishing a specifically distributed absolute temperature along the solid inner walls of the shaped tunnel, wherein the forcedly established specifically distributed absolute temperature along the solid inner walls of the shaped tunnel is specially adapted to the headway velocity and thermodynamic parameters of the fluid flow;
the solid inner walls forming:
   an open inlet allowing the fluid flow to enter the open inlet;
   an open outlet allowing the fluid flow to flow through the shaped tunnel and out of the open outlet; and
   a varying cross-sectional area, varying along the shaped tunnel length having a distance parameter x such that a stationary geometry of the shaped tunnel is either converging, or divergent, or convergent-divergent; wherein, a cross-sectional area profile function A(x) is given by an equation expressed as:

$$A(x) = \frac{A_x}{M(x)}\left(\frac{\gamma-1}{\gamma}\right)^{\frac{1}{2}}\left(\frac{2+\gamma(M(x))^2}{\gamma+1}\right)^{\frac{\gamma+1}{2(\gamma-1)}}$$

where $A_*$ is a constant, $\gamma$ is an adiabatic compressibility parameter of the flowing fluid, and M(x) is a gradually-smoothed monotonic function of x representing a distribution of headway velocity measured in Mach numbers;
and acting on the fluid flow to originate boundary layers adjacent to the solid inner walls; the acoustic thermoelectric device comprising:
   a multiplicity of elemental acoustic thermoelectric devices [5P.0] aggregated as a whole in a matrix of a phased array; and
   a common controller capable of interrelating operations of the multiplicity of elemental acoustic thermoelectric device;
the acoustic thermoelectric device is further specified as follows:
   the multiplicity of the elemental acoustic thermoelectric devices aggregated as a whole in a surface matrix arrangement having two opposite sides: first and second, wherein the first side having a thermoconductive bus being thermally in contact with the solid inner walls, in turn, contacting with the boundary layers, and the second side having a thermoconductive bus being thermally in contact with a solid outer surface of the geometrically configured corpus contacting with ambient fluid;
   each of the elemental acoustic thermoelectric devices is supplied with an individual integrated circuit comprising a sensor capable of detecting sound, an individual controller capable of manipulating by electric current, and a controllably manipulatable individual source of emf; and
   the common controller capable of controlling each of the elemental acoustic thermoelectric devices as well as the acoustic thermoelectric device as a whole;
the acoustic thermoelectric device is capable of at least one of:
   consuming electric power to trigger at least one of the Joule heating effect and the Peltier effect to provide a temperature difference between at least one of:
      the solid inner wall of the shaped tunnel and the solid outer surface of the geometrically configured corpus contacting with the ambient fluid, and
      different points of the solid inner wall,
   and
   triggering the Seebeck effect to harvest electric power induced by a temperature difference between at least one of:
      the solid walls of the shaped tunnel and solid surfaces of the geometrically configured corpus contacting with ambient fluid, and
      different points of the solid walls;
the common controller providing that the acoustic thermoelectric device causes forcedly established distributed absolute temperature along the solid inner walls such that gradually-smoothed monotonic function T(x) of x represents the distributed absolute temperature of the fluid flow along the shaped tunnel thereby providing for a degree of freedom to interrelate the functions A(x) and T(x) with function u(x) of x representing profile of the fluid flow's headway velocity varying form a value $u_{in}$ at the open inlet to a value $u_{ou}$ at the open outlet by a condition of flow continuity expressed as:

$$A(x) = \frac{A*\sqrt{(\gamma-1)RT(x)}}{u(x)}\left(\frac{2RT(x)+u^2(x)}{(\gamma+1)RT(x)}\right)^{\frac{\gamma+1}{2(\gamma-1)}}$$

where R is a specific gas constant characterizing the fluid flow, wherein the functions u(x) is gradually-smoothed monotonic, wherein:
   the gradually-smoothed monotonic function of the absolute temperature T(x) is determined by:
      an absolute temperature $T_{in}$ of the fluid flow at the open inlet;
      temperature change $\delta T_0(x)$ interrelated with adiabatic compression-expansion occurred due to an adiabatic action of the Coanda-effect, in turn, determined by a curvature of the stationary geometry of the shaped tunnel, and forcedly established temperature contribution $\delta T_1(x)$ to the absolute temperature $T(x)$ along the boundary layers subjected to controllable at least one of heating and coding actions of the acoustic thermoelectric device, such that $T(x)=T_{in}+\delta T_0(x)+\delta T_1(x)$, and the forcedly established distributed absolute temperature along the solid inner walls according to the gradually-smoothed monotonic function of the absolute temperature $T(x)$, in turn, controls the gradually-smoothed monotonic function of the fluid flow's headway velocity $u(x)$ that is determined by the headway velocity $u_{in}$ of the fluid flow at the open inlet, convective headway acceleration resulting in a velocity gradient along the shaped tunnel length as the fluid flow is subjected to the adiabatic Coanda-effect, and controllable headway acceleration occurred due to controllable heating and/or cooling action of the acoustic thermoelectric device;

thereby, configuring both the staionary geometry of the shaped tunnel and the forcedly established distributed absolute temperature along the solid inner walls providing for conditions for continuity and unbrokenness of the boundary layers and, as a result, for a laminar motion of the fluid flow.

2. A multi-stage nozzle composed of N nozzles of claim 1 consolidated as a whole;

wherein the N nozzles, and indexed by integer numbers n from 1 to N, $1 \leq n \leq N$, such that:

said number n is associated with said n-th nozzle;

said n-th nozzle comprises said n-th shaped tunnel having said n-th solid walls forming said n-th stationary geometry characterized by said n-th varying cross-sectional area and having said n-th open inlet and said n-th open outlet, correspondingly;

said n-th open inlet is characterized by said n-th open inlet cross-section, said n-th open outlet is characterized by said n-th open out cross-section, wherein the (n+1)-th open inlet cross-section and the n-th open outlet cross-section are identical for $1 \leq n \leq (N-1)$;

are united together wherein said (n+1)-th open inlet and said n-th open inlet for $1 \leq n \leq (N-1)$ are co-located to join the N shaped tunnels associated with the N nozzles, correspondingly, such that said n-th shaped tunnel is a fragment, indexed by said integer number n, of a resulting unbroken shaped tunnel formed thereby as a whole characterized by a united stationary geometry; said n-th fragment has said n-th varying cross-sectional area characterized by a cross-sectional area profile function $A(x)$ of x, and said n-th solid walls of said n-th shaped tunnel supplied with said n-th acoustic thermoelectric device providing forcedly established distributed absolute temperature along said n-th solid inner walls in accordance with the gradually-smoothed monotonic function of the absolute temperature $T_n(x)$, such that function $u_n(x)$ of the fluid flow's headway velocity along said n-th fragment of the resulting unbroken shaped tunnel length is gradually-smoothed monotonic and said n-th individual condition of flow continuity is:

$$A_n(x) = \frac{A_{*n}\sqrt{(\gamma-1)RT_n(x)}}{u_n(x)} \left( \frac{2RT_n(x)+u_n^2(x)}{(\gamma+1)RT_n(x)} \right)^{\frac{\gamma+1}{2(\gamma-1)}}$$

where $A_{*n}$ is n-th constant; the resulting unbroken shaped tunnel as a whole is either converging, or divergent, or convergent-divergent, or two-stage convergent-divergent; or multi-stage convergent-divergent; wherein the constants $A_{*n}$ are chosen such that piecewise-monotonic profile functions $A_{WHOLE}(x)$, and $T_{WHOLE}(x)$, composed of associated gradually-smoothed monotonic profile $A_n(x)$, $1 \leq n \leq N$, concatenated together and $T_n(x)$, $1 \leq n \leq N$, concatenated together, correspondingly, both remain gradually-smoothed along the resulting unbroken shaped tunnel as a whole, configured both:

the united stationary geometry of the resulting unbroken shaped tunnel, characterized by the gradually-smoothed piecewise-monotonic profile function $A_{WHOLE}(x)$, and the forcedly established distributed absolute temperature along all the solid inner walls of the resulting unbroken shaped tunnel, characterized by the gradually-smoothed piecewise-monotonic profile function $A_{WHOLE}(x)$;

providing conditions for continuity and unbrokenness of the boundary layers along the resulting unbroken shaped tunnel and, as a result, for a laminar motion of the fluid flow moving within and through the resulting unbroken shaped tunnel;

thereby, the multi-stage nozzle is applicable to convey:

in general, laminar flow to solve the problem of originated turbulence, and in particular, tiny portions of the fluid, associated with an acoustic wave incoming the open inlet and propagating within and along the resulting unbroken shaped-tunnel, to solve the problem of sound power dissipation.

* * * * *